US011352602B2

(12) United States Patent
Wee et al.

(10) Patent No.: US 11,352,602 B2
(45) Date of Patent: Jun. 7, 2022

(54) MICROALGAE ADAPTED FOR HETEROTROPHIC CULTURE CONDITIONS

(71) Applicant: Corbion Biotech, Inc., South San Francisco, CA (US)

(72) Inventors: Janice Lau Wee, South San Francisco, CA (US); Dawei Yuan, South San Francisco, CA (US); Wenhua Lu, South San Francisco, CA (US); Rika Regentin, South San Francisco, CA (US); Jeffrey Villari, South San Francisco, CA (US)

(73) Assignee: Corbion Biotech, Inc., South San Francisco, CA (US)

( * ) Notice: Subject to any disclaimer, the term of this patent is extended or adjusted under 35 U.S.C. 154(b) by 590 days.

(21) Appl. No.: 15/562,356

(22) PCT Filed: Mar. 30, 2016

(86) PCT No.: PCT/US2016/025023
§ 371 (c)(1),
(2) Date: Sep. 27, 2017

(87) PCT Pub. No.: WO2016/160999
PCT Pub. Date: Oct. 6, 2016

(65) Prior Publication Data
US 2018/0163170 A1    Jun. 14, 2018

Related U.S. Application Data

(60) Provisional application No. 62/141,167, filed on Mar. 31, 2015.

(51) Int. Cl.
*C12N 1/36* (2006.01)
*C12P 7/64* (2022.01)
*C12N 9/24* (2006.01)
*C12N 1/12* (2006.01)
*C12R 1/89* (2006.01)

(52) U.S. Cl.
CPC .............. *C12N 1/36* (2013.01); *C12N 1/125* (2021.05); *C12N 9/24* (2013.01); *C12P 7/64* (2013.01); *C12R 2001/89* (2021.05)

(58) Field of Classification Search
CPC .. C12N 1/36; C12N 9/24; C12N 1/125; C12P 7/64; C12R 1/89; C12R 2001/89
See application file for complete search history.

(56) References Cited

U.S. PATENT DOCUMENTS

| 8,278,090 | B1 | 10/2012 | Im et al. |
| 8,956,852 | B2 | 2/2015 | Im et al. |
| 2004/0209256 | A1 | 10/2004 | Dillon |
| 2010/0239712 | A1 | 9/2010 | Brooks et al. |
| 2011/0293785 | A1* | 12/2011 | Franklin ............... A23K 20/158 426/61 |
| 2011/0294174 | A1 | 12/2011 | Franklin et al. |
| 2012/0119862 | A1* | 5/2012 | Franklin ............... C12N 9/16 336/58 |
| 2012/0225472 | A1 | 9/2012 | Kuehnle |
| 2013/0071909 | A1 | 3/2013 | Im et al. |
| 2014/0113340 | A1 | 4/2014 | Harethi et al. |
| 2015/0125914 | A1* | 5/2015 | Franklin ........ C12Y 203/01041 435/134 |

FOREIGN PATENT DOCUMENTS

| DE | 10 2008 059562 A1 | 7/2009 | |
| WO | WO 2008/151149 A2 | 12/2008 | |
| WO | WO 2009/066142 A2 | 5/2009 | |
| WO | WO 2009/126843 A2 | 10/2009 | |
| WO | WO 2010/045368 A1 | 4/2010 | |
| WO | WO 2010/063031 A2 | 6/2010 | |
| WO | WO 2010/063032 A2 | 6/2010 | |
| WO | WO 2010/127182 A1 | 11/2010 | |
| WO | WO 2011/038463 A1 | 4/2011 | |
| WO | WO 2011/038464 A1 | 4/2011 | |
| WO | WO 2011/150411 A1 | 12/2011 | |
| WO | WO 2012/061647 A2 | 5/2012 | |
| WO | WO 2012/101459 A2 | 8/2012 | |
| WO | WO 2012/106560 A1 | 8/2012 | |
| WO | WO-2013071029 A1 * | 5/2013 | ................ C10L 1/08 |
| WO | WO 2013/138523 A1 | 9/2013 | |
| WO | WO 2013/158938 A1 | 10/2013 | |
| WO | WO 2014/060973 A1 | 4/2014 | |

(Continued)

OTHER PUBLICATIONS

U.S. Office Action dated Mar. 21, 2012 issued in U.S. Appl. No. 12/497,257.
U.S. Notice of Allowance dated Jul. 30, 2012 issued in U.S. Appl. No. 12/497,257.
U.S. Notice of Allowance dated Nov. 5, 2014 issued in U.S. Appl. No. 13/593,342.
International Preliminary Report on Patentability (IPRP/EP) dated Oct. 12, 2017 issued in Application No. PCT/US2016/025023.

(Continued)

*Primary Examiner* — Renee Claytor
*Assistant Examiner* — Susan E. Fernandez
(74) *Attorney, Agent, or Firm* — Leydig, Voit & Mayer

(57) ABSTRACT

The present invention provides methods for making microalgal strains with improved properties relative to the strains from which they are derived. In illustrative embodiments, the methods are performed to produce microalgal strains adapted for use in the industrial production of microalgae-derived biomass products, including but not limited to triglycerides and fatty acids. Also provided are microalgal strains, which can be obtained using the methods described herein, as wells microalgal-derived biomass products, which can be produced from such microalgal strains.

10 Claims, 4 Drawing Sheets
Specification includes a Sequence Listing.

(56) References Cited

FOREIGN PATENT DOCUMENTS

WO    WO 2014/089514 A1    6/2014
WO    WO 2015/051319 A2    4/2015

OTHER PUBLICATIONS

International Search Report and Written Opinion dated (ISR/EP) dated Sep. 8, 2016 issued in Application No. PCT/US2016/025023.
Invitation to Pay Additonal Fees w/Annex of Partial International Search (ISR/EP) dated Jul. 11, 2016 issued in Application PCT/US2016/025023.
Achitouv et al. (2004) "$C_{31}$-$C_{34}$ methylated squalenes from a Bolivian strain of Botryococcus braunii." *Phytochemistry* 65(23): 3159-3165.
Gusakov et al. (2007) "Design of highly efficient cellulase mixtures for enzymatic hydrolysis of cellulose" *Biotechnol Bioeng.* 97(5): 1028-38.
Inoue et al. (1994) "Analysis of oil derived from liquefaction of Botryococcus Braunii" *Biomass and Bioenergy* 6(4): 269-274.
Jeoh et al. (2007) "Cellulase digestibility of pretreated biomass is limited by cellulose accessibility" *Biotechnol Bioeng.* 98(1): 112-22.
Lane (2012) "CORBzyme, Bunge form JV for commercial-scale renewable oils plant in Brazil." Biofuels Digest pp. 1-2.
Largeau et al. (1980) "Sites of accumulation and composition of hydrocarbons in Botryococcus braunii" *Phytochemistry* 19: 1043-1051.
Lawford et al. (2002) "Performance testing of Zymomonas mobilis metabolically engineered for cofermentation of glucose, xylose, and arabinose" *Appl Biochem Biotechnol.* 98-100: 429-48.
Metzger et al. (1985) "Alkadiene- and botryococcene-producing races of wild strains of Botryococcus braunii" *Phytochemistry* 24(10): 2305-2312.
Sapp (2012) "USS Ford runs on CORBzyme marine diesel; first algal fuels used in operational fleet" Biofuels Digest pp. 1-4.
Tyystjärvi et al. (2005) "Mathematical modelling of the light response curve of photoinhibition of photosystem II." *Photosynth Res.* 84(1-3): 21-27.
Weetall et al. (1985) "Studies on the Nutritional Requirements of the Oil-Producing Alga Botryococcus braunii" *Applied Biochemistry and Biotechnology* 11: 377-391.
Wyman et al. (2005) "Comparative sugar recovery data from laboratory scale application of leading pretreatment technologies to corn stover" *Bioresource Technology* 96(18): 2026-32.
Zaslavskaia et al. (2001) "Trophic Conversion of an Obligate Photoautotrophic Organism Through Metabolic Engineering" *Science* 292: 2073-2075.
Marie-Mathilde Perrineau et al., "Evolution of Salt Tolerance in a Laboratory Reared Population of C Hlamydomonas Reinhardtil," Environmental Microbiology, vol. 16, No. 6, Jun. 23, 2014, pp. 1755-1766. <doi:10.1111/1462-2920.12372>.
European Office Action dated Jan. 14, 2019 issued in Application No. EP 16 715 970.6.
European Extended Search Report dated Nov. 21, 2018 issued in Application No. EP 18 199 852.7.
Office Action, dated May 11, 2018, for Thailand National Phase Application. No. 1701005926, with English translations of relevant portion thereof.
Chaung, Kai-Chung et al., "Effect of Culture Conditions on growth, Lipid content, and fatty acide composition of Aurantiochytrium mangrovei strain BL10", AMB Express, (Jan. 1, 2012), vol. 2, No. 1, p. 42, XP055078009, ISBN:2191-0855, DOI: 10.1186/2191-0855-2-42.

* cited by examiner

MICROALGAE ADAPTED FOR HETEROTROPHIC CULTURE CONDITIONS

CROSS-REFERENCE TO RELATED APPLICATIONS

This application is the U.S. national phase under 35 U.S.C. § 371 of Intl. Application No. PCT/US2016/025023, filed on Mar. 30, 2016, which claims the benefit under 35 U.S.C. § 119(e) of U.S. Provisional Application No. 62/141,167, filed on Mar. 31, 2015, which are hereby incorporated herein by reference in their entireties for all purposes.

GOVERNMENT FUNDING

Certain embodiments of this invention were made with State of California support under California Energy Commission Grant number pir-08-048. The energy commission has certain rights to this invention.

TECHNICAL FIELD

The present invention relates to microalgal strains adapted to heterotrophic culture conditions and methods for making such strains. These strains are particularly useful for the production of cultivation products such as triglycerides and fatty acids, as well as downstream products made from the cultivation products, such as oleochemicals.

BACKGROUND

Certain microalgae are capable of converting fixed-carbon energy sources into higher value products such as triglycerides, fatty acids, carbohydrates, and proteins. In addition, the microalgae themselves can be valuable as a food source. Certain species of microalgae have been genetically engineered to produce "tailored oils", which means that their triglyceride content shows altered distributions of fatty acid chain lengths and saturation relative to the strains from which they were derived. See PCT Pub. Nos. 2008/151149, 2009/126843, and 2010/045358. While *Chlorella* strains have been the focus of much effort in developing triglyceride production methods, more recently strains of the genus *Prototheca* have been identified as having even more promise as a new source of triglyceride, including tailored oils for specific applications. See PCT Pub. Nos. 2010/063031 and 2010/063032 and PCT App. Nos. U.S. Ser. No. 11/038,463 and U.S. Ser. No. 11/038,464.

A major challenge in using microalgae for the production of triglycerides and other valuable chemicals is the cost of using a fixed-carbon energy source. Fixed carbon feedstocks refer to carbon sources that are not carbon dioxide, which has a free energy that is too low to be optimal for use as the energetic input for heterotrophic microalgae culture. Fixed-carbon sources that have been used for microalgal cultivation include include glucose, fructose, sucrose, and glycerol. When using purified sugar (e.g., sucrose or glucose) as a fixed carbon feedstock for a cultivation, purification of the sugar from plant material such as sugar cane, sugar beets, and processed cellulosic materials is a major contributor to overall cultivation costs. Purification is often needed, because the fixed-carbon feedstock may contain substances that are inhibitory or toxic to the microalgae. For example, high levels of potassium and/or sodium salts and compounds such as xylose and furfurals present in these low-cost sources of sugar can be inhibitory to microalgal growth and triglyceride production.

Compounding these problems, the microalgae may not convert much of the fixed carbon source added to a cultivation to the desired product due to competing metabolic pathways in the microalgae.

Finally, many microalgal species exhibit optimal growth at temperatures requiring cooling of the cultivation medium, adding significant cost to the cultivation.

SUMMARY

In certain embodiments, the present invention provides a laboratory-adapted strain of microalga of a species that is capable of being heterotrophically cultivated. The laboratory-adapted strain is capable of growth in the presence of 100 mM potassium ion with a doubling time of less than 12 hours, wherein an unadapted or naturally occurring strain of microalga of that species is incapable of growth or has a doubling time of greater than or equal to 12 hours in the presence of 100 mM potassium ion. The laboratory-adapted strain can, for example, be capable of growth in the presence of 100 mM potassium ion with a doubling time of between 2 hours and 12 hours, e.g., about 2, 3, 4, 5, 6, 7, 8, 9, 10, 11 or 12 hours, e.g., about 4-5 hours. In various embodiments, the laboratory-adapted strain is capable of growth in the presence of at least about 200 mM, e.g., at least about 300, 400, 500, 600, 700, 800, 900 mM, up to about 1000 mM potassium or sodium ion. The laboratory-adapted strain can, in certain embodiments, be capable of producing at least about 10%, e.g., at least about 20%, 30%, 40%, 50%, 60%, 70%, 80%, up to about 90% triglyceride by dry cell weight. In particular embodiments, the laboratory-adapted strain is derived from a species that is a not a marine or halophilic species. Suitable species include those of the genus *Prototheca* or *Chlorella*, e.g., *Prototheca moriformis* or *Chlorella protothecoides*.

Another aspect of the invention includes, in certain embodiments, a laboratory-adapted strain of a microalgal species adapted under conditions of limiting sugar so as to have an increased yield of triglyceride relative to a parent strain under the same culture conditions. In illustrative embodiments, the laboratory-adapted strain has an increase in triglyceride yield (oil titer or lipid titer) of at least 3%. 5%, 7%, or 9% relative to the parent strain. The laboratory adapted strain is, in particular embodiments, capable of growth with a doubling time of between 2 hours and 24 hours, e.g., about 2, 3, 4, 5, 6, 7, 8, 9, 10, 11, 12, 13, 14, 15, 16, 17, 18, 19, 20, 21, 22, 23, 24 hours, e.g., about 4-5 hours. The laboratory-adapted strain can, in certain embodiments, be capable of producing at least about 10%, e.g., at least about 20%, 30%, 40%, 50%, 60%, 70%, 80%, up to about 90% triglyceride by dry cell weight. In particular embodiments, the laboratory-adapted strain is derived from a species that is a not a marine or halophilic species. Suitable species include those of the genus *Prototheca* or *Chlorella*, e.g., *Prototheca moriformis* or *Chlorella protothecoides*.

The invention also provides a method for producing a microalgal product. In certain embodiments, the method includes heterotrophically cultivating a microalga in a culture medium having a high salt concentration, wherein the microalga is adapted for growth in the high-salt condition, followed by recovery of the microalgal product from the culture. Where the microalgal product includes a triglyceride or fatty acid, the method can further include separating the triglyceride or fatty acid from the remaining microalgal biomass. In various embodiments, the microalga is capable of producing at least about 20% and up to about 90% triglyceride by dry cell weight, e.g., in the range of about 20-30%, 30-40%, 40-50%, 60-70%, 70-80%, or 80-90% triglyceride by dry cell weight. In certain embodiments, the microalga can be of the genus *Prototheca* or *Chlorella*, e.g., *Prototheca moriformis* or *Chlorella protothecoides*. The sodium or potassium condition employed in the method can be, in various embodiments, at least about 100 mM, 200 mM, 300 mM, 400 mM, 500 mM, up to about 600 mM, greater than the typical condition (e.g., fresh water salinity conditions, e.g., water with less than 500 parts per million (ppm) of dissolved salts, about 7 mg/L or less of sodium ions and about 3 mg/L or less of potassium ions) for growth of the parent or naturally occurring strain. In particular embodiments, the culture is fed with a feedstock that is a plant-derived product that is predominantly sucrose, glucose or fructose, a hydrolyzed cellulose and/or hydrolyzed hemicellulose. In various embodiments, the culture is fed with a feedstock that has a salt concentration of at least about 100 mM, e.g., at least about 150 mM, 200 mM, 250 mM, up to about 300 mM, total combined potassium or sodium ion so as to elevate the total combined potassium or sodium ion concentration of the culture medium to greater than 50 mM. In certain embodiments, the microalga is one that is adapted for growth in the high-salt condition by propagation under a high but sublethal concentration of salt, e.g., for at least 10 generations, e.g., at least 15, 20, 30, 40, 50, 60, 70, 80, 90, 100, 120, 130, 140 or 150 generations. In such embodiments, the the high but sublethal concentration of salt can be, for example, between about 100 mM to about 1000 mM, or from about 500 mM to about 900 mM, total combined sodium or potassium ion. In various embodiments, the high salt concentration is greater than or equal to about 100, 200, 300, 400, 500, 600, 700, 800, 900, or 1000 mM total combined sodium or potassium ion. In some embodiments, the method entails mutagenizing the microalga prior to propagation in the presence of the high but sublethal concentration of salt. In particular embodiments, the high salt concentration results from the addition of a high-salt sugar feedstock into the culture medium. The culture can, in certain embodiments, be fed with a sugar feedstock that is deionized to a lesser degree than would be required without the use of the adapted microalga. For example, the sugar feedstock can be deionized to a level of 300 mM or 150 mM total combined sodium and potassium ion, and the doubling time of the microalga at this salt concentration can be 5 or fewer hours, e.g., about 4, 3, 2 hours. In particular embodiments, the microalga is genetically engineered to produce an altered distribution of fatty acid chain lengths and/or fatty acid saturation, relative to the non-engineered microalga. For example, the microalga can include one or more of an exogenous acyl-ACP thioesterase, sucrose invertase, or desaturase and/or a knockout or knock-down of an endogenous fatty acid desaturase or acyl-ACP thioesterase. In varying embodiments, the exogenous acyl-ACP thioesterase is from a plant selected from the group consisting of *Cinnamomum camphora, Umbellularia californica, Cuphea hookeriana, Cuphea palustris, Cuphea lanceolata, Iris germanica, Myristica fragrans, Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. In illustrative embodiments, the microalga produces triglycerides having one of the following fatty acid distribution characteristics: >25% C12, >60% C18:1, >20% C18:0, or >30% C12-C14, and the method includes further separating the triglyceride or fatty acid from the remaining microalgal biomass.

Another aspect of the invention is a method for adapting a heterotrophic microalga including propagating the microalga in the presence of a high but sublethal concentration of salt so as to generate an adapted microalga capable of an increased growth rate in the presence of the high level of salt. In certain embodiments, the high but sublethal concentration of salt is between about 100 mM to about 1000 mM, or from about 500 mM to about 900 mM. In particular embodiments, the method entails selecting an adapted microalga capable of producing at least 50% triglycerides by dry cell weight in the presence of a high but sublethal concentration of salt. The microalga can, optionally, be genetically engineered to produce an altered fatty acid chain length and/or saturation distribution via one or more of the introduction of a gene encoding an active exogenous thioesterase, introduction of a gene encoding an active exogenous fatty acid desaturase, suppression of an endogenous thioesterase or suppression of an endogenous desaturase. In varying embodiments, the exogenous acyl-ACP thioesterase is from a plant selected from the group consisting of *Cinnamomum camphora, Umbellularia californica, Cuphea hookeriana, Cuphea palustris, Cuphea lanceolata, Iris germanica, Myristica fragrans, Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. The genetic engineering can be performed before or after the cultivation in the presence of the high salt. Related aspects of the invention include a microalgal strain produced by this method and a product produced using this strain.

The invention also provides a method for producing a microalgal product from a microalga that is adapted for growth in a low-sugar condition. In certain embodiments, the method includes heterotrophically cultivating a microalga in a culture medium, followed by recovery of the microalgal product from the culture. In certain embodiments, the adapted microalga is capable of producing at least 20% triglycerides by dry cell weight, and the adaptation of the microalga results in a higher efficiency of conversion of sugar into fatty acid, as compared to the parental strain, when both are cultivated under the same conditions. Where the microalgal product includes a triglyceride or fatty acid, the method can further include separating the triglyceride or fatty acid from the remaining microalgal biomass. In various embodiments, the adapted microalga is capable of producing at least about 20% and up to about 90% triglyceride by dry cell weight, e.g., in the range of about 20-30%, 30-40%, 40-50%, 60-70%, 70-80%, or 80-90% triglyceride by dry cell weight. In certain embodiments, the microalga can be of the genus *Prototheca* or *Chlorella*, e.g., *Prototheca moriformis* or *Chlorella protothecoides*. In particular embodiments, the the microalga is propagated in the presence of the low-sugar condition for at least 10 generations, e.g., at least 15, 20, 30, 40, 50, 60, 70, 80, 90, 100, 120, 130, 140 or 150 generations. In some embodiments, the method entails mutagenizing the microalga prior to propagation in the low-sugar condition. In illustrative embodiments, the low-sugar condition is a sugar concentration of less than about 1.0 g/L, e.g., less about 0.8 g/L, 0.5 g/L. 0.2 g/L, 0.1 g/L, 0.08 g/L, 0.05 g/L, 0.02 g/L, 0.01 g/L, as low as about 0.005 g/L. In particular embodiments, the microalga is genetically engineered to produce an altered distribution of fatty acid chain lengths and/or fatty acid saturation, relative to the non-engineered microalga. For example, the microalga can include one or more of an exogenous acyl-ACP thioesterase, sucrose invertase, or desaturase and/or a knockout or knock-down of an endogenous fatty acid desaturase or acyl-ACP thioesterase. In varying embodiments, the exogenous acyl-ACP thioesterase is from a plant selected from the group consisting of *Cinnamomum camphora*, *Umbellularia californica*, *Cuphea hookeriana*, *Cuphea palustris*, *Cuphea lanceolata*, *Iris germanica*, *Myristica fragrans*, *Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. In illustrative embodiments, the microalga produces triglycerides having one of the following fatty acid distribution characteristics: >25% C12, >60% C18:1, >20% C18:0, or >30% C12-C14, and the method includes further separating the triglyceride or fatty acid from the remaining microalgal biomass.

Another aspect of the invention is a method for adapting a heterotrophic microalga including propagating the microalga in the presence of a low concentration of sugar, for example at a concentration of less than about 1.0 g/L, e.g., less about 0.8 g/L, 0.5 g/L. 0.2 g/L, 0.1 g/L, 0.08 g/L, 0.05 g/L, 0.02 g/L, 0.01 g/L, as low as about 0.005 g/L. In particular embodiments, the method entails selecting an adapted microalga capable of producing at least 50% triglycerides by dry cell weight. The microalga can, optionally, be genetically engineered to produce an altered fatty acid chain length and/or saturation distribution via one or more of the introduction of a gene encoding an active exogenous thioesterase, introduction of a gene encoding an active exogenous fatty acid desaturase, suppression of an endogenous thioesterase or suppression of an endogenous desaturase. In varying embodiments, the exogenous acyl-ACP thioesterase is from a plant selected from the group consisting of *Cinnamomum camphora*, *Umbellularia californica*, *Cuphea hookeriana*, *Cuphea palustris*, *Cuphea lanceolata*, *Iris germanica*, *Myristica fragrans*, *Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. The genetic engineering can be performed before or after the cultivation in the presence of the low concentration of sugar. Related aspects of the invention include a microalgal strain produced by this method and a product produced using this strain.

In particular embodiments, the invention also provides a laboratory-adapted microalgal strain characterized by a growth rate that is 5% greater than a parent strain or a naturally occuring strain of that species, when cultured under the same conditions.

The invention further provides, in certain embodiments, a laboratory-adapted strain of microalga of a species capable of being heterotrophically cultivated in a culture medium including sugar cane juice, beet juice, or sorghum juice. The sugar cane juice, beet juice, or sorghum juice includes potassium and/or sodium ion, and the culture medium includes at least 100 mM total combined potassium ion and sodium ion. The laboratory-adapted strain possesses a doubling time of 12 or fewer hours, e.g., about 11, 10, 9, 8, 7, 6, 5, 4, 3 or 2 hours, under these conditions, whereas the naturally occurring strain is incapable of growth or has a doubling time of greater than or equal to 12 hours in the presence of 100 mM total combined potassium ion and sodium ion. In particular embodiments, the laboratory-adapted strain is capable of growth in the presence of 100 mM total combined potassium ion and sodium ion with a doubling time of between 2 hours and 12 hours e.g., about 2, 3, 4, 5, 6, 7, 8, 9, 10, 11, 12 hours, e.g., about 4-5 hours. Preferably, the laboratory-adapted strain is capable of growth in the presence of 100 mM total combined potassium ion and sodium ion with a doubling time of 8 or fewer hours, e.g., about 7, 6, 5, 4, 3 or 2 hours. In various embodiments, the laboratory-adapted strain is capable of growth in the presence of 250 mM, 350 mM, 450 mM, or 550 mM total combined potassium ion and sodium ion. In various embodiments, the sugar cane juice, beet juice, or sorghum juice is deionized, partially deionized, or not deionized. In various embodiments, the sugar cane juice, beet juice, or sorghum juice is deionized to a level of about 300 mM total combined potassium ion and sodium ion. The laboratory-adapted strain can, in certain embodiments, be capable of producing 10 to 90% triglyceride by dry cell weight. In particular embodiments, the laboratory-adapted strain is derived from a species that is a not a marine or halophilic species. Suitable species include those of the genus *Prototheca* or *Chlorella*, e.g., *Prototheca moriformis* or *Chlorella protothecoides*.

Another aspect of the invention includes, in certain embodiments, an improved microalgal strain having an improved efficiency in conversion of sugar to triglycerides produced by isolating a mutant of a parent microalgal strain exposed to an alternative oxidase inhibitor, e.g., a mitochondrial oxidase inhibitor. The improved microalgal strain can, in certain embodiments, be capable of producing 10% and up to about 90% triglyceride by dry cell weight, e.g., in the range of about 20-30%, 30-40%, 40-50%, 60-70%, 70-80%, or 80-90%. In particular embodiments, the improved microalgal strain is derived from a species that is a not a marine or halophilic species. Suitable species include those of the genus *Prototheca* or *Chlorella*, e.g., *Prototheca moriformis* or *Chlorella protothecoides*. The improved microalgal strain can, optionally, include at least one exogenous fatty acid biosynthesis gene, such as, for example, one or more of an exogenous acyl-ACP thioesterase and a fatty acid desaturase.

Another aspect of the invention includes, in certain embodiments, an improved microalgal strain having an improved oil titer, relative to a parental microalgal strain. In varying embodiments, the improved microalgal strain is produced by isolating a mutant of the parent microalgal strain which has been exposed to salicylhydroxamic acid (SHAM). In some embodiments, the improved microalgal strain is produced by isolating a mutant of the parent microalgal strain which has been exposed to an inhibitor of a monosaccharide transporter. In particular embodiments, the improved microalgal strain is produced by isolating a mutant of the parent microalgal strain which has been exposed to 2-deoxyglucose. In varying embodiments, the improved microalgal strain has at least a 5% improvement in oil titer, e.g., at least a 6%, 7%, 8%, 9%, 10%, or greater improvement in oil titer, relative to the parental microalgal strain.

Another aspect of the invention includes, in certain embodiments, an improved microalgal strain that is capable of producing oil having a higher percentage of C18:0 and/or C18:1 than a parental microalgal strain, wherein the improved microalgal strain is produced by isolating a mutant of the parent microalgal strain which has been exposed to an inhibitor of a β-ketoacyl-ACP synthase (KAS) and/or of an enoyl:acyl carrier protein (ACP) reductase. In some embodiments, the inhibitor includes cerulenin. In some embodiments, the inhibitor includes triclosan. In some embodiments, the improved microalgal strain has an at least 10% improvement in percentage of C18:0 and/or C18:1, e.g., at least 11%, 12%, 13%, 14%, 15%, 16%, 17%, 18%, 19%, 20% or greater, improvement in percentage of C18:0 and/or C18:1. In some embodiments, the microalgal strain is capable of producing fatty acids including at least 70% C18:0 and/or C18:1, e.g., at least 73%, 75%, 78%, 80%, 83%, 85%, or more, C18:0 and/or C18:1. In some embodiments, the oil titer is at least 98% of the parental microalgal strain, e.g., at least 99% or equivalent to the parental microalgal strain. In some embodiments, the oil titer is at least 5% greater, e.g., at least a 6%, 7%, 8%, 9%, 10% greater, than that of the parental microalgal strain.

In some embodiments, any of the improved microalgal strains discussed above is of a species that is not a marine or halophilic species. In some embodiments, the improved microalgal strain is capable of producing 10 to 90% triglyceride by dry cell weight. In some embodiments, the improved microalgal strain is of a species of the genus *Prototheca* or *Chlorella*. In varying embodiments, the species is *Prototheca moriformis* or *Chlorella protothecoides*. In varying embodiments, the improved microalgal strain is capable of producing at least 50% triglyceride by dry cell weight. In certain embodiments, the improved microalgal strain is a genetically engineered strain. In particular embodiments, the improved microalgal strain includes at least one exogenous fatty acid biosynthesis gene. In varying embodiments, the improved microalgal strain includes one or more of an exogenous acyl-ACP thioesterase, an exogenous fatty acid desaturase, and an exogenous β-ketoacyl-ACP synthase (KAS). In varying embodiments, the exogenous acyl-ACP thioesterase is from a plant selected from the group consisting of *Cinnamomum camphora, Umbellularia californica, Cuphea hookeriana, Cuphea palustris, Cuphea lanceolata, Iris germanica, Myristica fragrans, Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. In varying embodiments, the exogenous β-ketoacyl-ACP synthase (KAS) is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:59, SEQ ID NO:66 and SEQ ID NO:68. In some embodiments, the microalga is genetically engineered to produce an altered fatty acid chain length and/or saturation distribution via one or more of: (1) the introduction of a gene encoding an active exogenous thioesterase, (2) the introduction of a gene encoding an active exogenous fatty acid desaturase, (3) the introduction of a gene encoding an active exogenous β-ketoacyl-ACP synthase (KAS), (4) the suppression of an endogenous thioesterase, or (5) the suppression of an endogenous desaturase. In varying embodiments, the genetic engineering was performed before exposing the parent microalgal strain to the inhibitor of a monosaccharide transporter, 2-deoxyglucose, salicylhydroxamic acid (SHAM), or the inhibitor of a β-ketoacyl-ACP synthase (KAS) or of an enoyl:acyl carrier protein (ACP) reductase. In varying embodiments, the genetic engineering was performed after exposing the parent microalgal strain to the inhibitor of a monosaccharide transporter, 2-deoxyglucose, salicylhydroxamic acid (SHAM), or the inhibitor of a β-ketoacyl-ACP synthase (KAS) or of an enoyl:acyl carrier protein (ACP) reductase. Also provided are products produced by the improved microalgal strains described above.

Another aspect of the invention is a method for producing an improved microalgal strain. In some embodiments, the method entails cultivating a parental microalgal strain in the presence of an inhibitor of salicylhydroxamic acid (SHAM), and isolating a mutant of the parental microalgal strain that is capable of growth in the presence of salicylhydroxamic acid (SHAM). In some embodiments, the method entails cultivating a parental microalgal strain in the presence of an inhibitor of a monosaccharide transporter, and isolating a mutant of the parental microalgal strain that is capable of growth in the presence of the inhibitor of a monosaccharide transporter. In particular embodiments, the method entails cultivating a parental microalgal strain in the presence of 2-deoxyglucose, and isolating a mutant of the parental microalgal strain that is capable of growth in the presence of 2-deoxyglucose. In some embodiments, the method entails cultivating a parental microalgal strain in the presence of an inhibitor of a β-ketoacyl-ACP synthase (KAS) or of an enoyl:acyl carrier protein (ACP) reductase, and isolating a mutant of the parental microalgal strain that is capable of growth in the presence of the inhibitor. In variations of such embodiments, the inhibitor includes cerulenin or triclosan. In some embodiments of the method, the parental microalgal strain is of a species that is not a marine or halophilic species. In some embodiments, the improved microalgal strain is capable of producing 10 to 90% triglyceride by dry cell weight. In some embodiments, the improved microalgal strain is of a species of the genus *Prototheca* or *Chlorella*, for example, *Prototheca moriformis* or *Chlorella protothecoides*. In some embodiments, the improved microalgal strain is capable of producing at least 50% triglyceride by dry cell weight. In certain embodiments, the improved microalgal strain is a genetically engineered strain. In particular embodiments, the improved microalgal strain includes at least one exogenous fatty acid biosynthesis gene. In some embodiments, the improved microalgal strain includes one or more of an exogenous acyl-ACP thioesterase, a fatty acid desaturase, and an exogenous β-ketoacyl-ACP synthase (KAS). In some embodiments, the microalga is genetically engineered to produce an altered fatty acid chain length and/or saturation distribution via one or more of: (1) the introduction of a gene encoding an active exogenous thioesterase, (2) the introduction of a gene encoding an active exogenous fatty acid desaturase, (3) the introduction of a gene encoding an active exogenous β-ketoacyl-ACP synthase (KAS), (4) the suppression of an endogenous thioesterase, or (5) the suppression of an endogenous desaturase. In varying embodiments, the exogenous acyl-ACP thioesterase is from a plant selected from the group consisting of *Cinnamomum camphora, Umbellularia californica, Cuphea hookeriana, Cuphea palustris, Cuphea lanceolata, Iris germanica, Myristica fragrans, Cuphea palustris* and *Ulmus Americana*. In some embodiments, the exogenous acyl-ACP thioesterase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polypeptide selected from the group consisting of SEQ ID NO:15, SEQ ID NO:17, SEQ ID NO:19, SEQ ID NO:21, SEQ ID NO:23, SEQ ID NO:25, SEQ ID NO:27, SEQ ID NO:29 and SEQ ID NO:31. In varying embodiments, the exogenous acyl-ACP thioesterase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:35, SEQ ID NO:36, SEQ ID NO:37, SEQ ID NO:38, SEQ ID NO:39 and SEQ ID NO:58. In some embodiments, the exogenous fatty acid desaturase is selected from the group consisting of delta 12 fatty acid desaturase (d12FAD), stearoyl-ACP desaturase 2A (SAD2A) and stearoyl-ACP desaturase 2B (SAD2B). In some embodiments, the exogenous fatty acid desaturase is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:42, SEQ ID NO:45 and SEQ ID NO:48. In some embodiments, the exogenous sucrose invertase is expressed from a cassette having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide of SEQ ID NO:53. In some embodiments, the polynucleotide encoding a knockout or knock-down of an endogenous fatty acid desaturase has at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:40 and SEQ ID NO:41, SEQ ID NO:43 and SEQ ID NO:44, and SEQ ID NO:46 and SEQ ID NO:47. In varying embodiments, the exogenous β-ketoacyl-ACP synthase (KAS) is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:59, SEQ ID NO:66 and SEQ ID NO:68. In some embodiments, the genetic engineering was performed before exposing the parent microalgal strain to the inhibitor of a monosaccharide transporter, 2-deoxyglucose, salicylhydroxamic acid (SHAM), or the inhibitor of a β-ketoacyl-ACP synthase (KAS) or of an enoyl:acyl carrier protein (ACP) reductase. In some embodiments, the genetic engineering was performed after exposing the parent microalgal strain to the inhibitor of a monosaccharide transporter, 2-deoxyglucose, salicylhydroxamic acid (SHAM), or the inhibitor of a β-ketoacyl-ACP synthase (KAS) or of an enoyl:acyl carrier protein (ACP) reductase.

In illustrative embodiments of the above-described improved microalgal strain and related method, the microalga is genetically engineered to produce an altered fatty acid chain length and/or saturation distribution via suppression of an endogenous thioesterase and introduction of a gene encoding an active exogenous β-ketoacyl-ACP synthase (KAS). For example, an exogenous KASII can be introduced. In varying embodiments, the exogenous β-ketoacyl-ACP synthase (KAS) is encoded by a polynucleotide having at least about 60% sequence identity, e.g., at least about 65%, 70%, 75%, 80%, 85%, 90%, 91%, 92%, 93%, 94%, 95%, 96%, 97%, 98%, 99% or 100%, sequence identity, to a polynucleotide selected from the group consisting of SEQ ID NO:59, SEQ ID NO:66 and SEQ ID NO:68. In some embodiments, the microalgal strain is capable of producing fatty acids comprising at least 70% C18:0 and/or C18:1.

These and other aspects and embodiments of the invention are described in more detail below and illustrated in the accompanying drawings briefly described below.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

Definitions

Figure 1:
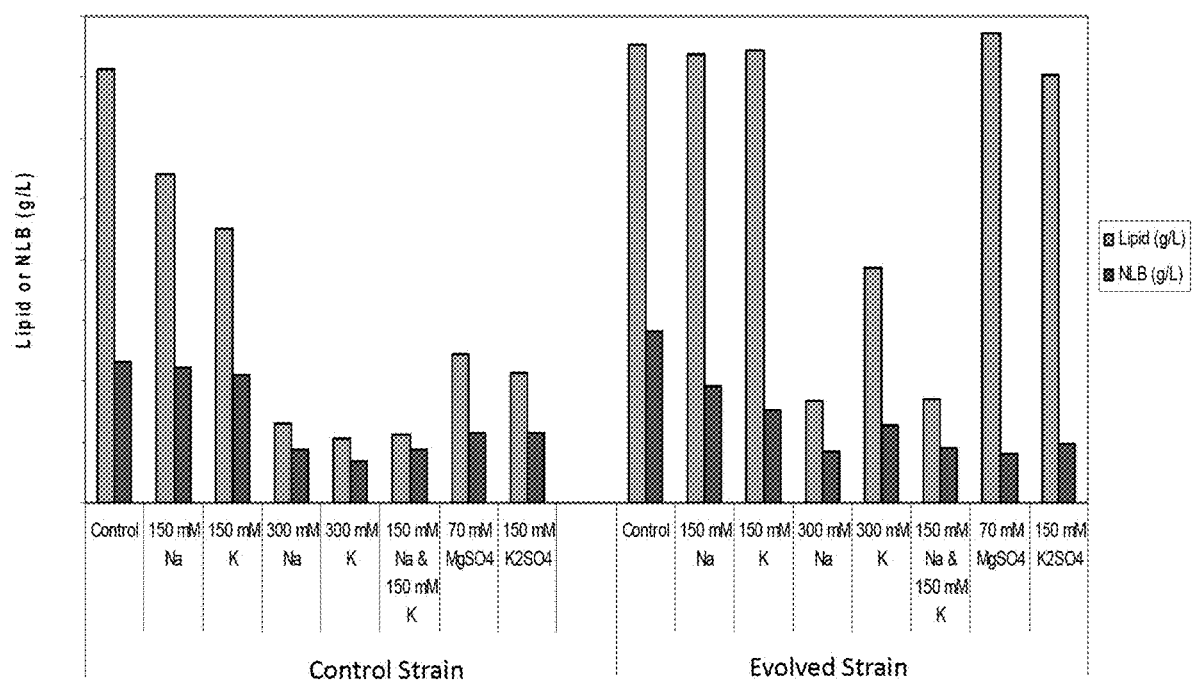
FIG. 1 is a bar graph showing triglyceride and non-triglyceride biomass (NTB) of an unadapted microalgal strain compared to that of an adapted strain in control and elevated salt concentration conditions.

As used herein, the term "adapt" or "adapted" refers to persistent changes in a microalgal strain resulting from exposure of a population of microalgae derived from the strain to a selection pressure. The changes include any persistent changes including genetic and epigenetic changes. The term "laboratory-adapted" refers to a microalgal strain produced by non-natural selection, i.e., resulting from deliberate exposure by humans to a selection pressue (regardless of whether this selection is literally carried out in a "laboratory" or some other facility).

As used herein, the phrase "improved microalgal strain" refers to a microalgal strain that has been derived from a parental strain and has at least one property that is enhanced with respect to the parental strain.

"Cultivated", and variants thereof such as "cultured" and "fermented", refer to the intentional fostering of growth of one or more cells by use of selected and/or controlled conditions. Examples of selected and/or controlled conditions include the use of a defined medium (with known characteristics such as pH, ionic strength, and carbon source), specified temperature, oxygen tension, carbon dioxide levels, and growth in a bioreactor. Cultivated does not refer to the growth or propagation of microorganisms in nature or otherwise without human intervention.

As used herein, "growth" encompasses increases in cell size, cellular contents, and/or cellular activity, and/or increases in cell numbers via mitosis.

"Doubling time" refers to the duration of time for a cell or culture of cells to double in number under selected conditions. Where the doubling time of a microalgal strain (e.g., an adapted strain) is expressed relative to the doubling time of another microalgal strain (e.g., a parental strain), it is understood that these doubling times are determined under the same culture conditions.

The term "total combined sodium and potassium ion" refers to the concentration value obtained by summing the sodium ion concentration and the potassium ion concentration of a solution, e.g., culture media, or sugar solution including sugar cane juice, beet juice, molasses, or sorghum juice, or depolymerized cellulose or depolymerized hemicellulose solutions. This term is not intended to imply that both ions must be present, but rather encompasses concentration values where all of the ions can be sodium or, conversely, all of the ions can be potassium, or both sodium ions and potassium ions are present.

The term "microalgal product" refers to any material produced by and/or derived from a microalga. The term encompasses secreted products, products that are extracted from the microalga (e.g., triglyceride and/or fatty acids), the residual biomass remaining after any extraction process, and any component of microalgal biomass. The term also encompasses any downstream product that incorporates any material produced by and/or derived from a microalga.

The term "feedstock" refers to a raw material (input) fed into a process for conversion into something different (output). This term is used herein to describe the organic substance(s) supplied to a microalgal culture to supply at least some of the algae's carbon and energy requirements when the culture is growth heterotorphically. A feedstock containing a sugar (simple mono- or disaccharides or complex oligo- or polysaccharides) is refered to herein as a "sugar feedstock."

As used herein, a material is described as "deionized" when the material (e.g., sugar cane juice) has been subjected to a processing step for removing ions, such as, e.g., ion exchange chromatography. The term does not imply that all ions are necessarily removed from the material.

The term "VHP sugar" refers to what is commonly referred to as very high polarity sugar, hi-pol sugar, or grade A sugar. For example, VHP sugar may have an ICUMSA value of between 600 and 1200.

The term "oil titer" is used herein to refer to the amount of oil in a microalga or microalgal culture. As used with reference to the adaptation methods herein, oil titer is often expressed as a percentage of the oil content of the parental microalgal strain.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using BLAST set to default parameters.

Methods for Making Improved Microalgal Strains

The present invention provides methods for making microalgal strains with improved properties relative to the strains from which they are derived. In illustrative embodiments, the methods are performed to produce microalgal strains adapted for use in the industrial production of microalgae-derived biomass products, including but not limited to triglycerides and fatty acids, or products derived therefrom including fuel, foodstuffs, surfactants, and oleochemicals.

In accordance with illustrative embodiments of the invention, heterotrophic microalgal strains are adapted for use in the industrial production of microalgae-derived biomass products, including triglycerides and fatty acids. Any heterotrophic microalgal strain can be employed in the methods described herein, and suitable starting (parental) strains may vary, depending upon the microalgae-derived biomass product to be produced. Suitable parental or unadapted strains for the applications described herein include those disclosed in US 2010/0239712, published Sep. 23, 2010 (which is hereby incorporated by reference in relevant partand specifically for this disclosure), and US 2011/0294174, published Dec. 1, 2011 (which is hereby incorporated by reference in relevant part and specifically for this disclosure). Specific examples of strains suitable for use in the methods described herein include species of the genus *Prototheca* or *Chlorella*, e.g., *Prototheca moriformis* or *Chlorella protothecoides*, e.g., any of UTEX strains 1435, 1806, 411, 264, 256, 255, 250, 249, 31, 29, 25, and CCAP strains 211/17 and 211/8d.

The chain length and saturation distribution of fatty acids produced by the microalgal cells may be tailored using genetic engineering methods including those taught in WO2008151149 (which is incorporated by reference herein for its description of genetic engineering methods and cultivation methods), WO2010063032 (which is incorporated by reference herein for its description of genetic engineering methods and cultivation methods), and PCT Application No. US11/38463 (which is incorporated by reference herein for its description of genetic engineering methods and cultivation methods), either before or after the adaptation. The microalgae may comprise one or more of an exogenous acyl-ACP thioesterase (including an acyl-ACP thioesterase with activity toward or specificity for C8, C10, C12, C14, C16, or C18), sucrose invertase, or fatty acid desaturase. Alternately, or in addition, the microalgae may comprise a knock-out or knock-down of an endogenous fatty acid desaturase or acyl-ACP thioesterase. A mutation (including knockout) or inhibition (e.g., using antisense or RNAi) of one or more endogenous desaturase genes (e.g., a steroyl-ACP desaturase or fatty acid desaturase including a delta 12 fatty acid desaturase) may reduce or eliminate desaturase activity to produce a more fully saturated triglyceride profile. The microalgae may also comprise a mutation (including a knockout) or inhibition (including via antisense or RNAi) of an edogenouse ketoacyl synthase gene and/or may comprise an exogenous ketoacyl synthase gene. In certain embodiments, strains are adapted in the laboratory to improve growth in high-salt media, growth on an alternative carbon source, growth at elevated temperature, to improve sugar to triglyceride conversion efficiency, to enhance oil titer, and/or to enhance C18:0 and/or C18:1 levels. In further embodiments, the adapted strains are used to produce products such as fatty acids or triglycerides.

Adaptation for Growth in Adverse Conditions

In an embodiment, the present invention provides methods for making microalgal strains adapted for growth or survival in an adverse condition. As a result of the adaptation of the strain, it may have a substantially unchanged or increased production of a desired product, such as microalgal triglyceride in the condition or even other conditions. In some embodiments, the method produces strains that exhibit increased growth rates relative to the unadapted strain (e.g., as may be measured by doubling time, specific growth rate, or rate constant), under cultivation conditions that are inhibitory to growth of an unadapted strain (i.e., a selection pressure). For example, a laboratory-adapted strain may be characterized by a growth rate that is 5% greater than a parent strain or a naturally occuring strain of that species, when cultured under the same conditions. In various embodiments, the method comprises culturing the unadapted strain under inhibitory growth conditions for multiple generations until an adapted strain is produced. Typically, the culturing will be continued for at least 10 to 20 generations, including, for example, at least 50 generations or at least 70, 80 or 150 generations. The culturing for multiple generations under the selection pressure can be conducted in a chemostat or by successive subculturing (e.g., in shake flasks). In some embodiments, the process involves adaptation of a mutagenized strain. Suitable mutation-inducing conditions include exposure to a chemical mutagen and/or UV or other irradiation. Typically, at the end of the adaptation period, isolates of the culture are obtained, characterized, and stored for future use. In an embodiment, an isolate is chosen that maintains a minimum level of triglyceride production (e.g., production comparable to the parent strain, e.g., production as measured by % dry cell weight of the final product, yield per volume of cultivation medium, and/or rate of triglyceride production per cell). In specific embodiments, the adapted strain is capable of producing between 10% and 90%, e.g., 20 to 30, 30 to 40, 40 to 50, 60 to 70, 70 to 80, 80 to 90, or 75 to 85% triglyceride by dry cell weight. As those of skill in the art readily appreciate, the capability of producing these levels of triglyceride can be determined using conditions suitable for triglyceride production. For example, nitrogen depletion/limitation is a known inducer of lipogenesis in oleaginous microorganisms, and therefore, triglyceride production can, in certain embodiments be carried out under low nitrogen conditions, e.g., as described in US 2011/0294174, published Dec. 1, 2011 (which is hereby incorporated by reference specifically for this disclosure).

High Salt

In various embodiments, the condition inhibitory to growth is a cultivation medium that has a higher salt concentration relative to a typical concentration for the parent strain, wherein the higher salt concentration limits growth (referred to herein as a "high salt concentration" or a "high-salt condition"). The high salt concentration may be a result of salts that include cations of potassium, sodium, calcium and/or magnesium. In various embodiments, a high salt concentration includes, for example and without limitation, potassium and/or sodium ion concentrations (e.g., "total combined sodium and potassium ion") of 10 to 1000, 50 to 900, or 100 to 800 mM higher than the typical concentration for growth of an unadapted strain (i.e., a parent strain or naturally occuring strain) under the same growth conditions. For example, the potassium or sodium ion concentration (individually, or in total) may be 10, 50, 100, 200, 300, 400, or 500 mM greater than the typical level for growth of an unadapted strain, when cultured under conventional culture conditions for that strain. Conventional conditions for species of *Prototheca* and *Chlorella* include, e.g., those disclosed in US 2010/0239712, published Sep. 23, 2010 (which is hereby incorporated by reference specifically for this disclosure), and US 2011/0294174, published Dec. 1, 2011 (which is hereby incorporated by reference specifically for this disclosure) (e.g., growth in 4.2 g/L $K_2HPO_4$, 3.1 g/L $NaH_2PO_4$, 0.24 g/L $MgSO_4.7H_2O$, 0.25 g/L Citric Acid monohydrate, 0.025 g/L $CaCl_2$ $2H_2O$, 2 g/L yeast extract plus 2% glucose for 7 days at 28° C. with agitation (200 rpm)). In particular embodiments, the "typical level" of the potassium and/or sodium ion concentration is the level that provides the highest growth rate (e.g., increase in cell number) of the unadapted strain under selected conditions. This level can be determined by growing the unadapted strain at a range of different salt concentrations and determining peak growth rate from a plot of growth rate versus salt concentration. As an example, the typical sodium and/or potassium concentration for an unadapted strain may be about 40 mM. In illustrative embodiments, the high but sublethal concentration of salt employed in the method is 100 to 1000 mM sodium and/or potassium ion, e.g., 100, 200, 300, 400, 500, 600, 700, 800, 900, or 1000 mM sodium and/or potassium ion. In some embodiments, salt is provided by the use of inexpensive carbon sources (e.g., sugar cane juice, VHP sugar, beet juice, sorghum juice, molasses, crude glycerol, or depolymerized cellusosic material including depolymerized cellulose and/or hemicellulose preparations). These sugar preparations may have salt concentrations that, when added to a culture, yield higher salt concentrations than the typical salt concentration for a given strain.

After multiple generations (e.g., 5-50, 100, 150, or more) of cultivation under high-salt conditions, the culture contains cells that multiply faster than the parent strain in the high-salt condition. One or more cells can then be isolated from the culture to establish a new adapted strain, which is then characterized for desired production characteristics, such as triglyceride productivity and distribution of fatty acid chain length and saturation. The adapted strain may then be used to produce triglycerides in the presence of high salt concentrations (including salt conditions elevated to a lesser degree than the evolution condition). As a result, lower cost, high-salt carbon sources can be used without expensive salt removal (deionization) steps or with a combination of low-salt and high-salt carbon sources for improved economy of triglyceride production. Such embodiments are particularly useful in connection with species of microalgae that have not naturally evolved to be salt-tolerant; i.e., species that are not marine or halophilic species.

Alternate Carbon Sources

In a specific embodiment, the cells are adapted for growth on VHP sugar as the primary or sole carbon source.

In various embodiments, the condition inhibitory to growth is a carbon source other than the typical carbon source such as purified glucose, as the primary carbon source. The alternate carbon sources can be glycerol, sucrose, particularly in the form of beet juice, VHP sugar, molasses, sorghum juice (typically extracted from the cane of the sorghum plant, e.g., by crushing, mashing, or cutting), sugar cane juice, and xylose, particularly xylose derived from cellulosic materials. Such "alternate" carbon sources yield lower growth rates than carbon sources that are conventionally employed for culturing, under defined culture conditions. In various embodiments, the carbon source is a plant-derived feedstock that is predominantly sucrose, glucose or fructose, or a hydrolyzed cellulosic material. Examples of such feedstocks include sugarcane extract (including thin juice or thick juice), sugar beet extract (including thin juice or thick juice), palm sugar, or depolymerized corn stover or sugar cane bagasse. In various embodiments, a strain is adapted to metabolize and/or tolerate five-carbon sugars, including, for example, xylose, arabinose, and ribose, or to tolerate inhibitory substances found in cellulosic material such as furfurals.

Inhibitory Substances

In various embodiments, the condition inhibitory to growth is a cultivation medium that contains a substance, other than sodium or potassium, that is inhibitory to growth. In a particular embodiment, the substance inhibitory to growth is a substance present in depolymerized cellulosic material. Cellulosic biomass is inexpensive and readily available and generally constitutes residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, miscanthus, fiber cane, and fiber sorghum.

Cellulosic biomass can be depolymerized to make sugar contained in it available to microalgae as an energy source, and the depolymerized cellulosic biomass resulting therefrom includes a number of materials that can be inhibitory to microalgal growth and triglyceride production. Such materials include, without limitation, lignin, hydroxymethylfurfural, acetate, high salt concentrations, and xylose. Microalgal strains adapted in accordance with the methods of the invention can be used to produce triglycerides from a sugar feedstock in the presence of inhibitory substances, including the high salt concentrations of many depolymerized cellulosic feedstocks. The high salt-levels are present naturally from the depolymerized cellulosic material or arise from the depolymerization process. For example, depolymerization of cellulosic materials may require highly acidic or alkaline conditions. The pH neutralization of the highly acidic or alkaline conditions results in sugar sources with high potassium and/or sodium concentrations. Using the adapted strains of the present invention, one can reduce or eliminate the need to deionize a sugar feedstock prior to adding it to the cultivation media. Deionization can be performed, for example, using ion exchange or reverse osmosis, and entails additional cost. In contrast, cultivations of strains of the present invention may be fed "raw" undeionized feedstock, or partially deionized feedstock (i.e., removing only a fraction of the salt in the feedstock or blending deionized feedstock with non-deionized feedstock). As a result, the production of biomass, including triglyceride and other products derived from the biomass becomes more cost-effective due to a growth rate or triglyceride production rate that is enhanced relative to the parent strain for a given elevated inhibitor concentration. (In this context, the term "elevated" encompasses the presence of an inhibitor that is not usually present in conventional cultures, as well as the presence of an inhibitor at a higher level than usual in conventional cultures.) In accordance with the adaptive methods of the invention, an unadapted strain is continuously cultured in cultivation media that contains an elevated level of one of more of these inhibitory materials or a composition comprising them, i.e., depolymerized cellulosic material, for multiple generations (e.g., 10-50, 100, 150, or more) or until the culture exhibits an increase in growth rate.

Atypical Temperature

In various embodiments, the condition inhibitory to growth is a temperature other than the typical growth temperature (about 32° C. for many microalgal strains). While the embodiment of the invention can be practiced to make strains adapted to growth and/or triglyceride production at temperatures below 32° C., more typically, these embodiments are practiced to make strains adapted to grow and produce triglycerides at temperatures above 32° C., i.e., 37° C. and higher. In accordance with the adaptive methods of the invention, an unadapted strain is continuously cultured at the desired temperature until the culture contains cells that grow faster and/or produce more triglycerides than does the unadapted strain at that temperature. Alternatively, a microalgal strain is adapted to a first elevated temperature for which the parent strain grows or produces triglycerides at a suboptimal rate (e.g., decreased by about 70%). After multiple generations, the strain is then adapted to a second elevated temperature that is higher than the first elevated temperature. If necessary or desired, the process may be repeated with further elevated temperatures. If a chemostat method is used, the temperature may be increased upon observation of an increase in cell density of the culture. As a result, an adapted strain is produced, which may exhibit improved growth and/or triglyceride production at an elevated temperature, thereby reducing energy, materials or capital equipment needed to cool an exothermic microalgal cultivation.

Atypical pH

In other embodiments, the condition inhibitory to growth is a pH other than the typical growth pH (e.g., 6.5-8 for many microalgal strains). In this embodiment of the invention, strains adapted to growth and/or triglyceride production at low or high pH are prepared. In accordance with an adaptive method of the present invention, an unadapted strain is continuously cultured at the desired pH until the culture contains cells that grow faster and/or produce more triglyceride than does the unadapted strain at that pH. Alternatively, a microalgal strain is adapted to a first pH for which the parent strain grows or produces triglycerides at a suboptimal rate (e.g., decreased by about 70%). After multiple generations, the strain is then adapted to a second pH that is lower or higher than the first pH. If necessary or desired, the process may be repeated at lower or higher pH. If a chemostat method is used, the pH may be decreased or increased upon observation of an increase in cell density of the culture. As a result, an adapted strain is produced, which may grow and/or produce triglyceride in culture media having a depressed or elevated pH. In a specific embodiment, the depressed or elevated pH is one that is lower than 6.5 or higher than 8, repectively. Cultivation of microalgae at a pH that is lower than 6.5 or higher than 8 can be useful in minimizing contamination of the culture medium during cultivation.

Adaptation for Enhanced Efficiency in Triglyceride Production

In an embodiment, the method is practiced to make a strain that converts a carbon source, e.g., a sugar such as glucose, sucrose, or sugar alcohol such as glycerol, to a desired end product, e.g., triglyceride, more efficiently than an unadapted counterpart strain. Efficiency is measured in the metabolic sense; the number of moles of triglyceride per mole of carbon source used is increased. In these embodiments, the method comprises culturing the unadapted strain under growth-limiting concentrations of the carbon source for multiple generations until an adapted strain is produced. When the carbon source is a sugar, a "growth-limiting concentration" of the sugar is referred to herein as a "low concentration of sugar" or a "low-sugar condition." For example, the concentration of useable sugars may be less than about 1.0 g/L, e.g., less about 0.8 g/L, 0.5 g/L. 0.2 g/L, 0.1 g/L, 0.08 g/L, 0.05 g/L, 0.02 g/L, 0.01 g/L, or as low as about 0.005 g/L. As in the other embodiments, the culturing under the adaptive conditions is continued for at least 10 to 20 or more generations, i.e., at least 70 generations, and sometimes for 150 generations or longer. In various embodiments, the method entails selecting an adapted microalgal strain capable of producing at least 50% triglycerides by dry cell weight under conventional culture conditions, where growth is not limited by the sugar concentration of the culture (i.e., where sugar is "non-limiting").

In an embodiment, the condition inhibitory to growth is an inhibition of alternative oxidase (AOX). The inhibition of AOX may be either chemical or by gene knockout or knockdown. Chemical inhibition may be accomplished with salicylhydroxamic acid (SHAM). For example, microalgal cells may be mutagenized chemically and/or using radiation. The mutagenized cells may then be plated on an inhibitor such as SHAM and robustly growing colonies selected. The selected colonies can then be analyzed for growth rates, triglyceride levels and efficiency in converting sugar to triglyceride. A mutant colony is then isolated that has a higher efficiency in converting sugar to triglyceride under conventional culture conditions. In particular embodiments, the mutant colony is capable of producing 10 to 90%, e.g., at least 50%, triglyceride by dry cell weight. Without being limited by the theory, the isolated strain may have one or more mutations that shunt more carbon to triglyceride and less carbon to $CO_2$. In various embodiments, these microalga subjected to this method are not of marine or halophilic species. Illustrative strains of *Chlorella* and strains of *Prototheca*, including but not limited to strains of *Chlorella protothecoides* and strains of *Prototheca moriformis*. The adapted strains can be produced using the adaptation methods provided herein. The mutant strain may be used to produce oil from sugar at high efficiency. The resulting oil may be used to make fuel, chemical, food, or other products.

Adaptation for Enhanced Oil Titer

In certain embodiments, the method is practiced to isolate an improved microalgal strain that has an enhanced oil titer relative to a parental strain. In some embodiments, the method entails cultivating a parental microalgal strain in the presence of an inhibitor of a monosaccharide transporter, and isolating a mutant of the parental microalgal strain that is capable of growth in the presence of the inhibitor of a monosaccharide transporter. Monosaccharide transporters include membrane transport proteins that bind monosaccharides (such as glucose) and sodium ions, which enter the cell together. The sodium ions are then pumped out of the cell by a sodium-potassium ATPase. The rate and extent of the sugar transport depends on the sodium ion concentration. Inhibitors of the monosaccharide transport system are well known and include phlorizin, cytochalasin B, 2-deoxyglucose, and inhibitors of the sodium-potassium ATPase system, such as cardiac glycosides (for example, digoxin and ouabain). Any inhibitor that is capable of inhibiting a microalgal monosaccharide transporter can be employed in the method.

Adaptation for Enhanced C18:0 and/or C18:1 Levels

In particular embodiments, the method is practiced to isolate an improved microalgal strain that has increased levels of C18:0 and/or C18:1 level(s) relative to a parental strain. In some embodiments, the method entails cultivating a parental microalgal strain in the presence of an inhibitor of a β-ketoacyl-ACP synthase (KAS) or of an enoyl:acyl carrier protein (ACP) reductase, and isolating a mutant of the parental microalgal strain that is capable of growth in the presence of the inhibitor. Any β-ketoacyl-ACP synthase (KAS) present in a microalgal cell can inhibited, including, e.g., KASI, KASII, and/or KASIII. The inhibitor can be selective for one of these enzymes or can inhibit more than one. Illustrative KAS inhibitors include cerulenin from the fungus *Cephalosporium caerulens*, thiolactomycin (TLM) from the actinomycete *Nocardia* spp., isoniazid (isonicotinic acid hydrazide), ethionamide, and triclosan [5-chloro-2-(2, 4-dichlorophenoxy)-phenol]. Alternatively, or in addition, to KAS inhibition, any enoyl:acyl carrier protein (ACP) reductase (ENR) present in a microalgal cell can be inhibited, including ENR (NADPH, A-specific) and/or ENR (NADPH, B-specific). The inhibitor can be selective for one of these enzymes or can inhibit more than one. Illustrative ENR inhibitors include triclosan, triclocarban, atromentin and leucomelone. In some embodiments, the inhibitor inhibits both a KAS and an ENR; triclosan, for example, inhibits both enzymes.

General Considerations for Methods

In embodiments of the adaptive methods of the invention, the condition inhibitory to growth and/or production of a desired product maintained during the adaptation process is not lethal to the cells and does not prevent cell division completely. Instead, the cultivation conditions are maintained such that cell division is slower than that observed under conventional conditions, such that there is selection pressure on the culture undergoing adaptation. For example, a condition that slows the growth rate (extends the doubling time) by from 5 to 95% may be used. In various embodiments, the growth rate is slowed by 20% to 90%, 30 to 85% 40 to 75%, or 50 to 70%. In a particular embodiment, the growth rate is slowed by about 70%.

In embodiments of the adaptive methods of the invention, the culturing for multiple generations can be conducted in a chemostat or by successive subculturing in shake flasks. Moreover, in these various embodiments, the strain to be adapted can be mutagenized prior to cultivation under the adaptive conditions or at any point or continuously throughout the adaptive process. Mutagenesis can be readily accomplished by means known to those of skill in the art, including, without limitation, exposure to a chemical mutagen; e.g., N-methyl-N'-nitro-N-nitrosoguanidine, ethyl methanesulfonate, or 2-methoxy-6-chloro-9-[3-(ethyl-2-chloroethyl) aminopropylamino] acridine dihydrochloride or UV, X-rays, gamma rays or other electromagnetic or particle irradiation.

In embodiments of the adaptive methods of the invention, the methods are practiced to adapt a microalgal strain to a number of different parameters, such as any two or more of the inhibitory conditions described above. For example and without limitation, a strain may be adapted to tolerate both high-temperature cultivation and high salt concentrations. In other embodiments, the strain may be adapted to utilize a carbon source more efficiently and to tolerate-high salt concentrations. In other embodiments, the strain may be adapted to high-temperature cultivation and high salt concentration as well as to utilize a carbon source more efficiently. In various embodiments, these multiply adapted strains are adapted in a process in which all adaptations are simultaneously made. In other embodiments, these multiply adapted strains are adapted in a series of sequential adaptation processes.

In embodiments of the adaptive methods of the invention, the practitioner can isolate single cells from an adapted culture. The single cell isolates will be characterized to confirm that they have one or more of the desired attributes of the adapted culture, such as an increase in triglyceride production, increase in the conversion efficiency of sugar to a triglycerides, or the ability to produce triglyceride with a desired fatty acid distribution, and isolates so confirmed will be stored or "banked" for future use, including for further adaptation.

Improved Microalgal Strains

In another aspect, the present invention also provides microalgal strains produced by the methods of the invention. These strains, which may be referred to herein as "laboratory-adapted strains" exhibit, relative to the strains from which they were derived, improved growth and/or triglyceride production under conditions inhibitory to growth and/or triglyceride production of the unadapted strains. In various embodiments, these adapted strains include strains that exhibit a faster growth rate and/or higher triglyceride production than unadapted counterpart strains for a particular condition. In various embodiments, these adapted strains exhibit a faster growth rate and/or higher triglyceride production relative to unadapted strains under one or more conditions such as higher culture temperature, e.g., temperatures of 37 degrees C. or higher where the unadapted strain is typically grown at temperatures of about 32 degrees C.; higher salt, e.g., potassium and/or sodium salt, concentrations, e.g., salt concentrations 100 to 800 mM higher than the salt concentration in typical growth media (e.g., 40 mM potassium); and conditions in which the primary carbon source is a carbon source other than glucose, e.g., glycerol. In various embodiments, these adapted strains are able to convert a specific type of carbon source into a desired end product, e.g., triglyceride, more efficiently than the unadapted strain from which they were derived. In various embodiments, these microalgal strains of the invention are not of marine or halophilic species. Illustrative strains of *Chlorella* and strains of *Prototheca*, including but not limited to strains of *Chlorella protothecoides* and strains of *Prototheca moriformis*. The adapted strains can be produced using the adaptation methods provided herein.

Salt-Tolerant

In one embodiment, the present invention provides an adapted strain of microalgae of a species that is capable of being heterotrophically cultivated. Due to the adaptation, the strain is capable of growth in the presence of high salt concentrations, e.g., 100 to 800 mM, or 700 mM higher than the typical concentration used to cultivate the microalgae. In some embodiments, the higher salt concentration is a concentration of a sodium and/or potassium salt that is at least 100 mM, at least 300 mM, or up to 800 mM higher than the typical concentration for the unadapted strain. For example, the elevated salt concentration may come from using a sugar feedstock having at least 50, 100, 150, or 200 mM sodium and/or potassium ion. In some embodiments, the strain exhibits a specific growth rate in the high salt concentrations that is at least 5%, at least 10%, 20%, at least 30% or at least 50% faster (e.g., as measured by approximation to first-order kinetics or doubling time) than that of the unadapted strain under the same salt concentrations.

In some embodiments, the adapted strain has a doubling time in the high salt concentrations that is 12 or fewer hours, e.g., about 2, 3, 4, 5, 6, 7, 8, 9, 10, 11 or 12 hours, e.g., about 4-5 hours, where the naturally occurring microalgae of that species has a doubling time of greater or equal to 12 hours in the high salt concentrations. In various embodiments, the reduction in doubling time may be at least 15 minutes, at least 30 minutes, at least 1 hour, or at least 2 hours or longer. In various embodiments, the reduction in doubling time may be in the range of 15 minutes to 8 hours, 2 to 48 hours, 3 to 24 hours, or 3.5 to 12 hours. Doubling time may conveniently be measured using optical density readings, as illustrated in the examples below and as is commonly practiced in the art for other applications, or by any other suitable method. In various embodiments, the adapted strain exhibits such decreased doubling time in media in which the salt concentration is in the range of 50 to 800 mM, 100 to 600 mM, or 200 to 400 mM higher than the typical salt concentration for the unadapted strain. For example, the combined sodium and potassium concentration may be 100 to 1000, 100 to 200, 200 to 300, 300 to 400, 400 to 500, 500 to 600, 700 to 800, 800 to 900, or 900 to 1000 mM.

In a particular embodiments, a laboratory-adapted strain of microalgae is capable of being cultivated heterotrophically so as to grow in the presence of 100 mM potassium ion with a doubling time of 12 or fewer hours, e.g., about 2, 3, 4, 5, 6, 7, 8, 9, 10, 11 or 12 hours, e.g., about 4-5 hours, whereas the unadapted parent strain of the adapted microalgae or the naturally occurring microalgae of that species is incapable of growth or has a doubling time of greater than or equal to 12 hours in the presence of 100 mM potassium ion. For example, in certain embodiments, the doubling time of the adapted strain is between 2 and 12 hours in the presence of 100 mM potassium ion. In various embodiments, the laboratory-adapted strain is capable of growth in the presence of 200, 300, 400, 500, 600, 700, 800, 900, or 1000 mM potassium and/or sodium ion. The laboratory-adapted strain is capable, in certain embodiments, of producing 10-90% triglyceride by dry cell weight.

Importantly, and as demonstrated by the examples below with respect to potassium and sodium salts, the methods for adapting microalgal strains to high salt concentrations can be practiced with one salt, such as potassium, a common growth inhibitor found in sugar feedstocks such as sugar cane juice, to generate an adapted strain that exhibits improved growth and/or triglyceride production characteristics in the presence of high concentrations of other salts, including but not limited to sodium, calcium or magnesium salts.

Alternate Carbon Source-Tolerant

In certain embodiments, a laboratory-adapted strain of microalgae is capable of being cultivated heterotrophically so as to grow in a culture medium comprising sugar cane juice, beet juice, or sorghum juice, wherein the sugar cane juice, beet juice, or sorghum juice comprises potassium and/or sodium ion, and wherein the culture medium comprises at least 100 mM total combined potassium ion and sodium ion. The adapted strain has a doubling time of 12 or fewer hours, e.g., about 2, 3, 4, 5, 6, 7, 8, 9, 10, 11 or 12 hours, e.g., about 4-5 hours, under these conditions, whereas the unadapted parent strain of the adapted microalgae or the naturally occurring microalgae of that species is incapable of growth or has a doubling time of greater than or equal to 12 hours in the presence of 100 mM potassium ion. For example, in certain embodiments, the doubling time of the adapted strain is between 2 and 12 hours, e.g., less than 8 hours, in the presence of 100 mM potassium ion. In various embodiments, the laboratory-adapted strain is capable of growth in the presence of 250, 350, 450, 550, 600, 700, 800, 900, or 1000 mM potassium and/or sodium ion. The sugar cane juice, beet juice, or sorghum juice can be deionized, partially deionized, or not deionized. In varying embodiments, the sugar cane juice, beet juice, or sorghum juice is deionized to a level of about 300 mM total combined potassium ion and sodium ion. The laboratory-adapted strain is capable, in certain embodiments, of producing 10-90% triglyceride by dry cell weight.

Enhanced Efficiency in Triglyceride Production

In one embodiment, the invention provides a laboratory-adapted strain of microalga of a species adapted under conditions of limiting sugar so as to have an increased yield, e.g., by at least 3%, of triglyceride relative to a parent strain under the same culture conditions. In various embodiments, this laboratory-adapted strain has a doubling time is between 2 hours and 24 hours under conventional culture conditions (i.e., where sugar is non-limiting). The laboratory-adapted strain is capable, in certain embodiments, of producing 10-90% triglyceride by dry cell weight.

Enhanced Oil Titer

Another aspect of the invention includes an improved microalgal strain having an improved oil titer, relative to a parental microalgal strain. In certain embodiments, the improved microalgal strain is a laboratory adapted strain produced by isolating a mutant of the parent microalgal strain which has been exposed to an inhibitor of a monosaccharide transporter, as described above. In particular embodiments, the improved microalgal strain is produced by isolating a mutant of the parent microalgal strain which has been exposed to 2-deoxyglucose. In varying embodiments, the improved microalgal strain has at least a 5% improvement in oil titer, e.g., at least a 6%, 7%, 8%, 9%, 10%, 11%, 12%, 13%, 14%, 15% or greater, e.g., up to 16%, 17%, 18%, 19%, 20%, 21%, 22%, 23%, 24%, or 25%, improvement in oil titer, relative to the parental microalgal strain. The improved microalgal strain can also have a percentage improvement in oil titer falling within any range bounded by any of these values, e.g., 5%-25%, 10%-20%, and 11%-15%. Oil titer can be measured using any conventional method; generally the same method is used for measuring oil titer in the improved versus the parental strain.

Enhanced C18:0 and/or C18:1 Levels

Another aspect of the invention includes an improved microalgal strain that is capable of producing oil having a higher percentage of C18:0 and/or C18:1 than a parental microalgal strain. In certain embodiments, the improved microalgal strain is a laboratory-adapted strain produced by isolating a mutant of the parent microalgal strain which has been exposed to an inhibitor of a β-ketoacyl-ACP synthase (KAS) and/or of an enoyl:acyl carrier protein (ACP) reductase. In some embodiments, the inhibitor includes cerulenin. In some embodiments, the inhibitor includes triclosan. In various embodiments, the improved microalgal strain has an at least 10% increase in percentage of C18:0 and/or C18:1, relative to the parental strain, e.g., at least 11%, 12%, 13%, 14%, 15%, 16%, 17%, 18%, 19%, 20%, 21%, 22%, 23%, 24%, 25%, 26%, 27%, 28%, 29%, 30% or greater, e.g., up to 35%, 40%, 45%, 50%, 55%, or 60%, increase in percentage of C18:0 and/or C18:1. The improved microalgal strain can also have a percentage increase in level(s) of C18:0 and/or C18:1 falling within any range bounded by any of these values, e.g., 10%-60%, 15%-50%, and 20%-30%. C18:0 and C18:1 levels can be can be measured using any conventional method; generally the same method is used for measuring oil titer in the improved versus the parental strain. The "increase in percentage of C18:0 and/or C18:1" can be an increase in percentage of C18:0 alone or an increase in percentage of C18:1 alone or an increase in the combined levels of C18:0 and C18:1.

In some embodiments, the improved microalgal strain is capable of producing fatty acids including at least 70% C18:0 and/or C18:1, e.g., at least 73%, 75%, 78%, 80%, 83%, 85%, 86%, 87%, 88%, 89%, 90%, or more, e.g., up to 93% or 95% C18:0 and/or C18:1. The improved microalgal strain can also have a percentage C18:0 and/or C18:1 falling within any range bounded by any of these values, e.g., 70%-95%, 75%-90%, and 80%-85%. As noted above, these percentages can be calculated based on C18:0 alone, C18:1 alone, or the combined levels of C18:0 and C18:1.

In some embodiments, the oil titer of the improved microalgal strain is at least 98% of the parental microalgal strain, e.g., at least 99% or equivalent to the parental microalgal strain. In some embodiments, the oil titer is at least 5% greater, e.g., at least 6%, 7%, 8%, 9%, 10%, 11%, 12%, 13%, 14%, 15% or greater, e.g., up to 16%, 17%, 18%, 19%, 20%, 21%, 22%, 23%, 24%, or 25%, greater than the parental microalgal strain. The improved microalgal strain can also have a percentage increase in oil titer falling within any range bounded by any of these values, e.g., 5%-25%, 10%-20%, and 11%-15%.

General Considerations for Improved Microalgal Strains

In some embodiments, any of the improved microalgal strains discussed above is of a species that is not a marine or halophilic species. In certain embodiments, the improved microalgal strain is capable of producing 10 to 90% triglyceride by dry cell weight. In particular embodiments, the improved microalgal strain is of a species of the genus Prototheca or Chlorella. In varying embodiments, the species is Prototheca moriformis or Chlorella protothecoides. In varying embodiments, the improved microalgal strain is capable of producing at least 50% triglyceride by dry cell weight.

Genetic Engineering of Parent or Improved Micoalgal Strains

In various embodiments of all of the methods of the invention, the parent or adapted strain is genetically engineered to express one or more exogenous genes, either before or after the adaptation process. For example, the parent or adapted strain can be genetically engineered to produce an altered distribution of fatty acid chain lengths and/or fatty acid saturation. In particular embodiments, the microalgal strain employed in the methods of the invention will have been genetically modified to express an exogenous sucrose invertase gene such that sufficient sucrose invertase is produced by the strain to enable it to metabolize sucrose efficiently. In many of these embodiments, the sucrose invertase gene will encode a sucrose invertase that is secreted into the cultivation media. Alternatively or in addition, the microalgal strain can be genetically engineered to express an exogenous acyl-ACP thioesterase, exogenous desaturase, or exogenous β-ketoacyl-ACP synthase (KAS) or to suppress an endogenous thioesterase or desaturase.

In illustrative embodiments of the above-described improved microalgal strains and related methods, the microalga is genetically engineered to produce an altered fatty acid chain length and/or saturation distribution via suppression of an endogenous thioesterase and introduction of a gene encoding an active exogenous β-ketoacyl-ACP synthase (KAS). For example, an exogenous KASII can be introduced.

Methods for Producing Products from Improved Microalgal Strains

In another aspect, the invention provides methods for producing useful products from adapted microalgal strains. In various embodiments, these methods are practiced to produce triglycerides that in turn are used as a food, chemical feedstock, cosmetic ingredient, or fuel. In various embodiments, these methods involve cultivating the adapted strain on a carbon source (e.g. a sugar) on which an unadapted strain would grow more slowly or produce less of the desired product than the adapted strain. In various embodiments, these methods involve cultivating the adapted strain in a cultivation medium in which an unadapted strain would grow more slowly than the adapted strain. In various embodiments, these methods involve cultivating the adapted strain at a temperature at which an unadapted strain would grow more slowly than the adapted strain. In certain embodiments, the methods involve cultivating an improved microalgal strain (e.g., one having enhanced oil titer or level(s) of C18:0 and/or C18:1). In various embodiments, two or more of the methods disclosed here are combined, i.e., an adapted strain that grows more rapidly on glucose and in high-salt cultivation media is cultivated on glucose in a high-salt cultivation media to produce triglyceride. In various embodiments, the desired product is microalgal biomass that is incorporated, directly or after processing, into a foodstuff. In various embodiments, the desired product is microalgal triglyceride that is isolated from the microalgal biomass and then incorporated directly, or after further processing, into food. In various embodiments, the desired product is microalgal triglyceride that is isolated from the microalgal biomass and then processed into a fuel, such as biodiesel, renewable diesel, or jet fuel, or oleochemical.

For example, in one embodiment, the invention provides a method for producing a microalgal product, wherein the method entails heterotrophically cultivating a microalga in a culture medium having a high salt concentration, wherein the microalga is adapted for growth in the high-salt condition, and recovering the microalgal product. The microalgal product can, for example, include a triglyceride or fatty acid, in which case, the method can include separating the triglyceride or fatty acid from the remaining microalgal biomass. In various embodiments, the microalga is capable of producing 20% and up to about 90% triglyceride by dry cell weight, e.g., in the range of about 20-30%, 30-40%, 40-50%, 60-70%, 70-80%, or 80-90%. In various embodiments, the microalga is not of marine or halophilic species. Illustrative suitable microalga include strains of Chlorella and strains of Prototheca, including but not limited to strains of Chlorella protothecoides and strains of Prototheca moriformis. The adapted microalga can cultured be at a sodium or potassium condition that is at least 100, 200, 300, 400 or 500 mM greater than the typical condition (e.g., fresh water salinity conditions, e.g., water with less than 500 parts per million (ppm) of dissolved salts, about 7 mg/L or less of sodium ions and about 3 mg/L or less of potassium ions) for growth of the parent or naturally occurring strain. In some embodiments, the culture is fed with a feedstock that is a plant-derived product that is predominantly sucrose, glucose or fructose, a hydrolyzed cellulose and/or hydrolyzed hemicellulose. The high salt concentration in the culture medium of this method can result from the addition of a high-salt sugar feedstock to the medium. In particular embodiments, the culture is fed with a feedstock that has a salt concentration of at least 100 mM, 150 mM, 200 mM, or 250 mM total combined potassium or sodium ion so as to elevate the total combined potassium or sodium ion concentration of the culture medium to greater than 50 mM. In some embodiments, the culture is fed with a sugar feedstock that is deionized to a lesser degree than would be required without the use of the adapted microalga. For example, the sugar feedstock can be deionized to a level of 300 mM or 150 mM total combined sodium ion and potassium ion, and, in certain embodiments, the doubling time of the microalga at this salt concentration is 5 or fewer hours, e.g., 4, 3 or 2 hours. The adapted microalga can be produced, as described herein, by propagation under a high but sublethal concentration of salt, which propogation can be carried out for at least 10 generations, e.g, at least 20, 30, 40, 50, 60, 70, 80, 90, 100, 110, 120, 130, 140, 150, or more, generations. In various embodiments, the high but sublethal concentration of salt is between 100 to 1000 or 500 to 900 mM total combined sodium or potassium ion. In various embodiments, the high salt concentration is greater than or equal to 100, 200, 300, 400, 500, 600, 700, 800, 900, or 1000 mM total combined sodium or potassium ion. In some embodiments, the adapted microalga is produced by mutagenizing the microalga prior to propagation in the presence of the high but sublethal concentration of salt.

In in another embodiment, the invention provides a method for producing a microalgal product, wherein the method entails heterotrophically cultivating a microalga in a culture medium, wherein the microalga is adapted for growth in a low-sugar condition, and recovering the microalgal product. In certain embodiments, the adapted microalga produces at least 20% triglycerides by dry cell weight under conventional culture conditions (i.e., where sugar is non-limiting), and the adaptation of the microalga results in a higher efficiency of conversion of sugar into fatty acid. The microalgal product can, for example, include a triglyceride or fatty acid, in which case, the method can include separating the triglyceride or fatty acid from the remaining microalgal biomass. In various embodiments, the microalga is capable of producing 20% and up to about 90% triglyceride by dry cell weight, e.g., in the range of about 20-30%, 30-40%, 40-50%, 60-70%, 70-80%, or 80-90% triglyceride by dry cell weight. Illustrative suitable microalga include strains of Chlorella and strains of Prototheca, including but not limited to strains of Chlorella protothecoides and strains of Prototheca moriformis. The adapted microalga can be produced, as described herein, by propagation in the presence of the low-sugar condition for at least 10 generations, e.g., at least 20, 30, 40, 50, 60, 70, 80, 90, 100, 110, 120, 130, 140, 150, or more, generations. In certain embodiments, the low-sugar condition is a sugar concentration of less than about 1.0 g/L, e.g., less about 0.8 g/L, 0.5 g/L. 0.2 g/L, 0.1 g/L, 0.08 g/L, 0.05 g/L, 0.02 g/L, 0.01 g/L, as low as about 0.005 g/L. In some embodiments, the adapted microalga is produced by mutagenizing the microalga prior to propagation in the presence of the low-sugar condition.

Optionally, after applying a selection pressure as described above to obtain a a strain with a faster growth rate under an inhibitor condition, and optional genetic engineering, multiple microalgal clones are isolated and tested for their ability to produce a desired product, such as a triglyceride of a certain chain-length or degree of saturation, or ability to produce increased amounts of the desired product. A clonal strain having both an increased growth rate and desired production capability is then selected and stored for future use.

In various embodiments, the microalgal strain produces triglycerides having >25%, >30%, >40%, >50%, >60%, >70%, >80%, >90%, C12. Alternatively, or in addition, the microalgal strain produces triglycerides having >60%, >70%, >80%, >90% C18:1. Alternatively or in addition, the microalgal strain produces triglycerides having >20%, >30%, >40%, >50%, >60%, >70%, >80%, >90% C18:0. Alternatively or in addition, the microalgal strain produces triglycerides having >30%, >40%, >50%, >60%, >70%, >80%, >90% C12-C14. In illustrative embodiments, the microalgal strain produces triglycerides having one of the following fatty acid distribution characteristics: >25% C12, >60% C18:1, >20% C18:0, or >30% C12-C14.

Fatty Acid Profiles of Improved Microalgal Cells

In some embodiments, the present invention provides an microalgal cell (e.g., a high-salt tolerant cell or a cell that has improved efficiency for converting sugar to triglyceride) comprising a triglyceride oil, wherein the fatty acid profile of the triglyceride oil is selected from the group consisting of: at least about 1%, at least about 2%, at least about 5%, at least about 7%, at least about 10%, or at least about 15% C8:0; at least about 1%, at least about 5%, at least about 15%, at least about 20%, at least about 25%, or at least about 30% C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% C12:0; at least about 2%, at least about 5%, at least about 10%, at least about 15%, at least about 20%, at least about 25%, at least about 30%, at least about 35%, at least about 40%, at least about 45%, or at least about 50% C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, C16:0; at least about 5%, at least about 10%, at least about 15%, at least about 20%, at least about 25%, at least about 30%, at least about 35%, at least about 40%, at least about 45%, or at least about 50% C18:0; at least about 60%, at least about 65%, at least about 70%, at least about 75%, at least about 80%, at least about 85%, or at least about 90% C18:1; less than about 7%, less than about 5%, less than about 3%, less than about 1%, or about 0% C18:2; and at least about 35%, at least about 40%, at least about 45%, at least about 50%, at least about 55%, at least about 60%, at least about 65%, at least about 70%, at least about 75%, at least about 80%, at least about 85%, or at least about 90% saturated fatty acids.

In some embodiments, the microalgal cell comprises triglyceride oil comprising a fatty acid profile selected from the group consisting of: total combined amounts of C8:0 and C10:0 of at least about 10%, at least about 20%, at least about 30%, at least about 40%, at least about 50%, at least about 60%, at least about 70%, at least about 80%, at least about 90%, or about 100%; total combined amounts of C10:0, C12:0, and C14:0 of at least about 50%, at least about 60%, at least about 70%, at least about 80%, at least about 90%, or about 100%; total combined amounts of C16:0, C18:0 and C18:1 of at least about 60%, at least about 70%, at least about 80%, at least about 90%, or about 100%; total combined amounts of C18:0, C18:1 and C18:2 of at least about 60%, at least about 70%, at least about 80%, at least about 90%, or about 100%; total combined amounts of C14:0, C16:0, C18:0 and C18:1 of at least about 60%, at least about 70%, at least about 80%, at least about 90%, or about 100%; and total combined amounts of C18:1 and C18:2 of less than about 30%, less than about 25%, less than about 20%, less than about 15%, less than about 10%, less than about 5%, or about 0%, In some embodiments, the microalgal cell comprises triglyceride oil having a fatty acid profile comprising a ratio of fatty acids selected from the group consisting of: a C8:0 to C10:0 ratio of at least about 5 to 1, at least 6 to 1, at least 7 to 1, at least 8 to 1, at least 9 to 1, or at least 10 to 1; a C10:0 to C12:0 ratio of at least about 6 to 1, at least 7 to 1, at least 8 to 1, at least 9 to 1, or at least 10 to 1; a C12:0 to C14:0 ratio of at least about 5 to 1, at least 6 to 1, at least 7 to 1, at least 8 to 1, at least 9 to 1, or at least 10 to 1; a C14:0 to C12:0 ratio of at least 7 to 1, at least 8 to 1, at least 9 to 1, or at least 10 to 1; and a C14:0 to C16:0 ratio of at least 1 to 2, at least 1 to 3, at least 1 to 4, at least 1 to 5, at least 1 to 6, at least 1 to 7, at least 1 to 8, at least 1 to 9, or at least 1 to 10.

Fatty Acid Profiles of Triglyceride Oil Compositions from Improved Microalgal Cells In some embodiments, the present invention provides an microalgal triglyceride oil composition, wherein the fatty acid profile of the triglyceride oil is selected from the group consisting of: at least about 1%, at least about 2%, at least about 5%, at least about 7%, at least about 10%, or at least about 15% C8:0; at least about 1%, at least about 5%, at least about 15%, at least about 20%, at least about 25%, or at least about 30% C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% C12:0; at least about 2%, at least about 5%, at least about 10%, at least about 15%, at least about 20%, at least about 25%, at least about 30%, at least about 35%, at least about 40%, at least about 45%, or at least about 50% C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% C16:0; at least about 5%, at least about 10%, at least about 15%, at least about 20%, at least about 25%, at least about 30%, at least about 35%, at least about 40%, at least about 45%, or at least about 50% C18:0; at least about 60%, at least about 65%, at least about 70%, at least about 75%, at least about 80%, at least about 85%, or at least about 90% C18:1; less than about 7%, less than about 5%, less than about 3%, less than about 1%, or about 0%, C18:2; and at least about 35%, at least about 40%, at least about 45%, at least about 50%, at least about 55%, at least about 60%, at least about 65%, at least about 70%, at least about 75%, at least about 80%, at least about 85%, or at least about 90% saturated fatty acids.

In some embodiments, the microalgal triglyceride oil composition comprises triglyceride oil comprising a fatty acid profile in which: the total combined amount of C10:0, C12:0 and C14:0 is at least about 50%, at least bout 60%, at least about 70%, at least about 80%, at least about 90%, or about 100%; the total combined amount of C16:0, C18:0 and C18:1 is at least about 60%, at least about 70%, at least about 80%, at least about 90%, or about 100%; the total combined amount of C18:0, C18:1 and C18:2 is at least about 60%, at least about 70%, at least about 80%, at least about 90%, or about 100%; the total combined amount of C14:0, C16:0, C18:0 and C18:1 is at least about 60%, at least about 70%, at least about 80%, at least about 90%, or about 100%; the total combined amounts of C8:0 and C10:0 is less than about 50%, less than about 45%, less than about 40%, less than about 35%, less than about 30%, less than about 25%, less than about 20%, less than about 15%, less than about 10%, less than about 5%, or about 0%.

In some embodiments, the microalgal triglyceride oil composition comprises triglyceride oil having a fatty acid profile comprising a ratio of fatty acids selected from the group consisting of: a C8:0 to C10:0 ratio of at least about 5 to 1, at least about 6 to 1, at least about 7 to 1, at least about 8 to 1, at least about 9 to 1, or at least about 10 to 1; a C10:0 to C12:0 ratio of at least about 6 to 1, at least about 7 to 1, at least about 8 to 1, at least about 9 to 1, or at least about 10 to 1; a C12:0 to C14:0 ratio of at least about 5 to 1, at least about 6 to 1, at least about 7 to 1, at least about 8 to 1, at least about 9 to 1, or at least about 10 to 1; a C14:0 to C12:0 ratio of at least about 7 to 1, at least about 8 to 1, at least about 9 to 1, or at least about 10 to 1; a C14:0 to C16:0 ratio of at least about 1 to 2, at least about 1 to 3, at least about 1 to 4, at least about 1 to 5, at least about 1 to 6, at least about 1 to 7, at least about 1 to 8, at least about 1 to 9, or at least about 1 to 10.

In some embodiments, the present invention provides a method of producing an microalgal triglyceride oil composition having a fatty acid profile selected from the group consisting of: at least about 1%, at least about 2%, at least about 5%, at least about 7%, at least about 10%, or at least about 15% C8:0; at least about 1%, at least about 5%, at least about 10%, at least about 15%, at least about 20%, at least about 25%, or at least about 30% C10:0; at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% C12:0; at least about 2%, at least about 5%, at least about 10%, at least about 15%, at least about 20%, at least about 25%, at least about 30%, at least about 35%, at least about 40%, at least about 45%, or at least about 50% C14:0; at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90% C16:0; at least about 5%, at least about 10%, at least about 15%, at least about 20%, at least about 25%, at least about 30%, at least about 35%, at least about 40%, at least about 45%, or at least about 50% C18:0; at least about 60%, at least about 65%, at least about 70%, at least about 75%, at least about 80%, at least about 85%, or at least about 90% C18:1; less than about 7%, less than about 5%, less than about 3%, less than about 1%, or about 0% C18:2; and at least about 35%, at least about 40%, at least about 45%, at least about 50%, at least about 55%, at least about 60%, at least about 65%, at least about 70%, at least about 75%, at least about 80%, at least about 85%, or at least about 90% saturated fatty acids, wherein the method comprises the steps of: (a) cultivating a population of microalgal cells in a culture medium until at least 10% of the dry cell weight of the microalgal cells is triglyceride oil; and (b) isolating the triglyceride oil composition from the microalgal cells.

In some embodiments, the method of producing microalgal triglyceride oil compositions yields triglyceride oils comprising a fatty acid profile in which: the total combined amount of C10:0, C12:0 and C14:0 is at least about 50%, at least about 60%, at least about 70%, at least about 80%, at least about 90%, or about 100%; the total combined amount of C16:0, C18:0 and C18:1 is at least about 60%, at least about 70%, at least about 80%, at least about 90%, or about 100%; the total combined amount of C18:0, C18:1 and C18:2 is at least about 60%, at least about 70%, at least about 80%, at least about 90%, or about 100%; the total combined amount of C14:0, C16:0, C18:0 and C18:1 is at least about 60%, at least about 70%, at least about 80%, at least about 90%, or about 100%; the total combined amount of C8:0 and C10:0 is less than about 50%, less than about 45%, less than about 40%, less than about 35%, less than about 30%, less than about 25%, less than about 20%, less than about 15%, less than about 10%, less than about 5%, or about 0%.

In some embodiments, the method of producing microalgal triglyceride oil compositions yields triglyceride oils having a fatty acid profile comprising a ratio of triglyceride oils selected from the group consisting of: a C8:0 to C10:0 ratio of at least about 5 to 1, at least about 6 to 1, at least about 7 to 1, at least about 8 to 1, at least about 9 to 1, or at least about 10 to 1; a C10:0 to C12:0 ratio of at least about 6 to 1, at least about 7 to 1, at least about 8 to 1, at least about 9 to 1, or at least about 10 to 1; a C12:0 to C14:0 ratio of at least about 5 to 1, at least about 6 to 1, at least about 7 to 1, at least about 8 to 1, at least about 9 to 1, or at least about 10 to 1; a C14:0 to C12:0 ratio of at least about 7 to 1, at least about 8 to 1, at least about 9 to 1, or at least about 10 to 1; and a C14:0 to C16:0 ratio of at least about 1 to 2, at least about 1 to 3, at least about 1 to 4, at least about 1 to 5, at least about 1 to 6, at least about 1 to 7, at least about 1 to 8, at least about 1 to 9, or at least about 1 to 10.

Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C24β stereochemistry. Thus, it is believed that the molecules detected as campesterol, stigmasterol, and β-sitosterol, are actually 22,23-dihydrobrassicasterol, proferasterol and clionasterol, respectively. Thus, in some embodiments the oils produced by the microalgae described above can be distinguished from plant oils by the presence of sterols with C24β stereochemistry and the absence of C24α stereochemistry in the sterols present. For example, the oils produced may contain 22,23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

Thus, the present invention includes a number of different aspects and embodiments. In an embodiment, the strains provided by the invention have been adapted in the laboratory to be capable of higher growth rates and/or triglyceride production under high-salt conditions, including those found in raw sugar cane juice. In other embodiments, the strains have been adapted to convert glucose or other sugar into fatty acid and/or triglyceride more efficiently. In other embodiments, the adapted strains are used to produce products such as triglycerides. The described embodiments of the invention are intended to be merely exemplary and numerous variations and modifications will be apparent to those skilled in the art. All such variations and modifications are intended to be within the scope of the present invention.

EXAMPLES

Example 1. Adaptation of *Prototheca* Strains to High-Salt Conditions

This example illustrates the methods of the invention with respect to adaptation of *Prototheca moriformis* Strain UTEX 1435 for growth at high potassium concentrations (540-640 mM). The strain was adapted in shake flasks. Five replicate flasks were set up for each condition tested. The cultures were maintained in the exponential growth phase and sub-cultured every 1-4 days, usually 1-3 days. The optical density at 750 nm (OD750) of the cultures was between 0.4 to 20.

Initial specific growth rates for all conditions were as follows: control (glucose carbon source)—0.21 $h^{-1}$; elevated temperature—0.07 $h^{-1}$; high [KCl]—0.08 $h^{-1}$; glycerol carbon source—0.15 $h^{-1}$.

The five cultures adapted to elevated temperature were adapted for 85 to 88 generations and exhibited growth rates in the range of 0.15 to 0.17 $h^{-1}$. The five cultures adapted to high KCl concentration were adapted for 70 to 73 generations and exhibited growth rates in the range of 0.08 to 0.10 $h^{-1}$; adaptation was continued to 161 to 165 generation for four of these cultures, which then exhibited growth rates in the range of 0.09 to 0.11 $h^{-1}$. The five cultures adapted to glycerol were adapted for 186 to 188 generations and exhibited growth rates in the range of 0.17 to 0.19 $h^{-1}$.

After adaptation for the number of generations indicated, the flask contents were banked and used as a source of inocula for triglyceride production testing. Under control conditions using glucose as a carbon source, the unadapted Strain UTEX 1435 produced about 17 g/L triglycerides and about 6 g/L non-triglyceride biomass (NTB).

Under control conditions using glycerol as a carbon source, the unadapted Strain UTEX 1435 produced about 6 g/L triglycerides and about 5 g/L non-triglyceride biomass (NTB). The adapted mixed-strain population similarly produced about 6 g/L triglycerides on glycerol and about 4 g/L of NTB.

Under control conditions of an elevated culture temperature of 37.6 degrees C. (optimal temperature is 32 degrees C.), the unadapted Strain UTEX 1435 produced about 15 g/L triglycerides and about 5 g/L NTB. The adapted mixed-strain population produced about 6 g/L triglycerides and about 5 g/L NTB at this temperature, indicating the adaptation did not result in increased triglyceride production with this strain.

Under assay conditions of high KCl concentration (300 mM higher than the optimal [KCl] of 40 mM), the unadapted Strain UTEX 1435 produced only about 2 g/L triglycerides and 1 g/L NTB, whereas the adapted mixed-strain population produced about 3 to 5 g/L triglycerides and 2 to 3 g/L NTB. In brief, the performance of all five high [KCl] cultures with respect to biomass and triglyceride production was superior to the unadapted strain.

To obtain a genetically pure clonal isolate, about 10 single colonies were isolated from each of the high [KCl] cultures adapted for 70 generations. Cell banks of the isolates were made, and the isolates were tested for triglyceride production. Of the resulting 50 isolates, the triglyceride titers of 47 were superior to the unadapted strain.

The top five isolates were then tested for triglyceride production in high KCl concentration and, separately, high NaCl concentration cultivations (300 mM excess of the salt). All of the isolates performed better than the unadapted strain, in terms of triglyceride production, in the high-salt conditions, and three of the isolates performed better, with respect to this parameter, than the unadapted strain even in the control (normal salt) conditions. Thus, in the control conditions, the unadapted Strain UTEX 1435 produced about 17 g/L of triglycerides, whereas this value for the 5 adapted strains ranged from about 11 to 19. In the high KCl medium, the unadapted strain produced about 3 g of triglycerides, whereas this value for the 5 adapted strains ranged from about 8 to 13. In the high NaCl medium, the unadapted strain produced about 4 g/L of triglycerides, whereas this value for the 5 adapted strains ranged from about 8 to 13.

Triglyceride production of one of the adapted strains was then compared to the unadapted parent strain in a variety of different salt conditions. The results are shown in FIG. 1. As can be seen in the figure, the adapted strain produced more triglycerides under all conditions tested, including not only the low salt condition optimal for the unadapted strain but in various high salt-concentration conditions (concentrations are in excess of optimal condition concentrations): 150 mM Na; 150 mM K; 300 mM Na; 300 mM K; 150 mM each of Na and K; 70 mM $MgSO_4$; and 150 mM $MgSO_4$.

This example demonstrates that methods of the invention can be used to make microalgal strains with improved characteristics, including decreased doubling time under growth inhibitory conditions and increased triglyceride production in conditions inhibitory to triglyceride production. The strains adapted to high-salt conditions have particular application to the production of triglycerides using inexpensive feedstocks, such as cane syrups, beet syrups, molasses, and many cellulosic-derived feedstocks, that have high salt concentrations. Moreover, some of these strains exhibited improved triglyceride production even under control (normal salt concentration) conditions. In addition, the altered phenotypes of some of the adapted cells, manifested as increased lysis under control conditions, could offer advantages with respect to downstream processing, as use of these strains could allow for efficient separation of the oil from the biomass/culture medium.

Example 2. Adaptation of *Prototheca* for Increased Sugar to Triglyceride Yield

This example illustrates a method of the invention with respect to the adaptation of a strain of an obligate heterotroph microalga, *Prototheca moriformis*, to increase growth rate and conversion yield of sugar to triglycerides in cultivation media containing glucose as the primary carbon source at growth-limiting concentrations. *Prototheca moriformis* Strain S1920 was used as the starting strain, and this strain was mutagenized by both physical (UV irradiation) and chemical means (EMS and NTG) prior to adaptation in culture. Culturing was conducted in a chemostat that allowed for a continuous cultivation. Fresh medium was added and cultivation broth removed at a controlled rate. Cell growth was limited by depletion of the glucose carbon source; the growth rate of the cells was thus controlled by the glucose feed rate, also known as the dilution rate. S1920 is a classically mutagenized strain selected for increased lipid titer obtained from a fee-for-service laboratory. The parent strain of S1920 is UTEX1435.

The mutagenized strain(s), as a mixed population, was first grown in batch culture. Then, culture medium containing glucose was continuously fed to the chemostat at a dilution rate of 0.05 $h^{-1}$, which allowed the cells to grow at 25% of the maximum specific growth rate. After growth for about 70 generations under these glucose-limited conditions, the mixed population was plated to isolate single colonies. Then, individual isolates were grown in flask cultures to measure triglyceride production and conversion yield of glucose to triglycerides.

Figure 2:
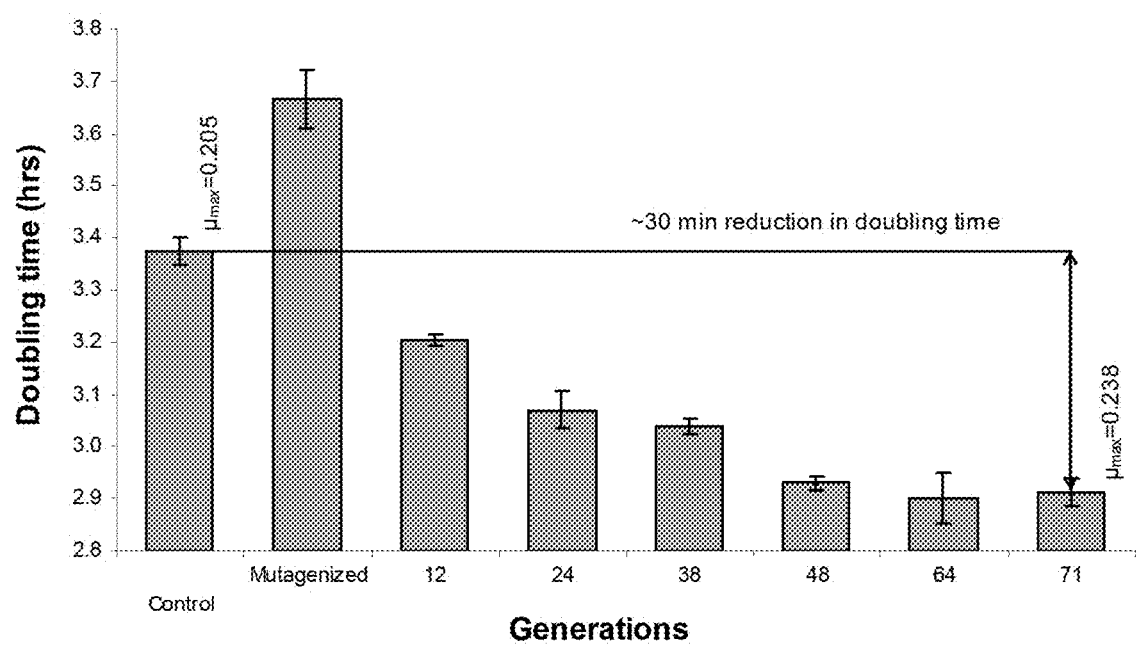
FIG. 2 is a bar graph showing the doubling time of an unadapted parent ("control") strain, a mutagenized culture of the parent strain, and a series of cultures of the mutagenized parent strain adapted to utilize glucose as a primary carbon source more efficiently (see Example 2)

Results are shown in FIG. 2. An increase in the growth rate of the adapted population was observed as the adaptation progressed. The doubling time of the unadapted, unmutagenized parent strain was about 3.4 hours (specific growth rate of 0.21 $h^{-1}$); the mutagenized population of the parent strain had a doubling time of about 3.7 hours. As the number of generations of adaptation increased, the doubling time decreased: 12 generations—~3.2 hours; 24 generations—~3.1 hours; 48 generations—~2.95 hours; and 71 generations—~2.9 hours, with the growth rate of the 71-generation adapted culture of 0.238. Thus, after 71 generations, the maximum specific growth rate of the resulting heterogenous population increased by 16%, and its doubling time decreased by about 30 minutes relative to the unmutagenized unadapted strain.

Isolated clones were obtained from the adapted culture, and over 50% of the 94 isolates tested had higher triglyceride titers (in shake flask screens) compared to the parent strain, and some isolates showed a yield increase relative to the parent strain of about 3.6% in terms of grams of triglyceride produced per gram of glucose consumed.

These two adapted isolates were then tested for triglyceride production at the 7 L scale using 70% reagent grade sucrose as the carbon feed. A control cultivation of the parent strain was performed for comparison. The total triglycerides produced in the adapted isolate cultivations exceeded that of the control throughout the cultivation, with the isolate cultivations showing a 9% increase at the end of day six. The peak yield of the isolate strains was about 3-7% greater than the control strain.

This example demonstrates that the method of the invention can be used to make microalgal strains that grow faster and produce more triglycerides on a given fixed carbon source, or more triglycerides per gram of carbon source, than unadapted strains. The method is applicable to carbon sources other than glucose, i.e., sources such as fructose, glycerol and xylose, as well as glucose-containing carbon sources such as sucrose, including sugar cane, beet juice, and cellulosics-derived carbon sources.

Example 3. Evolution of Salt-Tolerant *Prototheca* Strains and Evaluation on Crude Sugar Cane Syrup Through sequential batch fermentation of the high oil-producing strains, *Prototheca morifomis* Strains S1133 and S1331, in medium containing a high concentration of potassium, two evolved mutant strains (Strains S2939 and S2941) that are both salt tolerant and have high triglyceride productivities were obtained. The evolution process involved the cultivation of the parental strains in seed medium that was supplemented with 650 mM KCl. The potassium concentration was chosen to reduce the maximum specific growth rate of the parent strains by approximately 70%, which served as the selection pressure. Cell growth was maintained in the exponential phase for 70 generations through sequential subculturing. At the end of the evolution process, the mixed-culture population was plated for the isolation of single colonies, which were then screened in shake flasks to identify the mutants that show high triglyceride titers and yields in both a control medium and and medium supplemented with 300 mM KCl Strains S2939 (derived from strain S1133) and S2941 (derived from strain S1331) were found to be the best performers from our flask evaluation and were tested at the 7-L scale with reagent-grade sucrose or crude cane syrup as the carbon feed. The fermentable sugar content, potassium concentration, and sodium concentration of this cane syrup were 58% (w/w), 190 mM, and 25 mM, respectively. Control runs with a sucrose-metabolizing strain, S1868 engineered to express sucrose invertase, made according to Example 11, were conducted for performance comparison.

Figure 3:
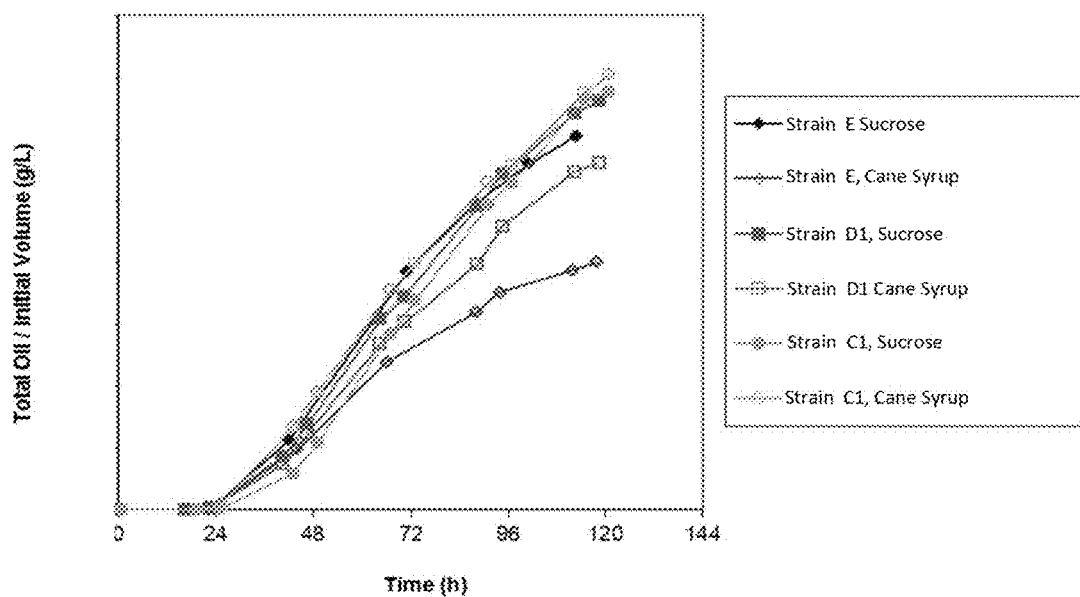
FIG. 3 shows oil production of various cell-adapted and control cultures over time using purified sucrose and cane syrup.

As shown in FIG. 3, the production of triglycerides by Strains S2939 and S2941 cultivated with crude cane syrup were comparable to that of Strain S1868 cultivated with reagent-grade sucrose, and far superior to that of Strain S1868 cultivated with the cane syrup. Despite the accumulation of >160 mM K in the fermentations with the crude cane syrup, the total triglycerides produced by S2939 and S2941 were 90-110% of that produced by Strain S1868 in the control fermentation with reagent-grade sucrose. The total triglycerides produced by Strains S2939 and S2941 on cane syrup were 70% and 40% higher, respectively, than that produced by Strain E on the same feedstock. Given that the accumulation of >50 mM K in the fermentation medium can significantly reduce the ability of Strain S1868 to produce triglycerides, these results clearly demonstrate the robustness of Strains S2939 and S2941.

Example 4: Selection of Mutants in the Presence of an Alternative Oxidase Inhibitor SHAM was used as a selection pressure for yield improvement in *Prototheca moriformis*. A high oil-producing strain S1920, of Example 2, was mutagenized by N-methyl-N'-nitro-N-nitrosoguanidine (NTG) or ethyl methanesulfonate (EMS) plus ultraviolet (UV) radiation to generate a heterogeneous cell population. The cells were then spread onto agar plates containing growth medium with a final SHAM concentration of 8 mM or 10 mM. Cells from the mutagenized population showed higher rates of survival on the SHAM-containing plates than those from the unmutagenized population, which served as the control. Furthermore, some of the colonies from the mutagenized population grew to a much larger size on the SHAM-containing plates than those from the control population. These larger colonies (a total of 96) were initially selected for evaluation in batch cultures to determine their triglyceride titers and glucose to triglyceride conversion yields. The five isolates that showed higher triglyceride titers, as well as conversion yields, compared to the parental strain were further tested in shake flasks to confirm their performance improvement. Among these mutants, Strain S3150 consistently exhibited a yield increase when compared to its parent, Strain S1920.

To assess its performance under high cell-density conditions, Strain S3150 was evaluated in 7-L fermentors using an optimized fed-batch process with sucrose as the carbon feed. Replicate control runs with its parent, Strain S1920, were also conducted for performance comparison. The performance of Strain S3150 was superior to that of its parent, Strain S1920, with Strain S3150 achieving a sugar/triglyceride yield increase of about 7% as compared to Strain S1920. Furthermore, the total amount of lipid produced by Strain S3150 was comparable to that observed for its parent, Strain S1920. These results suggest that the use of SHAM as a selection pressure for screening is an effective method for isolating mutants with improved yield.

Example 5: Genetic Engineering of *Chlorella protothecoides* to Express an Exogenous Sucrose Invertase Strains and Media:

*Chlorella protothecoides* (UTEX 250) was obtained from the Culture Collection of Alga at the University of Texas (Austin, Tex., USA). The stock cultures were maintained on modified Proteose medium. Modified Proteose medium consists of 0.25 g $NaNO_3$, 0.09 g $K_2HPO_4$, 0.175 g $KH_2PO_4$ 0.025 g, 0.025 g $CaCl_2.2H_2O$, 0.075 g $MgSO_4.7H_2O$, and 2 g yeast extract per liter (g/L).

Plasmid Construction:

To express the secreted form of invertase in *Chlorella protothecoides*, a *Saccharomyces cerevisiae* SUC2 gene was placed under the control of three different promoters: Cauliflower mosaic virus 35S promoter (CMV), *Chlorella* virus promoter (NC-1A), and *Chlorella* HUP1 promoter. A yeast SUC2 gene was synthesized to accommodate codon usage optimized for *C. protothecoides* and includes a signal sequence required for directing extracellular secretion of invertase. Each construct was built in pBluescript KS+, and EcoRI/AscI, AscI/XhoI, and XhoI/BamHI sites were introduced to each promoter, invertase gene, and CMV 3'UTR, respectively, by PCR ampilication using specific primers. Purified PCR products were cloned sequentially.

Transformation of *Chlorella protothecoides*:

A *Chlorella protothecoides* culture was grown in modified Proteose medium on a gyratory shaker under continuous light at 75 µmol photons $m^{-2}$ $sec^{-1}$ till it reached a cell density of of $6 \times 10^6$ cells/ml.

For biolistic transformation, S550d gold carriers from Seashell Technology were prepared according to the protocol from the manufacturer. Briefly, a linearized construct (20 µg) by BsaI was mixed with 50 µl of binding buffer and 60 µl (3 mg) of S550d gold carriers and incubated in ice for 1 min. Precipitation buffer (100 µl) was added, and the mixture was incubated in ice for another 1 min. After mild vortexing, DNA-coated particles were pelleted by spinning at 10,000 rpm in an Eppendorf microfuge for 10 seconds. The gold pellet was washed once with 500 µl of cold 100% ethanol, pelleted by brief spinning in the microfuge, and resuspended with 50 µl of ice-cold ethanol. After a brief (1-2 sec) sonication, 10 µl of DNA-coated particles were immediately transferred to the carrier membrane. The cells were harvested, washed once with sterile distilled water, resuspended in 50 µl of medium ($1 \times 10^7$ cells), and were spread in the center third of a non-selective Proteous plate. The cells were bombarded with the PDS-1000/He Biolistic Particle Delivery system (Bio-Rad). Rupture disks (1100 and 1350 psi) were used, and the plates were placed 9-12 cm below the screen/macrocarrier assembly. The cells were allowed to recover at 25° C. for 12-24 hours. Upon recovery, the cells were scraped from the plates with a rubber spatula, mixed with 100 µl of medium and spread on modified Proteose plates with 1% sucrose. After 7-10 days of incubation at 25° C. in the dark, colonies representing transformed cells were visible on the plates.

For transformation with electroporation, cells were harvested, washed once with sterile distilled water, and resuspended in a Tris-phosphate buffer (20 m M Tris-HCl, pH 7.0; 1 mM potassium phosphate) containing 50 mM sucrose to a density of $4 \times 10^8$ cells/ml. About 250 µl cell suspension ($1 \times 10^8$ cells) was placed in a disposable electroporation cuvette of 4 mm gap. To the cell suspension, 5 µg of linearized plasmid DNA and 200 µg of carrier DNA (sheared salmon sperm DNA) were added. The electroporation cuvette was then incubated in an ice water bath at 16° C. for 10 min. An electrical pulse (1100 V/cm) was then applied to the cuvette at a capacitance of 25 µF (no shunt resistor was used for the electroporation) using a Gene Pulser II (Bio-Rad Labs, Hercules, Calif.) electroporation apparatus. The cuvette was then incubated at room temperature for 5 minutes, following which the cell suspension was transferred to 50 ml of modified Proteose media, and shaken on a gyratory shaker for 2 days. Following recovery, the cells were harvested at low speed (4000 rpm), resuspended in modified Proteose media, and plated out at low density on modified Proteose plates with 1% sucrose. After 7-10 days of incubation at 25° C. in the dark, colonies representing transformed cells were visible on the plates.

Screening Transformants and Genotyping:

The colonies were picked from dark grown-modified Proteose plates with 1% sucrose, and approximately the same amount of cells were transferred to 24 well-plates containing 1 ml of modified Proteose liquid media with 1% sucrose. The cultures were kept in dark and agitated by orbital shaker from Labnet (Berkshire, UK) at 430 rpm for 5 days.

To verify the presence of the invertase gene introduced in *Chlorella* transformants, DNA of each transformant was isolated and amplified with a set of gene-specific primers (CMV construct: forward primer (CAACCACGTCTT-CAAAGCAA) (SEQ ID NO:1)/reverse primer (TCCGGTGTGTTGTAAGTCCA) (SEQ ID NO:2), CV constructs: forward primer (TTGTCGGAATGTCATAT-CAA) (SEQ ID NO:3)/reverse primer (TCCGGTGTGTTGTAAGTCCA) (SEQ ID NO:2) 171), and HUP1 construct: forward primer (AACGCCTTTGTA-CAACTGCA) (SEQ ID NO:4)/reverse primer (TCCGGTGTGTTGTAAGTCCA) (SEQ ID NO:2) 171)). For quick DNA isolation, a volume of cells (approximately 5-10 uL in size) were resuspended in 50 uL of 10 mM Na-EDTA. The cell suspension was incubated at 100° C. for 10 min and sonicated for 10 sec. After centrifugation at 12000 g for 1 min, 3 uL of supernatant was used for the PCR reaction. PCR amplification was performed in the DNA thermal cycler (Perkin-Elmer GeneAmp 9600). The reaction mixture (50 uL) contained 3 uL extracted DNA, 100 pmol each of the respective primers described above, 200 uM dNTP, 0.5 units of Taq DNA polymerase (NEB), and Taq DNA polymerase buffer according to the manufacturer's instructions. Denaturation of DNA was carried out at 95° C. for 5 min for the first cycle, and then for 30 sec. Primer annealing and extension reactions were carried out at 58° C. for 30 sec and 72° C. for 1 min respectively. The PCR products were then visualized on 1 agarose gels stained with ethidium bromide.

Growth in Liquid Culture:

After five days growth in darkness, the genotype-positive transformants showed growth on minimal liquid Proteose media+1% sucrose in darkness, while wild-type cells showed no growth in the same media in darkness.

Example 6: Transformation of Algal Strains with a Secreted Invertase Derived from S. cerevisiae Secreted Invertase:

A gene encoding a secreted sucrose invertase (Gen Bank Accession no. NP_012104 from Saccharomyces cerevisiae) was synthesized de-novo as a 1599 bp Asc I-Xho fragment that was subsequently sub-cloned into a pUC19 derivative possessing the Cauliflower Mosaic Virus 35s promoter and 3' UTR as EcoR I/Asc I and Xho/Sac I cassettes, respectively.

Growth of Algal Cells:

Media used in these experiments was liquid base media (2 g/L yeast extract, 2.94 mM $NaNO_3$, 0.17 mM $CaCl_2.2H_2O$, 0.3 mM $MgSO_4.7H_2O$, 0.4 mM $K_2HPO_4$, 1.28 mM $KH_2PO_4$, 0.43 mM NaCl) and solid base media (+1.5% agarose) containing fixed carbon in the form of sucrose or glucose (as designated) at 1% final concentration. The strains used in this experiment did not grow in the dark on base media in the absence of an additional fixed carbon source. Species were struck out on plates, and grown in the dark at 28° C. Single colonies were picked and used to inoculate 500 mL of liquid base media containing 1% glucose and allowed to grow in the dark until mid-log phase, measuring cell counts each day. Each of the following strains had been previously tested for growth on sucrose in the dark as a sole carbon source and exhibited no growth, and were thus chosen for transformation with a secreted invertase: (1) Chlorella protothecoides (UTEX 31); (2) Chlorella minutissima (UTEX 2341); and (3) Chlorella emersonii (CCAP 211/15).

Transformation of Algal Cells Via Particle Bombardment:

Sufficient culture was centrifuged to give approximately $1-5\times10^8$ total cells. The resulting pellet was washed with base media with no added fixed carbon source. Cells were centrifuged again and the pellet was resuspended in a volume of base media sufficient to give $5\times10^7$ to $2\times10^8$ cells/ml. 250-1000 µl of cells were then plated on solid base media supplemented with 1% sucrose and allowed to dry onto the plate in a sterile hood. Plasmid DNA was precipitated onto gold particles according to the manufacturer's recommendations (Seashell Technology, La Jolla, Calif.). Transformations were carried out using a BioRad PDS He-1000 particle delivery system using 1350 psi rupture disks with the macrocarrier assembly set at 9 cm from the rupture disk holder. Following transformations, plates were incubated in the dark at 28° C. All strains generated multiple transformant colonies. Control plates transformed with no invertase insert, but otherwise prepared in an identical fashion, contained no colonies.

Analysis of Chlorella protothecoides Transformants:

Genomic DNA was extracted from Chlorella protothecoides wild type cells and transformant colonies as follows: Cells were resuspended in 100 ul extraction buffer (87.5 mM Tris Cl, pH 8.0, 50 mM NaCl, 5 mM EDTA, pH 8.0, 0.25% SDS) and incubated at 60° C., with occasional mixing via inversion, for 30 minutes. For PCR, samples were diluted 1:100 in 20 mM Tris Cl, pH 8.0.

Genotyping was done on genomic DNA extracted from WT, the transformants and plasmid DNA. The samples were genotyped for the marker gene. Primers 2383 (5' CTGACCCGACCTATGGGAGCGCTCTTGGC 3') (SEQ ID NO:5) and 2279 (5' CTTGACTTCCCTCACCTGGAAT-TTGTCG 3') (SEQ ID NO:6) were used in this genotyping PCR. The PCR profile used was as follows: 94° C. denaturation for 5 min; 35 cycles of 94° C.—30 sec, 60° C.—30 sec, 72° C.—3 min; 72° C.—5 min. A band of identical size was amplified from the positive controls (plasmid) and two transformants of Chlorella protothecoides (UTEX 31).

Analysis of Chlorella minutissima and Chlorella emersonii transformants: Genomic DNA was extracted from Chlorella WT and the tranformants as follows: Cells were resuspended in 100 ul extraction buffer (87.5 mM Tris Cl, pH 8.0, 50 mM NaCl, 5 mM EDTA, pH 8.0, 0.25% SDS) and incubated at 60° C., with occasional mixing via inversion, for 30 minutes. For PCR, samples were diluted 1:100 in 20 mM Tris-Cl, pH 8.0. Genotyping was done on genomic DNA extracted from WT, the transformants and plasmid DNA. The samples were genotyped for the marker gene. Primers 2336 (5' GTGGCCATATGGACTTACAA 3') (SEQ ID NO:7) and 2279 (5' CTTGACTTCCCTCACCTGGAAT-TTGTCG 3') (SEQ ID NO:6) were designated primer set 2 (1215 bp expected product), while primers 2465 (5' CAAGGGCTGGATGAATGACCC-CAATGGACTGTGGTACGACG 3') (SEQ ID NO:8) and 2470 (5' CACCCGTCGTCATGTTCACG-GAGCCCAGTGCG 3') (SEQ ID NO:9) were designated primer set 4 (1442 bp expected product). The PCR profile used was as follows: 94° C. denaturation for 2 min; 29 cycles of 94° C.—30 sec, 60° C.—30 sec, 72° C.—1 min, 30 sec; 72° C.—5 min. A plasmid control containing the secreted invertase was used as a PCR control.

The sequence of the invertase construct corresponds to SEQ ID NO:10.

Example 7: Homologous Recombination in Prototheca Species

Homologous recombination of transgenes has several advantages. First, the introduction of transgenes without homologous recombination can be unpredictable because there is no control over the number of copies of the plasmid that gets introduced into the cell. Also, the introduction of transgenes without homologous recombination can be unstable because the plasmid may remain episomal and is lost over subsequent cell divisions. Another advantage of homologous recombination is the ability to "knock-out" gene targets, introduce epitope tags, switch promoters of endogenous genes and otherwise alter gene targets (e.g., the introduction of point mutations).

Two vectors were constructed using a specific region of the Prototheca moriformis (UTEX 1435) genome, designated KE858. KE858 is a 1.3 kb, genomic fragment that encompasses part of the coding region for a protein that shares homology with the transfer RNA (tRNA) family of proteins. Southern blots have shown that the KE858 sequence is present in a single copy in the *Prototheca moriformis* (UTEX 1435) genome. The first type of vector that was constructed, designated SZ725 (SEQ ID NO:11), consisted of the entire 1.3 kb KE858 fragment cloned into a pUC19 vector backbone that also contains the codon optimized yeast invertase (suc2) gene. The KE858 fragment contains a unique SnaB1 site that does not occur anywhere else in the targeting construct. The second type of vector that was constructed, designated SZ726 (SEQ ID NO:12), consisted of the KE858 sequence that had been disrupted by the insertion of the yeast invertase gene (suc2) at the SnaB1 site within the KE858 genomic sequence. The entire DNA fragment containing the KE858 sequences flanking the yeast invertase gene can be excised from the vector backbone by digestion with EcoRI, which cuts at either end of the KE858 region.

Both vectors were used to direct homologous recombination of the yeast invertase gene (suc2) into the corresponding KE858 region of the *Prototheca moriformis* (UTEX 1435) genome. The linear DNA ends homologous to the genomic region that was being targeted for homologous recombination were exposed by digesting the vector construct SZ725 with SnaB1 and vector construct SZ726 with EcoRI. The digested vector constructs were then introduced into *Prototheca moriformis* cultures using methods described above. Transformants from each vector construct were then selected using sucrose plates. Ten independent, clonally pure transformants from each vector transformation were analyzed for successful recombination of the yeast invertase gene into the desired genomic location (using Southern blots) and for transgene stability.

Southern blot analysis of the SZ725 transformants showed that 4 out of the 10 transformants picked for analysis contained the predicted recombinant bands, indicating that a single crossover event had occurred between the KE858 sequences on the vector and the KE858 sequences in the genome. In contrast, all ten of the SZ726 transformants contained the predicted recombinant bands, indicating that double crossover events had occurred between the EcoRI fragment of pSZ726 carrying KE858 sequence flanking the yeast invertase transgene and the corresponding KE858 region of the genome.

Sucrose invertase expression and transgene stability were assessed by growing the transformants for over 15 generations in the absence of selection. The four SZ725 transformants and the ten SZ276 transformants that were positive for the transgene by Southern blotting were selected and 48 single colonies from each of the transformants were grown serially: first without selection in glucose containing media and then with selection in media containing sucrose as the sole carbon source. All ten SZ276 transformants (100%) retained their ability to grow on sucrose after 15 generations, whereas about 97% of the SZ725 transformants retained their ability to grow on sucrose after 15 generations. Transgenes introduced by a double crossover event (SZ726 vector) have extremely high stability over generation doublings. In contrast, transgenes introduced by a single cross over event (SZ725 vector) can result in some instability over generation doublings because if tandem copies of the transgenes were introduced, the repeated homologous regions flanking the transgenes may recombine and excise the transgenic DNA located between them.

These experiments demonstrate the successful use of homologous recombination to generate *Prototheca* transformants containing a heterologous sucrose invertase gene that is stably integrated into the nuclear chromosomes of the organism. The success of the homologous recombination enables other genomic alterations in *Prototheca*, including gene deletions, point mutations and epitope tagging a desired gene product.

Use of Homologous Recombination to Knock-Out an Endogenous *Prototheca moriformis* Gene:

In a *Prototheca moriformis* cDNA/genomic screen, an endogenous stearoyl ACP desaturase (SAPD) cDNA was identified. Stearoyl ACP desaturase enzymes are part of the lipid synthesis pathway and they function to introduce double bonds into the fatty acyl chains. In some cases, it may be advantageous to knock-out or reduce the expression of lipid pathway enzymes in order to alter a fatty acid profile. A homologous recombination construct was created to assess whether the expression of an endogenous stearoyl ACP desaturase enzyme can be reduced (or knocked out) and if a corresponding reduction in unsaturated fatty acids can be observed in the lipid profile of the host cell. An approximately 1.5 kb coding sequence of a stearoyl ACP desaturase gene from *Prototheca moriformis* (UTEX 1435) was identified and cloned (SEQ ID NO:13). The homologous recombination construct was constructed using 0.5 kb of the SAPD coding sequence at the 5'end (5' targeting site), followed by the *Chlamydomonas reinhardtii* β-tublin promoter driving a codon-optimized yeast sucrose invertase suc2 gene with the *Chlorella vulgaris* 3'UTR. The rest (~1 kb) of the *Prototheca moriformis* SAPD coding sequence was then inserted after the *C. vulgaris* 3'UTR to make up the 3' targeting site. The sequence for this homologous recombination cassette is listed in SEQ ID NO:14. As shown above, the success-rate for integration of the homologous recombination cassette into the nuclear genome can be increased by linearizing the cassette before transforming the microalgae, leaving exposed ends. The homologous recombination cassette targeting an endogenous SAPD enzyme in *Prototheca moriformis* is linearized and then transformed into the host cell (*Prototheca moriformis*, UTEX 1435). A successful integration will eliminate the endogenous SAPD enzyme coding region from the host genome via a double reciprocal recombination event, while expression of the newly inserted suc2 gene will be regulated by the *C. reinhardtii* β-tubulin promoter. The resulting clones can be screened using plates/media containing sucrose as the sole carbon source. Clones containing a successful integration of the homologous recombination cassette will have the ability to grow on sucrose as the sole carbon source and changes in overall saturation of the fatty acids in the lipid profile will serve as a secondary confirmation factor. Additionally, Southern blotting assays using a probe specific for the yeast sucrose invertase suc2 gene and RT-PCR can also confirm the presence and expression of the invertase gene in positive clones. As an alternative, the same construct without the β-tubulin promoter can be used to excise the endogenous SAPD enzyme coding region. In this case, the newly inserted yeast sucrose invertase suc2 gene will be regulated by the endogenous SAPD promoter/5'UTR.

Example 8: Expression of Various Thioesterases in *Prototheca*

Methods and effects of expressing a heterologous thioesterase gene in *Prototheca* species have been previously described in PCT Application No. PCT/US2009/66142, hereby incorporated by reference in relevant part. The effect of other thioesterase genes/gene products from higher plants species was further investigated. These thioesterases include thioesterases from the following higher plants:

| Species | GenBank Accession No. | Specificity | SEQ ID NO: |
|---|---|---|---|
| Cinnamomum camphora | Q39473 | C14 | SEQ ID NOs: 15-16 |
| Umbellularia californica | Q41635 | C10-C12 | SEQ ID NOs: 17-18 |
| Cuphea hookeriana | AAC49269 | C8-C10 | SEQ ID NOs: 19-20 |
| Cuphea palustris | AAC49179 | C8 | SEQ ID NOs: 21-22 |
| Cuphea lanceolata | CAB60830 | C10 | SEQ ID NOs: 23-24 |
| Iris germanica | AAG43858.1 | C14 | SEQ ID NOs: 25-26 |
| Myristica fragrans | AAB717291.1 | C14 | SEQ ID NOs: 27-28 |
| Cuphea palustris | AAC49180 | C14 | SEQ ID NOs: 29-30 |
| Ulmus americana | AAB71731 | broad | SEQ ID NOs: 31-32 |

In all cases, each of the above thioesterase constructs was transformed in to *Prototheca moriformis* (UTEX 1435) using biolistic particle bombardment. Other transformation methods including homologous recombination as disclosed in PCT Application No. PCT/US2009/66142, would also be suitable for heterologous expression of genes of interest. Transformation of *Prototheca moriformis* (UTEX 1435) with each of the above thioesterase constructs was performed. Each of the constructs contained a NeoR gene and selection for positive clones was carried out using 100 µg/ml G418. All coding regions were codon optimized to reflect the codon bias inherent in *Prototheca moriformis* UTEX 1435 nuclear genes. Both amino acid sequences and the cDNA sequences for the construct used are listed in the sequence identity listing. The transit peptide for each of the higher plant thioesterase was replaced with an algal codon optimized transit peptide from *Prototheca moriformis* delta 12 fatty acid desaturase (SEQ ID NO:33) or from *Chlorella protothecoides* stearoyl ACP desaturase (SEQ ID NO:34). All thioesterase constructs were driven by the *Chlamydomanas reinhardtii* beta-tubulin promoter/5'UTR. Growth and lipid production of selected positive clones were compared to wildtype (untransformed) *Prototheca moriformis* (UTEX 1435). Wildtype and selected positive clones were grown on 2% glucose G418 plates. Lipid profiles analysis on selected positive clones for each construct is summarized below (expressed in Area %) in Table 1.

The results show that all of the thioesterases expressed impacted fatty acid profiles to some level. Looking at the "Total saturates" row, the degree of saturation was profoundly impacted by the expression of several of the thioesterases, including those from *U. californica*, *C. camphora*, and most notably, *U. americana*. These changes in the percentage of total saturates were unexpected in that the heterologous expression of thioesterases from higher plants can apparently impact more than just lipid chain lengths; it can also impact other attributes of lipid profiles produced by microalgae, namely the degree of saturation of the fatty acids.

Selected clones transformed with *C. palustris* C8 thioesterase, *C. hookeriana* thioesterase, *U. californica* and *C. camphora* thioesterase were further grown in varing amounts of G418 (from 25 mg/L to 50 mg/L) and at varying temperatures (from 22° C. to 25° C.) and the lipid profile was determined for these clones. Table 2 summarizes the lipid profile (in Area %) of representative clones containing each thioesterase. A second construct containing the *U. americana* thioesterase was constructed and transformed into *Prototheca moriformis* (UTEX 1435) using the biolistic methods described above. This second construct was introduced into the cell via homologous recombination. Methods of homologous recombination in *Prototheca* species were described previously in PCT Application No. PCT/US2009/66142. The homologous DNA that was used was from genomic DNA sequence of "6S" from *Prototheca moriformis* UTEX 1435. The selection agent was the ability to grow on sucrose, using a codon optimized suc2 gene from *S. cereveisiae* driven by the *C. reinhardtii* beta tubulin promoter. The native *U. americana* transit peptide was replaced by the *Chlorella protothecoides* (UTEX 250) stearoyl ACP desaturase transit peptide. The cDNA of this construct is listed in the Sequence Listing as SEQ ID NO:35. Selection of positive clones was performed on 2% sucrose plates and the resulting cultures for lipid profile determination was also grown on 2% sucrose containing medium. A representative lipid profile for this *Prototheca moriformis* strain containing a homologously recombined heterologous *U. americana* thioesterase is summarized in Table 2.

TABLE 1

Lipid profiles of *Prototheca moriformis* expressing various heterologous thioesterases.

| Fatty Acid | UTEX 1435 wt | Thioesterase | | | | | | | | |
|---|---|---|---|---|---|---|---|---|---|---|
| | | *U. californic* | *C. camphor* | *I. germanic* | *M. fragrans* | *C. palustris* | *C. hookeria* | *C. lanceolat* | *C. palustris* | *U. american* |
| C8:0 | 0 | 0 | 0 | 0 | | 3.1 | 1.8 | 0 | 0 | .09 |
| C10:0 | 0.02 | .07 | .02 | .01 | .09 | .56 | 6.85 | 1.91 | .01 | 2.85 |
| C12:0 | 0.05 | 14 | 1.82 | .09 | .05 | .25 | .2 | .29 | .06 | .74 |
| C14:0 | 1.65 | 3 | 17.3 | 2.59 | 5.31 | 1.45 | 1.8 | 1.83 | 2.87 | 10.45 |
| C16:0 | 28.0 | 21.4 | 24.3 | 26.52 | 31.08 | 22.84 | 23.9 | 25.55 | 27.23 | 33.3 |
| C18:0 | 2.9 | 2.9 | 2.7 | 3.11 | 2.71 | 3.24 | 2.8 | 3.26 | 3.62 | 3.47 |
| C18:1 | 53.8 | 45.2 | 41.3 | 49.96 | 39.77 | 56.62 | 49.8 | 55.43 | 51.04 | 38.71 |
| C18:2 | 10.95 | 10 | 9.7 | 11.86 | 14.17 | 8.24 | 9.7 | 8.17 | 10.81 | 7.38 |
| C18:3 α | 0.8 | .86 | .8 | .40 | .64 | .61 | .9 | .58 | .97 | .52 |
| Total saturates (area %) | 32.62 | 44.97 | 46.14 | 32.32 | 39.24 | 31.44 | 37.35 | 32.84 | 33.79 | 50.9 |

TABLE 2

Lipid profiles of Prototheca moriformis strains containing heterologous thioesterase genes.

| | C. palustris C8 | C. hookeriana | C. camphora | U. americana 2 |
|---|---|---|---|---|
| C8:0 | 12.28 | 2.37 | 0 | 0 |
| C10:0 | 2.17 | 12.09 | 0.02 | 4.69 |
| C12:0 | 0.34 | 0.33 | 3.81 | 1.02 |
| C14:0 | 1.59 | 2.08 | 32.73 | 16.21 |
| C16:0 | 15.91 | 20.07 | 24.03 | 38.39 |
| C18:0 | 1.59 | 1.57 | 1.21 | 2.83 |
| C18:1 | 50.64 | 41.80 | 18.64 | 27.22 |
| C18:2 | 13.02 | 16.37 | 16.57 | 7.65 |
| C18:3 α | 1.52 | 1.75 | 1.66 | 0.74 |
| Total saturates | 33.88 | 38.51 | 61.80 | 63.14 |

As with the clones described above, all transformants containing a heterologous thioesterase gene showed impacted fatty acid profiles to some level, and the total percent of saturated fatty acids were also changed, as compared to wildtype (untransformed) *Prototheca moriformis*. The *Prototheca moriformis* containing the *U. americana* thioesterase introduced by homologous recombination had the greatest increase in total saturates.

Additionally, transgenic clones containing the exogenous *C. hookeriana, C. camphora, U. californica* or *U. americana* thioesterase were assessed for novel lipid profiles. The *C. hookeriana* thioesterase containing clone achieved the following lipid profile when grown in 2% glucose, 25 mg/ml G418 at 22° C.: 5.10% C8:0; 18.28% C10:0; 0.41% C12:0; 1.76% C14:0; 16.31% C16:0; 1.40% C18:0; 40.49% C18:1; and 13.16% C18:2. The *C. camphora* thioesterase-containing clone (also containing an exogenous sucrose invertase) achieved the following lipid profile when grown in 2% sucrose at 25° C.: 0.04% C10:0; 6.01% C12:0; 35.98% C14:0; 19.42 C16:0; 1.48% C18:0; 25.44% C18:1; and 9.34% C18:2. The *U. calfornica* thioesterase containing clone achieved the following lipid profile when grown in 2% glucose, 25-100 mg/ml G418 at 22° C.: 0% C8:0; 0.11% C10:0; 34.01% C12:0; 5.75% C14:0; 14.02% C16:0; 1.10% C18:0; 28.93% C18:1; and 13.01% C18:2. The *U. americana* thioesterase containing clone achieved the following lipid profile when grown in 2% glucose at 28° C.: 1.54% C10:0; 0.43% C12:0; 7.56% C14:0; 39.45% C16:0; 2.49% C18:0; 38.49% C18:1; and 7.88% C18:2.

Example 9: Transformation of *Prototheca* with Multiple Exogenous Heterologous Thioesterase Genes Microalgae strain *Prototheca moriformis* (UTEX 1435) was transformed using the above disclosed methods to express multiple thioesterases in a single clone. The expression of multiple thioesterases in a single clone allows the microaglae to produce oils with fatty acid profiles completely different from those elaborated when any single thioesterase is expressed alone (as demonstrated in the preceding Examples). *Prototheca moriformis* (UTEX 1435) was first transformed with the *Cinnamomum camphora* thioesterase (a C14 preferring thioesterase) along with a sucrose invertase gene, the suc2 from *S. cerevisiae* (selection was the ability to grow on sucrose) using homologous recombination. The DNA used for this homologous recombination construct is from the KE858 region of *Prototheca moriformis* genomic DNA as described in the Section III above. The relevant portion of this construct is listed in the Sequence Listing as SEQ ID NO:36. Positive clones were screened on sucrose-containing plates. A positive clone was then re-transformed with one of three cassettes, each encoding resistance to the antibiotic G418 as well as an additional thioesterase: (1) thioesterase gene from *Cuphea hookeriana* (C8-10 preferring), SEQ ID NO:37; (2) thioesterase gene from *Umbellularia californica* (C12 preferring), SEQ ID NO:38; or thioesterase from *Ulmus americana* (broad; C10-C16 preferring), SEQ ID NO:39. Included in the Sequence Listing is the sequence of the relevant portion of each construct. Clones expressing both thioesterase genes were screened on sucrose containing medium with 50 μg/ml G418. Positive clones were selected and growth and lipid profile were assayed. Table 3 summarizes the lipid profile of representative positive clones (expressed in Area %).

TABLE 3

Lipid profiles of *Prototheca moriformis* transformed with multiple thioesterases.

| | UTEX | UTEX 1435 + C. camphora TE genetic background | | | |
|---|---|---|---|---|---|
| Fatty Acid | UTEX 1435 | 1435 + C. camphora TE | +C. hookeriana TE | +U. californica TE | +U. americana TE |
| C8:0 | 0 | 0 | 0.19 | 0 | 0.06 |
| C10:0 | 0.02 | 0.02 | 2.16 | 0.07 | 1.87 |
| C12:0 | 0.05 | 0.66 | 0.53 | 13.55 | 1.61 |
| C14:0 | 1.65 | 10.52 | 7.64 | 8.0 | 14.58 |
| C16:0 | 28.0 | 22.56 | 22.31 | 19.98 | 29.53 |
| C18:0 | 2.9 | 6.67 | 3.23 | 2.24 | 2.93 |
| C18:1 | 53.8 | 47.78 | 48.54 | 42.55 | 37.3 |
| C18:2 | 10.95 | 12.3 | 11.76 | 10.13 | 8.9 |
| C18:3 α | 0.8 | 0.93 | 0.91 | 0.91 | 0.76 |
| Total saturates (Area %) | 32.62 | 40.43 | 36.06 | 43.84 | 50.58 |

Additionally, a double thioesterase clone with *C. camphora* and *U. californica* thioesterases was grown in 2% sucrose containing medium with 50 mg/L G418 at 22° C. The fatty acid profile obtained from this strain under these growth conditions was: C8:0 (0); C10:0 (0.10); C12:0 (31.03); C14:0 (7.47); C16:0 (15.20); C18:0 (0.90); C18:1 (30.60); C18:2 (12.44); and C18:3a (1.38), with a total saturates of 54.7.

Double thioesterase clones with two homologous recombination constructs (one targeting the 6S region and the other targeting the KE858 region) containing the *C. camphora* thioestease were produced. A positive representative clone had a fatty acid profile of: 0% C8:0; 0.06% C10:0; 5.91% C12:0; 43.27% C14:0; 19.63% C16:0; 0.87% C18:0; 13.96% C18:1; and 13.78% C18:2, with a total saturates at 69.74%. This clone had a C12-C14 level at over 49%, which is over 37 times the C12-C14 level in wildtype cells.

The above data shows that multiple thioesterases can be successfully co-expressed in microalgae. The co-expression of multiple thioesterases results in altered fatty acid profiles that differ significantly not only from the wild type strain, but also from the fatty acid profile obtained by the expression of any one of the individual thioesterases. The expression of multiple thioesterases with overlapping chain length specificity can result in cumulative increases in those specific fatty acids.

The expression of heterologous thioesterases (either alone or in combination) in *Prototheca moriformis* not only alters the fatty acid/lipid profiles in the host strain, but when compared to oils currently available from a variety of seed crops, these profiles are of truly unique oils found in no other currently available system. Not only do the transgenic strains show significant differences from the untransformed wildtype strain, they have remarkably different profiles from many commercial oils. As an example, both coconut and palm kernel oils have levels of C8-C10 fatty acids ranging from 5.5-17%. Transgenic strain expressing the *C. palustris* C8-preferring thioesterase or the *C. hookeriana* C10-preferring thioesterase accumulates anywhere from 3.66 to 8.65%, respectively. These C8-C10 fatty acid levels are similar to coconut oil and palm kernel, however, the transgenic algal strains lack the significantly higher C12:0 fatty acids, and they have extremely high C16:0 (23% in transgenics versus 11-16% in coconut or palm kernel oil, respectively and/or 18:1 (50-57% in transgenics versus 8-19% in coconut or palm kernel oil, respectively.

Example 10: Altering the Levels of Saturated Fatty Acids in the Microalgae *Prototheca moriformis*

As part of a genomics screen using a bioinformatics based approach based on cDNAs, Illumia transcriptome and Roche 454 sequencing of genomic DNA from *Prototheca moriformis* (UTEX 1435), two specific groups of genes involved in fatty acid desaturation were identified: stearoyl ACP desaturases (SAD) and delta 12 fatty acid desaturases (412 FAD). Stearoyl ACP desaturase enzymes are part of the lipid synthesis pathway and they function to introduce double bonds into the fatty acyl chains, for example, the synthesis of C18:1 fatty acids from C18:0 fatty acids. Delta 12 fatty acid desaturases are also part of the lipid synthesis pathway and they function to introduce double bonds into already unsaturated fatty acids, for example, the synthesis of C18:2 fatty acids from C18:1 fatty acids. Southern blot analysis using probes based on the two classes of fatty acid desaturase genes identified during the bioinformatics efforts indicated that each class of desaturase genes was likely comprised of multiple family members. Additionally the genes encoding stearoyl ACP desaturases fell into two distinct families. Based on these results, three gene disruption constructs were designed to potentially disrupt multiple gene family members by targeting more highly conserved coding regions within each family of desaturase enzymes.

Three homologous recombination targeting constructs were designed using: (1) highly conserved portions of the coding sequence of delta 12 fatty acid desaturase (d12FAD) family members and (2) two constructs targeting each of the two distinct families of SAD, each with conserved regions of the coding sequences from each family. This strategy would embed a selectable marker gene (the suc2 sucrose invertase cassette from *S. cerevisiae* conferring the ability to hydrolyze sucrose) into these highly conserved coding regions (targeting multiple family members) rather than a classic gene replacement strategy where the homologous recombination would target flanking regions of the targeted gene.

All constructs were introduced into the cells by biolistic transformation using the methods described above and constructs were linearized before being shot into the cells. Transformants were selected on sucrose containing plates/ media and changes in lipid profile were assayed using the above-described method. Relevant sequences from each of the three targeting constructs are listed below.

| Description | SEQ ID NO: |
|---|---|
| 5' sequence from coding region of d12FAD from targeting construct | SEQ ID NO: 40 |
| 3' sequence from coding region of d12FAD from targeting construct | SEQ ID NO: 41 |
| d12FAD targeting construct cDNA sequence | SEQ ID NO: 42 |
| 5' sequence from coding region of SAD2A | SEQ ID NO: 43 |
| 3' sequence from coding region of SAD2A | SEQ ID NO: 44 |
| SAD2A targeting construct cDNA sequence | SEQ ID NO: 45 |
| 5' sequence from coding region os SAD2B | SEQ ID NO: 46 |
| 3' sequence from coding region of SAD2B | SEQ ID NO: 47 |
| SAD2B targeting construct cDNA sequence | SEQ ID NO: 48 |

Representative positive clones from transformations with each of the constructs were picked and the lipid profiles for these clones were determined (expressed in Area %) and summarized in Table 4 below.

TABLE 4

Lipid profiles for desaturase knockouts.

| Fatty Acid | d12FAD KO | SAD2A KO | SAD2B KO | wt UTEX 1435 |
|---|---|---|---|---|
| C8:0 | 0 | 0 | 0 | 0 |
| C10:0 | 0.01 | 0.01 | 0.01 | 0.01 |
| C12:0 | 0.03 | 0.03 | 0.03 | 0.03 |
| C14:0 | 1.08 | 0.985 | 0.795 | 1.46 |
| C16:0 | 24.42 | 25.335 | 23.66 | 29.87 |
| C18:0 | 6.85 | 12.89 | 19.555 | 3.345 |
| C18:1 | 58.35 | 47.865 | 43.115 | 54.09 |
| C18:2 | 7.33 | 10.27 | 9.83 | 9.1 |
| C18:3 alpha | 0.83 | 0.86 | 1 | 0.89 |
| C20:0 | 0.48 | 0.86 | 1.175 | 0.325 |

Each of the construct had a measurable impact on the desired class of fatty acid and in all three cases C18:0 levels increased markedly, particularly with the two SAD knockouts. Further comparison of multiple clones from the SAD knockouts indicated that the SAD2B knockout lines had significantly greater reductions in C18:1 fatty acids than the C18:1 fatty acid levels observed with the SAD2A knockout lines.

Additional Δ12 fatty acid desaturase (FAD) knockouts were generated in a *Prototheca moriformis* background using the methods described above. In order to identify potential homologous of Δ12FADs, the following primers were used in order to amplify a genomic region encoding a putative FAD:

Primer 1    5'-TCACTTCATGCCGGCGGTCC-3' SEQ ID NO: 49

Primer 2    5'-GCGCTCCTGCTTGGCTCGAA-3' SEQ ID NO: 50

The sequences resulting from the genomic amplification of *Prototheca moriformis* genomic DNA using the above primers were highly similar, but indicated that multiple genes or alleles of Δ12FADs exist in *Prototheca*.

Based on this result, two gene disruption constructs were designed that sought to inactivate one or more Δ12FAD genes. The strategy would to embed a sucrose invertase (suc2 from *S. cerevisiae*) cassette, thus conferring the ability to hydrolyze sucrose as a selectable marker, into highly conserved coding regions rather than use a classic gene replacement strategy. The first construct, termed pSZ1124, contained 5' and 3' genomic targeting sequences flanking a *C. reinhardtii* β-tubulin promoter driving the expression of the *S. cerevisiae* suc2 gene and a *Chlorella vulgaris* nitrate reductase 3'UTR (*S. cerevisiae* suc2 cassette). The second construct, termed pSZ1125, contained 5' and 3' genomic targeting sequences flanking a *C. reinhardtii* β-tubulin promoter driving the expression of the *S. cerevisiae* suc2 gene and a *Chlorella vulgaris* nitrate reductase 3'UTR. The relevant sequences of the constructs are listed in the Sequence Listing:

| | |
|---|---|
| pSZ1124 (FAD2B) 5' genomic targeting sequence | SEQ ID NO: 51 |
| pSZ1124 (FAD2B) 3' genomic targeting sequence | SEQ ID NO: 52 |
| *S. cerevisiae* suc2 cassette | SEQ ID NO: 53 |
| pSZ1125 (FAD2C) 5' genomic targeting sequence | SEQ ID NO: 54 |
| pSZ1125 (FAD2C) 3' genomic targeting sequence | SEQ ID NO: 55 | pSZ1124 and pSZ1125 were each introduced into a *Prototheca moriformis* background and positive clones were selected based on the ability to hydrolyze sucrose. Table 5 summarizes the lipid profiles (in Area %, generated using methods described above) obtained in two transgenic lines in which pSZ1124 and pSZ1125 targeting vectors were utilized.

TABLE 5

Lipid profiles of Δ12 FAD knockouts

| | C10:0 | C12:0 | C14:0 | C16:0 | C16:1 | C18:0 | C18:1 | C18:2 | C18:3α |
|---|---|---|---|---|---|---|---|---|---|
| parent | 0.01 | 0.03 | 1.15 | 26.13 | 1.32 | 4.39 | 57.20 | 8.13 | 0.61 |
| FAD2B | 0.02 | 0.03 | 0.80 | 12.84 | 1.92 | 0.86 | 74.74 | 7.08 | 0.33 |
| FAD2C | 0.02 | 0.04 | 1.42 | 25.85 | 1.65 | 2.44 | 66.11 | 1.39 | 0.22 |

The transgenic containing the FAD2B (pSZ1124) construct gave a very interesting and unexpected result in lipid profile, in that the C18:2 levels, which would be expected to decrease, only decreased by about one area %. However, the C18:1 fatty acid levels increased significantly, almost exclusively at the expense of the C16:0 levels, which decreased significantly. The transgenic containing the FAD2C (pSZ1125) construct also gave a change in lipid profile: the levels of C18:2 are reduced significantly along with a corresponding increase in C18:1 levels.

Beef Tallow Mimetic

One positive clone generated from the above SAD2B knockout experiment as described above was selected to be used as the background for the further introduction of a C14-preferring fatty acyl-ACP thioesterase gene. The construct introducing the *C. camphora* C14-preferring thioesterase contained targeting sequence to the 6S genomic region (allowing for targeted integration of the transforming DNA via homologous recombination) and the expression construct contained the *C. reinhardtii* β-tubulin promoter driving the expression of the neoR gene with the *Chlorella vulgaris* nitrate reductase 3'UTR, followed by a second *C. reinhardtii* β-tubulin promter driving the expression of a codon-optimized *C. camphora* thioesterase with a *Chlorella protothecoides* stearoyl ACP desaturase transit peptide with a second *Chlorella vulgaris* nitrate reductase 3'UTR. The 5' 6S genomic donor sequence is listed in SEQ ID NO:56; the 3' 6S genomic donor sequence is listed in SEQ ID NO:57; and the relevant expression construct for the *C. camphora* thioesterase is listed in SEQ ID NO:58.

Transformation was carried out using biolistic methods as described above and the cells were allowed to recover for 24 hours on plates containing 2% sucrose. After this time, the cells were re-suspended and re-plated on plates containing 2% sucrose and 50 μg/ml G418 for selection. Nine clones out of the positive clones generated were selected for lipid production and lipid profile. The nine transgenic clones (with the SAD2B KO and expressing *C. camphora* C14-preferring thioesterase) were cultured as described above and analyzed for lipid profile. The results are summarized below in Table 6. The lipid profile for tallow is also included in Table 6 below (National Research Council 1976: Fat Content and Composition of Animal Product).

TABLE 6

Lipid profile of thioesterase transformed clones.

| | C10:0 | C12:0 | C14:0 | C16:0 | C16:1 | C18:0 | C18:1 | C18:2 | C18:3 | C20 |
|---|---|---|---|---|---|---|---|---|---|---|
| SAD2BKO *C.camphora* TE clone 1 | 0.01 | 0.33 | 6.13 | 24.24 | 0.19 | 11.08 | 42.03 | 13.45 | 0.98 | 0.73 |
| SAD2BKO *C.camphora* TE clone 2 | 0.01 | 0.16 | 3.42 | 23.80 | 0.40 | 9.40 | 50.62 | 10.2 | 0.62 | 0.70 |
| SAD2BKO *C.camphora* TE clone 3 | 0.01 | 0.20 | 4.21 | 25.69 | 0.40 | 7.79 | 50.51 | 9.37 | 0.66 | 0.63 |
| SAD2BKO *C.camphora* TE clone 4 | 0.01 | 0.21 | 4.29 | 23.57 | 0.31 | 9.44 | 50.07 | 10.07 | 0.70 | 0.70 |
| SAD2BKO *C.camphora* TE clone 5 | 0.01 | 0.18 | 3.87 | 24.42 | 0.32 | 9.24 | 49.75 | 10.17 | 0.71 | 0.71 |
| SAD2BKO *C.camphora* TE clone 6 | 0.01 | 0.28 | 5.34 | 23.78 | 0.33 | 9.12 | 49.12 | 10.00 | 0.68 | 0.70 |
| SAD2BKO *C.camphora* TE clone 7 | 0.01 | 0.15 | 3.09 | 23.07 | 0.32 | 10.08 | 51.21 | 10.00 | 0.66 | 0.74 |
| SAD2BKO *C.camphora* TE clone 8 | 0.01 | 0.29 | 5.33 | 24.62 | 0.37 | 7.02 | 49.67 | 10.74 | 0.69 | 0.70 |
| SAD2BKO *C.camphora* TE clone 9 | 0.01 | 0.12 | 2.74 | 25.13 | 0.30 | 10.17 | 50.18 | 9.42 | 0.71 | 0.71 |
| wt UTEX 1435 | 0.01 | 0.02 | 0.96 | 23.06 | 0.79 | 3.14 | 61.82 | 9.06 | 0.46 | 0.27 |
| SAD2BKO | 0.01 | 0.03 | 0.80 | 23.66 | 0.13 | 19.56 | 43.12 | 9.83 | 1.00 | 1.18 |
| Tallow | 0.00 | 0.00 | 4.00 | 26.00 | 3.00 | 14.00 | 41.00 | 3.00 | 1.00 | 0.00 |

As can be seen in Table 6, the lipid profiles of the transgenic lines are quite similar to the lipid profile of tallow. Taken collectively, the data demonstrate the utility of combining specific transgenic backgrounds, in this case, a SAD2B knockout with a C14-preferring thioesterase (from *C. camphora*), to generate an transgenic algal strain that produce oil similar to the lipid profile of tallow.

Construct Used to Down Regulate the Expression of β-Ketoacyl Synthase II (KASII) by Targeted Knock-Out Approach Vector down-regulating KASII gene expression by targeted knock-out approach was introduced into a classically mutagenized derivative of UTEX 1435, S1331. The *Saccharomyces cerevisiae* invertase gene was utilized as a selectable marker, conferring the ability to grow on sucrose. The invertase expression cassette under control of *C. reinhardtii* B-tubulin promoter was inserted in the middle of the 315 bp long KASII genomic region to permit targeted integration (pSZ1503).

Relevant restriction sites in pSZ1503 are indicated in lowercase, bold and underlining and are 5'-3' BspQ 1, Kpn I, AscI, Xho I, Sac I, BspQ I, respectively. BspQI sites delimit the 5' and 3' ends of the transforming DNA. Bold, lowercase sequences represent genomic DNA from S1331 that permit targeted integration at KASII locus via homologous recombination. Proceeding in the 5' to 3' direction, the *C. reinhardtii* B-tubulin promoter driving the expression of the yeast sucrose invertase gene (conferring the ability of S1331 to metabolize sucrose) is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text.

Nucleotide sequence of transforming DNA contained in pSZ1503_[KASII_btub-y.inv-nr_KASII]:

(SEQ ID NO :59)

```
gctcttccgcaccggctggctccaccccaacttgaacctcgagaacccgcgcctggcgtcgacccgtcgtgctcgtggggccgc
ggaaggagcgcgccgaagacctggacgtcgtcctctccaactcctttggctttggcgggcacaattcgtgcgtcggtaccctttcttg
cgctatgacacttccagcaaaaggtagggcgggctgcgagacggcttcccggcgctgcatgcaacaccgatgatgcttcgaccccc
cgaagctccttcggggctgcatgggcgctccgatgccgctccagggcgagcgctgtttaaatagccaggccccgattgcaaagac
attatagcgagctaccaaagccatattcaaacacctagatcactaccacttctacacaggccactcgagcttgtgatcgcactccgct
aaggggggcgcctcttcctcttcgtttcagtcacaacccgcaaaggcgcgccATGctgctgcaggccttcctgttcctgctggcccgg
cttcgccgccaagatcagcgcctccatgacgaacgagacgtccgaccgcccctggtgcacttcacccccaacaagggctggat
gaacgaccccaacggcctgtggtacgacgagaaggacgccaagtggcacctgtacttccagtacaacccgaacgacaccgtc
tgggggacgcccttgttctggggccacgccacgtccgacgacctgaccaactgggaggaccagcccatcgccatcgccccgaa
gcgcaacgactccggcgccttctccggctccatggtggtggactacaacaacacctccggcttcttcaacgacaccatcgacccg
cgccagcgctgcgtggccatctggacctacaacaccccggagtccgaggagcagtacatctcctacagcctggacggcggcta
caccttcaccgagtaccagaagaaccccgtgctggccgccaactccacccagttccgcgacccgaaggtcttctggtacgagcc
ctcccagaagtggatcatgaccgcggccaagtcccaggactacaagatcgagatctactcctccgacgacctgaagtcctgga
agctggagtccgcgttcgccaacgagggcttcctcggctaccagtacgagtgccccgcctgatcgaggtccccaccgagcag
gaccccagcaagtcctactgggtgatgttcatctccatcaaccccggcgcccccggccggcggctccttcaaccagtacttcgtcg
gcagcttcaacggcacccacttcgaggccttcgacaaccagtcccgcgtggtggacttcggcaaggactactacgccctgcaga
ccttcttcaacaccgacccgacctacgggagcgccctgggcatcgcgtgggcctccaactgggagtactccgccttcgtgcccac
caaccctggcgctcctccatgtccctcgtgcgcaagttctccctcaacaccgagtaccaggccaacccggagacggagctgatc
aacctgaaggccgagccgatcctgaacatcagcaacgccggcccctggagccggttcgccaccaacaccacgttgacgaagg
ccaacagctacaacgtcgacctgtccaacagcaccggcacctggagttcgagctggtgtacgccgtcaacaccacccagacg
atctccaagtccgtgttcgcggacctctccctctggttcaagggcctggaggaccccgaggagtacctccgcatgggcttcgagg
tgtccgcgtcctccttcttcctggaccgcgggaacagcaaggtgaagttcgtgaaggagaaccctacttcaccaaccgcatga
gcgtgaacaaccagcccttcaagagcgagaacgacctgtcctactacaaggtgtacggcttgctggaccagaacatcctgga
gctgtacttcaacgacggcgacgtcgtgtccaccaacacctacttcatgaccaccgggaacgccctgggctccgtgaacatgac
gacgggggtggacaacctgttctacatcgacaagttccaggtgcgcgaggtcaagTGAcaattggcagcagcagctcggata
gtatcgacacactctggacgctggtcgtgtgatggactgttgccgccacacttgctgccttgacctgtgaatatccctgccgcttttatc
aaacagcctcagtgtgtttgatcttgtgtgtacgcgcttttgcgagttgctagctgcttgtgctatttgcgaataccaccccagcatcc
```

```
ccttccctcgtttcatatcgcttgcatcccaaccgcaacttatctacgctgtcctgctatccctcagcgctgctcctgctcctgctcactgc ccctcgcacagccttggtttgggctccgcctgtattctcctggtactgcaacctgtaaaccagcactgcaatgctgatgcacgggaagt agtgggatgggaacacaaatggaggatcgtagagctcatcttccgaaagtacgacgagtgagcgagctgattctctttgagcggg gtcgggtggttcggggagagtgcgcggaaaggcgcagagacgtgcggccggccgtgtccctccgtcttccoctggttggtgctata gtaacctgcctgtgtcgcgtgcgcgtcgggaagagc
```

The cDNAs of the KAS II allele 1 and allele 2 are identified in SEQ ID NOs: 66 and 68, respectively. The amino acid sequences of alleles 1 and 2 are identified in SEQ ID NOs: 67 and 69, respectively.

To determine the impact of KASII inactivation on lipid composition, pSZ1503 vector DNA was transformed into S1331 to generate a targeted KASII knock-out phenotype. Initial single clones were isolated and grown under standard lipid production conditions at pH5.0. The resulting profiles of the best representative clone and the wild-type cells are shown below in Table 7.

TABLE 7

Fatty acid profiles in S1331 and a derivative transgenic line transformed with pSZ1503 DNA.

| Sample ID | C10:0 | C12:0 | C14:0 | C16:0 | C16:1 | C18:0 | C18:1 | C18:2 | C18:3 α |
|---|---|---|---|---|---|---|---|---|---|
| 1331-5 | 0.01 | 0.03 | 0.96 | 24.28 | 0.64 | 3.94 | 62.69 | 6.21 | 0.49 |
| D698-2 | 0.01 | 0.01 | 0.83 | 38.36 | 1.38 | 2.21 | 48.31 | 7.60 | 0.55 |

Example 11. Genetic Engineering of a Microalga after Adaptation to High Salt A *Prototheca morifomis* strain, S2939, was identified as a salt tolerant mutant using the techniques described above. In order to confer the ability to grow on sucrose, the strain was transformed with sucrose invertase from *Saccharomyces cerevisiae* by recombination at one of two genomic integration sites according to the methods described in Example 7 herein and in co-owned applications WO2010/063031, WO2010/063032, WO2011/150411, WO2012/106560, WO2013/158938, PCT/US2014/059161, all of which are incorporated by reference. Twenty one transformants were tested for oil production in 10 mL cultures using sucrose as a sole carbon source. Multiple transformants, including S1868, were obtained that, when cultured on sucrose as a carbon source, produced 90% or more of the oil produced by the parent strain, which required added sucrose invertase enzyme for propagation and oil production on sucrose.

Example 12: Performance of Salt-Tolerant Strains on Cane Syrup in 7-L Fermentors Through sequential batch fermentation of a mutagenized population of the high oil-producing strain, *Prototheca morifomis* Strain S1920, in medium containing a high concentration of potassium, two mutant salt-tolerant mutant strains with high oil productivity were obtained, (Strain S3303 and Strain S3304). The evolution process involved the cultivation of the mutagenized cells in seed medium that was supplemented with 600-650 mM KCl. This potassium concentration was chosen to reduce the maximum specific growth rate of the parental strain, Strain S1920, by approximately 70%. The cells were grown in 10 mL of seed medium in 50-mL bioreactor tubes, and their growth was maintained in the exponential phase for approximately 70 generations through sequential subculturing. At the end of the evolution process, the mixed culture population was plated for the isolation of single colonies, which were then screened in shake flasks to identify the mutants that show high oil titers and yields in production media both with and without the supplementation of 300 mM KCl.

Strain S3303 and Strain S3304 were the two best performers in flasks and were then tested at the 7-L scale with a high cell-density process using both 60% (w/w) reagent-grade sucrose and crude cane syrup as the carbon source. The sucrose content, potassium concentration, and conductivity of this cane syrup were 60% (w/w), 214 mM potassium, and 42 mS/cm, respectively. Control runs with the parental strain were conducted for performance comparison. Invertase was added to the fermentations to catalyze the conversion of sucrose into glucose and fructose for their consumption.

Figure 4:
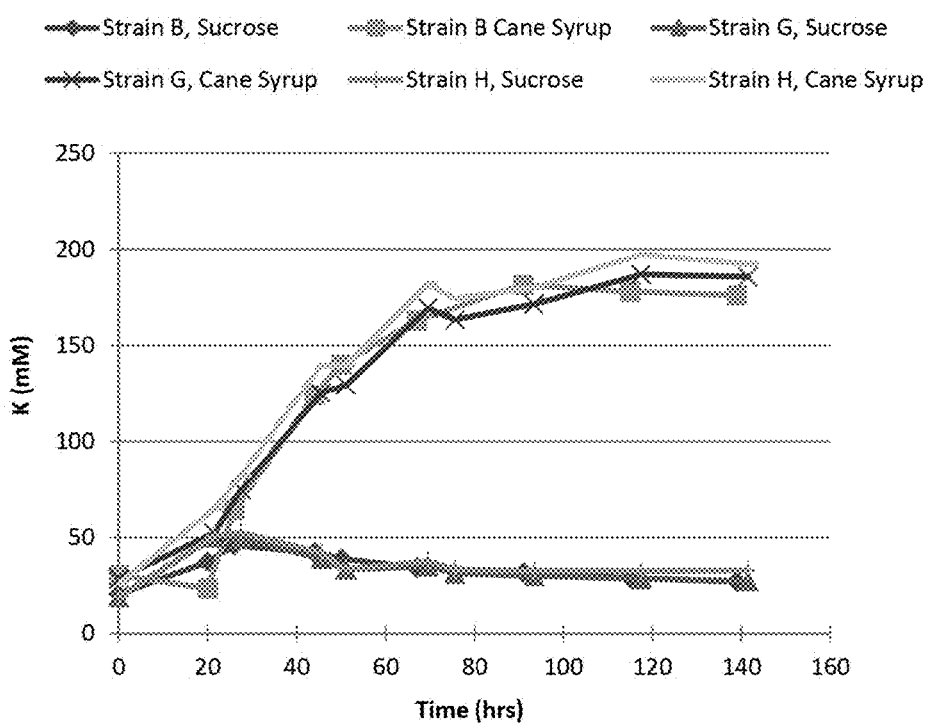
FIG. 4 shows a time-course for accumulation of potassium for several microalgal strains in sucrose and in cane syrup.
Figure 5:
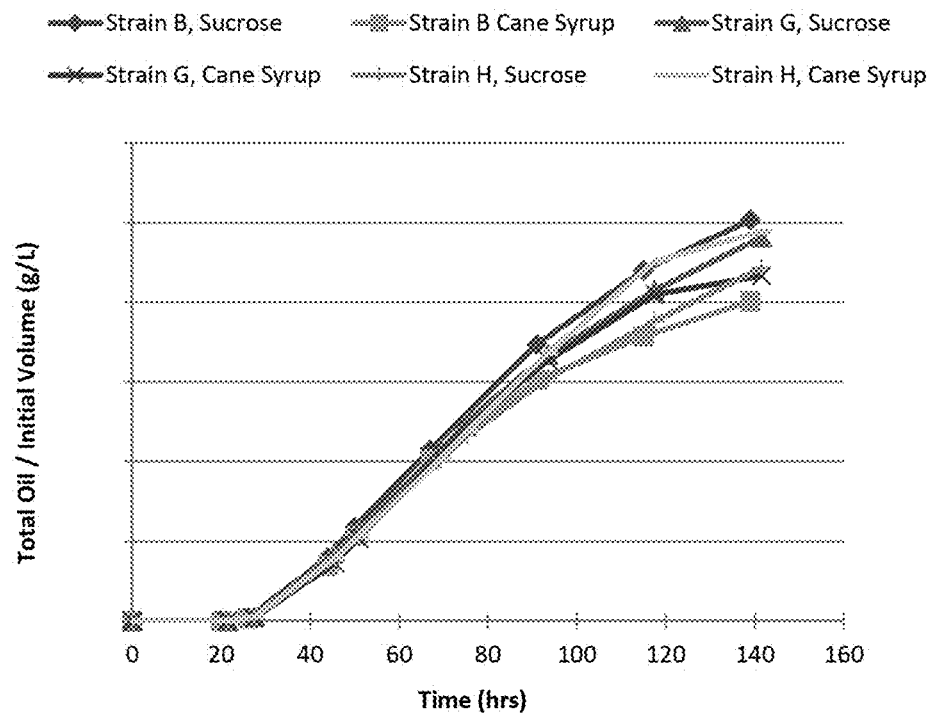
FIG. 5 shows a time course for oil production by the microalgal strains of FIG. 4 on sucrose and cane syrup.
Figure 6:
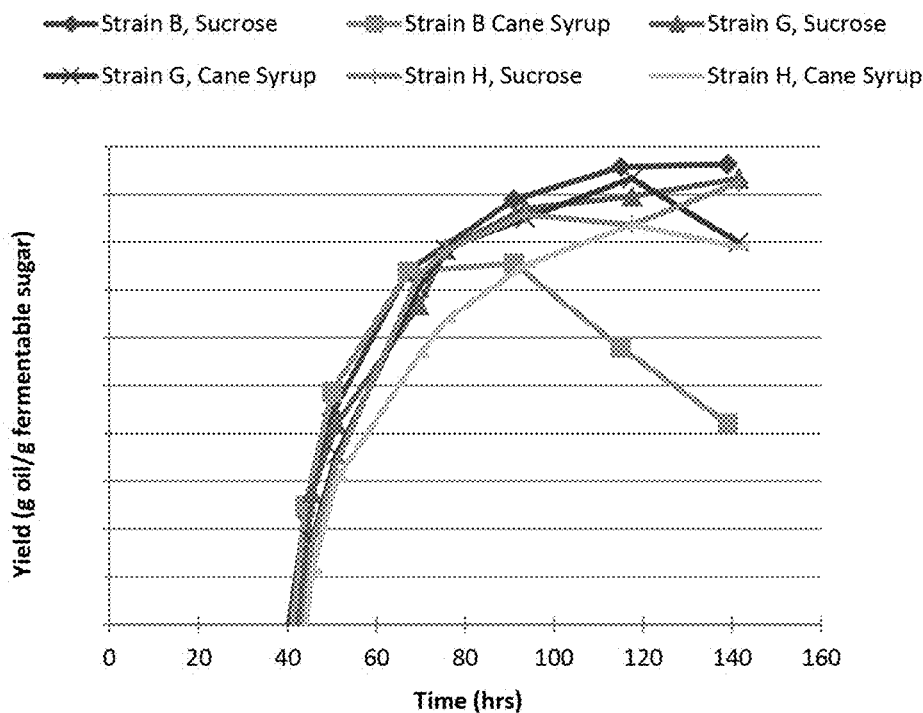
FIG. 6 shows a time course of yield in terms of grams of oil produced per gram of fermentable sugar for the strains of FIGS. 4 and 5.

As shown in FIGS. 4 and 5, the performances of Strains S3303 and S3304 are superior to that of Strain S1920 on cane syrup. Despite an accumulation of >170 mM K in the fermentation with cane syrup (FIG. 4), the total amounts of oil produced by Strains S3303 and S3304 were comparable to those observed in the fermentations with reagent-grade sucrose (FIG. 5). These were also 10% and 20% higher than the total amounts of oil produced by Strain S1920 in the runs with the same cane feedstock, respectively. In addition, as can be seen from FIG. 5, the total amount of oil produced by Strain S3304 on cane syrup was comparable to that produced by Strain S1331 on reagent-grade sucrose. Higher peak yields in terms of g oil/g fermentable sugar were achieved by Strains S3303 and S3304 on both cane syrup and reagent-grade sucrose, than for the parental strain S1920 (FIG. 6). Moreover, Strains S3303 and S3304 maintained their high yields until the end of the runs, while the yield of Strain S1920 dropped precipitously after 90 h of fermentation. These results demonstrate the robustness of the salt-tolerant strains in high cell-density fermentations with crude cane syrup.

Example 13: Selection of Mutants in the Presence of 2-Deoxyglucose to Increase Oil Titer The ability to increase oil production, maximize oil yield on carbon, and modulate the fatty acid profile of the oil produced, are critical for the development of a cost-effective, commercial manufacturing process with the heterotrophic oleaginous microalga, *Prothetheca moriformis*. This Example describes the use of 2-deoxyglucose (2-DG) as a selective agent for the identification of mutants with increased oil titers compared to the parental strain. 2-DG is an analog of glucose and an inhibitor of monosaccharide transporters.

To leverage the use of 2-DG for the identification of *P. moriformis* mutants with increased oil titers, the high oil-producing strains—Parental strains S2949, S2952, S3150, S3331 and S3332—were mutagenized by using N-methyl-N'-nitro-N-nitrosoguanidine (NTG) only, ethyl methanesulfonate (EMS) only, or EMS plus ultraviolet (UV) radiation to generate a heterogeneous mutant population as discussed above. The parental strains S2949, S2952, S3150, S3331 and S3332 all had similar lipid titers. The mutagenized cells obtained from the parental strains were then pooled and cultured either in seed medium containing 10 g/L fructose with 6-20 g/L 2-DG or in seed medium containing 10 g/L glucose with 30-50 g/L 2-DG for 5-7 days. The cells grown in the fructose culture were then spread onto TSA (tryptic soy agar) plates containing 20 g/L fructose and 12-20 g/L 2-DG, while the cells grown in the glucose culture were spread onto TSA plates containing 20 g/L glucose and 50 g/L 2-DG. Parental strains S2949, S2952, S3150, S3331, and S3332 were prepared according to Example 2.

The 2-DG resistant isolates that grew on the TSA plates supplemented with fructose or glucose were selected for evaluation in 50-mL bioreactor tubes. In this primary screen, the mutants were cultured in production medium that contained both glucose and fructose as carbon sources. Of the 192 isolates tested, five of them showed oil titers that were approximately 10% higher than that of the parental strain, Strain S3150 (Tables 8-9). Two of these mutants originated from the liquid culture that was supplemented with fructose, while the other three mutants originated from the liquid culture that was supplemented with glucose. Their improvements in oil titer compared to the parental strain were confirmed in the secondary screen (Table 10). The production cultures for this secondary screen were grown in 50-mL bioreactor tubes for 5 days and were fed glucose as the sole carbon source.

TABLE 8

Performances of the top 2-DG resistant mutants that were isolated from solid medium supplemented with fructose and 2-DG.

| 2-DG Resistant Mutants from Fructose Culture | Oil (% of Parent) |
|---|---|
| S2-F3_C6 | 110 |
| S2-F3_D10 | 111 |
| Strain S3150 (Parent) | 100 |

TABLE 9

Performance of the top 2-DG resistant mutants that were isolated from solid medium supplemented with glucose and 2-DG.

| 2-DG Resistant Mutants from Glucose Culture | Oil (% of Parent) |
|---|---|
| S2F7-C8 | 111 |
| S2F7-H5 | 109 |
| S2F7-H11 | 113 |
| Strain S3150 (Parent) | 100 |

TABLE 10

Performance of the top 2-DG resistant mutants in the secondary screen.

| 2-DG Resistant Mutants | Oil (% of Parent) |
|---|---|
| S2F3-C6 | 107 |
| S2F3-D10 | 106 |
| S2F7-C8 | 112 |

TABLE 10-continued

Performance of the top 2-DG resistant mutants in the secondary screen.

| 2-DG Resistant Mutants | Oil (% of Parent) |
|---|---|
| S2F7-H5 | 111 |
| S2F7-H11 | 108 |
| Strain S3150 (Parent) | 100 |

Example 14: Selection of Mutants in the Presence of Cerulenin or Triclosan to Increase Levels of C18:0 or C18:1 Fatty Acids This Example describes the use of cerulenin and triclosan as selective agents for the identification of mutants with increased levels of C18:0 or C18:1 fatty acids compared to the parental strains.

Cerulenin is an inhibitor of KASI and KASII, while triclosan is an inhibitor of the enoyl:ACP reductase in the fatty acid biosynthetic pathway. Microbial strains that are resistant to these inhibitors are likely to harbor mutations in their genome that enable them to over-express KASI, KASII, or the enoyl:ACP reductase. They may also express mutated forms of these enzymes that are more active than the wild-type ones. As a result, the resistant strains may possess an increased capacity for fatty acid biosynthesis.

To identify new strains of *P. moriformis* with improved oil titers, the lead base strains—Strains S22949, S2952, S3150, S3331 and S3332—were mutagenized by NTG, EMS, or EMS+UV and selected for cerulenin or triclosan resistance. The mutagenized cells were then pooled and spread onto TSA plates containing 15-35 μM cerulenin and/or 4 μM triclosan. The resistant isolates were then cultured in 50-mL bioreactor tubes for 5 days and were fed glucose as the carbon source, followed by oil titer and profile determination. None of the isolates showed oil titers that were higher than those of the parental strains. However, two of the cerulenin-resistant isolates (Strain S5100 and Strain S5226) produced oils that were significantly higher in C18:1 levels and lower in C16:0 levels than the oils produced by the parents (Table 11).

TABLE 11

Performance of two cerulenin-resistant mutants that showed increased levels of C18:1 and decreased levels of C16:0 compared to the parental strain, Strain S3150.

| | Fatty Acid Profile of Oil Produced (Area %) | | | | |
|---|---|---|---|---|---|
| Strain | C14:0 | C16:0 | C18:0 | C18:1 | C18:2 |
| S5100 | 0.7 | 17.3 | 4.4 | 70.1 | 5.7 |
| S5226 | 0.8 | 18.0 | 4.6 | 69.3 | 5.7 |
| S3150 (Parent) | 1.7 | 29.5 | 4.0 | 57.4 | 5.6 |

To confirm the ability of Strain S5100 to produce oil with an increased level of C18:1, its performance was further evaluated in a 7-L fermentor using a fed-batch process and 70% (w/w) sucrose as the carbon feed. Exogeneous invertase was added for sucrose hydrolysis. As shown in Table 12, the final yield and total oil production achieved by Strain S5100 were comparable to those achieved by the parental strain, Strain S3150. However, the C18:1 level of Strain S5100 was significantly higher than that for Strain S3150. By the end of the fermentation, it reached 75% of the total amount of fatty acids produced. Again, this elevated level of C18:1 was accompanied by a drop in the C16:0 level. These results are all consistent with those observed for the tube culture in the primary screen.

TABLE 12

Performance of the cerulenin-resistant mutant, Strain S5100, and its parental strain, Strain S3150, in high cell-density fermentations.

| Strain | Fatty Acid Profile of Oil (Area %) | | | | |
|---|---|---|---|---|---|
| | C14:0 | C16:0 | C18:0 | C18:1 | C18:2 |
| S5100 | 0.4 | 13.9 | 4.7 | 75.1 | 4.5 |
| S3150 | 1.4 | 27.6 | 4.0 | 60.1 | 4.8 |

*Normalized to initial volume of fermentation.

In addition to our work with the lead base strains, we also mutagenized the transgenic strain, Strain S3168, by NTG only or by EMS+UV and selected for isolates that were resistant to cerulenin or triclosan. Strain S3168 is a FATA (thioesterase knockout expressing invertase under control of beta tubulin promoter) and also has a *Cuphea wrightii* FATB under control of amt03 promoter (active at pH 7 but not at pH5). Plasmid pSZ1925: FatA1_Btub:inv:nr::amt03-CwTE2:nr_FatA1 and a recombinant microalgae engineered to express pSZ1925 were disclosed in co-owned application WO2012/061647, herein incorporated by reference. When cultured at low pH, this strain is a high oleic strain that is capable of producing oil with a C18:1 level of up to 77%. After the mutagenesis procedure, the cells were spread onto TSA plates containing 12 μM cerulenin or 4 μM triclosan. The resulting resistant isolates were then cultured in 50-mL bioreactor tubes for evaluation. From this primary screen, one of the triclosan-resistant mutants (Strain S5692) was found to exhibit an elevated level of C18:1 compared to Strain S3168, and its performance was subsequently evaluated in a 7-L fermentor with a fed-batch process and 70% (w/w) sucrose as the carbon feed. Exogeneous invertase was added for additional sucrose hydrolysis. As shown in Table 13, the final yield and total oil production achieved by Strain S5692 were very similar to those observed for the parental strain, Strain S3168. However, the C18:1 level of Strain T was considerably higher, reaching 84-85% by the end of the fermentations. Meanwhile, the C16:0 level accounted for only 6-7% of the total amount of fatty acids produced.

TABLE 13

Performance of the triclosan-resistant mutant, Strain S5692, and its parental strain, Strain S3168, in Solazyme's high cell-density fermentations.

| Strain | Fatty Acid Profile of Oil (Area %) | | | | |
|---|---|---|---|---|---|
| | C14:0 | C16:0 | C18:0 | C18:1 | C18:2 |
| Strain S5692 | 0.4 | 6.7 | 2.6 | 83.9 | 5.1 |
| Strain S5692 | 0.4 | 6.2 | 2.4 | 84.8 | 5.0 |
| S3168 | 0.4 | 12.7 | 1.8 | 77.3 | 6.0 |

*Normalized to initial volume of fermentation.

Since the formation of C18:0 is an intermediate step in the conversion of C16:0 to C18:1 in the fatty acid biosynthetic pathway, cerulenin and triclosan may also be used as selective agents for the identification of *P. moriformis* mutants with increased levels of C18:0. Hence, three different transgenic strains (Strain S4424, Strain S4440, and Strain S4442) that had already been genetically engineered to produce oils with elevated levels of C18:0 ranging from 38-44% were mutagenized by NTG only or EMS+UV. Strain S4424 (6SA::Cr(bTub)-syn(yInv)-Cv(nr):Pm(hxt_14757G)-Pm(SAD2hpC)-Cv(nr)::6SB), Strain S4440 (THI4a5'::Cr(bTub)-syn(yInv)-Cv(nr)::Cr(bTub)-Pm(SAD2hpD)-Cv(nr)::THI4a3), and Strain S4442_(DAO1b5'::Cr(bTub)-syn(yINV)-Cv(nr)::Cr(bTub)-Pm(SAD2hpD)-Cv(nr):: DAO1b3') all express a SAD2 hairpin RNAi construct and invertase, but at different integration sites. After mutagenisis, the resulting cells were spread onto TSA plates containing 15-35 μM cerulenin or 4 μM triclosan. Isolates that were resistant to either of these inhibitors were cultured in 50-mL bioreactor tubes for oil titer and profile determination. As shown in Tables 14-17, many of the isolates resistant to cerulenin or triclosan showed marked increases in their C18:0 levels compared to their parental strains—Strains S4424, S4440, or S4442. Although most of these isolates did not experience any improvements in their oil titers, three of them (JV33-1, JV33-104, and JV33-125) exhibited oil titers that were >10% higher than that of their parent, Strains S4424, S4440 or S4442. These results, together with those presented above, clearly indicate that 2-DG, cerulenin, and triclosan are effective selective agents for isolating mutants of *P. moriformis* with improved oil titers and/or are capable of producing oils with increased levels of long-chain fatty acids, such as C18:0 and C18:1.

TABLE 14

Performance of cerulenin-resistant mutants that showed increased levels of C18:0 and decreased levels of C16:0 compared to the parental strain, Strain S4424. The production cultures were grown in 50-mL bioreactor tubes for 5 days and were fed glucose as the carbon source.

| Selective Agent | Isolate/Strain | Oil (% of Parent) | Fatty Acid Profile of Oil Produced (Area %) | | | | |
|---|---|---|---|---|---|---|---|
| | | | C14:0 | C16:0 | C18:0 | C18:1 | C18:2 |
| 35 μM Cerulenin | JV32-40 | 62 | 1.8 | 20.2 | 46.1 | 20.2 | 6.9 |
| | JV32-44 | 76 | 0.6 | 18.9 | 45.9 | 24.2 | 5.9 |
| 15 μM Cerulenin | JV32-155 | 80 | 1.5 | 18.9 | 43.4 | 25.3 | 6.1 |
| — | S4424 (Parent) | 100 | 1.0 | 27.1 | 38.5 | 23.7 | 5.7 |

TABLE 15

Performance of triclosan-resistant mutants that showed increased levels of C18:0 and decreased levels of C16:0 compared to the parental strain, Strain S4424. The production cultures were grown in 50-mL bioreactor tubes for 5 days and were fed glucose as the carbon source.

| Selective Agent | Isolate/Strain | Oil (% of Parent) | Fatty Acid Profile of Oil Produced (Area %) | | | | |
|---|---|---|---|---|---|---|---|
| | | | C14:0 | C16:0 | C18:0 | C18:1 | C18:2 |
| 4 μM Triclosan | DY107-A7 | 83 | 0.4 | 19.2 | 47.5 | 22.4 | 6.6 |
| | DY107-D6 | 87 | 0.8 | 22.8 | 45.4 | 22.7 | 5.2 |
| | DY107-A12 | 92 | 1.1 | 20.2 | 44.5 | 24.0 | 6.2 |
| — | S4424 (Parent) | 100 | 1.0 | 28.3 | 38.9 | 23.0 | 5.4 |

TABLE 16

Performance of cerulenin-resistant mutants that showed increased levels of C18:0 and decreased levels of C16:0 compared to the parental strain, Strain S4440. The production cultures were grown in 50-mL bioreactor tubes for 5 days and were fed glucose as the carbon source.

| Selective Agent | Isolate/Strain | Oil (% of Parent) | Fatty Acid Profile of Oil Produced (Area %) | | | | |
|---|---|---|---|---|---|---|---|
| | | | C14:0 | C16:0 | C18:0 | C18:1 | C18:2 |
| 35 µM Cerulenin | JV33-47 | 93 | 0.5 | 16.2 | 47.7 | 24.5 | 6.5 |
| | JV33-1 | 110 | 0.5 | 16.3 | 47.7 | 24.9 | 6.1 |
| | JV33-7 | 93 | 0.5 | 16.3 | 47.3 | 24.9 | 6.4 |
| 15 µM Cerulenin | JV33-128 | 80 | 0.6 | 17.9 | 51.9 | 19.4 | 5.6 |
| | JV33-123 | 99 | 0.7 | 18.0 | 50.0 | 21.4 | 5.6 |
| | JV33-111 | 106 | 0.5 | 17.3 | 49.8 | 22.4 | 5.8 |
| | JV33-125 | 118 | 0.6 | 16.9 | 49.2 | 23.4 | 5.6 |
| | JV33-104 | 112 | 0.6 | 17.0 | 48.6 | 23.4 | 5.9 |
| — | S4440 (Parent) | 100 | 1.1 | 28.0 | 44.6 | 17.2 | 5.2 |

TABLE 17

Performance of cerulenin-resistant mutants that showed increased levels of C18:0 and decreased levels of C16:0 compared to the parental strain, Strain S4442. The production cultures were grown in 50-mL bioreactor tubes for 5 days and were fed glucose as the carbon source.

| Selective Agent | Isolate/Strain | Oil (% of Parent) | Fatty Acid Profile of Oil Produced (Area %) | | | | |
|---|---|---|---|---|---|---|---|
| | | | C14:0 | C16:0 | C18:0 | C18:1 | C18:2 |
| 35 µM Cerulenin | JV34-2 | 48 | 0.7 | 19.5 | 53.2 | 15.1 | 6.5 |
| | JV34-5 | 39 | 2.0 | 21.4 | 52.7 | 12.5 | 6.9 |
| | JV34-6 | 52 | 0.5 | 18.6 | 54.7 | 14.1 | 7.3 |
| | JV34-71 | 58 | 1.1 | 15.3 | 51.8 | 20.4 | 6.2 |
| 15 µM Cerulenin | JV34-103 | 79 | 0.8 | 21.4 | 52.1 | 16.0 | 5.5 |
| | JV34-113 | 58 | 0.7 | 20.0 | 53.1 | 15.4 | 6.2 |
| | JV34-121 | 63 | 0.6 | 18.8 | 53.5 | 15.9 | 6.4 |
| — | S4442 (Parent) | 100 | 1.1 | 29.3 | 44.9 | 15.7 | 5.2 |

Example 15: Down-Regulating FATA1 and Over Expressing Keto-Acyl-ACP Synthase II (PmKASII) in Cerulenin-Resistant *Prototheca moriformis* to Obtain an Oil Elevated in Unsaturated Fatty Acids Constructs that disrupt a single copy of the FATA1 allele while simultaneously overexpressing the *P. moriformis* KASII gene were introduced into a high oleic base strain (Strain S5100), obtained by classical mutagenesis and selection on 15 micromolar cerulenin. One of the resulting strains (S5587), produced 85% C18:1 (oleate) with total un-saturates around 93% in multiple fermentation runs. The strain S5587 has a significant improvement in both lipid profile and productivity over a similar strain that was not selected on cerulenin.

The *Saccharomyces cerevisiae* invertase gene (Accession no: NP 012104) was utilized as the selectable marker to introduce the PmKASII into the FATA1 locus of *P. moriformis* strain Strain S5100 by homologous recombination using biolistic transformation methods. To investigate the KASII activity when driven by different promoters, PmKASII was fused to the promoters such PmUAPA1, PmLDH1, and PmAMT3. Note that the integration constructs were all designed as reverse orientation to the FATA1 gene, because the most transformants resulting from the constructs with forward orientation were found to be unstable in sucrose invertase expression. Therefore, the constructs that have been expressed in Strain S5100 can be written as:

1) FATA1 3'::CrTUB2:ScSUC2:CvNR::PmUAPA1: PmKASII-CvNR::FATA1 5' (pSZ2533)
2) FATA1 3'::CrTUB2:ScSUC2:CvNR::PmLDH1: PmKASII-CvNR::FATA1 5' (pSZ2532)
3) FATA1 3'::CrTUB2:ScSUC2:CvNR::PmAMT3: PmKASII-CvNR::FATA1 5' (pSZ2750)

Refering to Table 18, relevant restriction sites in the construct pSZ2533 FATA13'::CrTUB2:ScSUC2:CvNR:: PmUAPA1:PmKASII-CvNR::FATA1 5' are indicated in lowercase, bold and underlining and are 5'-3' BspQ 1, Kpn I, Asc I, Mfe I, EcoRV, SpeI, AscI, ClaI, Sac I, BspQ I, respectively. BspQI sites delimit the 5' and 3' ends of the transforming DNA. Bold, lowercase sequences represent FATA1 3' genomic DNA that permit targeted integration at FATA1 locus via homologous recombination. Proceeding in the 5' to 3' direction, the *C. reinhardtii* β-tubulin promoter driving the expression of the yeast sucrose invertase gene is indicated by boxed text. The initiator ATG and terminator TGA for invertase are indicated by uppercase, bold italics while the coding region is indicated in lowercase italics. The *Chlorella vulgaris* nitrate reductase 3' UTR is indicated by lowercase underlined text followed by the *P. moriformis* UAPA1 promoter, indicated by boxed italics text. The Initiator ATG and terminator TGA codons of the PmKASII are indicated by uppercase, bold italics, while the remainder of the coding region is indicated by bold italics. The *Chlorella protothecoides* S106 stearoyl-ACP desaturase transit peptide is located between initiator ATG and the Asc I site. The *C. vulgaris* nitrate reductase 3' UTR is again indicated by lowercase underlined text followed by the FATA1 5' genomic region indicated by bold, lowercase text.

TABLE 18

Nucleotide sequence of transforming DNA contained in pSZ2533.

```
gctcttcacccaactcagataataccaataccctccttctcctcctcatccattcagtaccccccccttctcttcccaaagcagcaa
gcgcgtggcttacagaagaacaatcggcttccgccaaagtcgccgagcactgcccgacggcggcgcgcccagcagcccgcttggc
cacacaggcaacgaatacattcaatagggggcctcgcagaatggaaggagcggtaaagggtacaggagcactgcgcacaaggg
gcctgtgcaggagtgactgactgggcgggcagacggcgcaccgcgggcgcaggcaagcagggaagattgaagcggcagggagg
aggatgctgattgaggggggcatcgcagtctctcttggacccgggataaggaagcaaatattcggccggttgggttgtgtgtgtgc
acgttttcttcttcagagtcgtgggtgtgcttccagggaggatataagcagcaggatcgaatcccgcgaccagcgtttcccatcca gccaaccaccctgtcggtaccctttcttgcgctatgacacttccagcaaaaggtagggcgggctgcgagacggcttcccggcgctgc atgcaacaccgatgatgcttcgacccccgaagctccttcggggctgcatgggcgctccgatgccgctccagggcgagcgctgttta aatagccaggcccccgattgcaaagacattatagcgagctaccaaagccatattcaaacacctagatcactaccacttctacacag gccactcgagcttgtgatcgcactccgctaagggggcgcctcttcctcttcgtttcagtcacaacccgcaaaggcgcgccATGctg
```

TABLE 18-continued

Nucleotide sequence of transforming DNA contained in pSZ2533.

ctgcaggccttcctgttcctgctggccggcttcgccgccaagatcagcgcctccatgacgaacgagacgtccgaccgcccctgg
tgcacttcaccccaacaagggctggatgaacgaccccaacggcctgtggtacgacgagaaggacgccaagtggcacctgta
cttccagtacaacccgaacgacaccgtctggggacgcccttgttctggggccacgccacgtccgacgacctgaccaactggg
aggaccagccatcgccatcgccccgaagcgcaacgactccggcgccttctccggctccatggtggtggactacaacaacacct
ccggcttcttcaacgacaccatcgacccgcgccagcgctgcgtggccatctggacctacaacaccccggagtccgaggagcag
tacatctcctacagcctggacggcggctacaccttcaccgagtaccagaagaaccccgtgctggccgccaactccacccagttcc
gcgacccgaaggtcttctggtacgagccctcccagaagtggatcatgaccgcggccaagtcccaggactacaagatcgagat
ctactcctccgacgacctgaagtcctggaagctggagtccgcgttcgccaacgagggcttcctcggctaccagtacgagtgccc
cggcctgatcgaggtccccaccgagcaggaccccagcaagtcctactgggtgatgttcatctccatcaacccgcgcgccccggc
cggcggctccttcaaccagtacttcgtcggcagcttcaacggcaccacttcgaggccttcgacaaccagtcccgcgtggtggac
ttcggcaaggactactacgccctgcagaccttcttcaacaccgaccgacctacggggagcgccctgggcatcgcgtgggcctcc
aactgggagtactccgccttcgtgcccaccaacccctggcgctcctccatgtccctcgtgcgcaagttctccctcaacaccgagta
ccaggccaacccggagacggagctgatcaacctgaaggccgagccgatcctgaacatcagcaacgccggcccctggagccg
gttcgccaccaacaccacgttgacgaaggccaacagctacaacgtcgacctgtccaacagcaccggcacccctggagttcgagc
tggtgtacgccgtcaacaccacccagacgatctccaagtccgtgttcgcggacctctccctctggttcaaggcctggaggaccc
cgaggagtacctccgcatgggcttcgaggtgtccgcgtcctccttcttcctggaccgcgggaacagcaaggtgaagttcgtgaa
ggagaacccctacttcaccaaccgcatgagcgtgaacaaccagcccttcaagagcgagaacgacctgtcctactacaaggtgt
acggcttgctggaccagaacatcctggagctgtacttcaacgacggcgacgtcgtgtccaccaacacctacttcatgaccaccg
ggaacgcccctgggctccgtgaacatgacgacgggggtggacaacctgttctacatcgacaagttccaggtgcgcgaggtcaa g*TGA*caattggcagcagcagctcggatagtatcgacacactctggacgctggtcgtgtgatggactgttgccgccacacttgctgc cttgacctgtgaatatccctgccgcttttatcaaacagcctcagtgtgtttgatcttgtgtgtacgcgcttttgcgagttgctagctgcttg
tgctatttgcgaataccaccccagcatccccttccctcgtttcatatcgcttgcatcccaaccgcaacttatctacgctgtcctgctatc
cctcagcgctgctcctgctcctgctcactgccccctcgcacagccttggttttgggctccgcctgtattctcctggtactgcaacctgtaaa
ccagcactgcaatgctgatgcacgggaagtagtgggatgggaacacaaatggaggatcccgcgtctcgaacagagcgcgcagagg
aacgctgaaggtctcgcctctgtcgcacctcagcgcggcatacaccacaataaccacctgacgaatgcgcttggttcttcgtccatta
gcgaagcgtccggttcacacacgtgccacgttggcgaggtggcaggtgacaatgatcggtggagctgatggtcgaaacgttcacag cctagggatatcatagcgactgctaccccccgaccatgtgccgaggcagaaattatatacaagaagcagatcgcaattaggca
catcgctttgcattatccacacactattcatcgctgctgcggcaaggctgcagagtgtattttgtggcccaggagctgagtccga
agtcgacgcgacgagcggcgcaggatccgacccctagacgagctctgtcattttccaagcacgcagctaaatgcgctgagac
cgggtctaaatcatccgaaaagtgtcaaaatggccgattgggttcgcctaggacaatgcgctgcggattcgctcgagtccgct
gccggccaaaaggcggtggtacaggaaggcgcacggggccaaccctgcgaagccgggggcccgaacgccgaccgccggc
cttcgatctcgggtgtcccctcgtcaatttcctctctcgggtgcagccacgaaagtcgtgacgcaggtcacgaaatccggttac
gaaaaacgcaggtcttcgcaaaaacgtgagggtttcgcgtctcgccctagctattcgtatcgcgggtcagaccacgtgcag
aaaagcccttgaataacccgggaccgtggttaccgcgccgcctgcaccaggggggcttatataagcccacaccacacctgtctc
accacgcatttctccaactcgcgacttttcggaagaaattgttatccacctagtatagactgccacctgcaggaccttgtgtcttg
cagtttgtattggtcccggccgtcgagctcgacagatctgggctagggttggcctggccgctcggcactcccctttagccgcgcg
catccgcgttccagaggtgcgattcggtgtgtggagcattgtcatgcgcttgtggggtcgttccgtgcgcggcgggtccgccat
gggcgccgacctgggccctagggtttgttttcgggcaagcgagcccctctcacctcgtcgcccccgcattccctctctcttgca
gccttgcc*actagt*ATGgccaccgatccactttctcggcgttcaatgcccgctgcggcgacctgcgtcgctcggcgggctccg
ggccccggcgccagcgaggcccctcccgtgcgcgg*gcgcc*gccgccgccgccgacgccaaccccgcccgccccgagcg
ccgcgtggtgatcaccggccagggcgtggtgacctccctgggccagaccatcgagcagttctactcctccctgctggagggcg
tgtccgcatctcccagatccagaagttcgacaccaccggctacaccaccaccatcgccggcgagatcaagtccctgcagctg
gaccccacgtgcccaagcgctgggccaagcgcgtggacgacgtgatcaagtacgtgtacatcgccggcaagcaggccctg
gagtccgccggcctgcccatcgaggccgccgccctggccggcgccgcctggaccccgccctgtgcggcgtgctgatcggca
ccgccatggccggcatgacctccttcgccgccgcgcgtggaggccctgacccgcggcggcgtgcgcaagatgaacccttctgc
atcccttctccatctccaacatgggcggcgccatgctggccatggacatcggcttcatgggccccaactactcctctccaccg
cctgcgccaccggcaactactgcatcctgggcgccgccgaccacatccgccgcggcgacgccaacgtgatgctggccggcgg
cgccgacgccgccatcatccctccggcatcggcggcttcatcgcctgcaaggccctgtccaagcgcaacgacgagcccgagc
gcgcctcccgccctgggacgccgaccgcgacggcttcgtgatgggcgagggcgccggcgtgctggtgctggaggagctgg
agcacgccaagcgccgcggcgccaccatcctggccgagctggtgggcggcgccgccacctccgacgcccaccacatgaccg
agcccgaccccaagggccgcggcgtgcgcctgtgcctggagcgcgccctggagcgcgcccgcctggcccccgagcgcgtgg TABLE 18-continued Nucleotide sequence of transforming DNA contained in pSZ2533.

gctacgtgaacgcccacggcacctccaccccgcggcgacgtggccgagtaccgcgccatccgcgccgtgatcccccagga
ctccctgcgcatcaactccaccaagtccatgatcggccacctgctgggcggcgccggcgccgtggaggccgtggccgccatcc
aggccctcgcaccggctggctgcaccccaacctgaacctggagaacccgcccccggcgtggacccccgtggtgctggtggg
cccccgcaaggagcgcgccgaggacctggacgtggtgctgtccaactccttcggcttcggcggccacaactcctgcgtgatct
tccgcaagtacgacgagatggactacaaggaccacgacggcgactacaaggaccacgacatcgactacaaggacgacga
cgacaag*TGA*atcgatagatctcttaaggcagcagcagctcggatagtatcgacacactctggacgctggtcgtgtgatggactg ttgccgccacacttgctgccttgacctgtgaatatccctgccgcttttatcaaacagcctcagtgtgtttgatcttgtgtgtacgcgctttt
gcgagttgctagctgcttgtgctatttgcgaataccaccccagcatccccttccctcgtttcatatcgcttgcatcccaaccgcaactt
atctacgctgtcctgctatccctcagcgctgctcctgctcctgctcactgccccctcgcacaagccttggttttgggctccgcctgtattctcct
ggtactgcaacctgtaaaccagcactgcaatgctgatgcacgggaagtagtgggatgggaacacaaatggaaagcttaattaa*ga
gctc*ttgttttccagaaggagttgctccttgagcctttcattctcagcctcgataacctccaaagccgctctaattgtggaggggggttc
gaaccgaatgctgcgtgaacgggaaggaggaggagaaagagtgagcagggagggattcagaaatgagaaatgagaggtgaa
ggaacgcatccctatgcccttgcaatggacagtgtttctggccaccgccaccaagacttcgtgtcctctgatcatcatgcgattgatt
acgttgaatgcgacggccggtcagccccggacctccacgcaccggtgctcctccaggaagatgcgcttgtcctccgccatcttgcag
ggctcaagctgctcccaaaactcttgggcgggttccggacggacggctaccgcgggtgcggccctgaccgccactgttcggaagca
gcggcgctgcatgggcagcggccgctgcggtgcgccacggaccgcatgatccaccggaaaagcgcacgcgctggagcgcgcaga
ggaccacagagaagcggaagagacgccagtactggcaagcaggctggtcggtgccatggcgcgctactaccctcgctatgactc
gggtcctcggccggctggcggtgctgacaattcgtttagtggagcagcgactccattcagctaccagtcgaactcagtggcacagt
gactccgctcttc
(SEQ ID NO: 60)

In addition to the construct pSZ2533, PmKASII activity was investigated when the KASII gene driven by other promoters, including PmLDH1, and PmAMT3. The plasmid pSZ2532 can be written as FATA1 3'::CrTUB2:ScSUC2: CvNR::PmLDH1:PmKASII-CvNR::FATA1 5', while the plasmid pSZ2750 can be written as FATA1 3'::CrTUB2: ScSUC2: CvNR::PmAMT3:PmKASII-CvNR::FATA1 5'. Since the sequences of these two plasmids are same as pSZ2533 except for the promoter that drives the PmKASII, Table 19 and 20 only show the sequence of PmLDH1 and PmAMT3 promoters

TABLE 19

Nucleotide sequence of PmLDH1 promoter that drives the expression of PmKASII in pSZ2532.

gatatctccctccgtctctgcactctggcgcccctcctccgtctcgtggactgacggacgagagtctgggcgccgcttttctatcca
caccgccctttccgcatcgaagacaccacccatcgtgccgccaggtcttccccaatcacccgccctgtggtcctctctcccagccgt
gtttggtcgctgcgtccacattttttccattcgtgccccacgatcctcgcccatcttggcgccttggataggcacccttttttcagcac
gccctggtgtgtagcacaacctgacctctctctaccgcatcgcctccctcccacacctcagttgactccctcgtcgcacgttgcacc
cgcaagctccccattcatcctattgacaatcgcacactgtacatgtatgctcattattttgcaaaaaaacaggggtcggttcac
tcctggcagacgacgcggtgctgccgcgcgccgctgaggcggcgtcgcgacggcaacacccatcgcaccgcacgtcgacgag
tcaacccacccgtgctcaacggtgatctccccatcgcgacaccccccgtgaccgtactatgtgcgtccatacgcaacatgaaaag
gaccttggtccccggaggcggcgagctcgtaatcccgaggttggccccgcttccgctggacacccatcgcatcttccggctcgcc
cgctgtcgagcaagcgccctcgtgcgcgcaaccccttgtggtcctgcccgcagagccgggcataaaggcgagcaccacaccc
gaaccagtccaatttgctttctgcattcactcaccaacttttacatccacacatcgtactaccacacctgcccagtcgggtttgattt
ctattgcaaaggtgcggggggttggcgcactgcgtgggttgtgcagccggccgccgcggctgtacccagcgatcaggtagct
tgggctgtatcttctcaagcattaccttgtcctgggcgtaggtttgccactagt

(SEQ ID NO: 61)

TABLE 20

Nucleotide sequence of PmAMT3 promoter that drives the
expression of PmKASII in pSZ2750.

gatatcgaattcggccgacaggacgcgcgtcaaaggtgctggtcgtgtatgccctggccggcaggtcgttgctgctgctggttagtg
attccgcaaccctgattttggcgtcttattttggcgtggcaaacgctggcgcccgcgagccgggccggcggcgatgcggtgccccac
ggctgccggaatccaagggaggcaagagcgcccgggtcagttgaagggctttacgcgcaaggtacagccgctcctgcaaggctgc
gtggtggaattggacgtgcaggtcctgctgaagttcctccaccgcctcaccagcggacaaagcaccggtgtatcaggtccgtgtcat
ccactctaaagaactcgactacgacctactgatggccctagattcttcatcaaaaacgcctgagacacttgcccaggattgaaactc
cctgaagggaccaccagggggccctgagttgttccttccccccgtggcgagctgccagccaggctgtacctgtgatcgaggctggcgg
gaaaataggcttcgtgtgctcaggtcatgggaggtgcaggacagctcatgaaacgccaacaatcgcacaattcatgtcaagctaat
cagctatttcctcttcacgagctgtaattgtcccaaaattctggtctaccgggggtgatccttcgtgtacgggcccttccctcaaccct a
ggtatgcgcgcatgcggtcgccgcgcaactcgcgcgagggccgagggtttgggacgggccgtcccgaaatgcagttgcacccggat
gcgtggcacctttttgcgataatttatgcaatggactgctctgcaaaattctggctctgtcgccaaccctaggatcagcggcgtagga
tttcgtaatcattcgtcctgatggggagctaccgactaccctaatatcagcccgactgcctgacgccagcgtccacttttgtgcacaca
ttccattcgtgcccaagacatttcattgtggtgcgaagcgtccccagttacgctcacctgtttcccgacctccttactgttctgtcgaca
gagcgggcccacaggccggtcgcagccactagt

(SEQ ID NO: 62)

Results

Primary transformants were clonally purified and grown under standard lipid production conditions at either pH5.0 or pH7.0, depending on the promoters that drove the expression of the PmKASII gene (AMT3 is pH sensitive and inhibited at pH 5). Transgenic lines arising from the transformantions with pSZ2533 (D1636*) and pSZ2532 (D1637*) were assayed in lipid production media at pH5.0, because of the nature of the promoters and the fact that *P. moriformis* produces more lipid at pH5.0. Transgenic lines generated from the transformation of pSZ2750 (D1684*) were assayed at pH 7.0 to allow for maximal PmKASII gene expression when driven by the pH regulated PmAMT3 promoter. The resulting profiles from representative clones arising from transformations with D1636 (pSZ2533), D1637 (pSZ2532), and D1684 (pSZ2750) are shown in Table 21, 21, and 23, respectively.

The impact of FATA1 knock-out and simultaneously overexpression of the *P. moriformis* KASII gene is a clear diminution of C16:0 chain lengths with a significant increase in C18:1. At pH5.0, it appears that PmUAPA1 is stronger than PmLDH1, as the palmitate level in D1636 transformants is close to 3%, while none of the transformants in D1637 go below 7% at the same condition. Oleic acid (18:1) is elevated (e.g., above 70 or 75%) compared to the wild-type strain (e.g., about 54%).

TABLE 21

Lipid profile of representative clones arising
from transformation with D1636 (pSZ2533) DNA.

| Sample ID | C14:0 | C16:0 | C18:0 | C18:1 | C18:2 |
|---|---|---|---|---|---|
| pH 5; S5100; T523; D1636-3 | 0.53 | 3.31 | 6.15 | 79.89 | 7.19 |
| pH 5; S5100; T523; D1636-4 | 0.48 | 3.54 | 5.34 | 80.78 | 6.92 |
| pH 5; S5100; T523; D1636-5 | 0.48 | 3.59 | 5.41 | 81.37 | 6.55 |
| pH 5; S5100; T523; D1636-12 | 0.61 | 3.59 | 3.67 | 80.52 | 8.93 |
| pH 5; S5100; T523; D1636-13 | 0.55 | 3.80 | 4.88 | 81.83 | 6.61 |
| pH 5; S5100; T523; D1636-21 | 0.54 | 4.18 | 2.82 | 82.26 | 8.17 |
| pH 5; S5100 | 0.89 | 17.28 | 2.69 | 70.53 | 6.86 |

TABLE 22

Lipid profile of representative clones arising
from transformation with D1637 (pSZ2532) DNA.

| Sample ID | C14:0 | C16:0 | C18:0 | C18:1 | C18:2 |
|---|---|---|---|---|---|
| pH 5; S5100; T523; D1637-6 | 0.46 | 7.64 | 3.43 | 80.08 | 6.33 |
| pH 5; S5100; T523; D1637-12 | 0.66 | 8.49 | 1.90 | 77.06 | 9.59 |
| pH 5; S5100; T523; D1637-13 | 0.47 | 8.59 | 3.18 | 79.39 | 6.54 |
| pH 5; S5100; T523; D1637-15 | 0.60 | 9.60 | 2.51 | 76.41 | 8.85 |
| pH 5; S5100; T523; D1637-7 | 0.61 | 11.16 | 2.21 | 75.82 | 8.04 |
| pH 5; S5100; T523; D1637-8 | 0.93 | 11.29 | 3.61 | 74.84 | 6.61 |
| pH 5; S5100 | 0.89 | 17.28 | 2.69 | 70.53 | 6.86 |

TABLE 23

Lipid profile of representative clones arising from transformation with D1684 (pSZ2750) DNA.

| Sample ID | C14:0 | C16:0 | C18:0 | C18:1 | C18:2 |
|---|---|---|---|---|---|
| pH 7; S5100; T532; D1684-14 | 0.55 | 5.04 | 4.90 | 78.88 | 8.19 |
| pH 7; S5100; T532; D1684-23 | 0.58 | 5.80 | 4.98 | 77.51 | 8.69 |
| pH 7; S5100; T532; D1684-1 | 0.59 | 6.37 | 4.99 | 77.47 | 8.03 |
| pH 7; S5100; T532; D1684-24 | 0.55 | 6.37 | 4.83 | 77.98 | 7.73 |
| pH 7; S5100; T532; D1684-11 | 0.61 | 6.61 | 4.88 | 76.14 | 8.96 |
| pH 7; S5100; T532; D1684-16 | 0.57 | 6.61 | 5.01 | 77.74 | 7.83 |
| pH 7; S5100 | 0.84 | 20.12 | 3.52 | 66.86 | 6.77 |

Example 16: Down-Regulating/Knocking Out THI4a and Over Expressing CpalFATB1 or CpalFATB2 in Prototheca moriformis Constructs that disrupt a single copy of the THI4a allele while simultaneously overexpressing the *Cuphea palustris* FATB1 or FATB2 gene were introduced into *Prototheca moriformis*.

For plasmids pSZ4440 and pSZ4442, *Saccharomyces cerevisiae* invertase gene (Accession no: NP 012104) was utilized as the selectable marker to introduce CpalFATB2 into the THI4a locus of *P. moriformis* by homologous recombination using biolistic transformation methods. The constructs that have been expressed in Strain S5100 can be written as:

(pSZ4440): THI4a5'::CrTUB2_ScSUC2_PmPGH::AMT1-1p_CpSAD1tp-CpalFATB2_ExtB_Flag_PmEF1::THI4a3'

(pSZ4442): THI4a5'::CrTUB2_ScSUC2_PmPGH::PmSAD2-2ver2_CpSAD1tp-CpalFATB2_ExtB_Flag_PmAHCY::THI4a3'

(pSZ4424): THI4a::CrTUB2-NeoR-PmPGH:PmSAD2-2Ver3-CpSAD1tp_CpalFATB1ExtC_M230G_FLAG-CvNR::THI4a Proceeding in the 5' to 3' direction for pSZ4440 and pSZ4442, the THI4a5'-region for targeting precedes a selection expression cassette comprising the *C. reinhardtii* β-tubulin promoter driving the expression of the yeast sucrose invertase gene followed by the *Prototheca moriformis* PGH 3'-UTR. The AMT1-1p (pSZ4440) or PmSAD2-2ver2 (pSZ4442) promoters drive the expression of a *Chlorella protothecoides* S106 stearoyl-ACP desaturase transit peptide fused to *Cuphea palustris* CpalFATB2_ExtB. A Flag-tag precedes either the *Prototheca moriformis* EF1 or the *Prototheca moriformis* AHCY 3' UTR and the THI4a3'-region for targeting.

Proceeding in the 5' to 3' direction for pSZ4424, the THI4a5'-region for targeting precedes a selection expression cassette comprising the *C. reinhardtii* β-tubulin promoter driving the expression of the neomycin resistance gene followed by the *Prototheca moriformis* PGH 3'-UTR. The PmSAD2-2ver3 promoter drives the expression of a *Chlorella protothecoides* S106 stearoyl-ACP desaturase transit peptide fused to *Cuphea palustris* CpalFATB_ExtC with a Met to Gly substitution at position 230. A Flag-tag precedes the CvNR 3' UTR and the THI4a3'-region for targeting.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

SEQ ID NO: 1
CAACCACGTCTTCAAAGCAA

SEQ ID NO: 2
TCCGGTGTGTTGTAAGTCCA

SEQ ID NO: 3
TTGTCGGAATGTCATATCAA

SEQ ID NO: 4
AACGCCTTTGTACAACTGCA

SEQ ID NO: 5
CTGACCCGACCTATGGGAGCGCTCTTGGC

SEQ ID NO: 6
CTTGACTTCCCTCACCTGGAATTTGTCG

SEQ ID NO: 7
GTGGCCATATGGACTTACAA

SEQ ID NO: 8
CAAGGGCTGGATGAATGACCCCAATGGACTGTGGTACGACG

SEQ ID NO: 9
CACCCGTCGTCATGTTCACGGAGCCCAGTGCG

SEQ ID NO: 10
S. cerevisiae sucrose invertase NP_012104
GAATTCCCCAACATGGTGGAGCACGACACTCTCGTCTACTCCAAGAATATCAAAGATACAGTCTCAGAA
GACCAAAGGGCTATTGAGACTTTTCAACAAAGGGTAATATCGGGAAACCTCCTCGGATTCCATTGCCCA
GCTATCTGTCACTTCATCAAAAGGACAGTAGAAAAGGAAGGTGGCACCTACAAATGCCATCATTGCGAT
AAAGGAAAGGCTATCGTTCAAGATGCCTCTGCCGACAGTGGTCCCAAAGATGGACCCCCACCCACGAGG

INFORMAL SEQUENCE LISTING

```
AGCATCGTGGAAAAAGAAGACGTTCCAACCACGTCTTCAAAGCAAGTGGATTGATGTGAACATGGTGGA
GCACGACACTCTCGTCTACTCCAAGAATATCAAAGATACAGTCTCAGAAGACCAAAGGGCTATTGAGAC
TTTTCAACAAAGGGTAATATCGGGAAACCTCCTCGGATTCCATTGCCTATCTGTCACTTCATCAA
AAGGACAGTAGAAAAGGAAGGTGGCACCTACAAATGCCATCATTGCGATAAAGGAAAGGCTATCGTTCA
AGATGCCTCTGCCGACAGTGGTCCCAAAGATGGACCCCCACCCACGAGGAGCATCGTGGAAAAAGAAGA
CGTTCCAACCACGTCTTCAAAGCAAGTGGATTGATGTGATATCTCCACTGACGTAAGGGATGACGCACA
ATCCCACTATCCTTCGCAAGACCCTTCCTCTATATAAGGAAGTTCATTTCATTTGGAGAGGACACGCTG
AAATCACCAGTCTCTCTCTACAAATCTATCTCTGGCGCGCCATATCAATGCTTCTTCAGGCCTTTCTTT
TTCTTCTTGCTGGTTTTGCTGCCAAGATCAGCGCCTCTATGACGAACGAAACCTCGGATAGACCACTTG
TGCACTTTACACCAAACAAGGGCTGGATGAATGACCCCAATGGACTGTGGTACGACGAAAAAGATGCCA
AGTGGCATCTGTACTTTCAATACAACCCGAACGATACTGTCTGGGGGACGCCATTGTTTTGGGGCCACG
CCACGTCCGACGACCTGACCAATTGGGAGGACCAACCAATAGCTATCGCTCCGAAGAGGAACGACTCCG
GAGCATTCTCGGGTTCCATGGTGGTTGACTACAACAATACTTCCGGCTTTTTCAACGATACCATTGACC
CGAGACAACGCTGCGTGGCCATATGGACTTACAACACACCGGAGTCCGAGGAGCAGTACATCTCGTATA
GCCTGGACGGTGGATACACTTTTACAGAGTATCAGAAGAACCCTGTGCTTGCTGCAAATTCGACTCAGT
TCCGAGATCCGAAGGTCTTTTGGTACGAGCCCTCGCAGAAGTGGATCATGACAGCGGCAAAGTCACAGG
ACTACAAGATCGAAATTTACTCGTCTGACGACCTAAATCCTGGAAGCTCGAATCCGCGTTCGCAAACG
AGGGCTTTCTCGGCTACCAATACGAATGCCCAGGCCTGATAGAGGTCCCAACAGAGCAAGATCCCAGCA
AGTCCTACTGGGTGATGTTTATTTCCATTAATCCAGGAGCACCGGCAGGAGGTTCTTTTAATCAGTACT
TCGTCGGAAGCTTTAACGGAACTCATTTCGAGGCATTTGATAACCAATCAAGAGTAGTTGATTTTGGAA
AGGACTACTATGCCCTGCAGACTTTCTTCAATACTGACCCGACCTATGGGAGCGCTCTTGGCATTGCGT
GGGCTTCTAACTGGGAGTATTCCGCATTCGTTCCTACAAACCCTTGGAGGTCCTCCATGTCGCTCGTGA
GGAAATTCTCTCTCAACACTGAGTACCAGGCCAACCCGGAAACCGAACTCATAAACCTGAAAGCCGAAC
CGATCCTGAACATTAGCAACGCTGGCCCCTGGAGCCGGTTTGCAACCAACACCACGTTGACGAAAGCCA
ACAGCTACAACGTCGATCTTTCGAATAGCACCGGTACACTTGAATTTGAACTGGTGTATGCCGTCAATA
CCACCCAAACGATCTCGAAGTCGGTGTTCGCGGACCTCTCCCTCTGGTTTAAAGGCCTGGAAGACCCCG
AGGAGTACCTCAGAATGGGTTTCGAGGTTTCTGCGTCCTCCTTCTTCCTTGATCGCGGGAACAGCAAAG
TAAAATTTGTTAAGGAGAACCCATATTTTACCAACAGGATGAGCGTTAACAACCAACCATTCAAGAGCG
AAAACGACCTGTCGTACTACAAAGTGTATGGTTTGCTTGATCAAAATATCCTGGAACTCTACTTCAACG
ATGGTGATGTCGTGTCCACCAACACATACTTCATGACAACCGGGAACGCACTGGGCTCCGTGAACATGA
CGACGGGTGTGGATAACCTGTTCTACATCGACAAATTCCAGGTGAGGGAAGTCAAGTGAGATCTGTCGA
TCGACAAGCTCGAGTTTCTCCATAATAATGTGTGAGTAGTTCCCAGATAAGGGAATTAGGGTTCCTATA
GGGTTTCGCTCATGTGTTGAGCATATAAGAAACCCTTAGTATGTATTTGTATTTGTAAAATACTTCTAT
CAATAAAATTTCTAATTCCTAAAACCAAAATCCAGTACTAAAATCCAGATCCCCCGAATTAA

SEQ ID NO: 11
KE858 Homologous recombination construct SZ725
GCCCTTTGTCATCGTTGGCATGCTTTTTGCGTATGTACCATATGTTGAATGTATAATACGAACGGTTGA
CCGTCTGAGATGCGAGCTTTGGGTCTTGTCAAATGCGTGGCCGCACGGCTCCCTCGCACCCAGCCCCGA
GGCGTCGCGCACCTGGCGAGGAGCAGACCCACGCCAAGAAAGTCTAGTCCAGCATGTAACAACATCAGG
CAATGTGACGTTTTCGGTTCCCGATTTCTCTGCCGCTCTTTGACGGCAGGCACGGGCGAGCAACCGGCG
GCGCTCGCGTCAGGCACGATGGATGCGGCGCTGCCCACCTGTCAATGTACCCCACCAGTCTGTCGATCG
CTACAAGCAACCTTGTGCTCCACATTCCCACTTGCAGACAGTCTAGTCGATTTTGCCAAGCTGGATGTG
AGGATTGGCCATATCTTGGAGGCCAAGATTCACCCGGATGCTGATGGGTACGTACGCGAGCCAGGCAGG
CAGCTGCGTTGACTTTCTGATTGGCACAAAGCTTTGGCTACTCTCAATACCAACCACGTGCCCCTTCTG
CACACCTGCTTCCTTCTGATGACCACTCGCCACGCATGTCGCAGTCTGTACGTCGAGCAGATCGACCTC
GGCGAGGAGGGGGGCCCTCGCACCATCGTGAGTGGCCTGGTCCGGCACGTGACCCTGGAGGACCTTGTC
GGCCGGCGGGTGGTGGTGCTGGCCAACCTCAAGCCTCGGAGCATGCGCGGGGTCAAATCGGCTGGGATG
CTGCTCTGCGCCGCCAACGCGGATCACACCGCGGTGGAGCCGCTGCGGGTCCCGACGCCGCCGTGACG
GGGGAGCGGGTCTGGGCGGGGACGAGGCACTCCTGTCCACGGAGCCTGCCACACCCAATCAGGTAAGG
ACACGTTATTGGTGCGCATGGTGCGAATGCGTGGTCTGACCTGCTGTGGGTATGTGTTGTGGGATTGGA
AACCGAATGAGGGCCGTTCAGGATTGAGCCCTTGGCCCCACCCTGCTCATCCTCTCACGCCCGCAGGTC
CAGAAGAAGAAAATCTGGGAGGCAGTACAGCCGCTGCTGAGGAACGCCCAGGGGATCGCTACTGTG
GCAGGAGAGGCTATGGTGACCAGTGCGGGGCCACTGACCGCGCCCACGCTGGTTGACGCCGCGATTTCC
TGACGCGAGCGACTGATTCTTGACCTTTGAGAAGCCACCACAGCACCATTTTCATTGTTCATCCTTGAT
TTCAGTACGACTTCTCACCATTTCAGTACTGTAGGACCCCCAAAATAGTGTGATCACGCTCGCAAGGCA
CCTGTGTGATCACGGGGAAGGGCGAATTCCTTTCTTGCGCTATGACATTTCCAGCAAAAGGTAGGGCGG
GCTGCGAGACGGCTTCCCGGCGCTGCATGCAACACCGATGATGCTTCGACCCCCGAAGCTCCTTCGGG
GCTGCATGGCGCTCCGATGCCGCTCCAGGGCGAGCGCTGTTTAAATAGCCAGGCCCCCGATTGCAAAG
ACATTATAGCGAGCTACCAAAGCCATATTCAAACACCTAGATCACTACCACTTCTACACAGGCCACTCG
AGCTTGTGATCGCACTCCGCTAAGGGGGCGCCTCTTCCTCTTCGTTTCAGTCACAACCCGCAAACGGCG
CGCCATGCTGCTGCAGGCCTTCCTGTTCCTGCTGGCCGGCTTCGCCGCCAAGATCAGCGCCTCCATGAC
GAACGAGACGTCCGACCGCCCCTGGTGCACTTCACCCCAACAAGGGCTGGATGAACGACCCCAACGG
CCTGTGGTACGACGAGAAGGACGCCAAGTGGCACCTGTACTTCCAGTACAACCCGAACGACACCGTCTG
GGGGACGCCCTTGTTCTGGGGCCACGCCACGTCCGACGACCTGACCAACTGGGAGGACCAGCCCATCGC
CATCGCCCCGAAGCGCAACGACTCCGGCGCCTTCTCCGGCTCCATGGTGGTGGACTACAACAACACCTC
CGGCTTCTTCAACGACACCATCGACCCGCGCCAGCGCTGCGTGGCCATCTGGACCTACAACACCCCGGA
GTCCGAGGAGCAGTACATCTCCTACAGCCTGGACGGCGGCTACACCTTCACCGAGTACCAGAAGAACCC
CGTGCTGGCCGCCAACTCCACCCAGTTCCGCGACCCGAAGGTCTTCTGGTACGAGCCCTCCCAGAAGTG
GATCATGACCGCGGCCAAGTCCCAGGACTACAAGATCGAGATCTACTCCTCCGACGACCTGAAGTCCTG
GAAGCTGGAGTCCGCGTTCGCCAACGAGGGCTTCCTCGGCTACCAGTACGAGTGCCCCGGCCTGATCGA
GGTCCCCACCGAGCAGGACCCCAGCAAGTCCTACTGGGTGATGTTCATCTCCATCAACCCCGGCGCCCC
GGCCGGCGGCTCCTTCAACCAGTACTTCGTCGGCAGCTTCAACGGCACCCACTTCGAGGCCTTCGACAA
CCAGTCCCGCGTGGTGGACTTCGGCAAGGACTACTACGCCCTGCAGACCTTCTTCAACACCGACCCGAC
CTACGGGAGCGCCCTGGGCATCGCGTGGGCCTCCAACTGGGAGTACTCCGCCTTCGTGCCCACCAACCC
CTGGCGCTCCTCCATGTCCCTCGTGCGCAAGTTCTCCCTCAACACCGAGTACCAGGCCAACCCGGAGAC
GGAGCTGATCAACCTGAAGGCCGAGCCGATCCTGAACATCAGCAACGCCGGCCCCTGGAGCCGGTTCGC
```

INFORMAL SEQUENCE LISTING

```
CACCAACACCACGTTGACGAAGGCCAACAGCTACAACGTCGACCTGTCCAACAGCACCGGCACCCTGGA
GTTCGAGCTGGTGTACGCCGTCAACACCACCCAGACGATCTCCAAGTCCGTGTTCGCGGACCTCTCCCT
CTGGTTCAAGGGCCTGGAGGACCCCGAGGAGTACCTCCGCATGGGCTTCGAGGTGTCCGCGTCCTCCTT
CTTCCTGGACCGCGGGAACAGCAAGGTGAAGTTCGTGAAGGAGAACCCCTACTTCACCAACCGCATGAG
CGTGAACAACCAGCCCTTCAAGAGCGAGAACGACCTGTCCTACTACAAGGTGTACGGCTTGCTGGACCA
GAACATCCTGGAGCTGTACTTCAACGACGGCGACGTCGTGTCCACCAACACCTACTTCATGACCACCGG
GAACGCCCTGGGCTCCGTGAACATGACGACGGGGGTGGACAACCTGTTCTACATCGACAAGTTCCAGGT
GCGCGAGGTCAAGTGATTAATTAACTCGAGGCAGCAGCAGCTCGGATAGTATCGACACACTCTGGACGC
TGGTCGTGTGATGGACTGTTGCCGCCACACTTGCTGCCTTGACCTGTGAATATCCCTGCCGCTTTTATC
AAACAGCCTCAGTGTGTTTGATCTTGTGTGTACGCGCTTTTGCGAGTTGCTAGCTGCTTGTGCTATTTG
CGAATACCACCCCCAGCATCCCCTTCCCTCGTTTCATATCGCTTGCATCCCAACCGCAACTTATCTACG
CTGTCCTGCTATCCCTCAGCGCTGCTCCTGCTCCTGCTCACTGCCCCTCGCACAGCCTTGGTTTGGGCT
CCGCCTGTATTCTCCTGGTACTGCAACCTGTAAACCAGCACTGCAATGCTGATGCACGGGAAGTAGTGG
GATGGGAACACAAATGGAAAGCTT

SEQ ID NO: 12
Homologous recombination construct SZ726
CCCGTGATCACACAGGTGCCTTGCGAGCGTGATCACACTATTTTGGGGGTCCTACAGTACTGAAATGGT
GAGAAGTCGTACTGAAATCAAGGATGAACAATGAAAATGGTGCTGTGGTGGCTTCTCAAAGGTCAAGAA
TCAGTCGCTCGCGTCAGGAAATCGCGGCGTCAACCAGCGTGGGCGCGGTCAGTGGCCCCGCACTGGTCA
CCATAGCCTCTCCTGCCACAGTAGCGATCCCTGGGCGTTCACTCTCAGCAGCGGCTGTACTGCCTCCC
AGATTTTCTTCTTCTGGACCTGCGGGCGTGAGAGGATGAGCAGGGTGGGGCCAAGGGCTCAATCCTGAA
CGGCCCTCATTCGGTTTCCAATCCCACAACACATACCCACAGCAGGTCAGACCACGCATTCGCACCATG
CGCACCAAATAACGTGTCCTTACCTGATTGGGTGTGGCAGGCTCCGTGGACAGGAGTGCCTCGTCCCCC
GCCCAGACCCGCTCCCCCGTCACGGCGGCGTCCGGGACCCGCAGCGGCTCCACCGCGGTGTGATCCGCG
TTGGCGGCGCAGAGCAGCATCCCAGCCGATTTGACCCCGCGCATGCTCCGAGGCTTGAGGTTGGCCAGC
ACCACCACCCGCCGGCCGACAAGGTCCTCCAGGGTCACGTGCCGGACCAGGCCACTCACGATGGTGCGA
GGGCCCCCCTCCTCGCCGAGGTCGATCTGCTCGACGTACAGACTGCGACATGCGTGGCGAGTGGTCATC
AGAAGGAAGCAGGTGTGCAGAAGGGGCACGTGGTTGGTATTGAGAGTAGCCAAAGCTTTGTGCCAATCA
GAAAGTCAACGCAGCTGCCTGCCTGGCTCGCGTACAATTCCTTTCTTGCGCTATGACACTTCCAGCAAA
AGGTAGGGCGGGCTGCGAGACGGCTTCCCGGCGCTGCATGCAACACCGATGATGCTTCGACCCCCCGAA
GCTCCTTCGGGGCTGCATGGGCGCTCCGATGCCGCTCCAGGGCGAGCGCTGTTTAAATAGCCAGGCCCC
CGATTGCAAAGACATTATAGCGAGCTACCAAAGCCATATTCAAACACCTAGATCACTACCACTTCTACA
CAGGCCACTCGAGCTTGTGATCGCACTCCGCTAAGGGGGCGCCTCTTCCTCTTCGTTTCAGTCACAACC
CGCAAACGGCGCGCCATGCTGCTGCAGGCCTTCCTGTTCCTGCTGGCCGGCTTCGCCGCCAAGATCAGC
GCCTCCATGACGAACGAGACGTCCGACCGCCCCCTGGTGCACTTCACCCCCAACAAGGGCTGGATGAAC
GACCCCAACGGCCTGTGGTACGACGAGAAGGACGCCAAGTGGCACCTGTACTTCCAGTACAACCCGAAC
GACACCGTCTGGGGGACGCCCTTGTTCTGGGGCCACGCCACGTCCGACGACCTGACCAACTGGGAGGAC
CAGCCCATCGCCATCGCCCCGAAGCGCAACGACTCCGGCGCCTTCTCCGGCTCCATGGTGGTGGACTAC
AACAACACCTCCGGCTTCTTCAACGACACCATCGACCCGCGCCAGCGCTGCGTGGCCATCTGGACCTAC
AACACCCCGGAGTCCGAGGAGCAGTACATCTCCTACAGCCTGGACGGCGGCTACACCTTCACCGAGTAC
CAGAAGAACCCCGTGCTGGCCGCCAACTCCACCCAGTTCCGCGACCCGAAGGTCTTCTGGTACGAGCCC
TCCCAGAAGTGGATCATGACCGCGGCCAAGTCCCAGGACTACAAGATCGAGATCTACTCCTCCGACGAC
CTGAAGTCCTGGAAGCTGGAGTCCGCGTTCGCCAACGAGGGCTTCCTCGGCTACCAGTACGAGTGCCCC
GGCCTGATCGAGGTCCCCACCGAGCAGGACCCCAGCAAGTCCTACTGGGTGATGTTCATCTCCATCAAC
CCCGGCGCCCCGGCCGGCGGCTCCTTCAACCAGTACTTCGTCGGCAGCTTCAACGGCACCCACTTCGAG
GCCTTCGACAACCAGTCCCGCGTGGTGGACTTCGGCAAGGACTACTACGCCCTGCAGACCTTCTTCAAC
ACCGACCCGACCTACGGGAGCGCCCTGGGCATCGCGTGGGCCTCCAACTGGGAGTACTCCGCCTTCGTG
CCCACCAACCCCTGGCGCTCCTCCATGTCCCTCGTGCGCAAGTTCTCCCTCAACACCGAGTACCAGGCC
AACCCGGAGACGGAGCTGATCAACCTGAAGGCCGAGCCGATCCTGAACATCAGCAACGCCGGCCCCTGG
AGCCGGTTCGCCACCAACACCACGTTGACGAAGGCCAACAGCTACAACGTCGACCTGTCCAACAGCACC
GGCACCCTGGAGTTCGAGCTGGTGTACGCCGTCAACACCACCCAGACGATCTCCAAGTCCGTGTTCGCG
GACCTCTCCCTCTGGTTCAAGGGCCTGGAGGACCCCGAGGAGTACCTCCGCATGGGCTTCGAGGTGTCC
GCGTCCTCCTTCTTCCTGGACCGCGGGAACAGCAAGGTGAAGTTCGTGAAGGAGAACCCCTACTTCACC
AACCGCATGAGCGTGAACAACCAGCCCTTCAAGAGCGAGAACGACCTGTCCTACTACAAGGTGTACGGC
TTGCTGGACCAGAACATCCTGGAGCTGTACTTCAACGACGGCGACGTCGTGTCCACCAACACCTACTTC
ATGACCACCGGGAACGCCCTGGGCTCCGTGAACATGACGACGGGGGTGGACAACCTGTTCTACATCGAC
AAGTTCCAGGTGCGCGAGGTCAAGTGATTAATTAACTCGAGGCAGCAGCAGCTCGGATAGTATCGACAC
ACTCTGGACGCTGGTCGTGTGATGGACTGTTGCCGCCACACTTGCTGCCTTGACCTGTGAATATCCCTG
CCGCTTTTATCAAACAGCCTCAGTGTGTTTGATCTTGTGTGTACGCGCTTTTGCGAGTTGCTAGCTGCT
TGTGCTATTTGCGAATACCACCCCCAGCATCCCCTTCCCTCGTTTCATATCGCTTGCATCCCAACCGCA
ACTTATCTACGCTGTCCTGCTATCCCTCAGCGCTGCTCCTGCTCCTGCTCACTGCCCCTCGCACAGCCT
TGGTTTGGGCTCCGCCTGTATTCTCCTGGTACTGCAACCTGTAAACCAGCACTGCAATGCTGATGCACG
GGAAGTAGTGGGATGGGAACACAAATGGAAAGCTTGAGCTCGGTACCCGTACCCATCAGCATCCGGGTG
AATCTTGGCCTCCAAGATATGGCCAATCCTCACATCCAGCTTGGCAAAATCGACTAGACTGTCTGCAAG
TGGGAATGTGGAGCACAAGGTTGCTTGTAGCGATCGACAGACTGGTGGGGTACATTGACAGGTGGGCAG
CGCCGCATCCATCGTGCCTGACGCGAGCGCCGCCGGTTGCTCGCCCGTGCCTGCCGTCAAAGAGCGGCA
GAGAAATCGGGAACCGAAAACGTCACATTGCCTGATGTTGTTACATGCTGGACTAGACTTTCTTGGCGT
GGGTCTGCTCCTCGCCAGGTGCGCGACGCCTCGGGGCTGGGTGCGAGGGAGCCGTGCGGCCACGCATTT
GACAAGACCCAAAGCTCGCATCTCAGACGGTCAACCGTTCGTATTATACATTCAACATATGGTACATAC
GCAAAAAGCATG SEQ ID NO: 13
Homologous recombination: Targeting cassette for disruption of
Prototheca moriformis stearoyl ACP desaturase coding region (β-
tubulin driven suc2 cassette)
TTTGGCCCCGCTTTCCAGCTCCGGATCTGCTGGCGTCCGCCGCGAGACGTGACATCGCACGTCGCCGGG
```

| INFORMAL SEQUENCE LISTING |
|---|
| AGCGCCAGCTTGATCACTTGGCAGGGGGCCGTGCTCTACAAATACCAGGCCCCGCGGCGGTCAGTTCGC |
| ACATCCAATACCTGCCGAGCCATCTTGCCTACACTTTTTATCGACTCCTCTACTCTGTTCGCGAGAGCG |
| CTCGGTCCAGGCTTGGAATTCGCCGAATTCAGCTCGATCAGTCGCTTCTGCAACTGATCTCGGCCGTTC |
| GCAGACTGCCTTTTCTCAGCTTGTCAGGTAGCGAGTTGTTGTTTTATATTTATTCGATTTCATCTGTGT |
| TGCATGTCTTGTTCGTGCTGTGCGTTCTTTCTGGGCCGCGCTGTCGGGTCGCATGGGCTAGCTGTACTC |
| ATGTTAGTCATGCCGGTCCGACCTTGTTCGAGGAAGGCCCCACACTGAGCGTGCCCTCTTTCTACACCC |
| CTTGTGCAGAAATTAGATAGAAAGCAGAATTCCTTTCTTGCGCTATGACACTTCCAGCAAAAGGTAGGG |
| CGGGCTGCGAGACGGCTTCCCGGCGCTGCATGCAACACCGATGATGCTTCGACCCCCCGAAGCTCCTTC |
| GGGGCTGCATGGGCGCTCCGATGCCGCTCCAGGGCGAGCGCTGTTTAAATAGCCAGGCCCCCGATTGCA |
| AAGACATTATAGCGAGCTACCAAAGCCATATTCAAACACCTAGATCACTACCACTTCTACACAGGCCAC |
| TCGAGCTTGTGATCGCACTCCGCTAAGGGGGCGCCTCTTCCTCTTCGTTTCAGTCACAACCCGCAAACG |
| GCGCGCCATGCTGCTGCAGGCCTTCCTGTTCCTGCTGGCCGGCTTCGCCGCCAAGATCAGCGCCTCCAT |
| GACGAACGAGACGTCCGACCGCCCCTGGTGCACTTCACCCCCAACAAGGGCTGGATGAACGACCCCAA |
| CGGCCTGTGGTACGACGAGAAGGACGCCAAGTGGCACCTGTACTTCCAGTACAACCCGAACGACACCGT |
| CTGGGGGACGCCCTTGTTCTGGGGCCACGCCACGTCCGACGACCTGACCAACTGGAGGACCAGCCCAT |
| CGCCATCGCCCCGAAGCGCAACGACTCCGGCGCCTTCTCCGGCTCCATGGTGGTGGACTACAACAACAC |
| CTCCGGCTTCTTCAACGACACCATCGACCCGCGCCAGCGCTGCGTGGCCATCTGGACCTACAACACCCC |
| GGAGTCCGAGGAGCAGTACATCTCCTACAGCCTGGACGGCGGCTACACCTTCACCGAGTACCAGAAGAA |
| CCCCGTGCTGGCCGCCAACTCCACCCAGTTCCGCGACCCGAAGGTCTTCTGGTACGAGCCCTCCCAGAA |
| GTGGATCATGACCGCGGCCAAGTCCCAGGACTACAAGATCGAGATCTACCTCCTCCGACGACCTGAAGTC |
| CTGGAAGCTGGAGTCCGCGTTCGCCAACGAGGGCTTCCTCGGCTACCAGTACGAGTGCCCCGGCCTGAT |
| CGAGGTCCCCACCGAGCAGGACCCCAGCAAGTCCTACTGGGTGATGTTCATCTCCATCAACCCCGGCGC |
| CCCCGGCCGGCGGCTCCTTCAACCAGTACTTCGTCGGCAGCTTCAACGGCACCCACTTCGAGGCCTTCGA |
| CAACCAGTCCCGCGTGGTGGACTTCGGCAAGGACTACTACGCCCTGCAGACCTTCTTCAACCACCGACCC |
| GACCTACGGGAGCGCCCTGGGCATCGCGTGGGCCTCCAACTGGGAGTACTCCGCCTTCGTGCCCACCAA |
| CCCCTGGCGCTCCTCCATGTCCCTCGTGCGCAAGTTCTCCCTCAACACCGAGTACCAGGCCAACCCGGA |
| GACGGAGCTGATCAACCTGAAGGCCGAGCCGATCCTGAACATCAGCAACGCCGGCCCCTGGAGCCGGTT |
| CGCCACCAACACCACGTTGACGAAGGCCAACAGCTACAACGTCGACCTGTCCAACAGCACCGGCACCCT |
| GGAGTTCGAGCTGGTGTACGCCGTCAACACCACCCAGACGATCTCCAAGTCCGTGTTCGCGGACCTCTC |
| CCTCTGGTTCAAGGGCTGGAGGACCCCGAGGAGTACCTCCGCATGGGCTTCGAGGTGTCCGCGTCCTC |
| CTTCTTCCTGGACCGCGGGAACAGCAAGGTGAAGTTCGTGAAGGAGAACCCCTACTTCACCAACCGCAT |
| GAGCGTGAACAACCAGCCCTTCAAGAGCGAGAACGACCTGTCCTACTACAAGGTGTACGGCTTGCTGGA |
| CCAGAACATCCTGGAGCTGTACTTCAACGACGGCGACGTCGTGTCCACCAACACCTACTTCATGACCAC |
| CGGGAACGCCCTGGGCTCCGTGAACATGACGACGGGGTGGACAACCTGTTCTACATCGACAAGTTCCA |
| GGTGCGCGAGGTCAAGTGATTAATTAACTCGAGGCAGCAGCAGCTCGGATAGTATCGACACACTCTGGA |
| CGCTGGTCGTGTGATGGACTGTTGCCGCCACACTTGCTGCTTGACCTGTGAATATCCCTGCCGCTTTT |
| ATCAAACAGCCTCAGTGTGTTTGATCTTGTGTACGCGCTTTTGCGAGTTGCTAGCTGCTTGTGCTAT |
| TTGCGAATACCACCCCAGCATCCCCTTCCCTCGTTTCATATCGCTTGCATCCCAACCGCAACTTATCT |
| ACGCTGTCCTGCTATCCCTCAGCGCTGCTCCTGCTCCTGCTCACTGCCCCTCGCACAGCCTTGGTTTGG |
| GCTCCGCTGTATTCTCCTGGTACTGCAACCTGTAAACCAGCACTGCAATGCTGATGCACGGGAAGTAG |
| TGGGATGGGAACACAAATGGACCGACACGCCCCCGGCCCAGGTCCAGTTCTCCTGGGTCTTCCAGAGGC |
| CCGTCGCCATGTAAAGTGGCAGAGATTGGCGCCTGATTCGATTTGGATCCAAGGATCTCCAATCGGTGA |
| TGGGGACTGAGTGCCCAACTACCACCCTTGCACTATCGTCCTCGCACTATTTATTCCCACCTTCTGCTC |
| GCCCTGCCGGGCGATTGCGGGCGTTTCTGCCCTTGACGTATCAATTTCGCCCCTGCTGGCGCGAGGATT |
| CTTCATTCTAATAAGAACTCACTCCCGCCAGCTCTGTACTTTTCCTGCGGGGCCCCTGCATGGCTTGTT |
| CCCAATGCTTGCTCGATCGACGGCGCCCATTGCCCACGGCGCTGCCGCATCCATGTGAAGAACACGGA |
| AGAGTGCGAAGACTGGAAGTGAATTAAGAGTATAAGAAGAGGTACCAAGGGATTCTCAGGTGCTCTTAG |
| GAACGGCTTTTCCTTCGCCAAGAGAAACTGCTACTGCTCGTGTCGCCACGGTGGTCAAGCGCCCCATC |
| TGCGATCCACCAGGCCCATCCGCGGACTCGCGATCAGCCTGCTGGATCCGGACTGCCGACCTGACCGCT |
| CGCATCCACCATTACAACCCTCCAATTGGACACCACTCCCACGTCCTAAAGTTCACCATGCAAGCTGAT |
| CGATCGCATTCGCCGATGCACTCGCCTGCCACAGAGGTGTGCGCTTCGGACTAGCGTGCAGGCGCCCCG |
| AGGCCACCAGCATGCACCGATGGAAGCGGGCACGGCCGCTGCTCCAGGTCGCTGGCTCGCTCAGACCCA |
| TAGCAACCTCCGCTGCGTCCCTAAATGTCACACAGAGCGTCTTTGATGGGTACGGATGGGAGAGAATCT |
| GATTGGGCATTGCTGGTGCAGTGCAGGAAGATGGCAAGTGCACAGTCAGTCATGCTGTACAAACTGGTG |
| CCTCGTAGTATTGACTCGTATAGTGCATAGTATCATGCATGGTCGTTACTTGCAA |

SEQ ID NO: 14
Homologous recombination: Targeting cassette for disruption of
*Prototheca moriformis* stearoyl ACP desaturase coding region (suc2
cassette alone)
TTTGGCCCCGCTTTCCAGCTCCGGATCTGCTGGCGTCCGCCGCGAGACGTGACATCGCACGTCGCCGGG
AGCGCCAGCTTGATCACTTGGCAGGGGGCCGTGCTCTACAAATACCAGGCCCCGCGGCGGTCAGTTCGC
ACATCCAATACCTGCCGAGCCATCTTGCCTACACTTTTTATCGACTCCTCTACTCTGTTCGCGAGAGCG
CTCGGTCCAGGCTTGGAATTCGCCGAATTCAGCTCGATCAGTCGCTTCTGCAACTGATCTCGGCCGTTC
GCAGACTGCCTTTTCTCAGCTTGTCAGGTAGCGAGTTGTTGTTTTATATTTATTCGATTTCATCTGTGT
TGCATGTCTTGTTCGTGCTGTGCGTTCTTTCTGGGCCGCGCTGTCGGGTCGCATGGGCTAGCTGTACTC
ATGTTAGTCATGCCGGTCCGACCTTGTTCGAGGAAGGCCCCACACTGAGCGTGCCCTCTTTCTACACCC
CTTGTGCAGAAATTAGATAGAAAGCAATGCTGCTGCAGGCCTTCCTGTTCCTGCTGGCCGGCTTCGCCG
CCAAGATCAGCGCCTCCATGACGAACGAGACGTCCGACCGCCCCTGGTGCACTTCACCCCCAACAAGG
GCTGGATGAACGACCCCAACGGCCTGTGGTACGACGAGAAGGACGCCAAGTGGCACCTGTACTTCCAGT
ACAACCCGAACGACACCGTCTGGGGGACGCCCTTGTTCTGGGGCCACGCCACGTCCGACGACCTGACCA
ACTGGGAGGACCAGCCCATCGCCATCGCCCCGAAGCGCAACGACTCCGGCGCCTTCTCCGGCTCCATGG
TGGTGGACTACAACAACACCTCCGGCTTCTTCAACGACACCATCGACCCGCGCCAGCGCTGCGTGGCCA
TCTGGACCTACAACACCCCGGAGTCCGAGGAGCAGTACATCTCCTACAGCCTGGACGGCGGCTACACCT
TCACCGAGTACCAGAAGAACCCCGTGCTGGCCGCCAACTCCACCCAGTTCCGCGACCCGAAGGTCTTCT
GGTACGAGCCCTCCCAGAAGTGGATCATGACCGCGGCCAAGTCCCAGGACTACAAGATCGAGATCTACT
CCTCCGACGACCTGAAGTCCTGGAAGCTGGAGTCCGCGTTCGCCAACGAGGGCTTCCTCGGCTACCAGT

```
ACGAGTGCCCCGGCCTGATCGAGGTCCCCACCGAGCAGGACCCCAGCAAGTCCTACTGGGTGATGTTCA
TCTCCATCAACCCCGGCGCCCCGGCCGGCGGCTCCTTCAACCAGTACTTCGTCGGCAGCTTCAACGGCA
CCCACTTCGAGGGCTTCGACAACCAGTCCCGCGTGGTGGACTTCGGCAAGGACTACTACGCCCTGCAGA
CCTTCTTCAACACCGACCCGACCTACGGGAGCGCCCTGGGCATCGCGTGGGCCTCCAACTGGGAGTACT
CCGCCTTCGTGCCCACCAACCCCTGGCGCTCCTCCATGTCCCTCGTGCGCAAGTTCTCCCTCAACACCG
AGTACCAGGCCAACCCGGAGACGGAGCTGATCAACCTGAAGGCCGAGCCGATCCTGAACATCAGCAACG
CCGGCCCCTGGAGCCGGTTCGCCACCAACACCACGTTGACGAAGGCCAACAGCTACAACGTCGACCTGT
CCAACAGCACCGGCACCCTGGAGTTCGAGCTGGTGTACGCCGTCAACACCACCCAGACGATCTCCAAGT
CCGTGTTCGCGGACCTCTCCCTCTGGTTCAAGGGCCTGGAGGACCCCGAGGAGTACCTCCGCATGGGCT
TCGAGGTGTCCGCGTCCTCCTTCTTCCTGGACCGCGGGAACAGCAAGGTGAAGTTCGTGAAGGAGAACC
CCTACTTCACCAACCGCATGAGCGTGAACAACCAGCCCTTCAAGAGCGAGAACGACCTGTCCTACTACA
AGGTGTACGGCTTGCTGGACCAGAACATCCTGGAGCTGTACTTCAACGACGGCGACGTCGTGTCCACCA
ACACCTACTTCATGACCACCGGGAACGCCCTGGGCTCCGTGAACATGACGACGGGGGTGGACAACCTGT
TCTACATCGACAAGTTCCAGGTGCGCGAGGTCAAGTGACCGACACGCCCCGGCCCAGGTCCAGTTCTC
CTGGGTCTTCCAGAGGCCCGTCGCCATGTAAAGTGGCAGAGATTGGCGCCTGATTCGATTTGGATCCAA
GGATCTCCAATCGGTGATGGGGACTGAGTGCCCAACTACCACCCTTGCACTATCGTCCTCCGCACTATTT
ATTCCCACCTTCTGCTCGCCCTGCCGGGCGATTGCGGGCGTTTCTGCCCTTGACGTATCAATTTCGCCC
CTGCTGGCGCGAGGATTCTTCATTCTAATAAGAACTCACTCCCGCCAGCTCTGTACTTTTCCTGCGGGG
CCCCTGCATGGCTTGTTCCAATGCTTGCTCGATCGACGGCGCCCATTGCCCACGGCGCTGCCGCATCC
ATGTGAAGAAACACGGAAGAGTGCGAAGACTGGAAGTGAATTAAGAGTATAAGAAGAGGTACCAAGGGA
TTCTCAGGTGCTCTTAGGAACGGCTTTTCCTTCGCCAAGAGAAACTGCTACTGCTCGTGTCGCCACGGT
GGTCAAGCCGCCCCATCTGCGATCCACCAGGCCCATCCGCGGACTCGCGATCAGCCTGCTGGATCCGGA
CTGCCGACCTGACCGCTCGCATCCACCATTACAACCCTCCAATTGGACACCACTCCCACGTCCTAAAGT
TCACCATGCAAGCTGATCGATCGCATTCGCCGATGCACTTCGCCACAGAGGTGTGCGCTTCGGACT
AGCGTGCAGGCGCCCCGAGGCCACCAGCATGCACCGATGGAAGCGGGCACGGCCGCTGCTCCAGGTCGC
TGGCTCGCTCAGACCCATAGCAACCTCCGCTGCGTCCCTAAATGTCACACAGAGCGTCTTTGATGGGTA
CGGATGGAGAGAATCTGATTGGGCATTGCTGGTGCAGTGCAGGAAGATGGCAAGTGCACAGTCAGTCA
TGCTGTACAAACTGGTGCCTCGTAGTATTGACTCGTATAGTGCATAGTATCATGCATGGTCGTTACTTG
CAA

SEQ ID NO: 15
Cinnamomum camphora FATB1 (Genbank Q39473) amino acid sequence with
Prototheca moriformis delta 12 fatty acid desaturase transit peptide.
MAIKTNRQPVEKPPFTIGTLRKAIPAHCFERSALRGRAPDWSMLFAVITTIFSAAEKQWTNLEWKPKPN
PPQLLDDHFGPHGLVFRRTFAIRSYEVGPDRSTSIVAVMNHLQEAALNHAKSVGILGDGFGTTLEMSKR
DLIWVVKRTHVAVERYPAWGDTVEVECWVGASGNNGRRHDFLVRDCKTGEILTRCTSLSVMMNTRTRRL
SKIPEEVRGEIGPAFIDNVAVKDEEIKKPQKLNDSTADYIQGGLTPRWNDLDINQHVNNIKYVDWILET
VPDSIFESHHISSFTIEYRRECTMDSVLQSLTTVSGGSSEAGLVCEHLLQLEGGSEVLRAKTEWRPKLT
DSFRGISVIPAESSV SEQ ID NO: 16
Relevant codon optimized expression construct of Cinnamomum camphora
FATB1 cDNA with Prototheca moriformis delta 12 fatty acid desaturase
transit peptide.
GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGGCGTGATGCAAGCATGCC
TGGCGAAGACACATGGTGTGCGGATGCTGCCGGCTGCTGCCTGCTGCCAGCAGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGTGTCCACACTGTCACCAGGCCCGCAAG
CTTTGCAGAACCATGCTCATGGAGCGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCAGCGGCGGGGGCCACC
CTTCTTGCGGGGTCGCGCCCCAGCCAGCGGTGATGCGCTGATCCCAAACGAGTTCACATTCATTTGCAT
GCCTGGAGAAGCGAGGCTGGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGGACTGCATTTGGGTGGCAG
GCCGGCTGTTTCTTTCGTGTTGCAAAACGCGCCAGCTCAGCAACCTGTCCCGTGGGTCCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCTCCACGCCGGCTCCCCCGCCGC
CTGGGTGGAGCGCCTGTTCGGCTACGACTGGGCCCAGCAGACCATCGGCTGCTCCGACGCCGCCGTGTT
CCGCCTGTCCGCCCAGGGCCGCCCCGTGCTGTTCGTGAAGACGCCATCTGTCCGGCGCCCTGAACGACT
GCAGGACGAGGCCGCCCGCCTGTCCTGGCTGGCCACCACCGGCGTGCCTGCCGCCGTGCTGGACGT
GGTGACCGAGGCCGGCCGCGACTGGCTGCTGCTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT
GGTGGACCAGGACGACCTGGACGAGGAGCACCAGGGCCTGGCCCCCGCCGAGCTGTTCGCCCGCCTGAA
GGCCCGCATGCCCGACGGCGAGGACCTGGTGGTGACCCACGGCGACCTGCCTGCCAACATCATGGT
GGAGAACGGCCGCTTCTCCGGCTTCATCGACTGCGGCCGCCTGGGCGTGGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACCGCCTGCTGGACGAGTTCTTCTGACAATT
GGCAGCAGCAGCTCGGATAGTATCGACACACTCTGGACGCTGGTCGTGTGATGGACTGTTGCCGCCACA
CTTGCTGCCTTGACCTGTGAATATCCCTGCCGCTTTTATCAAACAGCCTCAGTGTGTTTGATCTTGTGT
```

| INFORMAL SEQUENCE LISTING |
|---|
| GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCTGTATTCTCCTGGTACTGCAACCT
GTAAACCAGCACTGCAATGCTGATGCACGGGAAGTAGTGGGATGGGAACACAAATGGAGGATCCCGCGT
CTCGAACAGAGCGCGCAGAGGAACGCTGAAGGTCTCGCCTCTGTCGCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACAGCCTAGGGATATC
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
GGGGGCGCCTCTTCCTCTTCGTTTCAGTCACAACCCGCAAACACTAGTATGGCTATCAAGACGAACAGG
CAGCCTGTGGAAGCTCCGTTCACGATCGGGACGCTGCGCAAGGCCATCCCCGCGCACTGTTTCGAG
CGCTCGGCGCTTCGTGGGCGCGCCCCCGACTGGTCCATGCTGTTCGCCGTGATCACCACCATCTTCTCC
GCCGCCGAGAAGCAGTGGACCAACCTGGAGTGGAAGCCCAAGCCCAACCCCCCCCAGCTGCTGGACGAC
CACTTCGGCCCCCACGGCCTGGTGTTCCGCCGCACCTTCGCCATCCGCAGCTACGAGGTGGGCCCCGAC
CGCTCCACCAGCATCGTGGCCGTGATGAACCACCTGCAGGAGGCCGCCTGAACCACGCCAAGTCCGTG
GGCATCCTGGGCGACGGCTTCGGCACCACCCTGGAGATGTCCAAGCGCGACCTGATCTGGGTGGTGAAG
CGCACCCACGTGGCCGTGGAGCGCTACCCCGCCTGGGGCGACACCGTGGAGGTGGAGTGCTGGGTGGGC
GCCTCCGGCAACAACGGCCGCCGCCACGACTTCCTGGTGCGCGACTGCAAGACCGGCGAGATCCTGACC
CGCTGCACCTCCCTGAGCGTGATGAATGAACACCCGCACCCGCCGCCTGAGCAAGATCCCCGAGGAGGTG
CGCGGCGAGATCGGCCCCGCCTTCATCGACAACGTGGCCGTGAAGGACGAGGAGATCAAGAAGCCCCAG
AAGCTGAACGACTCCACCGCCGACTACATCCAGGGCGGCCTGACCCCCGCTGGAACGACCTGGACATC
AACCAGCACGTGAACAACATCAAGTACGTGGACTGGATCCTGGAGACGCATCCGCCGACAGCATCTTCGAG
AGCCACCACATCTCCTCCTTCACCATCGAGTACCGCCGCGAGTGCACCATGGACAGCGTGCTGCAGTCC
CTGACCACCGTGAGCGGCGGCTCCTCCGAGGCCGGCCTGGTGTGCGAGCACCTGCTGCAGCTGGAGGGC
GGCAGCGAGGTGCTGCGCGCCAAGACCGAGTGGCGCCCCAAGCTGACCGACTCCTTCCGCGGCATCAGC
GTGATCCCCGCCGAGTCCAGCGTGATGGACTACAAGGACCACGACCGCGACTACAAGGACCACGACATC
GACTACAAGGACGACGACGACAAGTGATGACTCGAGGCAGCAGCAGCTCGGATAGTATCGACACACTCT
GGACGCTGGTCGTGTGATGGACTGTTGCCGCCACACTTGCTGCCTTGACCTGTGAATATCCCTGCCGCT
TTTATCAAACAGCCTCAGTGTGTTTGATCTTGTGTGTACGCGCTTTTGCGAGTTGCTAGCTGCTTGTGC
TATTTGCGAATACCACCCCCAGCATCCCCTTCCCTCGTTTCATATCGCTTGCATCCCAACCGCAACTTA
TCTACGCTGTCCTGCTATCCCTCAGCGCTGCTCCTGCTCCTGCTCACTGCCCCTCGCACAGCCTTGGTT
TGGGCTCCGCTGTATTCTCCTGGTACTGCAACCTGTAAACCAGCACTGCAATGCTGATGCACGGGAAG
TAGTGGGATGGGAACACAAATGGAAAGCTT |

SEQ ID NO: 17
*Umbellularia californica* FATB1 (Genbank Q41635) amino acid sequence
with *Prototheca moriformis* delta 12 fatty acid desaturase transit
peptide.
MAIKTNRQPVEKPPFTIGTLRKAIPAHCFERSALRGRAPDWSMLFAVITTIFSAAEKQWTNLEWKPKPK
LPQLLDDHFGLHGLVFRRTFAIRSYEVGPDRSTSILAVMNHMQEATLNHAKSVGILGDGFGTTLEMSKR
DLMWVVRRTHVAVERYPTWGDTVEVECWIGASGNNGMRRDFLVRDCKTGEILTRCTSLSVLMNTRTRRL
STIPDEVRGEIGPAFIDNVAVKDDEIKKLQKLNDSTADYIQGGLTPRWNDLDVNQHVNNLKYVAWVFET
VPDSIFESHHISSFTLEYRRECTRDSVLRSLTTVSGGSSEAGLVCDHLLQLEGGSEVLRARTEWRPKLT
DSFRGISVIPAEPRV SEQ ID NO: 18
Relevant codon optimized expression construct of *Umbellularia
californica* FATB1 cDNA with *Prototheca moriformis* delta 12 fatty acid
desaturase transit peptide.
GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGGCGTGATGCAAGCATGCC
TGGCAAGACACATGGTGTGCGGATGCTGCCGGCTGCTGCCTGCTGCGCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGTGTCCACACTGTCACCAGGCCCGCAAG
CTTTGCAGAACCATGCTCATGGACGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCAGCGGCGGGGGCCACC
CTTCTTGCGGGGTCGCGCCCCAGCCAGCGGTGATGCGTCGATCCCAAACGAGTTCACATTCATTTGCAT
GCCTGGAGAAGCGAGGCTGGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGGACTGCATTTGGGTGGGGCG
GCCGGCTGTTTCTTTCGTGTTGCAAAACGCGCCAGCTCAGCAACCTGTCCCGTGGGTCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCCTCCACGCCGGCTCCCCCGCCGC
CTGGGTGGAGCGCCTGTTCGGCTACGACTGGGCCCAGCAGACCATCGGCTGCTCCGACGCCGCCGTGTT
CCGCCTGTCCGCCCAGGGCCGCCCCGTGCTGTTCGTGAAGACCGACCTGTCCGGCGCCCTGAACGAGCT
GCAGGACGAGGCCGCCCGCCTGTCCTGGCTGGCCACCACCGGCGTGCCCTGCGCCGCCGTGCTGGACGT
GGTGACCGAGGCCGGCCGCGACTGGCTGCTGCTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT -continued

INFORMAL SEQUENCE LISTING

```
GGTGGACCAGGACGACCTGGACGAGGAGCACCAGGGCCTGGCCCCCGCCGAGCTGTTCGCCCGCCTGAA
GGCCCGCATGCCCGACGGCGAGGACCTGGTGGTGACCCACGGCGACGCCTGCCTGCCCAACATCATGGT
GGGAGAACGGCCGCTTCTCCGGCTTCATCGACTGCGGCCGCCTGGGCGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACCGCCTGCTGGACGAGTTCTTCTGACAATT
GGCAGCAGCAGCTCGGATAGTATCGACACACTCTGGACGCTGGTCGTGTGATGGACTGTTGCCGCCACA
CTTGCTGCCTTGACCTGTGAATATCCCTGCCGTCTTTTATCAAACAGCCTCAGTGTGTTTGATCTTGTGT
GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCCTGTATTCTCCTGGTACTGCAACCT
GTAAACCAGCACTGCAATGCTGATGCACGGGAAGTAGTGGGATGGGAACACAAATGGAGGATCCCGCGT
CTCGAACAGAGCGCGCAGAGGAACGCTGAAGGTCTCGCCTCTGTCGCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACAGCCTAGGGATATC
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
GGGGGCGCCTCTTCCTCTTCGTTTCAGTCACAACCCGCAAACACTAGTATGGCTATCAAGACGAACAGG
CAGCCTGTGGAGAAGCCTCCGTTCACGATCGGGACGCTGCGCAAGGCCATCCCCGCGCACTGTTTCGAG
CGCTCGGCGCTTCGTGGGCGCGCCCCGACTGGTCCATGCTGTTCGCCGTGATCACCACCATCTTCAGC
GCCGCCGAGAAGCAGTGGACCAACCTGGAGTGGAAGCCCAAGCCCAAGCTGCCCCAGCTGCTGGACGAC
CACTTCGGCCTGCACGGCCTGGTGTTCCGCCGCACCTTCGCCATCCGCTCCTACGAGGTGGGCCCCGAC
CGCAGCACCTCCATCCTGGCCGTGATGAACCACATGCAGGAGGCCACCTCGAACCACGCCAAGAGCGTG
GGCATCCTGGGCGACGGCTTCGGCACCACCCTGGAGATGTCCAAGCGCGACCTGATGTGGGTGGTGCGC
CGCACCCACGTGGCCGTGGAGCGCTACCCCCACCTGGGGCGACACCGTGGAGGTGGAGTGCTGGATCGGC
GCCAGCGGCAACAACGGCATGCGCCGCGACTTCCTGGTGCGCGACTGCAAGACCGGCGAGATCCTGACC
CGCTGCACCTCCCTGAGCGTGCTGATGAACACCCGCACCCGCCGCTGAGCACCATCCCCGACGAGGTG
CGCGGCGAGATCGGCCCCGCCTTCATCGACAACGTGGCCGTGAAGGACGACGAGATCAAGAAGCTGCAG
AAGCTGAACGACTCCACCGCCGACTACATCCAGGGCGGCCTGACCCCCCGCTGGAACGACCTGGACGTG
AACCAGCACGTGAACAACCTGAAGTACGTGGCCTGGGTGTTCGAGACCGTGCCCGACAGCATCTTCGAG
TCCCACCACATCAGCTCCTTCACCCTGGAGTACCGCCGCGAGTGCACCCGCGACTCCGGTGCTGCGCAGC
CTGACCACCGTGAGCGGCGGCAGCTCCGAGGCCGGCCTGGTGTGCGACCACCTGCTGCAGCTGGAGGGC
GGCAGCGAGGTGCTGCGCGCCCGCACCGAGTGGCGCCCCAAGCTGACCGACTCCTTCCGCGGCATCAGC
GTGATCCCCGCCGAGCCCCGCGTGATGGACTACAAGGACCACGACGGCGACTACAAGGACCACGACATC
GACTACAAGGACGACGACGACAAGTGATGACTCGAGGCAGCAGCGGCTCGGATAGTATCGACACACTCT
GGACGCTGGTCGTGTGATGGACTGTTGCCGCCACACTTGCTGCCTTGACCTGTGAATATCCCTGCCGCT
TTTATCAAACAGCCTCAGTGTGTTTGATCTTGTGTACGCGCTTTTGCGAGTTGCTAGCTGCTTGTGC
TATTTGCGAATACCACCCCCAGCATCCCCTTCCCTCGTTTCATATCGCTTGCATCCCAACCGCAACTTA
TCTACGCTGTCCTGCTATCCCTCAGCGCTGCTCCTGCTCCTGCTCACTGCCCCTCGCACAGCCTTGGTT
TGGGCTCCGCCTGTATTCTCCTGGTACTGCAACCTGTAAACCAGCACTGCAATGCTGATGCACGGGAAG
TAGTGGGATGGGAACACAAATGGAAAGCTT
```

SEQ ID NO: 19
*Cuphea hookeriana* FATB2 (Genbank AAC49269) amino acid sequence with
*Prototheca moriformis* delta 12 fatty acid desaturase transit peptide.
```
MAIKTNRQPVEKPPFTIGTLRKAIPAHCFERSALRGRAQLPDWSRLLTAITTVFVKSKRPDMHDRKSKR
PDMLVDSFGLESTVQDGLVFRQSFSIRSYEIGTDRTASIETLMNHLQETSLNHCKSTGILLDGFGRTLE
MCKRDLIWVVIKMQIKVNRYPAWGDTVEINTRFSRLGKIGMGRDWLISDCNTGEILVRATSAYAMMNQK
TRRLSKLPYEVHQEIVPLFVDSPVIEDSDLKVHKFKVKTGDSIQKGLTPGWNDLDVNQHVSNVKYIGWI
LESMPTEVLETQELCSLALEYRRECGRDSVLESVTAMDPSKVGVRSQYQHLLRLEDGTAIVNGATEWRP
KNAGANGAISTGKTSNGNSVS
```

SEQ ID NO: 20
Relevant codon optimized expression construct of *Cuphea hookeriana*
FATB2 cDNA with *Prototheca moriformis* delta 12 fatty acid desaturase
transit peptide.
```
GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGCTGGGCTTGCATGCCGGGCAATGCGCATGGTGGCAAGAG
GGCGGCGACACTTGCTGGAGCTGCCGCGGTGCCTCCAGGTGGTTCAATCGCGGCAGCCAGAGGGATTTC
AGATGATCGCGCGCTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGCGGGCGTGATGCAAGCATGCC
TGGCGAAGACACATGGTGTGCGGATGCTGCCGGCTGCTGCCTGCTGCCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGTGTCCACACTGTCACCAGGCCCGCAAG
CTTTGCAGAACCATGCTCATGGACGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCACCGGCGGGGCCACC
CTTCTTGCGGGGTCGCGCCCCAGCCAGCGGTGATGCGCTGATCCCAAACGAGTTCACATTCATTTGCAT
GCCTGGAGAAGCGAGGCTGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGACTGCATTTGGGTGGGGCG
GCCGGCTGTTTCTTTCGTGTTGCAAAACGCGCCAGCTCAGCAACCTGTCCCGTGGGTCCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCCTCCACGCCGGCTCCCCCGCCGC
```

-continued

INFORMAL SEQUENCE LISTING

CTGGGTGGAGCGCCTGTTCGGCTACGACTGGGCCCAGCAGACCATCGGCTGCTCCGACGCCGCCGTGTT
CCGCCTGTCCGCCCAGGGCCGCCCCGTGCTGTTCGTGAAGACCGACCTGTCCGGCGCCCTGAACGAGCT
GCAGGACGAGGCCGCCCGCCTGTCCTGGCTGGCCACCACCGGCGTGCCCTGCGCCGCCGTGCTGGACGT
GGTGACCGAGGCCGGCCGCGACTGGCTGCTGCTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT
GGTGGACCAGGACGACCTGGACGAGGAGCACCAGGGCCTGGCCCCCGCCGAGCTGTTCGCCCGCCTGAA
GGCCCGCATGCCCGACGGCGAGGACCTGGTGGTGACCCACGGCGACGCCTGCCTGCCCAACATCATGGT
GGAGAACGGCCGCTTCTCCGGCTTCATCGACTGCGGCCGCCTGGGCGTGGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACCGCCTGCTGGACGAGTTCTTCTGACAATT
GGCAGCAGCAGCTCGGATAGTATCGACACACTCTGGACGCTGGTCGTGTGATGGACTGTTGCCGCCACA
CTTGCTGCCTTGACCTGTGAATATCCCTGCCGCTTTTATCAAACAGCCTCAGTGTGTTTGATCTTGTGT
GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCCTGTATTCTCCTGGTACTGCAACCT
GTAAACCAGCACTGCAATGCTGATGCACGGGAAGTAGTGGGATGGGAACACAAATGGAGGATCCCGCGT
CTCGAACAGAGCGCGCAGAGGAACGCTGAAGGTCTCGCCTCTGTCGCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACAGCCTAGGGATATC
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
GGGGGCGCCTCTTCCTCTTCGTTTCAGTCACAACCCGCAAACACTAGTATGGCTATCAAGACGAACAGG
CAGCCTGTGGAGAAGCCTCCGTTCACGATCGGGACGCTGCGCAAGGCCATCCCCGCGCACTGTTTCGAG
CGCTCGGCGCTTCGTGGGCGCGCCCAGCTGCCCGACTGGAGCCGCCTGCTGACCGCCATCACCACCGTG
TTCGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACGAG
ATCGGCACCGACCGCACCGCCAGCATCGAGACCCTGATGAACCACCTGCAGGAGACCTCCCTGAACCAC
TGCAAGAGCACCGGCATCCTGCTGGACGGCTTCGGCCGCACCCTGGAGATGTGCAAGCGCGACCTGATC
TGGGTGGTGATCAAGATGCAGATCAAGGTGAACCGCTACCCCGCCTGGGGCGACACCGTGGAGATCAAC
ACCCGCTTCAGCCGCCTGGGCAAGATCGGCATGGGCCGCGACTGGCTGATCTCCGACTGCAACACCGGC
GAGATCCTGGTGCGCGCCACCAGCGCCTACGCCATGATGAACCAGAAGACCCGCCGCCTGTCCAAGCTG
CCCTACGAGGTGCACCAGGAGATCGTGCCCCTGTTCGTGGACAGCCCCGTGATCGAGGACTCCGACCTG
AAGGTGCACAAGTTCAAGGTGAAGACCGGCGACAGCATCCAGAAGGGCCTGACCCCCGGCTGGAACGAC
CTGGACGTGAACCAGCACGTGTCCAACGTGAAGTACATCGGCTGGATCCTGGAGAGCATGCCCACCGAG
GTGCTGGAGACCCAGGAGCTGTGCTCCCTGGCCCTGGAGTACCGCCGCGAGTGCGGCCGCGACTCCGTG
CTGGAGAGCGTGACCGCCATGGACCCCAGCAAGGTGGGCGTGCGCTCCCAGTACCAGCACCTGCTGCGC
CTGGAGGACGGCACCGCCATCGTGAACGGCGCCACCGAGTGGCGCCCCAAGAACGCCGGCGCCAACGGC
GCCATCTCCACCGGCAAGACCAGCAACGGCAACTCCGTGTCCATGGACTACAAGGACCACGACGGCGAC
TACAAGGACCACGACATCGACTACAAGGACGACGACGACAAGTGACTCGAGGCAGCAGCAGCTCGGATA
GTATCGACACACTCTGGACGCTGGTCGTGTGATGGACTGTTGCCGCCACACTTGCTGCCTTGACCTGTG
AATATCCCTGCCGCTTTTATCAAACAGCCTCAGTGTGTTTGATCTTGTGTGTACGCGCTTTTGCGAGTT
GCTAGCTGCTTGTGCTATTTGCGAATACCACCCCCAGCATCCCCTTCCCTCGTTTCATATCGCTTGCAT
CCCAACCGCAACTTATCTACGCTGTCCTGCTATCCCTCAGCGCTGCTCCTGCTCCTGCTCACTGCCCCT
CGCACAGCCTTGGTTTGGGCTCCGCCTGTATTCTCCTGGTACTGCAACCTGTAAACCAGCACTGCAATG
CTGATGCACGGGAAGTAGTGGGATGGGAACACAAATGGAAAGCTT

SEQ ID NO: 21
*Cuphea palustris* C8 preferring thioesterase (Genbank AAC49179) amino acid sequence with *Prototheca moriformis* delta 12 fatty acid desaturase transit peptide.
MAIKTNRQPVEKPPFTIGTLRKAIPAHCFERSALRGRAPANGSAVTLKSGSLNTQEDTLSSSPPPRAFF
NQLPDWSMLLTAITTVFVAPEKRWTMFDRKSKRPNMLMDSFGLERVVQDGLVFRQSFSIRSYEICADRT
ASIETVMNHVQETSLNQCKSIGLLDDGFGRSPEMCKRDLIWVVTRMKIMVNRYPTWGDTIEVSTWLSQS
GKIGMGRDWLISDCNTGEILVRATSVYAMMNQKTRRFSKLPHEVRQEFAPHFLDSPPAIEDNDGKLQKF
DVKTGDSIRKGLTPGWYDLDVNQHVSNVKYIGWILESMPTEVLETQELCSLTLEYRRECGRDSVLESVT
SMDPSKVGDRFQYRHLLRLEDGADIMKGRTEWRPKNAGTNGAISTGKT SEQ ID NO: 22
Relevant codon optimized expression construct of *Cuphea palustris* C8 preferring thioesterase cDNA with *Prototheca moriformis* delta 12 fatty acid desaturase transit peptide.
GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGGCGTGATGCAAGCATGCC
TGGCGAAGACACATGGTGTGCGGATGCTGCCGGCTGCTGCCTGCTGCGCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGTGTCCACACTGTCACCAGGCCCGCAAG
CTTTGCAGAACCATGCTCATGGACGCATGTAGCGCTGACGTCCCTTGACGGCGCTCCTCTCGGGTGTGG

| INFORMAL SEQUENCE LISTING |
| --- |
| GAAACGCAATGCAGCACAGGCAGCAGAGGCGGCGGCAGCAGAGCGGCGGCAGCAGCGGCGGGGGCCACC |
| CTTCTTGCGGGGTCGCGCCCCAGCCAGCGGTGATGCGCTGATCCCAAACGAGTTCACATTCATTTGCAT |
| GCCTGGAGAAGCGAGGCTGGGGCCTTTGGGCTGGTGCAGCCGCAATGGAATGCGGGACCGCCAGGCTA |
| GCAGCAAAGGCGCCTCCCCTACTCCGCATCGATGTTCCATAGTGCATTGGACTGCATTTGGGTGGGGCG |
| GCCGGCTGTTTCTTTCGTGTTGCAAAACGCGCCAGCTCAGCAACCTGTCCCGTGGGTCCCCCGTGCCGA |
| TGAAATCGTGTGCACGCCGATCAGCTGATTGCCCGGCTCGCGAAGTAGGCGCCCTCCTTTCTGCTCGCC |
| CTCTCTCCGTCCCGCCTCTAGAATATCAATGATCGAGCAGGACGGCCCTCCACGCCGGCTCCCCCGCGC |
| CTGGGTGGAGCGCCTGTTCGGCTACGACTGGGCCCAGCAGACCATCGGCTGCTCCGACGCGCCGTGTT |
| CCGCCTGTCCGCCCAGGGCCGCCCCGTGCTGTTCGTGAAGACCGACCTGTCCGGCGCCCTGAACGAGCT |
| GCAGGACGAGGCCGCCCGCCTGTCCTGGCTGGCCACCACCGGCGTGCCCTGCGCCGCCGTGCTGGACGT |
| GGTGACCGAGGCCGGCCGCGACTGGCTGCTGCTGGGCGAGGTGCCCGGCCAGGACCTGCTGTCCTCCCA |
| CCTGGCCCCCGCCGAGAAGGTGTCCATCATGGCCGACGCCATGCGCCGCCTGCACACCCTGGACCCCGC |
| CACCTGCCCCTTCGACCACCAGGCCAAGCACCGCATCGAGCGCGCCCGCACCCGCATGGAGGCCGGCCT |
| GGTGGACCAGGACGACCTGGACGAGGAGCACCAGGGCCTGGCCCCCGCCGAGCTGTTCGCCCGCCTGAA |
| GGCCCGCATGCCCGACGGCGAGGACCTGGTGGTGACCCACGGCGACGCCTGCCTGCCCAACATCATGGT |
| GGAGAACGGCCGCTTCTCCGGCTTCATCGACTGCGGCCGCCTGGGCGTGGCCGACCGCTACCAGGACAT |
| CGCCCTGGCCACCCGCGACATCGCCGAGGAGCTGGGCGGCGAGTGGGCCGACCGCTTCCTGGTGCTGTA |
| CGGCATCGCCGCCCCCGACTCCCAGCGCATCGCCTTCTACCGCCTGCTGGACGAGTTCTTCTGACAATT |
| GGCAGCAGCAGCTCGGATAGTATCGACACACTCTGGACGCTGGTCGTGTGATGGACTGTTGCCGCCACA |
| CTTGCTGCCTTGACCTGTGAATATCCCTGCCGCTTTTATCAAACAGCCTCAGTGTGTTTGATCTTGTGT |
| GTACGCGCTTTTGCGAGTTGCTAGCTGCTTGTGCTATTTGCGAATACCACCCCCAGCATCCCCTTCCCT |
| CGTTTCATATCGCTTGCATCCCAACCGCAACTTATCTACGCTGTCCTGCTATCCCTCAGCGCTGCTCCT |
| GCTCCTGCTCACTGCCCCTCGCACAGCCTTGGTTTGGGCTCCGCCTGTATTCTCCTGGTACTGCAACCT |
| GTAAACCAGCACTGCAATGCTGATGCACGGGAAGTAGTGGGATGGGAACACAAATGGAGGATCCCGCGT |
| CTCGAACAGAGCGCGCAGAGGAACGCTGAAGGTCTCGCCTCTGTCGCACCTCAGCGCGGCATACACCAC |
| AATAACCACCTGACGAATGCGCTTGGTTCTTCGTCCATTAGCGAAGCGTCCGGTTCACACACGTGCCAC |
| GTTGGCGAGGTGGCAGGTGACAATGATCGGTGGAGCTGATGGTCGAAACGTTCACAGCCTAGGGATATC |
| GAATTCCTTTCTTGCGCTATGACACTTCCAGCAAAAGGTAGGGGCTGCTGGACGCTTCCCGGCCTGCAT |
| GCAACACCGATGATGCTTCGACCCCCCGAAGCTCCTTCGGGGCTGCATGGGCGCTCCGATGCCGCTCCA |
| GGGCGAGCGCTGTTTAAATAGCCAGGCCCCCGATTGCAAAGACATTATAGCGAGCTACCAAAGCCATAT |
| TCAAACACCTAGATCACTACCACTTCTACACAGGCCACTCGAGCTTGTGATCGCACTCCGCTAAGGGGG |
| CGCCTCTTCCTCTTCGTTTCAGTCACAACCCGCAAACACTAGTATGGCTATCAAGACGAACAGGCAGCC |
| TGTGGAGAAGCCTCCGTTCACGATCGGGACGCTGCGCAAGGCCATCCCCGCGCACTGTTTCGAGCGCTC |
| GGCGCTTCGTGGGCGCGCCCCCGCGAACGGCAGCGCGGTGACCCTGAAGTCGGGCTCCCTGAACACCCA |
| GGAGGACACGCTGAGCTCGTCCCCCCCCCCCGCGCGTTCTTCAACCAGCTGCCCGACTGGAGCATGCTG |
| CTGACCGCGATCACCACGGTCTTCGTGGCGCCCGAGAAGCAGTCTGGACCATGTTCGACCGCAAGTCGA |
| AGCGCCCCAACATGCTGATGGACTCCTTCGGCCTGGAGCGCGTGGTCCAGGACGGCCTGGTGTTCCGCC |
| AGAGCTTCTCGATCCGCTCCTACGAGATCTGCGCGGACCGCACCGCGAGCATCGAGACGGTGATGAACC |
| ACGTCCAGGAGACCTCGCTGAACAGTGCAAGTCCATCGGCCTGCTGGACGACGGCTTCGGCCGCAGCCC |
| CGAGATGTGCAAGCGCGACCTGATCTGGGTGGTCACCCGCATGAAGATCATGGTGAACCGCTACCCCAC |
| GTGGGGCGACACCATCGAGGTCTCGACGTGGCTGTCCCAGAGCGGCAAGATCGGCATGGGCCCGACTGG |
| CTGATCTCGGACTGCAACACCGGCGAGATCTTGGTGCGCGCGACGTCCGTCTACGCGATGATGAACCAG |
| AAGACCCGCCGCTTCAGCAAGCTGCCCCACGAGGTGCGCCAGGAGTTCGCGCCCCACTTCCTGGACTCG |
| CCCCCGCGATCGAGGACAACGACGGCAAGCTGCAGAAGTTCGACGTCAAGACGGGCGACTCCATCCGCA |
| AGGGCCTGACCCCCGGCTGGTACGACCTGGACGTGAACCAGCACGTGAGCAACGTCAAGTACATCGGCT |
| GGATCCTGGAGTCGATGCCCACCGAGGTCCTGGAGACGCAGGAGCTGTGCTCCCTGACCCTGGAGTACC |
| GCCGCGAGTGCGGCCGCGACTCGGTGCTGGAGAGCGTCACCAGCATGGACCCCTCGAAGGTGGGCGACC |
| GCTTCCAGTACCGCCACCTGCTGCGCCTGGAGGACGGCGCGGACATCATGAAGGGCGCACCGAGTGGCG |
| CCCCAAGAACGCGGGCACGAACGGCGCGATCTCCACCGGCAAGACGTGACTCGAGGCAGCAGCAGCTCG |
| GATAGTATCGACACACTCTGGACGCTGGTCGTGTGATGGACTGTTGCCGCCACACTTGCTGCCTTGACC |
| TGTGAATATCCCTGCCGCTTTTATCAAACAGCCTCAGTGTGTTTGATCTTGTGTGTACGCGCTTTTGCG |
| AGTTGCTAGCTGCTTGTGCTATTTGCGAATACCACCCCCAGCATCCCCTTCCCTCGTTTCATATCGCTT |
| GCATCCCAACCGCAACTTATCTACGCTGTCCTGCTATCCCTCAGCGCTGCTCCTGCTCCTGCTCACTGC |
| CCCTCGCACAGCCTTGGTTTGGGCTCCGCCTGTATTCTCCTGGTACTGCAACCTGTAAACC |
| AGCACTGCAATGCTGATGCACGGGAAGTAGTGGGATGGGAACACAAATGGAAAGCTTGAGCTC |

SEQ ID NO: 23
*Cuphea lanceolata* C10 preferring thioesterase (Genbank CAB60830)
amino acid sequence with *Prototheca moriformis* delta 12 fatty acid
desaturase transit peptide.
MAIKTNRQPVEKPPFTIGTLRKAIPAHCFERSALRGRAPANGSAVNLKSGSLNTQEDTSSSPPPRAFLN
QLPDWSMLLTAITTVFVAAEKQWTMLDRKSKRPDMLVDSVGLKSIVRDGLVSRQSFLIRSYEIGADRTA
SIETLMNHLQETSINHCKSLGLLNDGFGRTPGMCKNDLIWVLTKMQIMVNRYPTWGDTVEINTWFSQSG
KIGMASDWLISDCNTGEILIRATSVWAMMNQKTRRFSRLPYEVRQELTPHFVDSPHVIEDNDQKLHKFD
VKTGDSIRKGLTPRWNDLDVNQHVSNVKYIGWILESMPIEVLETQELCSLTVEYRRECGMDSVLESVTA
VDPSENGGRSQYKHLLRLEDGTDIVKSRTEWRPKNAGTNGAISTSTAKTSNGNSASDDDDKLG SEQ ID NO: 24
Relevant codon optimized coding region of *Cuphea lanceolata* C10
preferring thioesterase with *Prototheca moriformis* delta 12 fatty
acid desaturase transit peptide.
ACTAGTATGGCTATCAAGACGAACAGGCAGCCTGTGGAGAAGCCTCCGTTCACGATCGGGACGCTGCGC
AAGGCCATCCCCGCGCACTGTTTCGAGCGCTCGGCGCTTCGTGGGCGCGCCCCCGCGAACGGCAGCGCG
GTGAACCTGAAGTCGGGCTCCCTGAACACCCAGGAGGACACGAGCTCGTCCCCCCCCCCCGCGCGTTC
CTGAACCAGCTGCCCGACTGGAGCATGCTGCTGACCGCGATCACCACCGTCTTCGTGGCGGCGGAGAAG
CAGTGGACGATGCTGGACCGCAAGTCGAAGCGCCCCGACATGCTGGTGGACTCCGTCGGCCTGAAGAGC
ATCGTGCGCGACGGCCTGGTCTCGCGCCAGTCCTTCCTGATCCGCAGCTACGAGATCGGCGCGGACCGC

| INFORMAL SEQUENCE LISTING |
|---|
| ACCGCGTCGATCGAGACCCTGATGAACCACCTGCAGGAGACGTCCATCAACCACTGCAAGAGCCTGGGC
CTGCTGAACGACGGCTTCGGCCGCACCCCCGGCATGTGCAAGAACGACCTGATCTGGGTGCTGACCAAG
ATGCAGATCATGGTCAACCGCTACCCCACGTGGGGCGACACCGTCGATCAACACGTGGTTCTCGCAG
TCCGGCAAGATCGGCATGGCGAGCGACTGGCTGATCTCGGACTGCAACACCGGCGAGATCCTGATCCGC
GCGACCTCCGTGTGGGCGATGATGAACCAGAAGACGCGCCGCTTCAGCCGCCTGCCCTACGAGGTCCGC
CAGGAGCTGACCCCCCACTTCGTGGACTCGCCCCACGTCATCGAGGACAACGACCAGAAGCTGCACAAG
TTCGACGTGAAGACCGGCGACTCCATCCGCAAGGGCCTGACGCCCCGCTGGAGCGACCTGGACGTCAAC
CAGCACGTGTCGAACGTGAAGTACATCGGCTGGATCCTGGAGTCCATGCCCATCGAGGTCCTGGAGACC
CAGGAGCTGTGCTCGCTGACCGTGGAGTACCGCCGCGAGTGCGGCATGGACTCCGTGCTGGAGTCGGTC
ACGGCGGTGGACCCCAGCGAGAACGGCGGCCGCAGCCAGTACAAGCACCTGCTGCGCCTGGAGGACGGC
ACCGACATCGTCAAGTCGCGCACCGAGTGGCGCCCCAAGAACGCGGGCACGAACGGCGCGATCTCCACC
AGCACCGCGAAGACGTCGAACGGCAACTCCGCGAGCGATGACGATGACAAGCTGGGATGACTCGAG

SEQ ID NO: 25
*Iris germanica* C14 preferring thioesterase (Genbank AAG43858.1) amino
acid sequence with *Chlorella* protothecoides stearoyl ACP desaturase
chloroplast transit peptide.
MATASTFSAFNARCGDLRRSAGSGPRRPARPLPVRGRAAQAATRVNGSKVGLKTDTNKLEDAPFIPSSA
PRTFYNQLPDWSVLLAAITTIFLAAEKQWTLIDWKRGGPDMLSDAFGLPKIIENGLLYRQKFSIRSYEI
GADQTASIETLMNHLQETALDWHVKCAGLLGNGFGSTPEMSKMNLIWVVTKMQVLVEHYPSWGDVIEVDT
WAAASGKNGMRRDWHVRDWQTGQTIMRASSNWVMMNQNTRRLSKFPEEVRAEIEPYFMERAPVIDDDNR
KLPKLDDDTADHVRNGLTPRWSDLDVNQHVKNVKYIGWILESAPISILESHELASMTLEYRRECGRDSV
LQSLTSVSNNCTDGSEELPIECQHLLRNEGGSEIVKGRTEWRPKKCGPFGAGRP SEQ ID NO: 26
Relevant codon optimized coding region of *Iris germanica* C14
preferring thioesterase with *Chlorella* protothecoides stearoyl ACP
desaturase transit peptide.
ACTAGTATGGCCACCGCATCCACTTTCTCGGCGTTCAATGCCCGCTGCGGCGACCTGCGTCGCTCGGCG
GGCTCCGGGCCCCGGCGCCCAGCGAGGCCCCTCCCCGTGCGCGGGCGCGCCGCCCAGGCGGCCACCCGC
GTGAACGGCAGCAAGGTGGGCCTGAAGACCGACACCAACAAGCTGGAGGACGCGCCCTTCATCCCCTCG
TCCGCCCCCCGCACCTTCTACAACCAGCTGCCCGACTGGAGCGTCCTGCTGGCGGCCATCACCACCATC
TTCCTGGCGGCCGAGAAGCAGTGGACCCTGATCGACTGGAAGCGCGGCGGCCCCGACATGCTGTCGGAC
GCGTTCGGCCTGCCCAAGATCATCGAGAACGGCCTGCTGTACCGCCAGAAGTTCTCCATCCGCAGCTAC
GAGATCGGCGCCGACCAGACCGCCTCGATCGAGACCCTGATGAACCACCTGCAGGAGACCGCGCTGAAC
CACGTCAAGTGCGCCGGCCTGCTGGGCAACGGCTTCGGCTCCACCCCCGAGATGAGCAAGATGAACCTG
ATCTGGGTGGTCACCAAGATGCAGGTGCTGGTCGAGCACTACCCCTCGTGGGGCGACGTGATCGAGGTG
GACACCTGGGCGGCCGCGTCCGGCAAGAACGGCATGCGCCGCGACTGGCACGTCCGCGACTGGCAGACC
GGCCAGACCATCATGCGCGCCAGCTCGAACTGGGTGATGATGAACCAGAACACCCGCCGCCTGTCCAAG
TTCCCCGAGGAGGTCCGCGCCGAGATCGAGCCCTACTTCATGGAGCGCGCCCCCGTGATCGACGACGAC
AACCGCAAGCTGCCCAAGCTGGACGACGACACCGCGGACCACGTCCGCAACGGCCTGACCCCCCGCTGG
AGCGACCTGGACGTGAACCAGCACGTCAAGAACGTGAAGTACATCGGCTGGATCCTGGAGTCGGCCCCC
ATCTCCATCCTGGAGAGCCACGAGCTGGCCTCGATGACCCTGGAGTACCGCCGCGAGTGCGGCCGCGAC
TCCGTCCTGCAGAGCCTGACCTCGGTGTCCAACAACTGCACCGACGGCAGCGAGGAGCTGCCCATCGAG
TGCCAGCACCTGCTGCGCAACGAGGGCGGCTCGGAGATCGTCAAGGGCCGCACCGAGTGGCGCCCCAAG
AAGTGCGGCCCCTTCGGCGCCGGCCGCCCCTGACTCGAG SEQ ID NO: 27
*Myristica fragrans* fatty acyl thioesterase (Genbank AAB717291.1)
amino acid sequence with *Prototheca moriformis* delta 12 fatty acid
desaturase chloroplast transit peptide.
MAIKTNRQPVEKPPFTIGTLRKAIPAHCFERSALRGRAANAHTVPKINGNKAGLLTPMESTKDEDIVAA
PTVAPKRTFINQLPDWSMLLAAITTIFLAAEKQWTNLDWKPRRPDMLVDFDPFSLGRFVQDGLIFRQNF
SIRSYEIGADRTASIETLMNHLQETALNHVRCIGLLDDGFGSTPEMTRRDLIWVVTRMQVLVDRYPSWG
DVIEVDSWVTPSGKNGMKREWFLRDCKTGEILTRATSVWVMMNKRTRRLSKIPEEVRVEIEPYFVEHGV
LDEDSRKLPKLNDNTANYIRRGLAPRWSDLDVNQHVNNVKYIGWILESVPSSLLESHELYGMTLEYRKE
CGKDGLLQSLTAVASDYGGGSLEAGVECDHLLRLEDGSEIMRGKTEWRPKRAANTTYFGSVDDIPPANN
A SEQ ID NO: 28
Relevant codon optimized coding region of *Mysistica fragrans* fatty
acyl thioesterase with *Prototheca moriformis* delta 12 fatty acid
desaturase chloroplast transit peptide.
ACTAGTATGGCTATCAAGACGAACAGGCAGCCTGTGGAGAAGCCTCCGTTCACGATCGGGACGCTGCGC
AAGGCCATCCCCGCGCACTGTTTCGAGCGCTCGGCGCTTCGTGGGCGCGCCGCCAACGCCCACACCGTG
CCCAAGATCAACGGCAACAAGGCCGGCCTGCTGACCCCCATGGAGAGCACCAAGGACGAGGACATCGTC
GCGGCCCCCACCGTGGCGCCCAAGCGCACCTTCATCAACCAGCTGCCCGACTGGTCGATGCTGCTGGCC
GCGATCACCACCATCTTCCTGGCGGCCGAGAAGCAGTGGACCAACCTGGACTGGAAGCCCCGCCGCCCC
GACATGCTGGTCGACTTCGACCCCTTCTCCCTGGGCCGCTTCGTGCAGGACGGCCTGATCTTCCGCCAG
AACTTCAGCATCCGCTCGTACGAGATCGGCGCGGACCGCACCGCCTCCATCGAGACCCTGATGAACCAC
CTGCAGGAGACCGCGCTGAACCACGTCCGCTGCATCGGCCTGCTGGACGACGGCTTCGGCAGCACCCCC
GAGATGACCCGCCGCGACCTGATCTGGGTGGTCACCCGCATGCAGGTCCTGGTGGACCGCTACCCCTCG
TGGGGCGACGTGATCGAGGTCGACTCCTGGGTGACCCCCAGCGGCAAGAACGGCATGAAGCGCGAGTGG
TTCCTGCGCGACTGCAAGACCGGCGAGATCCTGACCCGCGCCACCTCGGTCTGGGTGATGATGAACAAG
CGCACCCGCCGCCTGTCCAAGATCCCCGAGGAGGTCCGCGTGGAGATCGAGCCCTACTTCGTCGAGCAC
GGCGTGCTGGACGAGGACTCGCGCAAGCTGCCCAAGCTGAACGACAACACCGCCAACTACATCCGCCGC
GGCCTGGCGCCCCGCTGGTCCGACCTGGACGTCAACCAGCACGTGAACAACGTCAAGTACATCGGCTGG |

| INFORMAL SEQUENCE LISTING |
| --- |
| ATCCTGGAGAGCGTGCCCAGCAGCCTGCTGGAGTCGCACGAGCTGTACGGCATGACCCTGGAGTACCGC
AAGGAGTGCGGCAAGGACGGCCTGCTGCAGTCCCTGACCGCCGTCGCCAGCGACTACGGCGGCGGCTCG
CTGGAGGCCGGCGTGGAGTGCGACCACCTGCTGCGCCTGGAGGACGGCTCCGAGATCATGCGCGGCAAG
ACCGAGTGGCGCCCCAAGCGCGCCGCGAACACCACCTACTTCGGCAGCGTCGACGACATCCCCCCCGCC
AACAACGCGTGACTCGAG

SEQ ID NO: 29
*Cuphea palustris* C14 preferring thioesterase (Genbank AAC49180) amino
acid sequence with *Chlorella protothecoides* stearoyl ACP desaturase
transit peptide.
MATASTFSAFNARCGDLRRSAGSGPRRPARPLPVRGRASMLLSAVTTVFGVAEKQWPMLDRKSKRPDML
VEPLGVDRIVYDGVSFRQSFSIRSYEIGADRTASIETLMNMFQETSLNHCKIIGLLNDGFGRTPEMCKR
DLIWVVTKMQIEVNRYPTWGDTIEVNTWVSASGKHGMGRDWLISDCHTGEILIRATSVWAMMNQKTRRL
SKIPYEVRQEIEPQFVDSAPVIVDDRKFHKLDLKTGDSICNGLTPRWTDLDVNQHVNNVKYIGWILQSV
PTEVFETQELCGLTLEYRRECGRDSVLESVTAMDPSKEGDRSLYQHLLRLEDGADIVKGRTEWRPKNAG
AKGAILTGKTSNGNSIS SEQ ID NO: 30
Relevant codon optimized coding region of *Cuphea palustris* C14
preferring thioesterase with *Chlorella protothecoides* stearoyl ACP
desaturase transit peptide.
ACTAGTATGGCCACCGCATCCACTTTCTCGGCGTTCAATGCCCGCTGCGGCGACCTGCGTCGCTCGGCG
GGCTCCGGGCCCCGGCGCCCAGCGAGGCCCCTCCCCGTGCGCGGGCGCGCCAGCATGCTGCTGTCGGCG
GTGACCACGGTCTTCGGCGTGGCCGAGAAGCAGTGGCCCATGCTGGACCGCAAGTCCAAGCGCCCCGAC
ATGCTGGTCGAGCCCCTGGGCGTGGACCGCATCGTCTACGACGGCGTGAGCTTCCGCCAGTCGTTCTCC
ATCCGCAGCTACGAGATCGGCGCCGACCGCACCGCCTCGATCGAGACGCTGATGAACATGTTCCAGGAG
ACCTCCCTGAACCACTGCAAGATCATCGGCCTGCTGAACGACGGCTTCGGCCGCACGCCCGAGATGTGC
AAGCGCGACCTGATCTGGGTCGTGACCAAGATGCAGATCGAGGTGAACCGCTACCCCACGTGGGGCGAC
ACCATCGAGGTCAACACGTGGGTGAGCGCCTCGGGCAAGCACGGCATGGGCCGCGACTGGCTGATCTCC
GACTGCCACACCGGCGAGATCCTGATCCGCGCGACGAGCGTCTGGGCGATGATGAACCAGAAGACCCGC
CGCCTGTCGAAGATCCCCTACGAGGTGCGCCAGGAGATCGAGCCCCAGTTCGTCGACTCCGCCCCCGTG
ATCGTGGACGACCGCAAGTTCCACAAGCTGGACCTGAAGACGGGCGACAGCATCTGCAACGGCCTGACC
CCCCGCTGGACGGACCTGGACGTGAACCAGCACGTCAACAACGTGAAGTACATCGGCTGGATCCTGCAG
TCGGTCCCCACCGAGGTGTTCGAGACGCAGGAGCTGTGCGGCCTGACCCTGGAGTACCGCCGCGAGTGC
GGCCGCGACTCCGTGCTGGAGAGCGTCACGGCCATGGACCCCTCGAAGGAGGGCGACCGCTCCCTGTAC
CAGCACCTGCTGCGCCTGGAGGACGGCGCGGACATCGTGAAGGGCCGCACCGAGTGGCGCCCCAAGAAC
GCCGGCGCCAAGGGCGCCATCCTGACGGGCAAGACCAGCAACGGCAACTCGATCTCCTGACTCGAG SEQ ID NO: 31
*Ulmus americana* broad specificity thioesterase (Genbank AAB71731)
amino acid sequence with *Chlorella protothecoides* stearoyl ACP
desaturase transit peptide.
MATASTFSAFNARCGDLRRSAGSGPRRPARPLPVRGRAQLPDWSMLLAAITTLFLAAEKQWMMLDWKPK
RPDMLVDPFGLGRFVQDGLVFRNNFSIRSYEIGADRTASIETLMNHLQETALNHVKSVGLLEDGLGSTR
EMSLRNLIWVVTKMQVAVDRYPTWGDEVQVSSWATAIGKNGMRREWIVTDFRTGETLLRATSVWVMMNK
LTRRISKIPEEVWHEIGPSFIDAPPLPTVEDDGRKLTRFDESSADFIRKGLTPRWSDLDINQHVNNVKY
IGWLLESAPPEIHESHEIASLTLEYRRECGRDSVLNSATKVSDSSQLGKSAVECNHLVRLQNGGEIVKG
RTVWRPKRPLYNDGAVVDVPAKTS SEQ ID NO: 32
Relevant codon optimized coding region of *Ulmus americana* broad
specificity thioesterase with *Chlorella protothecoides* stearoyl ACP
desaturase transit peptide.
ACTAGTATGGCCACCGCATCCACTTTCTCGGCGTTCAATGCCCGCTGCGGCGACCTGCGTCGCTCGGCG
GGCTCCGGGCCCCGGCGCCCAGCGAGGCCCCTCCCCGTGCGCGGGCGCGCCAGCTGCCCGACTGGAGC
ATGCTGCTGGCCGCGATCACCACCCTGTTCCTGGCGGCCGAGAAGCAGTGGATGATGCTGGACTGGAAG
CCCAAGCGCCCCGACATGCTGGTGGACCCCTTCGGCCTGGGCCGCTTCGTGCAGGACGGCCTGGTGTTC
CGCAACAACTTCAGCATCCGCAGCTACGAGATCGGCGCGGACCGCACCGCCAGCATCGAGACCCTGATG
AACCACCTGCAGGAGACGCCCCTGAACCACGTGAAGAGCGTGGGCCTGCTGGAGGACGGCCTGGGCAGC
ACCCGCGAGATGAGCCTGCGCAACCTGATCTGGGTGGTGACCAAGATGCAGGTGGCGGTGGACCGCTAC
CCCACCTGGGGCGACGAGGTGCAGGTGAGCAGCTGGGCGACCGCCATCGGCAAGAACGGCATGCGCCGC
GAGTGGATCGTGACCGACTTCCGCACCGGCGAGACCCTGCTGCGCGCCACCAGCGTGTGGGTGATGATG
AACAAGCTGACCCGCCGCATCAGCAAGATCCCCGAGGAGGTGTGGCACGAGATCGGCCCCAGCTTCATC
GACGCGCCCCCCCTGCCCACCGTGGAGGACGACGGCCGCAAGCTGACCCGCTTCGACGAGAGCAGCGCC
GACTTCATCCGCAAGGGCCTGACCCCCCGCTGGAGCGACCTGGACATCAACCAGCACGTGAACAACGTG
AAGTACATCGGCTGGCTGCTGGAGAGCGCGCCCCCCGAGATCCACGAGGCGCACGAGATCGCCAGCCTG
ACCCTGGAGTACCGCCGCGAGTGCGGCCGCGACAGCGTGCTGAACAGCGCCACCAAGGTGAGCGACAGC
AGCCAGCTGGGCAAGAGCGCCGTGGAGTGCAACCACCTGGTGCGCCTGCAGAACGGCGGCGAGATCGTG
AAGGGCCGCACCGTGTGGCGCCCCAAGCGCCCCCTGTACAACGACGGCGCCGTGGTGGACGTGCCCGCC
AAGACCAGCTGACTCGAG SEQ ID NO: 33
Codon optimized *Prototheca moriformis* (UTEX 1435) delta 12 fatty acid
desaturase transit peptide cDNA sequence.
ACTAGTATGGCTATCAAGACGAACAGGCAGCCTGTGGAGAAGCCTCCGTTCACGATCGGGACGCTGCGC
AAGGCCATCCCCGCGCACTGTTTCGAGCGCTCGGCGCTTCGTGGGCGCGCC |

INFORMAL SEQUENCE LISTING

SEQ ID NO: 34
Codon optimized *Chlorella* protothecoides (UTEX 250) stearoyl ACP
desaturase transit peptide cDNA sequence.
ACTAGTATGGCCACCGCATCCACTTTCTCGGCGTTCAATGCCCGCTGCGGCGACCTGCGTCGCTCGGCG
GGCTCCGGGCCCCGGCGCCCAGCGAGGCCCCTCCCCGTGCGCGGGCGCGCC SEQ ID NO: 35
Revelant homologous recombination expression construct of codon
optimized coding region of *Ulmus americana* broad specificity
thioesterase.
GCTCTTCGGCCGCCGCCACTCCTGCTCGAGCGCGCCCGACTCGCGCTCCGCCTGCGCCCGCGCGTGCGC
CGCCAGCGCCTTGGCCTTTTCGCGCGCGCTCGTGCGCGTCGCTGATGTCCATCACCAGGTCCATGAGGTC
TGCCTTGCGCCGGCTGAGCCACTGCTTCGTCCGGGCGGCCAAGAGGAGCATGAGGGAGGACTCCTGGTC
CAGGGTCCTGACGTGGTCGCGGCTCTGGGAGCGGGCCAGCATCATCTGGCTCTGCCGCACCGAGGCCGC
CTCCAACTGGTCCTCCAGCAGCCGCAGTCGCCGCCGACCCTGGCAGAGGAAGACAGGTGAGGGGGGTAT
GAATTGTACAGAACAACCACGAGCCTTGTCTAGGCAGAATCCCTACCAGTCATGGCTTTACCTGGATGA
CGGCCTGCGAACAGCTGTCCAGCGACCCTCGCTGCCGCCGCTTCTCCCGCACGCTTCTTTCCAGCACCG
TGATGGCGCGAGCCAGCGCCGCACGCTGGCGCTGCGCTTCGCCGATCTGAGGACAGTCGGGGAACTCTG
ATCAGTCTAAACCCCCTTGCGCGTTAGTGTTGCCATCCTTTGCAGACCGGTGAGAGCCGACTTGTTGTG
CGCCACCCCCCACACCACCTCCTCCCAGACCAATTCTGTCACCTTTTTGGCGAAGGCATCGGCCTCGGC
CTGCAGAGAGGACAGCAGTGCCCAGCCGCTGGGGGTTGGCGGATGCACGCTCAGGTACCCTTTCTTGCG
CTATGACACTTCCAGCAAAGGTAGGGCGGGCTGCGAGACGGCTTCCCGGCGCTGCATGCAACACCGAT
GATGCTTCGACCCCCCGAAGCTCCTTCGGGGCTGCATGGGCGCTCCGATGCCGCTCCAGGGCGAGCGCT
GTTTAAATAGCCAGGCCCCCGATTGCAAAGACATTATAGCGAGCTACCAAAGCCATATTCAAACACCTA
GATCACTACCACTTCTACACAGGCCACTCGAGCTTGTGATCGCACTCCGCTAAGGGGGCGCCTCTTCCT
CTTCGTTTCAGTCACAACCCGCAAACGGCGCGCCATGCTGCTGCAGGCCTTCCTGTTCCTGCTGGCCGG
CTTCGCCGCCAAGATCAGCGCCTCCATGACGAACGAGACGTCCGACCGCCCCTGGTGCACTTCACCCC
CAACAAGGGCTGGATGAACGACCCCAACGGCCTGTGGTACGACGAGAAGGACGCCAAGTGGCACCTGTA
CTTCCAGTACAACCCGAACGACACCGTCTGGGGGACGCCCTTGTTCTGGGGCCACGCCACGTCCGACGA
CCTGACCAACTGGGAGGACCAGCCCATCGCCATCGCCCGAAGCGCAACGACTCCGGCGCCTTCTCCGG
CTCCATGGTGGTGGACTACAACAACACCTCCGGCTTCTTCAACGACACCATCGACCCGCGCCAGCGCTG
CGTGGCCATCTGGACCTACAACACCCCGGAGTCCGAGGAGCGACTACTCCTACAGCCTGGACGGCGG
CTACACCTTCACCGAGTACCAGAAGAACCCCGTGCTGGCCGCCAACTCCACCCAGTTCCGCGACCCGAA
GGTCTTCTGGTACGAGCCCTCCCAGAAGTGGATCATGACCGCGGCCAAGTCCCAGGACTACAAGATCGA
GATCTACTCCTCCGACGACCTGAAGTCCTGGAAGCTGGAGTCCGCGTTCGCCAACGAGGGCTTCCTCGG
CTACCAGTACGAGTGCCCCGGCCTGATCGAGGTCCCCACCGAGCGAGGTACCCCAGCAAGTCCTACTGGGT
GATGTTCATCTCCATCAACCCCGGCGCCCCGGCCGGCGGCTCCTTCAACCAGTACTTCGTCGGCAGCTT
CAACGGCACCCACTTCGAGGCCTTCGACAACCAGTCCCGCGTGGTGGACTTCGGCAAGGACTACTACGC
CCTGCAGACCTTCTTCAACACCGACCCGACCTACGGGAGCGCCCTGGGCATCGCGTGGGCCTCCAACTG
GGAGTACTCCGCCTTCGTGCCCACCAACCCCTGGCGCTCCTCCATGTCCCTCGTGCGCAAGTTCTCCCT
CAACACCGAGTACCAGGCCAACCCGGAGACGGAGCTGATCAACCTCGAAGGCCGAGCCGATCCTGAACAT
CAGCAACGCCGGCCCCTGGAGCCGGTTCGCCACCAACACCACGTTGACGAAGGCCAACAGCTACAACGT
CGACCTGTCCAACAGCACCGGCACCCTGGAGTTCGAGCTGGTGTACGCCGTCAACACCACCCAGACGAT
CTCCAAGTCCGTGTTCGCGGACCTCTCCCTCTGGTTCAAGGGCCTGGAGGACCCCGAGGAGTACCTCCG
CATGGGCTTCGAGGTGTCCGCGTCCTCCTTCTTCCTGGACCGCGGGAACAGCAAGGTGAAGTTCGTGAA
GGAGAACCCCTACTTCACCAACCGCATGAGCGTGAACAACCAGCCCTTCAAGAGCGAGAACGACCTGTC
CTACTACAAGGTGTACGGCTTGCTGGACCAGAACATCCTGGAGCTGTACTTCAACGACGGCGACGTCGT
GTCCACCAACACCTACTTCATGACCACCGGGAACGCCCTGGGCTCCGTGAACATGACGACGGGGGTGGA
CAACCTGTTCTACATCGACAAGTTCCAGGTGCGCGAGGTCAAGTGACAATTGGCAGCAGCTCGGAT
AGTATCGACACACTCTGGACGCTGGTCGTGTGATGGACTGTTGCCGCCACACTTGCTGCCTTGACCTGT
GAATATCCCTGCCGCTTTTATCAAACAGCCTCAGTGTGTTTGATCTTGTGTGTACGCGCTTTTGCGAGT
TGCTAGCTGCTTGTGCTATTTGCGAATACCACCCCAGCATCCCCTTCCCTCGTTTCATATCGCTTGCA
TCCCAACCGCAACTTATCTACGCTGTCCTGCTATCCCTCAGCGCTCCTGCTCCTTGCTCACTGCCCC
TCGCACAGCCTTGGTTTGGGCTCCGCCTGTATTCTCCTGGTACTGCAACCTGTAAACCAGCACTGCAAT
GCTGATGCACGGGAAGTAGTGGGATGGGAACACAAATGGAGGATCCCGCGTCTCGAACAGAGCGCGCAG
AGGAACGCTGAAGGTCTCGCCTCTGTCGCACCTCAGCGCGGCATACACCACAATAACCACCTGACGAAT
GCGCTTGGTTCTTCGTCCATTAGCGAAGCGTCCGGTTCACACACGTGCCACGTTGGCGAGGTGGCAGGT
GACAATGATCGGTGGAGCTGATGGTCGAAACGTTCACAGCCTAGGGATATCGAATTCCTTTCTTGCGCT
ATGACACTTCCAGCAAAGGTAGGGCGGGCTGCGAGACGGCTTCCCGGCGCTGCATGCAACACCGATGA
TGCTTCGACCCCCCGAAGCTCCTTCGGGGCTGCATGGGCGCTCCGATGCCGCTCCAGGGCGAGCGCTGT
TTAAATAGCCAGGCCCCCGATTGCAAAGACATTATAGCGAGCTACCAAAGCCATATTCAAACACCTAGA
TCACTACCACTTCTACACAGGCCACTCGAGCTTGTGATCGCACTCCGCTAAGGGGGCGCCTCTTCCTCT
TCGTTTCAGTCACAACCCGCAAACACTAGTATGGCCACCGCATCCACTTTCTCGGCGTTCAATGCCCGC
TGCGGCGACCTGCGTCGCTCGGCGGGCTCCGGGCCCCGGCGCCCAGCGAGGCCCCTCCCCGTGCGCGGG
CGCGCCCAGCTGCCCGACTGGAGCATGCTGCTGGCCGCGATCACCACCCTGTTCCTGGCGGCCGAGAAG
CAGTGGATGATGCTGGACTGGAAGCCCAAGCGCCCCGACATGCTGGTGGACCCCTTCGGCCTGGGCCGC
TTCGTGCAGGACGGCCTGGTGTTCCGCAACAACTTCAGCATCCGCAGCTACGAGATCGGCGCGGACCGC
ACCGCCAGCATCGAGACCCTGATGAACCACCTGCAGGAGACCGCCCTGAACCACGTGAAGAGCGTGGGC
CTGCTGGAGGACGGCCTGGGCAGCACCCGCGAGATGAGCCTGCGCAACCTGATCTGGGTGGTGACCAAG
ATGCAGGTGGCGGTGGACCGCTACCCCACCTGGGGCGACGAGGTGCAGGTGAGCAGCTGGGCGACCGCC
ATCGGCAAGAACGGCATGCGCCGCGAGTGGATCGTGACCGACTTCCGCACCGGCGAGACCCTGCTGCGC
GCCACCAGCGTGTGGGTGATGATGAACAAGCTGACCCGCCGCATCAGCAAGATCCCCGAGGAGGTGTGG
CACGAGATCGGCCCCAGCTTCATCGACGCGCCCCCCTGCCCACCGTGGAGGACGACGGCCGCAAGCTG
ACCCGCTTCGACGAGAGCAGCGCCGACTTCATCCGCAAGGGCCTGACCCCCGCTGGAGCGACCTGGAC
ATCAACCAGCACGTGAACAACGTGAAGTACATCGGCTGGCTGCTGGAGAGCGCGCCCCCGAGATCCAC
GAGAGCCACGAGATCGCCAGCCTGACCCTGGAGTACCGCCGCGAGTGCGGCCGCGACAGCGTGCTGAAC
AGCGCCACCAAGGTGAGCGACAGCAGCCAGCTGGGCAAGAGCGCCGTGGAGTGCAACCACCTGGTGCGC

| INFORMAL SEQUENCE LISTING |
| --- |
| CTGCAGAACGGCGGCGAGATCGTGAAGGGCCGCACCGTGTGGCGCCCCAAGCGCCCCCTGTACAACGAC
GGCGCCGTGGTGGACGTGCCCGCCAAGACCAGCGATGACGATGACAAGCTGGGATGACTCGAGTTAATT
AACTCGAGGCAGCAGCAGCTCGGATAGTATCGACACACTCTGGACGCTGGTCGTGTGATGGACTGTTGC
CGCCACACTTGCTGCCTTGACCTGTAATATCCCTGCCGCTTTTATCAAACAGCCTCAGTGTGTTTGAT
CTTGTGTGTACGCGCTTTTGCGAGTTGCTAGCTGCTTGTGCTATTTGCGAATACCACCCCCAGCATCCC
CTTCCCTCGTTTCATATCGCTTGCATCCCAACCGCAACTTATCTACGCTGTCCTGCTATCCCTCAGCGC
TGCTCCTGCTCCTGCTCACTGCCCCTCGCACAGCCTTGGTTTGGGCTCCGCCTGTATTCTCCTGGTACT
GCAACCTGTAAACCAGCACTGCAATGCTGATGCACGGGAAGTAGTGGGATGGGAACACAAATGGAAAGC
TGTAGAGCTCCTTGTTTTCCAGAAGGAGTTGCTCCTTGAGCCTTTCATTCTCAGCCTCGATAACCTCCA
AAGCCGCTCTAATTGTGGAGGGGGTTCGAATTTAAAAGCTTGGAATGTTGGTTCGTGCGTCTGGAACAA
GCCCAGACTTGTTGCTCACTGGGAAAAGGACCATCAGCTCCAAAAAACTTGCCGCTCAAACCGCGTACC
TCTGCTTTCGCGCAATCTGCCCTGTTGAAATCGCCACCACATTCATATTGTGACGCTTGAGCAGTCTGT
AATTGCCTCAGAATGTGGAATCATCTGCCCCCTGTGCGAGCCCATGCCAGGCATGTCGCGGGCGAGGAC
ACCCGCCACTCGTACAGCAGACCATTATGCTACCTCACAATAGTTCATAACAGTGACCATATTTCTCGA
AGCTCCCCAACGAGCACCTCCATGCTCTGAGTGGCCACCCCCGGCCCTGGTGCTTGCGGAGGGCAGGT
CAACCGGCATGGGGCTACCGAAATCCCCGACCGGATCCCACCACCCCCCGCGATGGGAAGAATCTCTCC
CGGGATGTGGGCCCACCACCAGCACAACCTGCTGGCCCAGGCGAGCGTCAAACCATACCACACAAATAT
CCTTGGCATCGGCCCTGAATTCCTTCTGCCGCTCTGCTACCCGGTGCTTCTGTCCGAAGCAGGGGTTGC
TAGGGATCGCTCCGAGTCCGCAAACCCTTGTCGCGTGGCGGGGCTTGTTCGAGCTTGTTCGAGCTTGAA
GAGCCTCTAGAGTCGACCTGCAGGCATGCAAGCTTGGCGTAATCATGGTCATAGCTGTTTCCTGTGTGA
AATTGTTATCCGCTCACAATTCCACACAACATACGAGCCGGAAGCATAAAGTGTAAAGCCTGGGGTGCC
TAATGAGTGAGCTAACTCACATTAATTGCGTTGCGCTCACTGCCCGCTTTCCAGTCGGGAAACCTGTCG
TGCCAGCTGCATTAATGAATCGGCCAACGCGCGGGGAGAGGCGGTTTGCGTATTGGGCGCTCTTCC

SEQ ID NO: 36
Revelant homologous recombination expression construct of codon
optimized coding region of *Cinnamomum camphora* C14 preferring
thioesterase.
GAATTCGCCCTCCCGTGATCACACAGGTGCCTTGCGAGCGTGATCACACTATTTTGGGGGTCCTACAGT
ACTGAAATGGTGAGAAGTCGTACTGAAATCAAGGATGAACAATGAAAATGGTGCTGTGGTGGCTTCTCA
AAGGTCAAGAATCAGTCGCTCGCGTCAGGAAATCGCGGCGTCAACCAGCGTGGGCGCGGTCAGTGGCCC
CGCACTGGTCACCATAGCCTCTCCTGCCACAGTAGCGATCCCCTGGGCGTTCACTCTCAGCAGCGGCTG
TACTGCCTCCCAGATTTTCTTCTTCTGGACCTGCGGGCGTGAGAGGATGAGCAGGGTGGGCCAAGGGCT
CAATCCTGAACGGCCCTCATTCGGTTTCCAATCCCACAACACATACCCACAGCAGGTCAGACCACGCAT
TCCACCATGCGCACCAATAACGTGTCCTTACCTGATTGGGTGTGGCAGGCTCCGTGGACAGGAGTGCCT
CGTCCCCCGCCCAGACCCGCTCCCCCGTCACGGCGGCGTCCGGGACCGCCAGCGGCTCCACCGCGGTGT
GATCCGCGTTGGCGGCGCAGAGCAGCATCCCAGCCGATTTGACCCCGCGCATGCTCCGAGGCTTGAGGT
TGGCCAGCACCACCACCCGCCGGCCGACAAGGTCCTCCAGGGTCACGTGCCGGACCAGGCCACTCACGA
TGGTGCGAGGGCCCCCCTCCTCGCCGAGGTCGATCTGCTCGACGTACAGACTGCGACATGCGTGGCGAG
TGGTCATCAGAAGGAAGCAGGTGTGCAGAAGGGGCACGTGGTTGGTATTGAGAGTAGCCAAAGCTTGGT
GCCAATCAGAAAGTCAACGCAGCTGCCTGCCTGGCTCGCGTACAATTCCTTTCTTGCGTATGACACTT
CCAGCAAAAGGTAGGGCGGGCTGCGAGACGGCTTCCCGGCGCTGCATGCAACACCGATGATGCTTCGAC
CCCCCGAAGCTCCTTCGGGGCTGCATGGGCGCTCCGATGCCGCTCCAGGGCGAGCGCTGTTTAAATAGC
CAGGCCCCCGATTGCAAAGACATTATAGCGAGCTACCAAAGCATATTCAAACACCTAGATCACTACCAC
TTCTACACAGGCCACTCGAGCTTGTGATCGCACTCCGCTAAGGGGCGCTCTTCCCTTCGTTTCAGTC
ACAACCCGCAAACGGCGCGCCATGCTGCTGCAGGCCTTCCTGTTCCTGCTGGCCGGCTTCGCCGCCAAG
ATCAGCGCCTCCATGACGAACGAGACGTCCGACCGCCCCCTGGTGCACTTCACCCCCAACAAGGGCTGG
ATGAACGACCCCAACGGCCTGTGGTACGACGAGAAGGACGCCAAGTGGCACCTGTACTTCCAGTACAAC
CCGAACGACACCGTCTGGGGGACGCCCTTGTTCTGGGGCCACGCCACGTCCGACGACCTGACCAACTGG
GAGGACCAGCCCATCGCCATCGCCCCGAAGCGCAACGACTCCGGCGCCTTCTCCGGCTCCATGGTGGTG
GACTACAACAACACCTCCGGCTTCTTCAACGACACCATCGACCCGCGCCAGCGCTGCGTGGCCATCTGG
ACCTACAACACCCCGGAGTCCGAGGAGCAGTACATCCTCTACAGCCTGGACGGCGGCTACACCTTCACC
GAGTACCAGAAGAACCCCGTGCTGGCCGCCAACTCCACCCAGTTCCGCGACTGCTGGTCCGGAAGGTCTTCTGGTAC
GAGCCCTCCCAGAAGTGGATCATGACCGCGGCCAAGTCCCAGGACTACAAGATCGAGATCTACTCCTCC
GACGACCTGAAGTCCTGGAAGCTGGAGTCCGCGTTCGCCAACGAGGGCTTCCTCGGCTACCAGTACGAG
TGCCCCGGCCTGATCGAGGTCCCCACCGAGCAGGACCCCAGCAAGTCCTACTGGGTGATGTTCATCTCC
ATCAACCCCGGCGCCCGGCCGGCGGCTCCTTCAACCAGTACTTCGTCGGCAGCTTCAACGGCACCCAC
TTCGAGGCCTTCGACAACCAGTCCCGCGTGGTGGACTTCGGCAAGGACTACTACGCCCTGCAGACCTTC
TTCAACACCGACCCGACCTACGGGAGCGCCCTGGGCATCGCGTGGGCCTCCAACTGGGAGTACTCCGCC
TTCGTGCCCACCAACCCCTGGCGCTCCTCCATGTCCCTCGTGCGCAAGTTCTCCCTCAACACCGAGTAC
CAGGCCAACCCGGAGACGGAGCTGATCAACCTGAAGGCCGACCGATCCTGAACATCAGCAACGCCGGC
CCCTGGAGCCGGTTCGCCACCAACACCACGTTGACGAAGGCCAACAGCTACAACGTCGACCTGTCCAAC
AGCACCGGCACCCTGGAGTTCGAGCTGGTGTACGCCGTCAACACCACCCAGACGATCTCCAAGTCCGTG
TTCGCGGACCTCTCCCTCTGGTTCAAGGGCCTGGAGGACCCCGAGGAGTACCTCCGCATGGGCTTCGAG
GTGTCCGCGTCCTCCTTCTTCCTGGACGCGGGAACAGCAAGGTGAAGTTCGTGAAGGAGAACCCCTAC
TTCACCAACCGCATGAGCGTGAACAACGCCAGCCCTTCAAGAGCGAGAAGGACCGTCGTCCTACTACAAGGTG
TACGGCTTGCTGGACCAGAACATCCTGGAGCTGTACTTCAACGACGGCGACTCGTGTCCACCAACACC
TACTTCATGACCACCGGGAACGCCCTGGGCTCCGTGAACATGACGACGGGGGTGGACAACCTGTTCTAC
ATCGACAAGTTCCAGGTGCGCGAGGTCAAGTGATTAATTAACTCGAGGCAGCAGCAGCTCGGATAGTAT
CGACACACTCTGGACGCTGGTCGTGTGATGGACTGTTGCCGCCACACTTGCTGCCTTGACCTGTAATA
TCCCTGCCGCTTTTATCAAACAGCCTCAGTGTGTTTGATCTTGTGTGTACGCGCTTTTGCGAGTTGCTA
GCTGCTTGTGCTATTTGCGAATACCACCCCCAGCATCCCCTTCCCTCGTTTCATATCGCTTGCATCCCAA
CCGCAACTTATCTACGCTGTCCTGCTATCCCTCAGCGCTGCTCCTGCTCCTGCTCACTGCCCCTCGCAC
AGCCTTGGTTTGGGCTCCGCCTGTATTCTCCTGGTACTGCAACCTGTAAACCAGCACTGCAATGCTGAT
GCACGGGAAGTAGTGGGATGGGAACACAAATGGAAAGCTTGAGCTCCTTTCTTGCGCTATGACACTTCC
AGCAAAAGGTAGGGCGGGCTGCGAGACGGCTTCCCGGCGCTGCATGCAACACCGATGATGCTTCGACCC
CCCGAAGCTCCTTCGGGGCTGCATGGGCGCTCCGATGCCGCTCCAGGGCGAGCGCTGTTTAAATAGCCA |

| INFORMAL SEQUENCE LISTING |
| --- |
| GGCCCCCGATTGCAAAGACATTATAGCGAGCTACCAAAGCCATATTCAAACACCTAGATCACTACCACT
TCTACACAGGCCACTCGAGCTTGTGATCGCACTCCGCTAAGGGGCGCCTCTTCCTCTTCGTTTCAGTC
ACAACCCGCAAACACTAGTATGACGTTCGGGGTCGCCTCCCGGCCATGGGCCGCGGTGTCTCCCTTCC
CCGGCCCAGGGTCGCGGTGCGCGCCCAGTCGGCGAGTCAGGTTTTGGAGAGCGGGCGCGCCCCCGACTG
GTCCATGCTGTTCGCCGTGATCACCACCATCTTCTCCGCCGCCGAGAAGCAGTGGACCAACCTGGAGTG
GAAGCCCAAGCCCAACCCCCCCAGCTGCTGGACGACCACTTCGGCCCCCACGGCCTGGTGTTCCGCCG
CACCTTCGCCATCCGCAGCTACGAGGTGGGCCCCGACCGCTCCACCAGCATCGTGGCCGTGATGAACCA
CCTGCAGGAGGCCGCCCTGAACCACGCCAAGTCCGTGGGCATCCTGGGCGACGGCTTCGGCACCACCCT
GGGAGATGTCCAAGCGCGACCTGATCTGGGTGGTGAAGCGCACCCACGTGGCCGTGGAGCGCTACCCCGC
CTGGGGCGACACCGTGGAGGTGGAGTGCTGGGTGGGCGCCTCCGGCAACAACGGCCGCCGCCACGACTT
CCTGGTGCGCGACTGCAAGACCGGCGAGATCCTGACCCGCTGCACCTCCCTGAGCGTGATGATGAACAC
CCGCACCCGCCGCCTGAGCAAGATCCCCGAGGAGGTGCGCGGCGAGATCGGCCCCGCCTTCATCGACAA
CGTGGCCGTGAAGGACGAGGAGATCAAGAAGCCCCAGAAGCTGAACGACTCCACCGCCGACTACATCCA
GGGCGGCCTGACCCCCGCTGGAACGACCTGGACATCAACCAGCACGTGAACAACATCAAGTACGTGGA
CTGGATCCTGGAGACCGTGCCCGACACGCATCTTCGAGAGCCACCACATCTCCTCCTTCACCATCGAGTA
CCGCCGCGAGTGCACCATGGACAGCGTGCTGCAGTCCCTGACCACCGTGAGCGGCGGCTCCTCCGAGGC
CGGCCTGGTGTGCGAGCACCTGCTGCAGCTGGAGGGCGGCAGCGAGGTGCTGCGCGCCAAGACCGAGTG
GCGCCCCAAGCTGACCGACTCCTTCCGCGGCATCAGCGTGATCCCCGCCGAGTCCAGCGTGATGGACTA
CAAGGACCACGACGGCGACTACAAGGACCACGACATCGACTACAAGGACGACGACGACAAGTGACTCGA
GGCAGCAGCAGCTCGGATAGTATCGACACACTCTGGACGCTGGTCGTGTGATGGACTGTTGCCGCCACA
CTTGCTGCCTTGACCTGTGAATATCCCTGCCGCTTTTATCAAACAGCCTCAGTGTGTTTGATCTTGTGT
GTACGCGCTTTTGCGAGTTGCTAGCTCTTGTGCTATTTGCGAATACCACCCCCAGCATCCCCTTCCCTC
GTTTCATATCGCTTGCATCCCAACCGCAACTTATCTACGCTGTCCTGCTATCCCTCAGCGCTGCTCCTG
CTCCTGCTCACTGCCCCTCGCACAGCCTTGGTTTGGGCTCCGCCTGTATTCTCCTGGTACTGCAACCTG
TAAACCAGCACTGCAATGCTGATGCACGGGAAGTAGTGGGATGGGAACACAAATGGAAAGCTGGTACCC
GTACCCATCAGCATCCGGGTGAATCTTGGCCTCCAAGATATGGCCAATCCTCACATCCAGCTTGGCAAA
ATCGACTAGACTGTCTGCAAGTGGGAATGTGGAGCACAAGGTTGCTTGTAGCGATCGACAGACTGGTGG
GGTACATTGACAGGTGGGCAGCGCCGCATCCATCGTGCCTGACGCGAGCGCCGCCGGTTGCTCGCCCGT
GCCTGCCGTCAAAGAGCGGCAGAGAAATCGGGAACCGAAAACGTCACATTGCCTGATGTTGTTACATGC
TGGACTAGACTTTCTTGGCGTGGGTCTGCTCCTCGCCAGGTGCGCGACGCCTCGGGGCTGGGTGCGAGG
GAGCCGTGCGGCCACGCATTTGACAAGACCCAAAGCTCGCATCTCAGACGGTCAACCGTTCGTATTATA
CATTCAACATATGGTACATACGCAAAAAGCATGCCAACGATGACATAGGCGAATTC |

SEQ ID NO: 37
Relevant expression construct for codon optimized coding region of
*Cuphea hookeriana* C10 preferring thioesterase with *Chlorella*
*protothecoides* stearoyl ACP desaturase transit peptide.

GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGCGTGATGCAAGCATGCC
TGGCGAAGACACATGGTGTGCGGATGCTGCCGGCTGCTGCCTGCTGCGCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGTGCTCCACACTGTCACCAGGCCCGCAAG
CTTTGCAGAACCATGCTCATGGACGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCAGCGGCGGGGGCCACC
CTTCTTGCGGGGTCGCGCCCCAGCCAGCGGTGATGCGCTGATCCCAAACGAGTTCACATTCATTTGCAT
GCCTGGAGAAGCGAGGCTGGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGGACTGCATTTGGGTGGGGCG
GCCGGCTGTTTCTTTCGTGTTGCAAAACGCGCCAGCTCAGCAACCTGTCCCGTGGGTCCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCCTCCACGCCGGCTCCCCCGCCGC
CTGGGTGGAGCGCCTGTTCGGCTACGACTGGGCCCAGCAGACCATCGGCTGCTCCGACGCCGCCGTGTT
CCGCCTGTCCGCCCAGGGCCGCCCCGTGCTGTTCGTGAAGACCGACCTGTCCGGCGCCCTGAACGAGCT
GCAGGACGAGGCCGCCCGCCTGTCCTGGCTGGCCACCACCGGCGTGCCCTGCGCCGCCGTGCTGGACGT
GGTGACCGAGGCCGGCCGCGACTGGCTGCTGCTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT
GGTGGACCAGGACGACCTGGACGAGGAGCACCAGGGCCTGGCCCCCGCCGAGCTGTTCGCCCGCCTGAA
GGCCCGCATGCCCGACGGCGAGGACCTGGTGGTGACCCACGGCGACGCCTGCCTGCCCAACATCATGGT
GGAGAACGGCCGCTTCTCCGGCTTCATCGACTGCGGCCGCCTGGGCGTGGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACCGCCTGCTGGACGAGTTCTTCTGACAATT
GGCAGCAGCAGCTCGGATAGTATCGACACACTCTGGACGCTGGTCGTGTGATGGACTGTTGCCGCCACA
CTTGCTGCCTTGACCTGTGAATATCCCTGCCGCTTTTATCAAACAGCCTCAGTGTGTTTGATCTTGTGT
GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCCTGTATTCTCCTGGTACTGCAACCT
GTAAACCAGCACTGCAATGCTGATGCACGGGAAGTAGTGGGATGGGAACACAAATGGAGGATCCCGCGT
CTCGAACAGAGCGCGCAGAGGAACGCTGAAGGTCTCGCCTCTGTCGCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACAGCCTAGGGATATC

```
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
GGGGGCGCCTCTTCCTCTTCGTTTCAGTCACAACCCGCAAACACTAGTATGGCCACCGCATCCACTTTC
TCGGCGTTCAATGCCCGCTGCGGCGACCTGCGTCGCTCGGCGGGCTCCGGGCCCGGCGCCCAGCGAGG
CCCCTCCCCGTGCGCGGGCGCGCCCAGCTGCCCGACTGGAGCCGCCTGCTGACCGCCATCACCACCGTG
TTCGTGAAGTCCAAGCGCCCCGACATGCACGACCGCAAGTCCAAGCGCCCCGACATGCTGGTGGACAGC
TTCGGCCTGGAGTCCACCGTGCAGGACGGCCTGGTGTTCCGCCAGTCCTTCTCCATCCGCTCCTACGAG
ATCGGCACCGACCGCACCGCCAGCATCGAGACCCTGATGAACCACCTGCAGGAGACCTCCCTGAACCAC
TGCCAAGAGCACCGGCATCCTGCTGGACGGCTTCGGCCGCACCCTGGAGATGTGCAAGCGCGACCTGATC
TGGGTGGTGATCAAGATGCAGATCAAGGTGAACCGCTACCCCGCCTGGGGCGACACCGTGGAGATCAAC
ACCCGCTTCAGCCGCCTGGGCAAGATCGGCATGGGCCGCGACTGGCTGATCTCCGACTGCAACACCGGC
GAGATCCTGGTGCGCGCCACCAGCGCCTACGCCATGATGAACCAGAAGACCCGCCGCCTGTCCAAGCTG
CCCTACGAGGTGCACCAGGAGATCGTGCCCCTGTTCGTGGACAGCCCCGTGATCGAGGACTCCGACCTG
AAGGTGCACAAGTTCAAGGTGAAGACCGGCGACAGCATCCAGAAGGGCCTGACCCCCGGCTGGAACGAC
CTGGACGTGAACCAGCACGTGTCCAACGTGAAGTACATCGGCTGGATCCTGGAGAGCATGCCCACCGAG
GTGCTGGAGACCCAGGAGCTGTGCTCCCTGGCCCTGGAGTACCGCCGCGAGTGCGGCCGCGACTCCGTG
CTGGAGAGCGTGACCGCCATGGACCCCAGCAAGGTGGGCGTGCGCTCCCAGTACCAGCACCTGCTGCGC
CTGGAGGACGGCACCGCCATCGTGAACGGCGCCACCGAGTGGCGCCCCAAGAACGCCGGCGCCAACGGC
GCCATCTCCACCGGCAAGACCAGCAACGGCAACTCCGTGTCCATGGACTACAAGGACCACGACGGCGAC
TACAAGGACCACGACATCGACTACAAGGACGACGACGACAAGTGACTCGAGGCAGCAGCAGCTCGGATA
GTATCGACACACTCTGGACGCTGGTCGTGTGATGGACTGTTGCCGCCACACTTGCTGCCTTGACCTGTG
AATATCCTGCCGCTTTTATCAAACAGCCTCAGTGTGTTTGATCTTGTGTGTACGCGCTTTTGCGAGTT
GCTAGCTGCTTGTGCTATTTGCGAATACCACCCCCAGCATCCCCTTCCCTCGTTTCATATCGCTTGCAT
CCCAACCGCAACTTATCTACGCTGTCCTGCTATCCCTCAGCGCTGCTCCTGCTCCTGCTCACTGCCCCT
CGCACAGCCTTGGTTTGGGCTCCGCCTGTATTCTCCTGGTACTGCAACCTGTAAACCAGCACTGCAATG
CTGATGCACGGGAAGTAGTGGGATGGGAACACAAATGGAAAGCTTGAGCTC

SEQ ID NO: 38
Relevant expression construct for codon optimized coding region of
Umbellularia californica C12 preferring thioesterase with Chlorella
protothecoides stearoyl ACP desaturase transit peptide.
GGTACCCGCCTGCAACGCAAGGGCAGCCACAGCCGCTCCCACCCGCCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGGCGTGATGCAAGCATGCC
TGGCGAAGACACATGGTGTGCGGATGCTGCCGGCTGCTGCCTGCTGCGCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCACCATCAGCAGGAGCGCATGCGAAGG
GACTGGCCCCATGCACGCCATGCCAAACCGGAGCGCACCGAGGCTCCACACTGTCACCAGGCCCGCAAG
CTTTGCAGAACCATGCTCATGGACGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCAGCGGCGGGGGCCACC
CTTCTTGCGGGGTCGCGCCCCAGCCAGCGGTGATGCGCTGATCCCAAACGAGTTCACATTCATTTGCAT
GCCTGGAGAAGCGAGGCTGGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGGACTGCATTTGGGTGGGGCG
GCCGGCTGTTTCTTTCGTGTTGCAAAACGCGCCAGCTCAGCAACCTGTCCCGTGGGTCCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCCTCCACGCCGGCTCCCCCGCCAG
CTGGGTGGAGCGCCTGTTCGGCTACGACTGGGCCCAGCAGACCATCGGCTGCTCCGACGCGCCGTGTT
CCGCCTGTCCGCCCAGGGCCGCCCCGTGCTGTTCGTGAAGACCGACCTGTCCGGCGCCCTGAACGAGCT
GCAGGACGAGGCCGCCCGCCTGTCCTGGCTGGCCACCACCGGCGTGCCCTGCGCCGCCGTGCTGGACGT
GGTGACCGAGGCCGGCCGCGACTGGCTGCTGTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT
GGTGGACCAGGACGACCTGGACGAGGAGCACCAGGGCCTGGCCCCCGCCGAGCTGTTCGCCCGCCTGAA
GGCCCGCATGCCCGACGGCGAAGGACCTGGTGGTGACCCACGGCGACGCCTGCCTGCCCAACATCATGGT
GGAGAACGGCCGCTTCTCCGGCTTCATCGACTGCGGCCGCCTGGGCGTGGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACGCCGCTGCTGGACGAGTTCTTCTGACAATT
GGCAGCAGCAGCTCGGATAGTATCGACACACTCTGGACGCTGGTCGTGTGATGGACTGTTGCCGCCACA
CTTGCTGCCTTGACCTGTGAATATCCTGCCGCTTTTATCAAACAGCCTCAGTGTGTTTGATCTTGTGT
GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCCTGTATTCTCCTGGTACTGCAACCT
GTAAACCAGCACTGCAATGCTGATGCACGGGAAGTAGTGGGATGGGAACACAAATGGAGGATCCCGCGT
CTCGAACAGAGCGCGCAGAGGAACGCTGAAGGTCTCGCCTCTGCCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACAGCCTAGGGATATC
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
```

-continued

INFORMAL SEQUENCE LISTING

```
GGGGGCGCCTCTTCCTCTTCGTTTCAGTCACAACCCGCAAACACTAGTATGGCCACCGCATCCACTTTC
TCGGCGTTCAATGCCCGCTGCGGCGACCTGCGTCGCTCGGCGGGCTCCGGGCCCGGCGCCCAGCGAGG
CCCCTCCCCGTGCGCGGGCGCGCCCCCGACTGGTCCATGCTGTTCGCCGTGATCACCACCATCTTCAGC
GCCGCCGAGAAGCAGTGGACCAACCTGGAGTGGAAGCCCAAGCCCAAGCTGCCCCAGCTGCTGGACGAC
CACTTCGGCCTGCACGGCCTGGTGTTCCGCCGCACCTTCGCCATCCGCTCCTACGAGGTGGGCCCCGAC
CGCAGCACCTCCATCCTGGCCGTGATGAACCACATGCAGGAGGCCACCCTGAACCACGCCAAGAGCGTG
GGCATCCTGGGCGACGGCTTCGGCACCACCCTGGAGATGTCCAAGCGCGACCTGATGTGGGTGGTGCGC
CGCACCCACGTGGCCGTGGAGCGCTACCCCACCTGGGGCGACACCGTGGAGGTGGAGTGCTGGATCGGC
GCCAGCGGCAACAACGGCATGCGCCGCGACTTCCTGGTGCGCGACTGCAAGACCGGCGAGATCCTGACC
CGCTGCACCTCCCTGAGCGTGCTGATGAACACCCGCACCCGCCGCCTGAGCACCATCCCCGACGAGGTG
CGCGGCGAGATCGGCCCCGCCTTCATCGACAACGTGGCCGTGAAGGACGACGAGATCAAGAAGCTGCAG
AAGCTGAACGACTCCACCGCCGACTACATCCAGGGCGGCCTGACCCCCCGCTGGAACGACCTGGACGTG
AACCAGCACGTGAACAACCTGAAGTACGTGGCCTGGGTGTTCGAGACCGTGCCCGACAGCATCTTCGAG
TCCCACCACATCAGCTCCTTCACCCTGGAGTACCGCCGCGAGTGCACCCGCGACTCCGTGCTGCGCAGC
CTGACCACCGTGAGCGGCGGCAGCTCCGAGGCCGGCCTGGTGTGCGACCACCTGCTGCAGCTGGAGGGC
GGCAGCGAGGTGCTGCGCGCCCGCACCGAGTGGCGCCCCAAGCTGACCGACTCCTTCCGCGGCATCAGC
GTGATCCCCGCCGAGCCCCGCGTGATGGACTACAAGGACCACGACGGCGACTACAAGGACCACGACATC
GACTACAAGGACGACGACGACAAGTGACTCGAGGCAGCAGCAGCTCGGATAGTATCGACACACTCTGGA
CGCTGGTCGTGTGATGGACTGTTGCCGCCACACTTGCTGCCTTGACCTGTGAATATCCCTGCCGCTTTT
ATCAAACAGCCTCAGTGTGTTTGATCTTGTGTGTACGCGCTTTTGCGAGTTGCTAGCTGCTTGTGCTAT
TTGCGAATACCACCCCCAGCATCCCCTTCCCTCGTTTCATATCGCTTGCATCCCAACCGCAACTTATCT
ACGCTGTCCTGCTATCCCTCAGCGCTGCTCCTGCTCCTGCTCACTGCCCCTCGCACAGCCTTGGTTTGG
GCTCCGCCTGTATTCTCCTGGTACTGCAACCTGTAAACCAGCACTGCAATGCTGATGCACGGGAAGTAG
TGGGATGGGAACACAAATGGAAAGCTTGAGCTC

SEQ ID NO: 39
Relevant expression construct for codon optimized coding region of
Ulmus americana broad specificity thioesterase with Chlorella
protothecoides stearoyl ACP desaturase transit peptide.
GGTACCCGCCTGCAACGCAAGGGCAGCCACAGCCGCTCCCACCCGCGCTGAACCGACACGTGCTTGGG
CGCCTGCCGCCTGCCTGCCGCATGCTTGTGCTGGTGAGGCTGGGCAGTGCTGCCATGCTGATTGAGGCT
TGGTTCATCGGGTGGAAGCTTATGTGTGTGCTGGGCTTGCATGCCGGGCAATGCGCATGGTGGCAAGAG
GGCGGCAGCACTTGCTGGAGCTGCCGCGGTGCCTCCAGGTGGTTCAATCGCGGCAGCCAGAGGGATTTC
AGATGATCGCGCGTACAGGTTGAGCAGCAGTGTCAGCAAAGGTAGCAGTTTGCCAGAATGATCGGTTCA
GCTGTTAATCAATGCCAGCAAGAGAAGGGGTCAAGTGCAAACACGGGCATGCCACAGCACGGGCACCGG
GGAGTGGAATGGCACCACCAAGTGTGTGCGAGCCAGCATCGCCGCCTGGCTGTTTCAGCTACAACGGCA
GGAGTCATCCAACGTAACCATGAGCTGATCAACACTGCAATCATCGGGCGGGCGTGATGCAAGCATGCC
TGGCGAAGACACATGGTGTGCGGATGCTGCCGGCTGCTGCCTGCTGCGCACGCCGTTGAGTTGGCAGCA
GGCTCAGCCATGCACTGGATGGCAGCTGGGCTGCCACTGCAATGTGGTGGATAGGATGCAAGTGGAGCG
AATACCAAACCCTCTGGCTGCTTGCTGGGTTGCATGGCATCGCCACCATCAGCAGGAGCGCATGCGAAGG
GACTGGCCCCATGCACGCCATGCCAAACCGGAGCGCACCGAGTGTCCACACTGTCACCAGGCCCGCAAG
CTTTGCAGAACCATGCTCATGGACGCATGTAGCGCTGACGTCCCTTGACGGCGCTCCTCTCGGGTGTGG
GAAACGCAATGCAGCACAGGCAGCAGAGGCGGCGGCAGCAGAGCGGCGGCAGCAGCGGCGGGGGCCACC
CTTCTTGCGGGGTCGCGCCCCAGCCAGCGGTGATGCGCTGATCCCAAACGAGTTCACATTCATTTGCAT
GCCTGGAGAAGCGAGGCTGGGGCCTTTGGGCTGGTGCAGCCCGCAATGGAATGCGGGACCGCCAGGCTA
GCAGCAAAGGCGCCTCCCCTACTCCGCATCGATGTTCCATAGTGCATTGGACTGCATTTGGGTGGGGCG
GCCGGCTGTTTCTTTCGTGTTGCAAAACGCGCCAGCTCAGCAACCTGTCCCGTGGGTCCCCCGTGCCGA
TGAAATCGTGTGCACGCCGATCAGCTGATTGCCCGGCTCGCGAAGTAGGCGCCCTCCTTTCTGCTCGCC
CTCTCTCCGTCCCGCCTCTAGAATATCAATGATCGAGCAGGACGGCCTCCACGCCGGCTCCCCCGCCGC
CTGGGTGGAGCGCCTGTTCGGCTACGACTGGGCCCAGCAGACCATCGGCTGCTCCGACGCCGCCGTGTT
CCGCCTGTCCGCCCAGGGCCGCCCCGTGCTGTTCGTGAAGACCGACCTGTCCGGCGCCCTGAACGAGCT
GCAGGACGAGGCCGCCCGCCTGTCCTGGCTGGCCACCACCGGCGTGCCCTGCGCCGCCGTGCTGGACGT
GGTGACCGAGGCCGGCCGCGACTGGCTGCTGCTGGGCGAGGTGCCCGGCCAGGACCTGCTGTCCTCCCA
CCTGGCCCCCGCCGAGAAGGTGTCCATCATGGCCGACGCCATGCGCCGCCTGCACACCCTGGACCCCGC
CACCTGCCCCTTCGACCACCAGGCCAAGCACCGCATCGAGCGCGCCCGCACCCGCATGGAGGCCGGCCT
GGTGGACCAGGACGACCTGGACGAGGAGCACCAGGGCCTGGCCCCCGCCGAGCTGTTCGCCCGCCTGAA
GGCCCGCATGCCCGACGGCGAGGACCTGGTGGTGACCCACGGCGACGCCTGCCTGCCCAACATCATGGT
GGAGAACGGCCGCTTCTCCGGCTTCATCGACTGCGGCCGCCTGGGCGTGGCCGACCGCTACCAGGACAT
CGCCCTGGCCACCCGCGACATCGCCGAGGAGCTGGGCGGCGAGTGGGCCGACCGCTTCCTGGTGCTGTA
CGGCATCGCCGCCCCCGACTCCCAGCGCATCGCCTTCTACCGCCTGCTGGACGAGTTCTTCTGACAATT
GGCAGCAGCAGCTCGGATAGTATCGACACACTCTGGACGCTGGTCGTGATGGACTGTTGCCGCCACACA
CTTGCTGCCTTGACCTGTGAATATCCCTGCCGCTTTTATCAAACAGCCTCAGTGTGTTTGATCTTGTGT
GTACGCGCTTTTGCGAGTTGCTAGCTGCTTGTGCTATTTGCGAATACCACCCCCAGCATCCCCTTCCCT
CGTTTCATATCGCTTGCATCCCAACCGCAACTTATCTACGCTGTCCTGCTATCCCTCAGCGCTGCTCCT
GCTCCTGCTCACTGCCCCTCGCACAGCCTTGGTTTGGGCTCCGCCTGTATTCTCCTGGTACTGCAACCT
GTAAACCAGCACTGCAATGCTGATGCACGGGAAGTAGTGGGATGGGAACACAAATGGAAAGCTTCCCGT
CTCGAACAGAGCGCGCAGAGGAACGCTGAAGGTCTCGCCTCTGTCGCACCTCAGCGCGGCATACACCAC
AATAACCACCTGACGAATGCGCTTGGTTCTTCGTCCATTAGCGAAGCGTCCGGTTCACACACGTGCCAC
GTTGGCGAGGTGGCAGGTGACAATGATCGGTGGAGCTGATGGTCGAAACGTTCACGCCTAGGGATATC
GAATTCCTTTCTTGCGCTATGACACTTCCAGCAAAAGGTAGGGCGGGCTGCGAGACGGCTTCCCGGCGC
TGCATGCAACACCGATGATGCTTCGACCCCCCGAAGCTCCTTCGGGGCTGCATGGGCGCTCCGATGCCG
CTCCAGGGCGAGCGCTGTTTAAATAGCCAGGCCCCCGATTGCAAAGACATTATAGCGAGCTACCAAAGC
CATATTCAAACACCTAGATCACTACCACTTCTACACAGGCCACTCGAGCTTGTGATCGCACTCCGCTAA
GGGGGCGCCTCTTCCTCTTCGTTTCAGTCACAACCCGCAAACACTAGTATGGCCACCGCATCCACTTTC
TCGGCGTTCAATGCCCGCTGCGGCGACCTGCGTCGCTCGGCGGGCTCCGGGCCCGGCGCCCAGCGAGG
CCCCTCCCCGTGCGCGGGCGCGCCCAGCTGCCCGACTGGAGCATGCTGCTGGCCGCGATCACCACCCTG
TTCCTGGCGGCCGAGAAGCAGTGGATGATGCTGGACTGGAAGCCCAAGCGCCCCGACATGCTGGTGGAC
```

```
CCCTTCGGCCTGGGCCGCTTCGTGCAGGACGGCCTGGTGTTCCGCAACAACTTCAGCATCCGCAGCTAC
GAGATCGGCGCGGACCGCACCGCCAGCATCGAGACCCTGATGAACCACCTGCAGGAGACCGCCCTGAAC
CACGTGAAGAGCGTGGGCCTGCTGGAGGACGGCCTGGGCGACCACCCGCGAGATGAGCCTGCGCAACCTG
ATCTGGGTGGTGACCAAGATGCAGGTGGCGGTGGACCGCTACCCCACCTGGGGCGACGAGGTGCAGGTG
AGCAGCTGGGCGACCGCCATCGGCAAGAACGGCATGCGCCGCGAGTGGATCGTGACCGACTTCCGCACC
GGCGAGACCCTGCTGCGCGCCACCAGCGTGTGGGTGATGATGAACAAGCTGACCCGCCGCATCAGCAAG
ATCCCCGAGGAGGTGTGGCACGAGATCGGCCCCAGCTTCATCGACGCGCCCCCCCTGCCCACCGTGGAG
GACGACGGCCGCAAGCTGACCCGCTTCGACGAGAGCAGCGCCGACTTCATCCGCAAGGGCCTGACCCCC
CGCTGGAGCGACCTGGACATCAACCAGCACGTGAACAACGTGAAGTACATCGGCTGGCTGCTGGAGAGC
GCGCCCCCCGAGATCCACGAGAGCCACGAGATCGCCAGCCTGACCCTGGAGTACCGCCGCGAGTGCGGC
CGCGACAGCGTGCTGAACAGCGCCACCAAGGTGAGCGACAGCAGCCAGCTGGGCAAGAGCGCCGTGGAG
TGCAACCACCTGGTGCGCCTGCAGAACGGCGGCGAGATCGTGAAGGGCCGCACCGTGTGGCGCCCCAAG
CGCCCCCTGTACAACGACGGCGCCGTGGTGGACGTGCCCGCCAAGACCAGCGATGACGATGACAAGCTG
GGATGACTCGAGGCAGCAGCAGCTCGGATAGTATCGACACACTCTGGACGCTGGTCGTGTGATGGACTG
TTGCCGCCACACTTGCTGCCTTGACCTGTGAATATCCCTGCCGCTTTTATCAAACAGCCTCAGTGTGTT
TGATCTTGTGTGTACGCGCTTTTGCGAGTTGCTAGCTGCTTGTGCTATTTGCGAATACCACCCCCAGCA
TCCCCTTCCCTCGTTTCATATCGCTTGCATCCCAACCGCAACTTATCTACGCTGTCCTGCTATCCCTCA
GCGCTGCTCCTGCTCCTGCTCACTGCCCCTCGCACAGCCTTGGTTTGGGCTCCGCCTGTATTCTCCTGG
TACTGCAACCTGTAAACCAGCACTGCAATGCTGATGCACGGGAAGTAGTGGGATGGGAACACAAATGGA
AAGCTTGAGCTC

SEQ ID NO: 40
5' donor DNA sequence of Prototheca moriformis delta 12 FAD knockout
homologous recombination targeting construct
GCTCTTCGGGTTTGCTCACCCGCGAGGTCGACGCCCAGCATGGCTATCAAGACGAACAGGCAGCCTGTG
GAGAAGCCTCCGTTCACGATCGGGACGCTGCGCAAGGCCATCCCCGCGCACTGTTTCGAGCGCTCGGCG
CTTCGTAGCAGCATGTACCTGGCCTTTGACATCGCGGTCATGTCCCTGCTCTACGTCGCGTCGACGTAC
ATCGACCCTGCGCCGGTGCCTACGTGGGTCAAGTATGGCGTCATGTGGCCGCTCTACTGGTTCTTCCAG
GTGTGTGTGAGGGTTGTGGTTGCCCGTATCGAGGTCCTGGTGGCGCGCATGGGGAGAAGGCGCCTGTC
CCGCTGACCCCCCCGGCTACCCTCCCGGCACCTTCCAGGGCGCCTTCGGCACGGGTGTCTGGGTGTGCG
CGCACGAGTGCGGCCACCAGGCCTTTTCCTCCAGCCAGGCCATCAACGACGGCGTGGGCCTGGTGTTCC
ACAGCCTGCTGCTGGTGCCCTACTACTCCTGGAAGCACTCGCACCGCCGCCACCACTCCAACACGGGGT
GCCTGGACAAGGACGAGGTGTTTGTGCCGCCGCACCGCGCAGTGGCGCACGAGGGCCTGGAGTGGGAGG
AGTGGCTGCCCATCCGCATGGGCAAGGTGCTGGTCACCCTGACCCTGGGCTGGCCGCTGTACCTCATGT
TCAACGTCGCCTCGCGGCCGTACCCGCGCTTCGCCAACCACTTTGACCCGTGGTCGCCCATCTTCAGCA
AGCGCGAGGTACCCTTTCTTGCGTATGACACTTCCAGCAAAAGGTAGGGCGGGCTGCGAGACGGCTTC
CCGGCGCTGCATGCAACACCGATGATGCTTCGACCCCCCGAAGCTCCTTCGGGGCTGCATGGGCGCTCC
GATGCCGCTCCAGGGCGAGCGCTGTTTAAATAGCCAGGCCCCCGATTGCAAAGACATTATAGCGAGCTA
CCAAAGCCATATTCAAACACCTAGATCACTACCACTTCTACACAGGCCACTCGAGCTTGTGATCGCACT
CCGCTAAGGGGGCGCCTCTTCCTCTTCGTTTCAGTCACAACCCGCAAACGGCGCGCC SEQ ID NO: 41
3' donor DNA sequence of Prototheca moriformis delta 12 FAD knockout
homologous recombination targeting construct
CAATTGGCAGCAGCAGCTCGGATAGTATCGACACACTCTGGACGCTGGTCGTGTGATGGACTGTTGCCG
CCACACTTGCTGCCTTGACCTGTGAATATCCCTGCCGCTTTTATCAAACAGCCTCAGTGTGTTTGATCT
TGTGTGTACGCGCTTTTGCGAGTTGCTAGCTGCTTGTGCTATTTGCGAATACCACCCCCAGCATCCCCT
TCCCTCGTTTCATATCGCTTGCATCCCAACCGCAACTTATCTACGCTGTCCTGCTATCCCTCAGCGCTG
CTCCTGCTCCTGCTCACTGCCCCTCGCACAGCCTTGGTTTGGGCTCCGCCTGTATTCTCCTGGTACTGC
AACCTGTAAACCAGCACTGCAATGCTGATGCACGGGAAGTAGTGGGATGGGAACACAAATGGAGCATCG
AGGTGGTCATCTCCGACCTCGCGTTGGTGGCGGTGCTCAGCGGGCTCAGCGTGCTGGGCCGCACCATGG
GCTGGGCCTGGTGGTCAAGACCTACGTGGTGCCCTACATGATCGTGAACATGTGGCTGGTGCTCATCA
CGCTGCTCCAGCACACGCACCCGGCCCTGCCGCACTACTTCGAGAAGGACTGGGACTGGCTACGCGGCG
CCATGGCCACCGTCGACCGCTCCATGGGCCCGCCCTTCATGGACAGCATCCTGCACCACATCTCCGACA
CCCACGTGCTGCACCACCTCTTCAGCACCATCCCGCACTACCACGCCGAGGAGGCCTCCGCCGCCATCC
GGCCCATCCTGGGCAAGTACTACCAATCCGACAGCCGCTGGGTCGGCCGCGCCCTGTGGGAGGACTGGC
GCGACTGCCGCTACGTCGTCCCCGACGCGCCCGAGGACGACTCCGCGCTCTGGTTCCACAAGTGAGCGC
GCCTGCGCGAGGACGCAGAACAACGCTGCCGCCGTGTCTTTTGCACGCGCGACTCCGGCGCTTCGCTGG
TGGCACCCCCATAAAGAAACCCTCAATTCTGTTTGTGGAAGACACGGTGTACCCCCACCCACCCACCTG
CACCTCTATTATTGGTATTATTGACGCGGGAGTGGGCGTTGTACCCTACAACGTAGCTTCTCTAGTTTT
CAGCTGGCTCCCACCATTGTAAAGAGCCTCTAGAGTCGACCTGCAGCTCGAAGCTTGGCGTAATCAT
GGTCATAGCTGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGAGAGGCGGTT
TGCGTATTGGGCGCTCTTCC SEQ ID NO: 42
Prototheca moriformis delta 12 FAD knockout homologous recombination
targeting construct
GCTCTTCGGGTTTGCTCACCCGCGAGGTCGACGCCCAGCATGGCTATCAAGACGAACAGGCAGCCTGTG
GAGAAGCCTCCGTTCACGATCGGGACGCTGCGCAAGGCCATCCCCGCGCACTGTTTCGAGCGCTCGGCG
CTTCGTAGCAGCATGTACCTGGCCTTTGACATCGCGGTCATGTCCCTGCTCTACGTCGCGTCGACGTAC
ATCGACCCTGCGCCGGTGCCTACGTGGGTCAAGTATGGCGTCATGTGGCCGCTCTACTGGTTCTTCCAG
GTGTGTGTGAGGGTTGTGGTTGCCCGTATCGAGGTCCTGGTGGCGCGCATGGGGAGAAGGCGCCTGTC
CCGCTGACCCCCCCGGCTACCCTCCCGGCACCTTCCAGGGCGCCTTCGGCACGGGTGTCTGGGTGTGCG
CGCACGAGTGCGGCCACCAGGCCTTTTCCTCCAGCCAGGCCATCAACGACGCGTGGGCCTGGTGTTCC
ACAGCCTGCTGCTGGTGCCCTACTACTCCTGGAAGCACTCGCACCGCCGCCACCACTCCAACACGGGT
```

| INFORMAL SEQUENCE LISTING |
| --- |
| GCCTGGACAAGGACGAGGTGTTTGTGCCGCCGCACCGCGCAGTGGCGCACGAGGGCCTGGAGTGGGAGG
AGTGGCTGCCCATCCGCATGGGCAAGGTGCTGGTCACCCTGACCCTGGGCTGGCCGCTGTACCTCATGT
TCAACGTCGCCTCGCGGCCGTACCCGCGCTTCGCCAACCACTTTGACCCGTGGTCGCCCATCTTCAGCA
AGCGCGAGGTACCCTTTCTTGCGCTATGACACTTCCAGCAAAAGGTAGGGCGGGCTGCGAGACGGCTTC
CCGGCGCTGCATGCAACACCGATGATGCTTCGACCCCCCGAAGCTCCTTCGGGGCTGCATGGGCGCTCC
GATGCCGCTCCAGGGCGAGCGCTGTTTAAATAGCCAGGCCCCCGATTGCAAAGACATTATAGCGAGCTA
CCAAAGCCATATTCAAACACCTAGATCACTACCACTTCTACACAGGCCACTCGAGCTTGTGATCGCACT
CCGCTAAGGGGGCGCCTCTTCCTCTTCGTTTCAGTCACAACCCGCAAACGGCGCGCCATGCTGCTGCAG
GCCTTCCTGTTCCTGCTGGCCGGCTTCGCCGCCAAGATCAGCGCCTCCATGACGAACGAGACGTCCGAC
CGCCCCCTGGTGCACTTCACCCCCAACAAGGGCTGGATGAACGACCCCAACGGCCTGTGGTACGACGAG
AAGGACGCCAAGTGGCACCTGTACTTCCAGTACAACCCGAACGACACCGTCTGGGGGACGCCCTTGTTC
TGGGGCCACGCCACGTCCGACGACCTGACCAACTGGGAGGACCAGCCCATCGCCATCGCCCCGAAGCGC
AACGACTCCGGCGCCTTCTCCGGCTCCATGGTGGTGGACTACAACAACACCTCCGGCTTCTTCAACGAC
ACCATCGACCCGCGCCAGCGCTGCGTGGCCATCTGGACCTACAACACCCCGGAGTCCGAGGAGCAGTAC
ATCTCCTACAGCCTGGACGGCGGCTACACCTTCACCGAGTACCAGAAGAACCCCGTGCTGGCCGCCAAC
TCCACCCAGTTCCGCGACCCGAAGGTCTTCTGGTACGAGCCCTCCCAGAAGTGGATCATGACCGCGAAC
AAGTCCAGGACTACAAGATCGAGATCTACTCCTCCGACGACCTGAAGTCCTGGAAGCTGGAGTCCGCG
TTCGCCAACGAGGGCTTCCTCGGCTACCAGTACGAGTGCCCCGGCCTGATCGAGGTCCCCACCGAGCAG
GACCCCAGCAAGTCCTACTGGGTGATGTTCATCTCCATCAACCCCGGCGCCCGGCCGGCGGCTCCTTC
AACCAGTACTTCGTCGGCAGCTTCAACGGCACCCACTTCGAGGCCTTCGACAACCAGTCCCGCGTGGTG
GACTTCGGCAAGGACTACTACGCCCTGCAGACCTTCTTCAACACCGACCCGACCTACGGGAGCGCCCTG
GGCATCGCGTGGGCCTCCAACTGGGAGTACTCCGCCTTCGTGCCCACCAACCCCTGGCGCTCCTCCATG
TCCCTCGTGCGCAAGTTCTCCCTCAACACCGAGTACCAGGCCAACCCGGAGACGGAGCTGATCAACCTG
AAGGCCGAGCCGATCCTGAACATCAGCAACGCCGGCCCCTGGAGCGCGGTTCGCCACCAACCACGTTG
ACGAAGGCCAACAGCTACAACGTCGACCTGTCCAACAGCACCGGCACCCTGGAGTTCGAGCTGGTGTAC
GCCGTCAACACCACCCAGACGATCTCCAAGTCCGTGTTCGCGGACCTCTCCCTCTGGTTCAAGGGCCTG
GAGGACCCCGAGGAGTACCTCCGCATGGGCTTCGAGGTGTCCGCGTCCTCCTTCTTCCTGGACCGCGGG
AACAGCAAGGTGAAGTTCGTGAAGGAGAACCCCTACTTCACCAACGCCATGAGCGTGAACAACCAGCCC
TTCAAGAGCGAGAACGACCTGTCCTACTACAAGGTGTACCGGCTTGCTGGACCAGAACATCCTGGAGCTG
TACTTCAACGACGGCGACGTCGTGTCCACCAACACCTACTTCATGACCACCGGGAACGCCCTGGGCTCC
GTGAACATGACGACGGGGGTGGACAACCTGTTCTACATCGACAAGTTCCAGGTGCGCGAGGTCAAGTGA
CAATTGGCAGCAGCAGCTCGGATAGTATCGACACACTCTGGACGCTGGTCGTGTGATGGACTGTTGCCG
CCACACTTGCTGCCTTGACCTGTGAATATCCCTGCCGCTTTTATCAAACAGCCTCAGTGTGTTTGATCT
TGTGTGTACGCGCTTTTGCGAGTTGCTAGCTGCTTGTGCTATTTGCGAATACCACCCCAGCATCCCCT
TCCCTCGTTTCATATCGCTTGCATCCCAACCGCAACTTATCTACGCTGTCCTGCTATCCCTCAGCGCTG
CTCCTGCTCCTGCTCACTGCCCCTCGCACAGCCTTGGTTTGGGCTCCGCCTGTATTCTCCTGGTACTGC
AACCTGTAAACCAGCACTGCAATGCTGATGCACGGGAAGTAGTGGGATGGGAACACAAATGGAGCATCG
AGGTGGTCATCTCCGACCTCGCGTTGGTGGCGGTGCTCAGCGGGCTCAGCGTGCTGGGCCGCACCATGG
GCTGGGCCTGGCTGGTCAAGACCTACGTGGTGCCCTACATGATCGTGAACATGTGGCTGGTGCTCATCA
CGCTGCTCCAGCACACGCACCCGGCCCTGCCGCACTACTTCGAGAAGGACTGGGACTGGCTACGCGGCG
CCATGGCCACCGTCGACCGCTCCATGGGCCCGCCCTTCATGGACAGCATCCTGCACCACATCTCCGACA
CCCACGTGCTGCACCACCTCTTCAGCACCATCCCGCACTACCACGCCGAGGAGGCCTCCGCCGCCATCC
GGCCCATCCTGGGCAAGTACTACCAATCCGACAGCCGCTGGGTCGGCCGCGCCCTGTGGGAGGACTGGC
GCGACTGCCGCTACGTCGTCCCCGACGCGCCCGAGGACGACTCCGCGCTCTGGTTCCACAAGTGAGCGC
GCCTGCGCGAGGACGCAGAACAACGCTGCCGCCGTGTCTTTTGCACGCGGACTCCGGCGCTTCGCTGG
TGGCACCCCCATAAAGAAACCCTCAATTCTGTTTGTGGAAGACACGGTGTACCCCACCCACCCACCTG
CACCTCTATTATTGGTATTATTGACGCGGGAGTGGGCGTTGTACCCTACAACGTAGCTTCTCTAGTTTT
CAGCTGGCTCCCACCATTGTAAAGAGCCTCTAGAGTCGACCTGCAGGCATGCAAGCTTGGCGTAATCAT
GGTCATAGCTGTTTCCTGTGTGAAATTGTTATCCGCTCACAATTCCACACAACATACGAGCCGGAAGCA
TAAAGTGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGAGAGGCGGTT
TGCGTATTGGGCGCTCTTCC |

SEQ ID NO: 43
5' donor DNA sequence of *Prototheca moriformis* SAD2A knockout
homologous recombination targeting construct
GCTCTTCCGCCTGGAGCTGGTGCAGAGCATGGGTCAGTTTGCGGAGGAGAGGGTGCTCCCCGTGCTGCA
CCCCGTGGACAAGCTGTGGCAGCCGCAGGACTTCCTGCCCGACCCCGAGTCGCCCGACTTCGAGGACCA
GGTGGCGGAGCTGCGCGCGCGCGCCAAGGACCTGCCCGACGAGTACTTTGTGGTGCTGGTGGGCGACAT
GATCACGGAGGAGGCGCTGCCGACCTACATGGCCATGCTCAACACCTTGGACGGTGTGCGCGACGACAC
GGGCGCGGCTGACCACCCGTGGGCGCGCTGGACGCGGCAGTGGGTGGCCGAGGAGAACCGGCACGGCGA
CCTGCTGAACAAGTACTGTTGGCTGACGGGGCGCGTCAACATGCGGGCCGTGGAGGTGACCATCAACAA
CCTGATCAAGAGCGGCATGAACCCGCAGACGGACAACAACCCTTACTTGGGCTTCGTCTACACCTCCTT
CCAGGAGCGCGCCACCAAGTAGGTACC SEQ ID NO: 44
3' donor DNA sequence of *Prototheca moriformis* SAD2A knockout
homologous recombination targeting construct
CAATTGGCAGCAGCAGCTCGGATAGTATCGACACACTCTGGACGCTGGTCGTGTGATGGACTGTTGCCG
CCACACTTGCTGCCTTGACCTGTGAATATCCCTGCCGCTTTTATCAAACAGCCTCAGTGTGTTTGATCT
TGTGTGTACGCGCTTTTGCGAGTTGCTAGCTGCTTGTGCTATTTGCGAATACCACCCCAGCATCCCCT
TCCCTCGTTTCATATCGCTTGCATCCCAACCGCAACTTATCTACGCTGTCCTGCTATCCCTCAGCGCTG
CTCCTGCTCCTGCTCACTGCCCCTCGCACAGCCTTGGTTTGGGCTCCGCCTGTATTCTCCTGGTACTGC
AACCTGTAAACCAGCACTGCAATGCTGATGCACGGGAAGTAGTGGGATGGGAACACAAATGAAGGATC
GTAGAGCTCCAGCCACGGCAACACCGCGCGCCTGGCGGCCGAGCACGGCGACAAGGGCCTGAGCAAGAT
CTGCGGGCTGATCGCCAGCGACGAGGGCCGGCACGAGATCGCCTACACGCGCATCGTGGACGAGTTCTT
CCGCCTCGACCCCGAGGGCGCCGTCGCCGCCTACGCCAACATGATGCGCAAGCAGATCACCATGCCCGC

| INFORMAL SEQUENCE LISTING |
|---|
| GCACCTCATGGACGACATGGGCCACGGCGAGGCCAACCCGGGCCGCAACCTCTTCGCCGACTTCTCCGC |
| CGTCGCCGAGAAGATCGACGTCTACGACGCCGAGGACTACTGCCGCATCCTGGAGCACCTCAACGCGCG |
| CTGGAAGGTGGACGAGCGCCAGGTCAGCGGCCAGGCCGCCGCGGACCAGGAGTACGTTCTGGGCCTGCC |
| CCAGCGCTTCCGGAAACTCGCCGAGAAGACCGCCGCCAAGCGCAAGCGCGTCGCGCGCAGGCCCGTCGC |
| CTTCTCCTGGAGAGAAGAGCCTCTAGAGTCGACCTGCAGGCATGCAAGCTTGGCGTAATCATGGTCATA |
| GCTGTTTCCTGTGTGAAATTGTTATCCGCTCACAATTCCACACAACATACGAGCCGGAAGCATAAAGTG |
| TAAAGCCTGGGGTGCCTAATGAGTGAGCTAACTCACATTAATTGCGTTGCGCTCACTGCCCGCTTTCCA |
| GTCGGGAAACCTGTCGTGCCAGCTGCATTAATGAATCGGCCAACGCGCGGGGAGAGGCGGTTTGCGTAT |
| TGGGCGCTCTTCC |

SEQ ID NO: 45
*Prototheca moriformis* SAD2A knockout homologous recombination
targeting construct
GCTCTTCCGCCTGGAGCTGGTGCAGAGCATGGGTCAGTTTGCGGAGGAGAGGGTGCTCCCCGTGCTGCA
CCCCGTGGACAAGCTGTGGCAGCCGCAGGACTTCCTGCCCGACCCCGAGTCGCCCGACTTCGAGGACCA
GGTGGCGGAGCTGCGCGCGCGCGCCAAGGACCTGCCCGACGAGTACTTTGTGGTGCTGGTGGGCGACAT
GATCACGGAGGAGGCGCTGCCGACCTACATGGCCATGCTCAACACCTTGGACGGTGTGCGCGACGACAC
GGGCGCGGCTGACCACCCGTGGGCGCGCTGGACGCGGCAGTGGGTGGCCGAGGAGAACCGGCACGGCGA
CCTGCTGAACAAGTACTGTTGGCTGACGGGGCGCGTCAACATGCGGGCCGTGGAGGTGACCATCAACAA
CCTGATCAAGAGCGGCATGAACCCGCAGACGGACAACAACCCTTACTTGGGCTTCGTCTACACCTCCTT
CCAGGAGCGCGCCACCAAGTAGGGTACCCTTTCTTGCGCTATGACACTTCCAGCAAAAGGTAGGGCGGGC
TGCGAGACGGCTTCCCGGCGCTGCATGCAACACCGATGATGCTTCGACCCCCGAAGCTCCTTCGGGGC
TGCATGGGCGCTCCGATGCCGCTCCAGGGCGAGCGCTGTTTAAATAGCCAGGCCCCCGATTGCAAAGAC
ATTATAGCGAGCTACCAAAGCCATATTCAAACACCTAGATCACTACCACTTCTACACAGGCCACTCGAG
CTTGTGATCGCACTCCGCTAAGGGGCGCCTCTTCCTCTTCGTTTCAGTCACAACCCGCAAACGGCGCG
CCATGCTGCTGCAGGCCTTCCTGTTCCTGCTGGCCGGCTTCGCCGCCAAGATCAGCGCCTCCATGACGA
ACGAGACGTCCGACCGCCCCTGGTGCACTTCACCCCCAACAAGGGCTGGATGAACGACCCCAACGGCC
TGTGGTACGACGAGAAGGACGCCAAGTGGCACCTGTACTTCCAGTACAACCCGAACGACACCGTCTGGG
GGACGCCCTTGTTCTGGGGCCACGCCACGTCCGACGACCTGACCAACTGGGAGGACCAGCCCATCGCCA
TCGCCCCGAAGCGCAACGACTCCGGCGCCTTCTCCGGCTCCATGGTGGTGACTACAACAACACCTCCG
GCTTCTTCAACGACACCATCGACCCGCGCCAGCGCTGCGTGGCCATCTGGACCTACAACACCCCGGAGT
CCGAGGAGCAGTACATCTCCTACAGCCTGGACGGCGGCTACACCTTCACCGAGTACCAGAAGAACCCCG
TGCTGGCCGCCAACTCCACCCAGTTCCGCGACCCGAAGGTCTTCTGGTACGAGCCCTCCCAGAAGTGGA
TCATGACCGCGGCCAAGTCCCAGGACTACAAGATCGAGATCTACTCCTCCGACGACCTGAAGTCCTGGA
AGCTGGAGTCCGCGTTCGCCAACGAGGGCTTCCTCGGCTACCAGTACGAGTGCCCCGGCCTGATCGAGG
TCCCCACCGAGCAGGACCCCAGCAAGTCCTACTGGGTGATGTTCATCTCCATCAACCCCGGCGCCCGG
CCGGCGGCTCCTTCAACCAGTACTTCGTCGGCAGCTTCAACGGCACCCACTTCGAGGCCTTCGACAACC
AGTCCCGCGTGGTGGACTTCGGCAAGGACTACTACGCCCTGCAGACCTTCTTCAACACCGACCCGACCT
ACGGGAGCGCCCTGGGCATCGCGTGGGCCTCCAACTGGGAGTACTCCGCCTTCGTGCCCACCAACCCCT
GGCGCTCCTCCATGTCCCTCGTGCGCAAGTTCTCCCTCAACACCGAGTACCAGGCCAACCCGGAGACGG
AGCTGATCAACCTGAAGGCCGAGCCGATCCTGAACATCAGCAACGCCGGCCCCTGGAGCCGGTTCGCCA
CCAACACCACGTTGACGAAGGCCAACAGCTACAACGTCGACCTGTCCAACAGCACCGGCACCCTGGAGT
TCGAGCTGGTGTACGCCGTCAACACCACCCAGACGATCTCCAAGTCCGTGTTCGCGGACCTCTCCCTCT
GGTTCAAGGGCCTGGAGGACCCCGAGGAGTACCTCCGCATGGGCTTCGAGGTGTCCGCGTCCTCCTTCT
TCCTGGACCGCGGGAACAGCAAGGTGAAGTTCGTGAAGGAGAACCCCTACTTCACCAACCGCATGAGCG
TGAACAACCAGCCCTTCAAGAGCGAGAACGACCTGTCCTACTACAAGGTGTACGGCTTGCTGGACCAGA
ACATCCTGGAGCTGTACTTCAACGACGGCGACGTCGTGTCCACCAACACCTACTTCATGACCACCGGGA
ACGCCCTGGGCTCCGTGAACATGACGACGGGGGTGGACAACCTGTTCTACATCGACAAGTTCCAGGTGC
GCGAGGTCAAGTGACAATTGGCAGCAGCAGCTCGGATAGTATCGACACACTCTGGACGCTGGTCGTGTG
ATGGACTGTTGCCGCCACACTTGCTGCCTTGACCTGTGAATATCCCTGCCGCTTTTATCAAACAGCCTC
AGTGTGTTTGATCTTGTGTGTACGCGCTTTTGCGAGTTGCTAGCTGCTTGTGCTATTTGCGAATACCAC
CCCCAGCATCCCCTTCCCTCGTTTCATATCGCTTGCATCCCAACCGCAACTTATCTACGCTGTCCTGCT
ATCCCTCAGCCGCTGCTCCTGCTCCTGCTCACTGCCCCTCGCACAGCCTTGGTTTGGGCTCCGCCTGTAT
TCTCCTGGTACTGCAACCTGTAAACCAGCACTGCAATGCTGATGCACGGGAAGTAGTGGGATGGGAACA
CAAATGGAAGGATCGTAGAGCTCCAGCCACGGCAACACCGCGCGCCTGGCGGCCGAGCACGGCGACAAG
GGCCTGAGCAAGATCTGCGGGCTGATCGCCAGCGACGAGGGCCGACATCGCCTACACGCGCATC
GTGGACGAGTTCTTCCGCCTCGACCCCGAGGGCGCCGTCGCCGCCTACGCCAACATGATGCGCAAGCAG
ATCACCATGCCCGCGCACCTCATGGACGACATGGGCCACGGCGAGGCCAACCCGGGCCGCAACCTCTTC
GCCGACTTCTCCGCCGTCGCCGAGAAGATCGACGTCTACGACGCCGAGGACTACTGCCGCATCCTGGAG
CACCTCAACGCGCGCTGGAAGGTGGACGAGCGCCAGGTCAGCGGCCAGGCCGCCGCGGACCAGGAGTAC
GTTCTGGGCCTGCCCCAGCGCTTCCGGAAACTCGCCGAGAAGACCGCCGCCAAGCGCAAGCGTCGCG
CGCAGGCCCGTCGCCTTCTCCTGGAGAGAAGAGCCTCTAGAGTCGACCTGCAGGCATGCAAGCTTGGCG
TAATCATGGTCATAGCTGTTTCCTGTGTGAAATTGTTATCCGCTCACAATTCCACACAACATACGAGCC
GGAAGCATAAAGTGTAAAGCCTGGGGTGCCTAATGAGTGAGCTAACTCACATTAATTGCGTTGCGCTCA
CTGCCCGCTTTCCAGTCGGGAAACCTGTCGTGCCAGCTGCATTAATGAATCGGCCAACGCGCGGGGAGA
GGCGGTTTGCGTATTGGGCGCTCTTCC SEQ ID NO: 46
5' donor DNA sequence of *Prototheca moriformis* SAD2B knockout
homologous recombination targeting construct
GCTCTTCCCGCCTGGAGCTGGTGCAGAGCATGGGCAGTTTGCGGAGGAGAGGGTGCTCCCCGTGCTGC
ACCCCGTGGACAAGCTGTGGCAGCCGCAGGACTTCCTGCCCGACCCCGAGTCGCCCGACTTCGAGGACC
AGGTGGCGGAGCTGCGCGCGCGCGCCAAGGACCTGCCCGACGAGTACTTTGTGGTGCTGGTGGGCGACA

| INFORMAL SEQUENCE LISTING |
|---|

TGATCACGGAGGAGGCGCTGCCGACCTACATGGCCATGCTCAACACCTTGGACGGTGTGCGCGACGACA
CGGGCGCGGCTGACCACCCGTGGGCGCGCTGGACGCGGCAGTGGGTGGCCGAGGAGAACCGGCACGGCG
ACCTGCTGAACAAGTACTGTTGGCTGACGGGGCGCGTCAACATGCGGGCCGTGGAGGTGACCATCAACA
ACCTGATCAAGAGCGGCATGAACCCGCAGACGGACAACAACCCTTACTTGGGCTTCGTCTACACCTCCT
TCCAGGAGCGCGCCACCAAGTAGGTACC

SEQ ID NO: 47
3' donor DNA sequence of Prototheca moriformis SAD2B knockout
homologous recombination targeting construct
CAGCCACGGCAACACCGCGCGCCTTGCGGCCGAGCACGGCGACAAGAACCTGAGCAAGATCTGCGGGCT
GATCGCCAGCGACGAGGGCCGGCACGAGATCGCCTACACGCGCATCGTGGACGAGTTCTTCCGCCTCGA
CCCCGAGGGCGCCGTCGCCGCCTACGCCAACATGATGCGCAAGCAGATCACCATGCCCGCGCACCTCAT
GGACGACATGGGCCACGGCGAGGCCAACCCGGGCCGCAACCTCTTCGCCGACTTCTCCGCGGTCGCCGA
GAAGATCGACGTCTACGACGCCGAGGACTACTGCCGCATCCTGGAGCACCTCAACGCGCGCTGGAAGGT
GGACGAGCGCCAGGTCAGCGGCCAGGCCGCCGCGGACCAGGAGTACGTCCTGGGCCTGCCCCAGCGCTT
CCGGAAACTCGCCGAGAAGACCGCCGCCAAGCGCAAGCGCGTCGCGCGCAGGCCCGTCGCCTTCTCCTG
GAGAAGAGCCTCTAGAGTCGACCTGCAGGCATGCAAGCTTGGCGTAATCATGGTCATAGCTGTTTCCTG
TGTGAAATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGTTTGCGTATTGGGCGCTCTT
CC SEQ ID NO: 48
Prototheca moriformis SAD2B knockout homologous recombination
targeting construct
GCTCTTCCCGCCTGGAGCTGGTGCAGAGCATGGGGCAGTTTGCGGAGGAGAGGGTGCTCCCCGTGCTGC
ACCCCGTGGACAAGCTGTGGCAGCCGCAGGACTTCCTGCCCGACCCCGAGTCGCCCGACTTCGAGGACC
AGGTGGCGGAGCTGCGCGCGCGCGCCAAGGACCTGCCCGACGAGTACTTTGTGGTGCTGGTGGGCGACA
TGATCACGGAGGAGGCGCTGCCGACCTACATGGCCATGCTCAACACCTTGGACGGTGTGCGCGACGACA
CGGGCGCGGCTGACCACCCGTGGGCGCGCTGGACGCGGCAGTGGGTGGCCGAGGAGAACCGGCACGGCG
ACCTGCTGAACAAGTACTGTTGGCTGACGGGGCGCGTCAACATGCGGGCCGTGGAGGTGACCATCAACA
ACCTGATCAAGAGCGGCATGAACCCGCAGACGGACAACAACCCTTACTTGGGCTTCGTCTACACCTCCT
TCCAGGAGCGCGCCACCAAGTAGGTACCCTTTCTTGCGCTATGACACTTCCAGCAAAGGTAGGGCGGG
CTGCAGAGACGGCTTCCCGGCGCTGCATGCAACACCGATGATGCTTCGACCCCCCGAAGCTCCTTCGGGG
CTGCATGGGCGCTCCGATGCCGCTCCAGGGCGAGCGCTGTTTAAATAGCCAGGCCCCCGATTGCAAAGA
CATTATAGCGAGCTACCAAAGCCATATTCAAACACCTAGATCACTACCACTTCTACACAGGCCACTCGA
GCTTGTGATCGCACTCCGCTAAGGGGGCGCCTCTTCCTCTTCGTTTCAGTCACAACCCGCAAACGGCGC
GCCATGCTGCTGCAGGCCTTCCTGTTCCTGCTGGCCGGCTTCGCCGCCAAGATCAGCGCCTCCATGACG
AACGAGACGTCCGACCGCCCCCTGGTGCACTTCACCCCCAACAAGGGCTGGATGAACGACCCCAACGGC
CTGTGGTACGACGAGAAGGACGCCAAGTGGCACCTGTACTTCCAGTACAACCCGAACGACACCGTCTGG
GGGACGCCCTTGTTCTGGGGCCACGCCACGTCCGACGACCTGACCAACTGGGAGGACCAGCCCATCGCC
ATCGCCCCGAAGCGCAACGACTCCGGCGCCTTCTCCGGCTCCATGGTGGTGGACTACAACAACACCTCC
GGCTTCTTCAACGACACCATCGACCCGCGCCAGCGCTGCGTGGCCATCTGGACCTACAACACCCCGGAG
TCCGAGGAGCAGTACATCTCCTACAGCCTGGACGGCGGCTACACCTTCACCGAGTACGAGAAGAACCCC
GTGCTGGCCGCCAACTCCACCCAGTTCCGCGACCCGAAGGTCTTCTGGTACGAGCCCTCCCAGAAGTGG
ATCATGACCGCGGCCAAGTCCCAGGACTACAAGATCGAGATCTACTCCTCCGACGACCTGAAGTCCTGG
AAGCTGGAGTCCGCGTTCGCCAACGAGGGCTTCCTCGGCTACCAGTACGAGTGCCCCGGCCTGATCGAG
GTCCCCACCGAGCAGGACCCCAGCAAGTCCTACTGGGTGATGTTCATCTCCATCAACCCCGGCGCCCCG
GCCGGCGGCTCCTTCAACCAGTACTTCGTCGGCAGCTTCAACGGCACCCACTTCGAGGCCTTCGACAAC
CAGTCCCGCGTGGTGGACTTCGGCAAGGACTACTACGCCCTGCAGACCTTCTTCAACACCGACCCGACC
TACGGGAGCGCCCTGGGCATCGCGTGGGCCTCCAACTGGGAGTACTCCGCCTTCGTGCCCACCAACCCC
TGGCGCTCCTCCATGTCCCTCGTGCGCAAGTTCTCCCTCAACACCGAGTACCAGGCCAACCCGGAGACG
GAGCTGATCAACCTGAAGGCCGAGCCGATCCTGAACATCAGCAACGCCGGCCCCTGGAGCGGTTCGCC
ACCAACACCACGTTGACGAAGGCCAACAGCTACAACGTCGACCTGTCCAACAGCACCGGCACCCTGGAG
TTCGAGCTGGTGTACGCCGTCAACACCACCCAGACGATCTCCAAGTCCGTGTTCGCGGACCTCTCCCTC
TGGTTCAAGGGCCTGGAGGACCCCGAGGAGTACCTCCGCATGGGCTTCGAGGTGTCCGCGTCCTCCTTC
TTCCTGGACCGCGGGAACAGCAAGGTGAAGTTCGTGAAGGAGAACCCCTACTTCACCAACCGCATGAGC
GTGAACAACCAGCCCTTCAAGAGCGAGAACGACCTGTCCTACTACAAGGTGTACGGCTTGCTGGACCAG
AACATCCTGGAGCTGTACTTCAACGACGGCGACGTCGTGTCCACCAACACCTACTTCATGACCACCGGG
AACGCCCTGGGCTCCGTGAACATGACGACGGGGGTGGACAACCTGTTCTACATCGACAAGTTCCAGGTG
CGCGAGGTCAAGTGACAATTGGCAGCAGCAGCTCGGATAGTATCGACACACTCTGGACGCTGGTCGTGT
GATGGACTGTTGCCGCCACACTTGCTGCCTTGACCTGTGAATATCCCTGCCGCTTTTATCAAACAGCCT
CAGTGTGTTTGATCTTGTGTGTACGCGCTTTTGCGAGTTGCTAGCTGCTTGTGCTATTTGCGAATACCA
CCCCCAGCATCCCCTTCCCTCGTTTCATATCGCTTGCATCCCAACCGCAACTTATCTACGCTGTCCTGC
TATCCCTCAGCGCTGCTCCTGCTCCTGCTCACTGCCCCTCGCACAGCCTTGGTTTGGGCTCCGCCTGTA
TTCTCCTGGTACTGCAACCTGTAAACCAGCACTGCAATGCTGATGCACGGGAAGTAGTGGGATGGGAAC -continued

INFORMAL SEQUENCE LISTING

ACAAATGGACAGCCACGGCAACACCGCGCGCCTTGCGGCCGAGCACGGCGACAAGAACCTGAGCAAGAT
CTGCGGGCTGATCGCCAGCGACGAGGGCCGGCACGAGATCGCCTACACGCGCATCGTGGACGAGTTCTT
CCGCCTCGACCCCGAGGGCGCCGTCGCCGCCTACGCCAACATGATGCGCAAGCAGATCACCATGCCCGC
GCACCTCATGGACGACATGGGCCACGGCGAGGCCAACCCGGGCCGCAACCTCTTCGCCGACTTCTCCGC
GGTCGCCGAGAAGATCGACGTCTACGACGCCGAGGACTACTGCCGCATCCTGGAGCACCTCAACGCGCG
CTGGAAGGTGGACGAGCGCCAGGTCAGCGGCCAGGCCGCCGCGGACCAGGAGTACGTCCTGGGCCTGCC
CCAGCGCGCTTCCGGAAACTCGCCGAGAAGACCGCCGCCAAGCGCAAGCGCGTCGCGCGCAGGCCCGCGC
CTTCTCCTGGAGAAGAGCCTCTAGAGTCGACCTGCAGGCATGCAAGCTTGGCGTAATCATGGTCATAGC
TGTTTCCTGTGTGAAATTGTTATCCGCTCACAATTCCACACAACATACGAGCCGGAAGCATAAAGTGTA
AAGCCTGGGGTGCCTAATGAGTGAGCTAACTCACATTAATTGCGTTGCGCTCACTGCCCGCTTTCCAGT
CGGGAAACCTGTCGTGCCAGCTGCATTAATGAATCGGCCAACGCGCGGGGAGAGGCGGTTTGCGTATTG
GGCGCTCTTCC

SEQ ID NO: 49
FAD primer 1
5'-TCACTTCATGCCGGCGGTCC-3'

SEQ ID NO: 50
FAD primer 2
5'-GCGCTCCTGCTTGGCTCGAA-3'

SEQ ID NO: 51
pSZ1124 (FAD2B) 5' genomic targeting sequence
GCTCTTCGAGACGTGGTCTGAATCCTCCAGGCGGGTTTCCCCGAGAAAGAAAGGGTGCCGATTTCAAAG
CAGAGCCATGTGCCGGGCCCTGTGGCCTGTGTTGGCGCCTATGTAGTCACCCCCCCTCACCCAATTGTC
GCCAGTTTGCGCAATCCATAAACTCAAACTGCAGCTTCTGAGCTGCGCTGTTCAAGAACACCTCTGGG
GTTTGCTCACCCGCGAGGTCGACGCCCAGCATGGCTATCAAGACGAACAGGCAGCCTGTGGAGAAGCCT
CCGTTCACGATCGGGACGCTGCGCAAGGCCATCCCCGCGCACTGTTTCGAGCGCTCGGCGCTTCGTAGC
AGCATGTACCTGGCCTTTGACATCGCGGTCATGTCCCTGCTCTACGTCGCGTCGACGTACATCGACCCT
GCGCCGGTGCCTACGTGGGTCAAGTATGGCGTCATGTGGCCGCTCTACTGGTTCTTCCAGGTGTGTGTG
AGGGTTGTGGTTGCCCGTATCGAGGTCCTGGTGGCGCGCATGGGGGAGAAGGCGCCTGTCCCGCTGACC
CCCCCGGCTACCCTCCCGGCACCTTCCAGGGCGCCTTCGGCACGGGTGTCTGGGTGTGCGCGCACGAGT
GCGGCCACCAGGCCTTTTCCTCCAGGCCATCAACGACGGCGTGGGCCTGGTGTTCCACAGCCTGC
TGCTGGTGCCCTACTACTCCTGGAAGCACTCGCACCGGGTACC SEQ ID NO: 52
pSZ1124 (FAD2B) 3' genomic targeting sequence
CCGCCACCACTCCAACACGGGGTGCCTGGACAAGGACGAGGTGTTTGTGCCGCCGCACCGCGCAGTGGC
GCACGAGGGCCTGGAGTGGGAGGAGTGGCTGCCCATCCGCATGGGCAAGGTGCTGGTCACCCTGACCCT
GGGCTGGCCGCTGTACCTCATGTTCAACGTCGCCTCGCGGCCGTACCCGCGCTTCGCCAACCACTTTGA
CCCGTGGTCGCCCATCTTCAGCAAGCGCGAGCGCATCGAGGTGGTCATCTCCGACCTGGCTGGTGGC
GGTGCTCAGCGGGCTCAGCGTGCTGGGCCGCACCATGGGCTGGGCCTGGCTGGTCAAGACCTACGTGGT
GCCCTACCTGATCGTGAACATGTGGCTCGTGCTCATCACGCTGCTCCAGCACACGCACCCGGCGCTGCC
GCACTACTTCGAGAAGGACTGGGACTGGCTGCGCGGCGCCATGGCCACCGTGGACCGCTCCATGGGCCC
GCCCTTCATGGACAACATCCTGCACCACATCTCCGACACCCACGTCCTGCACCACCTCTTCAGCACCAT
CCCGCACTACCACGCCGAGGAGGCCTCCGCCGCCATCAGGCCCATCCTGGGCAAGTACTACCAGTCCGA
CAGCCGCTGGGTCGGCCGCGCCCTGTGGGAGGACTGGCGCGACTGCCGCTACGTCGTCCCGGACGCGCC
CGAGGACGACTCCGCGCTCTGGTTCCACAAGTGAGTGAGTGAGAAGAGC SEQ ID NO: 53
S. cerevisiae suc2 cassette
CTTTCTTGCGCTATGACACTTCCAGCAAAAGGTAGGGCGGGCTGCGAGACGGCTTCCCGGCGCTGCATG
CAACACCGATGATGCTTCGACCCCCCGAAGCTCCTTCGGGGCTGCATGGGCGCTCCGATGCCGCTCCAG
GGCGAGCGCTGTTTAAATAGCCAGGCCCCCGATTGCAAAGACATTATAGCGAGCTACCAAAGCCATATT
CAAACACCTAGATCACTACCACTTCTACACAGGCCACTCGAGCTTGTGATCGCACTCCGCTAAGGGGGC
GCCTCTTCCTCTTCGTTTCAGTCACAACCCGCAAACGGCGCGCCATGCTGCTGCAGGCCTTCCTGTTCC
TGCTGGCCGGCTTCGCCGCCAAGATCAGCGCCTCCATGACGAACGAGACGTCCGACCGCCCCCTGGTGC
ACTTCACCCCCAACAAGGGCTGGATGAACGACCCCAACGGCCTGTGGTACGACGAGAAGGACGCCAAGT
GGCACCTGTACTTCCAGTACAACCCGAACGACACCGTCTGGGGACGCCCTTGTTCTGGGGCCACGCCA
CGTCCGACGACCTGACCAACTGGGAGGACCAGCCCATCGCCATCGCCCCGAAGCGCAACGACTCCGGCG
CCTTCTCCGGCTCCATGGTGGTGGACTACAACAACACCTCCGGCTTCTTCAACGACACCATCGACCCGC
GCCAGCGCTGCGTGGCCATCTGGACCTACAACACCCCGGAGTCCGAGGAGCAGTACATCTCCTACAGCC
TGGACGGCGGCTACACCTTCACCGAGTACCAGAAGAACCCCGTGCTGGCCGCCAACTCCACCCAGTTCC
GCGACCCGAAGGTCTTCTGGTACGAGCCCTCCCAGAAGTGGATCATGACCGCGGCCAAGTCCCAGGACT
ACAAGATCGAGATCTACTCCTCCGACGACCTGAAGTCCTGGAAGCTGGAGTCCGCGTTCGCCAACGAGG
GCTTCCTCGGCTACCAGTACGAGTGCCCCGGCCTGATCGAGGTCCCCACCGAGCAGGACCCCAGCAAGT
CCTACTGGGTGATGTTCATCTCCATCAACCCCGGCGCCCCGGCCGGCGGCTCCTTCAACCAGTACTTCG
TCGGCAGCTTCAACGGCACCCACTTCGAGGCCTTCGACAACCAGTCCCGCGTGGTGGACTTCGGCAAGG
ACTACTACGCCCTGCAGACCTTCTTCAACACCGACCCGACCTACGGGAGCGCCCTGGGCATCGCGTGGG
CCTCCAACTGGGAGTACTCCGCCTTCGTGCCCACCAACCCCTGGCGCTCCTCCATGTCCCTCGTGCGCA
AGTTCTCCCTCAACACCGAGTACCAGGCCAACCCGGAGACGGAGCTGATCAACCTGAAGGCCGAGCCGA
TCCTGAACATCAGCAACGCCGGCCCCTGGAGCCGGTTCGCCACCAACACCACGTTGACGAAGGCCAACA
GCTACAACGTCGACCTGTCCAACAGCACCGGCACCCTGGAGTTCGAGCTGGTGTACGCCGTCAACACCA
CCCAGACGATCTCCAAGTCCGTGTTCGCGGACCTCTCCCTCTGGTTCAAGGGCCTGGAGGACCCCGAGG
AGTACCTCCGCATGGGCTTCGAGGTGTCCGCGTCCTCCTTCTTCCTGGACCGCGGGAACAGCAAGGTGA
AGTTCGTGAAGGAGAACCCCTACTTCACCAACCGCATGAGCGTGAACAACCAGCCCTTCAAGAGCGAGA
ACGACCTGTCCTACTACAAGGTGTACGGCTTGCTGGACCAGAACATCCTGGAGCTGTACTTCAACGACG

```
GCGACGTCGTGTCCACCAACACCTACTTCATGACCACCGGGAACGCCCTGGGCTCCGTGAACATGACGA
CGGGGGTGGACAACCTGTTCTACATCGACAAGTTCCAGGTGCGCGAGGTCAAGTGACAATTGGCAGCAG
CAGCTCGGATAGTATCGACACACTCTGGACGCTGGTCGTGTGATGGACGTGTTGCCGCCACACTTGCTGC
CTTGACCTGTGAATATCCCTGCCGCTTTTATCAAACAGCCTCAGTGTGTTTGATCTTGTGTGTACGCGC
TTTTGCGAGTTGCTAGCTGCTTGTGCTATTTGCGAATACCACCCCCAGCATCCCCTTCCCTCGTTTCAT
ATCGCTTGCATCCCAACCGCAACTTATCTACGCTGTCCTGCTATCCCTCAGCGCTGCTCCTGCTCCTGC
TCACTGCCCCTCGCACAGCCTTGGTTTGGGCTCCGCCTGTATTCTCCTGGTACTGCAACCTGTAAACCA
GCACTGCAATGCTGATGCACGGGAAGTAGTGGGATGGGAACACAAATGGA

SEQ ID NO: 54
pSZ1125 (FAD2C) 5' genomic targeting sequence
GCTCTTCGAGGGGCTGGTCTGAATCCTTCAGGCGGGTGTTACCCGAGAAAGAAAGGGTGCCGATTTCAA
AGCAGACCCATGTGCCGGGCCCTGTGCCCTGTGTTGGCGCCTATGTAGTCACCCCCCCTCACCCAATTG
TCGCCAGTTTGCGCACTCCATAAACTCAAAACAGCAGCTTCTGAGCTGCGCTGTTCAAGAACACCTCTG
GGGTTTGCTCACCCGCGAGGTCGACGCCCAGCATGGCTATCAAGACGAACAGGCAGCCTGTGGAGAAGC
CTCCGTTCACGATCGGGACGCTGCGCAAGGCCATCCCCGCGCACTGTTTCGAGCGCTCGGCGCTTCGTA
GCAGCATGTACCTGGCCTTTGACATCGCGGTCATGTCCCTGCTCTACGTCGCGTCGACGTACATCGACC
CTGCACCGGTGCCTACGTGGGTCAAGTACGGCATCATGTGGCCGCTCTACTGGTTCTTCCAGGTGTGTT
TGAGGGTTTTGGTTGCCCGTATTGAGGTCCTGGTGGCGCGCATGGAGGAGAAGGCGCCTGTCCCGCTGA
CCCCCCCGGCTACCCTCCCGGCACCTTCCAGGGCGCCTTCGGCACGGGTGTCTGGGTGTGCGCGCACGA
GTGCGGCCACCAGGCCTTTTCCTCCAGCCAGGCCATCAACGACGGCGTGGGCCTGGTGTTCCACAGCCT
GCTGCTGGTGCCCTACTACTCCTGGAAGCACTCGCACCGGGTACC SEQ ID NO: 55
pSZ1125 (FAD2C) 3' genomic targeting sequence
CCGCCACCACTCCAACACGGGGTGCCTGGACAAGGACGAGGTGTTTGTGCCGCCGCACCGCGCAGTGGC
GCACGAGGGCCTGGAGTGGGAGGAGTGGCTGCCCATCCGCATGGGCAAGGTGCTGGTCACCCTGACCCT
GGGCTGGCCGCTGTACCTCATGTTCAACGTCGCCTCGCGCGCCGTACCCGCGCTTCGCCAACCACTTTGA
CCCGTGGTCGCCCATCTTCAGCAAGCGCGAGCGCATCGAGGTGGTCATCTCCGACCTGGCGCTGGTGGC
GGTGCTCAGCGGGCTCAGCGTGCTGGGCCGCACCATGGGCTGGGCCTGGCTGGTCAAGACCTACGTGGT
GCCCTACCTGATCGTGAACATGTGGCTCGTGCTCATCACGCTGCTCCAGCACACGCACCCGGCGCTGCC
GCACTACTTCGAGAAGGACTGGGACTGGCTGCGCGGCGCCATGGCCACCGTGGACCGCTCCATGGGCCC
GCCCTTCATGGACAACATCCTGCACCACATCTCCGACACCCACGTGCTGCACCACCTCTTCAGCACCAT
CCCGCACTACCACGCCGAGGAGGCCTCCGCCGCCATCAGGCCCATCCTGGGCAAGTACTACCAGTCCGA
CAGCCGCTGGGTCGGCCGCGCCCTGTGGGAGGACTGGCGCGACTGCCGCTACGTCGTCCCGGACGCGCC
CGAGGACGACTCCGCGCTCTGGTTCCACAAGTGAGTGAGTGAGAAGAGC SEQ ID NO: 56
5' 6S genomic donor sequence
GCTCTTCGCCGCCGCCACTCCTGCTCGAGCGCGCCCGCGCGTGCGCCGCCAGCGCCTTGGCCTTTTCGC
CGCCGCTCGTGCGCGTCGCTGATGTCCATCACCAGGTCCATGAGGTCTGCCTTGCGCCGGCTGAGCCACT
GCTTCGTCCGGGCGGCCAAGAGGAGCATGAGGGAGGACTCCTGGTCCAGGGTCCTGACGTGGTCGCGGC
TCTGGGAGCGGGCCAGCATCATCTGGCTCTGCCGCACCGAGGCCGCCTCCAACTGGTCCTCCAGCAGCC
GCAGTCGCCGCCGACCCTGGCAGAGGAAGACAGGTGAGGGGGGTATGAATTGTACAGAACAACCACGAG
CCTTGTCTAGGCAGAATCCCTACCAGTCATGGCTTTACCTGGATGACGGCCTGCGAACAGCTGTCCAGC
GACCCTCGCTGCCGCCGCTTCTCCCGCACGCTTCTTTCCAGCACCGTGATGGCGCGAGCCAGCGCCGCA
CGCTGGCGCTGCGCTTCGCCGATCTGAGGACAGTCGGGGAACTCTGATCAGTCTAAACCCCCTTGCGCG
TTAGTGTTGCCATCCTTTGCAGACCGGTGAGAGCCGACTTGTTGTGCGCCACCCCCCACACCACCTCCT
CCCAGACCAATTCTGTCACCTTTTTGGCGAAGGCATCGGCCTCGGCCTGCAGAGAGGACAGCAGTGCCC
AGCCGCTGGGGGTTGGCGGATGCACGCTCAGGTACC SEQ ID NO: 57
3' 6S genomic donor sequence
GAGCTCCTTGTTTTCCAGAAGGAGTTGCTCCTTGAGCCTTTCATTCTCAGCCTCGATAACCTCCAAAGC
CGCTCTAATTGTGGAGGGGGTTCGAATTTAAAAGCTTGGAATGTTGGTTCGTGCGTCTGGAACAAGCCC
AGACTTGTTGCTCACTGGGAAAAGGACCATCAGCTCCAAAAAACTTGCCGCTCAAACCGCGTACCTCTG
CTTTCGCGCAATCTGCCCTGTTGAAATCGCCACCACATTCATATTGTGACGCTTGAGCAGTCTGTAATT
GCCTCAGAATGTGGAATCATCTGCCCCCTGTGCGAGCCCATGCCAGGCATGTCGCGGGCGAGGACACCC
GCCACTCGTACAGCAGACCATTATGCTACCTCACAATAGTTCATAACAGTGACCATATTTCTCGAAGCT
CCCCAACGAGCACCTCCATGCTCTGAGTGGCCACCCCCCGGCCCTGGTGCTTGCGGAGGGCAGGTCAAC
CGGCATGGGGCTACCGAAATCCCCGACCGGATCCCACCACCCCCGCGATGGGAAGAATCTCTCCCCGGG
ATGTGGGCCCACCACCAGCACAACCTGCTGGCCCAGGCGAGCGTCAAACCATACCACACAAATATCCTT
GGCATCGGCCCTGAATTCCTTCTGCCGCTCTGCTACCCGGTGCTTCTGTCCGAAGCAGGGGTTGCTAGG
GATCGCTCCGAGTCCGCAAACCCTTGTCGCGTGGCGGGGCTTGTTCGAGCTTGAAGAGC SEQ ID NO: 58
Relevant expression construct for Cinnamomum camphora thioesterase
(βtub::neo::nitred::βtub::C. camphora TE::nitred)
CTTTCTTGCGCTATGACACTTCCAGCAAAAGGTAGGGCGGGCTGCGAGACGCTTCCCGGCGCTGCATG
CAACACCGATGATGCTTCGACCCCCCGAAGCTCCTTCGGGGCTGCATGGGCGCTCCGATGCCGCTCCAG
GGCGAGCGCTGTTTAAATAGCCAGGCCCCCGATTGCAAAGACATTATAGCGAGCTACCAAAGCCATATT
CAAACACCTAGATCACTACCACTTCTACACAGGCCACTCGAGCTTGATCGCACTCCGCTAAGGGGGC
GCCTCTTCCTCTTCGTTTCAGTCACAACCCGCAAACTCTAGAATATCAATGATCGAGCAGGACGGCCTC
CACGCCGGCTCCCCCGCCGCCTGGGTGGAGCGCCTGTTCGGCTACGACTGGGCCCAGCAGACCATCGGC
TGCTCCGACGCCGCCGTGTTCCGCCTGTCCGCCCAGGGCCGCCCCGTGCTGTTCGTGAAGACCGACCTG
TCCGGCGCCCTGAACGAGCTGCAGGACGAGGCCGCCCGCCTGTCCTGGCTGGCCACCACCGGCGTGCCC
TGCGCCGCCGTGCTGGACGTGGTGACCGAGGCCGGCCGCGACTGGCTGCTGCTGGGCGAGGTGCCCGGC
```

CAGGACCTGCTGTCCTCCCACCTGGCCCCGCCGAGAAGGTGTCCATCATGGCCGACGCCATGCGCCGC
CTGCACACCCTGGACCCCGCCACCTGCCCCTTCGACCACCAGGCCAAGCACCGCATCGAGCGCGCCGC
ACCCGCATGGAGGCCGGCCTGGTGGACCAGGACGACCTGGACGAGGACGCACCAGGGCCTGGCCCCGCC
GAGCTGTTCGCCCGCCTGAAGGCCCGCATGCCCGACGGCGAGGACCTGGTGGTGACCCACGGCGACGCC
TGCCTGCCCAACATCATGGTGGAGAACGGCCGCTTCTCCGGCTTCATCGACTGCGGCCGCCTGGGCGTG
GCCGACCGCTACCAGGACATCGCCCTGGCCACCCGCGACATCGCCGAGGAGCTGGGCGGCGAGTGGGCC
GACCGCTTCCTGGTGCTGTACGGCATCGCCGCCCCCGACTCCCAGCGCATCGCCTTCTACCGCCTGCTG
GACGAGTTCTTCTGACAATTGGCAGCAGCAGCTCGGATAGTATCGACACACTCTGGACGCTGGTCGTGT
GATGGACTGTTGCCGCCACACTTGCTGCCTTGACCTGTGAATATCCCTGCCGCTTTTATCAAACAGCCT
CAGTGTGTTTGATCTTGTGTGTACGCGCTTTTGCGAGTTGCTAGCTGCTTGTGCTATTTGCGAATACCA
CCCCCAGCATCCCCTTCCCTCGTTTCATATCGCTTGCATCCCAACCGCAACTTATCTACGCTGTCCTGC
TATCCCTCAGCGCTGCTCCTGCTCCTGCTCACTGCCCCTCGCACAGCCTTGGTTTGGGCTCCGCCTGTA
TTCTCCTGGTACTGCAACCTGTAAACCAGCACTGCAATGCTGATGCACGGGAAGTAGTGGGATGGGAAC
ACAAATGGAGGATCCCGCGTCTCGAACAGAGCGCGCAGAGGAACGCTGAAGGTCTCGCCTCTGTCGCAC
CTCAGCGCGGCATACACCACAATAACCACCTGACGAATGCGCTTGGTTCTTCGTCCATTAGCGAAGCGT
CCGGTTCACACACGTGCCACGTTGGCGAGGTGGCAGGTGACAATGATCGGTGGAGCTGATGGTCGAAAC
GTTCACAGCCTAGGGATATCGAATTCCTTTCTTGCGCTATGACACTTCCAGCAAAAGGTAGGGCGGGCT
GCGAGACGGCTTCCCGGCGCTGCATGCAACACCGATGATGCTTCGACCCCCCGAAGCTCCTTCGGGGCT
GCATGGGCGCTCCGATGCCGCTCCAGGGCGAGCGCTGTTTAAATAGCCAGGCCCCCGATTGCAAAGACA
TTATAGCGAGCTACCAAAGCCATATTCAAACACCTAGATCACTACCACTTCTACACAGGCCACTCGAGC
TTGTGATCGCACTCCGCTAAGGGGGCGCCTCTTCCTCTTCGTTTCAGTCACAACCCGCAAACACTAGTA
TGGCCACCGCATCCACTTTCTCGGCGTTCAATGCCCGCTGCGGCGACCTGCGTCGCTCGGCGGGCTCCG
GGCCCCGGCGCCCAGCGAGGCCCCTCCCCGTGCGCGGGCGCGCCCCCGACTGGTCCATGCTGTTCGCCG
TGATCACCACCATCTTCTCCGCGCCGAGAAGCAGTGGACCAACCTGGAGTGGAAGCCCAAGCCCAACC
CCCCCCAGCTGCTGGACGACCACTTCGGCCCCCACGGCCTGGTGTTCCGCCGCACCTTCGCCATCCGCA
GCTACGAGGTGGGCCCCGACCGCTCCACCAGCATCGTGGCCGTGATGAACCACCTGCAGGAGGCCGCC
TGAACCACGCCAAGTCCGTGGGCATCCTGGGCGACGGCTTCGGCACCACCCTGGAGATGTCCAAGCGCG
ACCTGATCTGGGTGGTGAAGCGCACCCACGTGGCCGTGGAGCGCTACCCCGCCTGGGGCGACACCGTGG
AGGTGGAGTGCTGGGTGGGCGCCTCCGGCAACAACGGCCGCCGCCACGACTTCCTGGTGCGCGACTGCA
AGACCGGCGAGATCCTGACCCGCTGCACCTCCCTGAGCGTGATGATGAACACCCGCACCCGCCGCCTGA
GCAAGATCCCCGAGGAGGTGCGCGGCGAGATCGGCCCCGCCTTCATCGACAACGTGGCCGTGAAGGACG
AGGAGATCAAGAAGCCCCAGAAGCTGAACGACTCCACCGCCGACTACATCCAGGGCGGCCTGACCCCCC
GCTGGAACGACCTGGACATCAACCAGCACGTGAACAACATCAAGTACGTGGACTGGATCCTGGAGACCG
TGCCCGACAGCATCTTCGAGAGCCACCACATCTCCTCCTTCACCATCGAGTACCGCCGCGAGTGCACCA
TGGACAGCGTGCTGCAGTCCCTGACCACCGTGAGCGGCGGCTCCTCCGAGGCCGGCCTGGTGTGCGAGC
ACCTGCTGCAGCTGGAGGGCGGCAGCGAGGTGCTGCGCGCCAAGACCGAGTGGCGCCCCAAGCTGACCG
ACTCCTTCCGCGGCATCAGCGTGATCCCCGCCGAGTCCAGCGTGATGGACTACAAGGACCACGACGGCG
ACTACAAGGACCACGACATCGACTACAAGGACGACGACGACAAGTGACTCGAGGCAGCAGCAGCTCGGA
TAGTATCGACACACTCTGGACGCTGGTCGTGTGATGGACTGTTGCCGCCACACTTGCTGCCTTGACCTG
TGAATATCCCTGCCGCTTTTATCAAACAGCCTCAGTGTGTTTGATCTTGTGTGTACGCGCTTTTGCGAG
TTGCTAGCTGCTTGTGCTATTTGCGAATACCACCCCCAGCATCCCCTTCCCTCGTTTCATATCGCTTGC
ATCCCAACCGCAACTTATCTACGCTGTCCTGCTATCCCTCAGCGCTGCTCCTGCTCCTGCTCACTGCCC
CTCGCACAGCCTTGGTTTGGGCTCCGCCTGTATTCTCCTGGTACTGCAACCTGTAAACCAGCACTGCAA
TGCTGATGCACGGGAAGTAGTGGGATGGGAACACAAATGGAAAGCTT

SEQ ID NO: 59
Nucleotide sequence of transforming DNA contained in
pSZ1503 [KASII_btub-y.inv-nr_KASII]
gctcttcccgcaccggctggctccaccccaacttgaacctcgagaacccccgcgcctggcgtcgacccccg
tcgtgctcgtggggccgcggaaggagcgcgccgaagacctggacgtcgtcctctccaactcctttggct
ttggcgggcacaattcgtcgtcggtaccctttcttgcgctatgacacttccagcaaaaggtagggcgg
gctgcgagacggcttcccggcgctgcatgcaacaccgatgatgcttcgaccccccgaagctccttcggg
gctgcatgggcgctccgatgccgctccagggcgagcgctgtttaaatagccaggcccccgattgcaaag
acattatagcgagctaccaaagccatattcaaacacctagatcactaccacttctacacaggccactcg
agcttgtgatcgcactccgctaaggggcgcctcttcctcttcgtttcagtcacaacccgcaaacggcg
cgccATGctgctgcaggccttcctgttcctgctggccggcttcgccgccaagatcagcgcctccatgac
gaacgagacgtcgaccgccccctggtgcacttcaccccaacaagggctggatgaacgaccccaacg
cctgtggtacgacgagaaggacgccaagtggcacctgtacttccagtacaaccgaacgacaccgtctg
ggggacgcccttgttctggggccacgccacgtccgacgacctgaccaactgggaggaccagcccatcgc
catcgccccgaagcgcaacgactccggcgcctctccggctccatggtggtggactacaacaacacctc
cggcttcttcaacgacaccatcgaccgcgccagcgctgcgtggccatctggacctacaacaccccgga
gtccgaggagcagtacatctcctacagcctggacaggcggtcacccttcaccgagtaccagaagaaccc
cgtgctggccgccaactccacccagttccgcgacccgaaggtcttctggtacgagccctcccagaagtg
gatcatgaccgcggccaagtcccaggactacaagatcgagatctactcctccgacgacctgaagtcctg
gaagctggagtccgcgttcgccaacgagggcttcctcggctaccagtacgagtgccccggcctgatcga
ggtccccaccgagcaggaccccagcaagtcctactgggtgatgttcatctccatcaaccccggcgcccc
ggccggcggctccttcaaccagtacttcgtcggcagcttcaacggcacccacttcgaggccttcgacaa
ccagtcccgcgtggtggacttcggcaaggactactacgccctgcagaccttcttcaacaccgacccgac
ctacgggagcgccctgggcatcgcgtgggcctccaactgggagtactccgccttcgtgcccaccaaccc
ctggcgctcctccatgtccctcgtgcgcaagttctccctcaacaccgagtaccaggccaacccggagac
ggagctgatcaacctgaaggccgagccgatcctgaacatcagcaacgccggccctggagccggttcgc
caccaacaccacgttgacgaaggccaacagctacaacgtcgacctgtccaacagcaccgccaccctgga
gttcgagctggtgtacgccgtcaacaccacccagacgatctccaagtccgtgttcgcggacctctccct
ctggttcaagggcctggaggacccccgaggagtacctccgcatgggcttcgaggtgtccgcgtcctccttt
cttcctggaccgcgggaacagcaaggtgaagttcgtgaaggagaaccctacttcaccaaccgcatgag
cgtgaacaaccagcccttcaagagcgagaacgacctgtcctactacaaggtgtacgcgcttgctggacca
gaacatcctggagctgtacttcaacgacggcgacgtcgtgtccaccaacacctacttcatgaccaccggg -continued

INFORMAL SEQUENCE LISTING

```
gaacgccctgggctccgtgaacatgacgacgggggtggacaacctgttctacatcgacaagttccaggt
gcgcgaggtcaagTGAcaattggcagcagcagctcggatagtatcgacacactctggacgctggtcgtg
tgatggactgttgccgccacacttgctgccttgacctgtgaatatccctgccgcttttatcaaacagcc
tcagtgtgtttgatcttgtgtgtacgcgcttttgcgagttgctagctgcttgtgctatttgcgaatacc
accccagcatccccttccctcgtttcatatcgcttgcatcccaaccgcaacttatctacgctgtcctg
ctatccctcagcgctgctcctgctcctgctcactgccctcgcacagccttggtttgggctccgcctgt
attctcctggtactgcaacctgtaaaccagcactgcaatgctgatgcacgggaagtagtgggatgggaa
cacaaatggaggatcgtagagctcatcttccgaaagtacgacgagtgagcgagctgattctctttgagc
ggggtcgggtggttcggggagagtgcgcgaaaggcgcagagacgtgcggccggccgtgtccctccgtc
ttcccctggttggtgctatagtaacctgcctgtgtcgcgtgcgcgtcgggaagagc
```

SEQ ID NO: 60
Nucleotide sequence of transforming DNA contained in pSZ2533

<u>gctcttcaccccaactcagataataccaataccctccttctcctcctcatccattcagtaccccccc</u>
<u>ttctcttcccaaagcagcaagcgcgtggcttacagaagaacaatcggcttccgccaaagtcgccgagca</u>
<u>ctgccgacggcggcgcgcccagcagcccgcttggccacacaggcaacgaatacattcaataggggcc</u>
<u>tcgcagaatggaaggagcggtaaagggtacaggagcactgcgcacaaggggcctgtgcaggagtgactg</u>
<u>actgggcgggcagacggcgcaccgcgggcgcaggcaagcagggaagattgaacggcagggaggaggat</u>
<u>gctgattgaggggggcatcgcagtctctcttggacccgggataaggaagcaaatattcggccggttggg</u>
<u>ttgtgtgtgtgcacgtttctcttcagagtcgtgggtgtgcttccagggaggatataagcagcaggat</u> cgaatcccgcgaccagcgtttccccatccagccaaccaccctgtc<u>ggtacc</u>ctttcttgcgctatgaca
cttccagcaaaaggtagggcgggctgcgagacggcttcccggcgctgcatgcaacaccgatgatgcttc
gaccccccgaagctccttcggggctgcatgggcgctccgatgccgctccagggcgagcgctgtttaaat
agccaggcccccgattgcaaagacattatagcgagctaccaaagccatattcaaacacctagatcacta
ccacttctacacaggccactcgagcttgtgatcgcactccgctaagggggcgcctcttcctcttcgttt
cagtcacaacccgcaaacggcgcgccATGctgctgcaggccttcctgttcctgctggccggcttcgccg

*ccaagatcagcgcctccatgacgaacgagacgtccgaccgcccctggtgcacttcacccccaacaagg
gctggatgaacgaccccaacggcctgtggtacgacgagaaggacgccaagtggcacctgtacttccagt
acaacccgaacgacaccgtctggggacgcccttgttctggggcacgccacgtccgacgacctgacca
actgggagaccagccatcgccatcgccccgaagcgcaacgatccggcgccttctccggctccatgg
tggtggactacaacaacacctccggcttcttcaacgacaccatcgaccgcgccagcgctgcgtggcca
tctggacctacaacaccccggagtccgaggagcagtacatctcctacagcctggacggcggctacacct
tcaccgagtaccagaagaacccccgtgctggccgccaactccacccagttccgcgacccgaaggtcttct
ggtacgagccctcccagaagtggatcatgaccgcggccagtccaggactacaagatcgagatctact
cctccgacgacctgaagtcctggaagctggagtccgcgttcgccaacgagggcttcctcggctaccagt
acgagtgccccggcctgatcgaggtccccaccgagcaggaccccagcaagtcctactgggtgatgttca
tctccatcaaccccggcgccccggccggcggctcttcaaccagtacttcgtcggcagcttcaacggca
cccacttcgaggccttcgacaaccagtcccgcgtggtggacttcggcaaggactactacgccctgcaga
ccttcttcaacaccgacccgacctacgggagcgccctgggcatcgcgtgggcctccaactgggagtact
ccgccttcgtgcccaccaaccctggcgctcctccatgtccctcgtgcgcaagttctccctcaacaccg
agtaccaggccaacccggagacggagctgatcaacctgaaggccgagccgatcctgaacatcagcaacg
ccggccctgggagccggttcgccaccaacaccacgttgacgaaggccaacagctacaacgtcgactgt
ccaacagcaccggcaccctggagttcgagctggtgtacgccgtcaacaccaccagacgatctccaagt
ccgtgttcgcggacctctccctctggttcaagggcctggaggaccccgaggagtacctccgcatgggct
tcgaggtgtccgcgtcctccttcttcctggaccgcgggaacagcaaggtgaagttcgtgaaggagaacc
cctacttcaccaaccgcatgagcgtgaacaaccagcccttcaagagcgagaacgacctgtcctactaca
aggtgtacggcttgctggaccagaacatcctggagctgtacttcaacgacggcgacgtcgtgtccacca
acacctacttcatgaccaccgggaacgccctgggctccgtgaacatgacgacgggggtggacaacctgt* tctacatcgacaagttccaggtgcgcgaggtcaagTGA<u>caattg</u>gcagcagcagctcggatagtatcga <u>cacactctggacgctggtcgtgtgatggactgttgccgccacacttgctgccttgacctgtgaatatcc</u>
<u>ctgccgcttttatcaaacagcctcagtgtgtttgatcttgtgtgtacgcgcttttgcgagttgctagct</u>
<u>gcttgtgctatttgcgaataccacccccagcatccccttccctcgtttcatatcgcttgcatcccaacc</u>
<u>gcaacttatctacgctgtcctgctatccctcagcgctgctcctgctcctgctcactgccctcgcacag</u>
<u>ccttggtttgggctccgcctgtattctcctggtactgcaacctgtaaaccagcactgcaatgctgatgc</u>
<u>acgggaagtagtgggatgggaacacaaatggaggatcccgcgtctcgaacagagcgcgcagaggaacgc</u>
<u>tgaaggtctcgcctctgtcgcacctcagcgcggcatacaccacaataaccacctgacgaatgcgcttgg</u>
<u>ttcttcgtccattagcgaagcgtccggttcacacacgtgccacgttggcgaggtggcaggtgacaatga</u> tcggtggagctgatggtcgaaacgttcacagcctagggatatcatagcgactgctaccccccgaccatg
tgccgaggcagaaattatatacaagaagcagatcgcaattaggcacatcgctttgcattatccacacac
tattcatcgctgctgcggcaaggctgcagagtgtattttgtgccaggagctgagtccgaagtcgac
gcgacgagcggcgcaggatccgacccctagacgagctctgtcattttccaagcacgcagctaaatgcgc
tgagaccgggtctaaatcatccgaaaagtgtcaaaatggccgattgggttcgcctaggacaatgcgctg

INFORMAL SEQUENCE LISTING cggattcgctcgagtccgctgccggccaaaaggcggtggtacaggaaggcgcacggggccaaccctgcg aagccggggccccgaacgccgaccgccggccttcgatctcgggtgtcccctcgtcaatttcctctctc gggtgcagccacgaaagtcgtgacgcaggtcacgaaatccggttacgaaaaacgcaggtcttcgcaaaa acgtgagggtttcgcgtctcgccctagctattcgtatcgccgggtcagacccacgtgcagaaaagccct tgaataacccgggaccgtggttaccgcgccgcctgcaccaggggcttatataagcccacaccacacct gtctcaccacgcatttctccaactcgcgacttttcggaagaaattgttatccacctagtatagactgcc acctgcaggaccttgtgtcttgcagtttgtattggtcccggccgtcgagctcgacagatctgggctagg gttggcctggccgctcggcactccccttagccgcgcgcatccgcgttccagaggtgcgattcggtgtg tggagcattgtcatgcgcttgtgggggtcgttccgtgcgcggcgggtccgccatgggcgccgacctggg ccctagggtttgttttcgggccaagcgagcccctctcacctcgtcgccccccgcattcctctctctt gcagccttgccactagtATGgccaccgcatccactttctcggcgttcaatgcccgctgcggcgacctgc gtcgctcggcgggctccggccccggcgcccagcgaggcccctccccgtgcgcgggcgcgccgccgccg ccgccgacgccaacccgccgccccgagcgccgcgtggtgatcaccggccagggcgtggtgacctccc tgggccagaccatcgagcagttctactcctccctgctggagggcgtgtccggcatctcccagatccaga agttcgacaccaccggctacaccaccaccatcgccggcgagatcaagtccctgcagctggaccctacg tgcccaagcgctgggccaagcgcgtggacgacgtgatcaagtacgtgtacatcgccggcaagcaggccc tggagtccgccggcctgcccatcgaggccgccggcctggccggcgccggcctggaccccgccctgtgcg gcgtgctgatcggcaccgccatggccggcatgacctccttcgccgccggcgtggaggccctgacccgcg gcggcgtgcgcaagatgaacccctttctgcatcccttctccatctccaacatgggcggcgccatgctgg ccatggacatcggcttcatgggccccaactactccatctccaccgcctgcgccaccggcaactactgca tcctgggcgccgccgaccacatccgccgcggcgacgccaacgtgatgctggccggcggcgccgacgccg ccatcatcccctccggcatcggcggcttcatcgcctgcaaggccctgtccaagcgcaacgacgagcccg agcgcgcctcccgcccctgggacgccgaccgcgacggcttcgtgatgggcgagggcgccggcgtgctgg tgctggaggagctggagcacgccaagcgccgcggcgccaccatcctggccgagctggtgggcggcgccg ccacctccgacgccaccacatgaccgagcccgaccccagggccgcggcgtgcgcctgtgcctggagc gcgccctggagcgcgcccgcctggccccgagcgcgtgggctacgtgaacgccacggcacctccaccc ccgccggcgacgtggccgagtaccgcgccatccgcgccgtgatccccaggactccctgcgcatcaact ccaccaagtccatgatcggccacctgctgggcggcgccggcgccgtggaggccgtggccgccatccagg ccctgcgcaccggctggctgcaccccaacctgaacctggagaacccgccccggcgtggaccccgtgg tgctggtgggccccgcaaggagcgcgccgaggacctggacgtggtgctgtccaactccttcggcttcg gcggccacaactcctgcgtgatcttccgcaagtacgacgagatggactacaaggaccacgacggcgact acaaggaccacgacatcgactacaaggacgacgacgacaagTGAatcgatagatctcttaaggcagcag cagctcggatagtatcgacacactctggacgctggtcgtgtgatggactgttgccgccacacttgctgc
cttgacctgtgaatatccctgccgcttttatcaaacagcctcagtgtgtttgatcttgtgtgtacgcgc
ttttgcgagttgctagctgcttgtgctatttgcgaataccacccccagcatcccttccctcgtttcat
atcgcttgcatcccaaccgcaacttatctacgctgtcctgctatccctcagcgctgctcctgctcctgc
tcactgcccctcgcacagccttggtttgggctccgcctgtattctcctggtactgcaacctgtaaacca
gcactgcaatgctgatgcacgggaagtagtgggatgggaacacaaatggaaagcttaattaagagctct
tgttttccagaaggagttgctccttgagcctttcattctcagcctcgataacctccaaagccgctctaa
ttgtggaggggggttcgaaccgaatgctgcgtgaacgggaaggaggaggagaaagagtgagcagggaggg
attcagaaatgagaaatgagaggtgaaggaacgcatccctatgcccttgcaatggacagtgtttctggc
caccgccaccaagacttcgtgtcctctgatcatcatgcgattgattacgttgaatgcgacggccggtca
gccccggacctccacgcaccggtgctcctccaggaagatgcgcttgtcctccgccatcttgcagggctc
aagctgctcccaaaactcttgggcgggttccggacgggacggctaccgcgggtgcggccctgaccgccac
tgttcggaagcagcggcgctgcatgggcagcggccgctgcggtgcgccacggaccgcatgatccaccgg
aaaagcgcacgcgctggagcgcgcagaggaccacagagaagcggaagagacgccagtactggcaagcag
gctggtcggtgccatggcgcgctactaccctcgctatgactcgggtcctcggccggctggcggtgctga
caattcgtttagtggagcagcgactccattcagctaccagtcgaactcagtggcacagtgactccgctc
ttc

INFORMAL SEQUENCE LISTING

SEQ ID NO: 61
Nucleotide sequence of PmLDH1 promoter that drives the expression of PmKASII in pSZ2532 gatatctccctccgtctctgcactctggcgcccctcctccgtctcgtggactgacggacgagagtctgg
gcgccgcttttctatccacaccgcccttccgcatcgaagacaccacccatcgtgccgccaggtcttcc
ccaatcacccgccctgtggtcctctctcccagccgtgtttggtcgctgcgtccacattttccattcgt
gccccacgatcctcgcccatcttggcgccttggataggcaccctttttcagcacgccctggtgtgtag
cacaacctgacctctctaccgcatcgcctccctccacacctcagttgactcctcgtcgcacgttg
cacccgcaagctccccatttcatcctattgacaatcgcacactgtacatgtatgctcattattttgcaa
aaaaacaggggtcggttcactcctggcagacgacgcggtgctgccgcgcgccgctgaggcggcgtcgc
gacggcaacacccatcgcaccgcacgtcgacgagtcaacccaccctgctcaacggtgatctccccatcg
cgacaccccccgtgaccgtactatgtgcgtccatacgcaacatgaaaaggaccttggtccccggaggcg
gcgagctcgtaatcccgaggttggccccgcttccgctggacacccatcgcatcttccggctcgcccgct
gtcgagcaagcgccctcgtgcgcgcaacccttgtggtgcctgcccgcagagccgggcataaaggcgagc
accacaccgaaccagtccaatttgctttctgcattcactcaccaacttttacatccacacatcgtact
accacacctgcccagtcgggtttgatttctattgcaaaggtgcgggggggttggcgcactgcgtgggtt
gtgcagccggccgccgcggctgtacccagcgatcaggtagcttgggctgtatcttctcaagcattacct
tgtcctgggcgtaggtttgccactagt

SEQ ID NO: 62
Nucleotide sequence of PmAMT3 promoter that drives the expression of PmKASII in pSZ2750 gatatcgaattcggccgacaggacgcgcgtcaaaggtgctggtcgtgtatgccctggccggcaggtcgt
tgctgctgctggttagtgattccgcaaccctgattttggcgtcttattttggcgtggcaaacgctggcg
cccgcgagccgggccggcggcgatgcggtgccccacggctgccggaatccaagggaggcaagagcgccc
gggtcagttgaagggctttacgcgcaaggtacagccgctcctgcaaggctgcgtggtggaattggacgt
gcaggtcctgctgaagttcctccaccgcctcaccagcggacaaagcaccggtgtatcaggtccgtgtca
tccactctaaagaactcgactacgacctactgatggccctagattcttcatcaaaaacgcctgagacac
ttgcccaggattgaaactccctgaagggaccaccaggggccctgagttgttccttcccccgtggcgag
ctgccagccaggctgtacctgtgatcgaggctggcgggaaaataggcttcgtgtgctcaggtcatggga
ggtgcaggacagctcatgaaacgccaacaatcgcacaattcatgtcaagctaatcagctatttcctctt
cacgagctgtaattgtcccaaaattctggtctaccggggtgatccttcgtgtacgggcccttccctca
accctaggtatgcgcgcatgcggtcgccgcgcaactcgcgcgagggccgagggtttgggacgggccgtc
ccgaaatgcagttgcaccggatgcgtggcacctttttgcgataatttatgcaatggactgctctgca
aaattctggctctgtcgccaaccctaggatcagcggcgtaggatttcgtaatcattcgtcctgatgggg
agctaccgactaccctaatatcagcccgactgcctgacgccagcgtccacttttgtgcacacattccat
tcgtgcccaagacatttcattgtggtgcgaagcgtccccagttacgctcacctgtttcccgacctcctt
actgttctgtcgacagagcgggcccacaggccggtcgcagccactagt

SEQ ID NO: 63
Nucleotide sequence of pSZ4424 - for expression of C8 CpalFATB1 ExtC with M230G mutation
THI4a::CrTUB2-NeoR-PmPGH:PmSAD2-2Ver3-
CpSAD1tp_CpalFATB1ExtC_M230G_FLAG-CvNR::THI4a

| Nucleotide positions | Element name |
| --- | --- |
| 794-1105 | CrTUB2 promoter |
| 2581-3146 | PmSAD22 ver3 promoter |
| 1919-2362 | UTR04424PmPGH 3'-UTR |
| 4506-4907 | CvNR 3'-UTR |
| 1-787 | THI4a 5' target flanking sequence |
| 4920-5622 | THI4a 3' target flanking sequence |
| 3271-4419 | CpalC8 ExtC |
| 1118-1912 | NeoR |
| 3157-3261 | CpSAD1tp (tp = transit peptide) |
| 4420-4491 | FLAG |

```
   1 ccctcaactg cgacgctggg aaccttctcc gggcaggcga tgtgcgtggg tttgcctcct
  61 tggcacggct ctacaccgtc gagtacgcca tgaggcggtg atggctgtgt cggttgccac
 121 ttcgtccaga gacggcaagt cgtccatcct ctgcgtgtgt ggcgcgacgc tgcagcagtc
 181 cctctgcagc agatgagcgt gactttggcc atttcacgca ctcgagtgta cacaatccat
 241 ttttcttaaa gcaaatgact gctgattgac cagatactgt aacgctgatt tcgctccaga
 301 tcgcacagat agcgaccatg ttgctgcgtc tgaaaatctg gattccgaat tcgaccctgg
 361 cgctccatcc atgcaacaga tggcgacact tgttacaatt cctgtcaccc atcggcatgg
 421 agcaggtcca cttagattcc cgatcaccca cgcacatctc gctaatagtc attcgttcgt
 481 gtcttcgatc aatctcaagt gagtgtgcat ggatcttggt tgacgatgcg gtatgggttt
 541 gcgccgctgg ctgcagggtc tgcccaaggc aagctaaccc agctcctctc ccgacaata
 601 ctctcgcagg caaagccggt cacttgcctt ccagattgcc aataaactca attatggcct
 661 ctgtcatgcc atccatgggc ctgatgaatg tcacgctcg tgtcctgacc gttcccagc
 721 ctctggcgtc ccctgccccg cccaccagcc cacgccgcgc ggcagtcgct gccaaggctg
 781 tctcggaggt accctttctt gcgctatgac acttccagca aaaggtaggg cgggctgcga
 841 gacggcttcc cggcgctgca tgcaacaccg atgatgcttc gacccccga agctccttcg
 901 gggctgcatg ggcgctccga tgccgctcca gggcgagcgc tgtttaaata gccaggcccc
 961 cgattgcaaa gacattatag cgagctacca aagccatatt caaacaccta gatcactacc
1021 acttctacac aggccactcg agcttgtgat cgcactccgc taaggggcg cctcttcctc
1081 ttcgtttcag tcacaacccg caaactctag aatatcaatg atcgagcagg acggcctcca
1141 cgccggctcc cccgccgcct gggtggagcg cctgttcggc tacgactggg cccagcagac
1201 catcggctgc tccgacgccg ccgtgttccg cctgtccgcc cagggccgcc ccgtgctgtt
1261 cgtgaagacc gacctgtccg gcgccctgaa cgagctgcag gacgaggccg cccgcctgtc
1321 ctggctggcc accaccggcg tgccctgcgc cgccgtgctg gacgtggtga ccgaggccgg
1381 ccgcgactgg ctgctgctgg gcgaggtgcc cggccaggac ctgctgtcct cccacctggc
1441 ccccgccgag aaggtgtcca tcatggccga cgccatgcgc cgcctgcaca ccctggaccc
1501 cgccacctgc cccttcgacc accaggccaa gcaccgcatc gagcgcgccc gcacccgcat
1561 ggaggccggc ctggtggacc aggacgacct ggacgaggag caccaggccc tggcccccgc
1621 cgagctgttc gcccgcctga aggcccgcat gcccgacggc gaggacctgg tggtgaccca
1681 cggcgacgcc tgcctgccca acatcatggt ggagaacggc cgcttctccg gcttcatcga
1741 ctgcggccgc ctgggcgtgg ccgaccgcta ccaggacatc gccctggcca cccgcgacat
1801 cgccgaggag ctgggcggcg agtgggccga ccgcttcctg gtgctgtacg gcatcgccgc
1861 ccccgactcc cagcgcatcg ccttctaccg cctgctggac gagttcttct gacaattgac
1921 gccgcgcgg cgcacctgac ctgttctctc gagggcgcct gttctgcctt gcgaaacaag
1981 ccctggagc atgcgtgcat gatcgtctct ggcgccccgc cgcgcggttt gtcgccctcg
2041 cgggcgccgc ggccgcgggg gcgcattgaa attgttgcaa accccacctg acagattgag
```

-continued

```
2101 ggcccaggca ggaaggcgtt gagatggagg tacaggagtc aagtaactga aagtttttat 2161 gataactaac aacaaagggt cgtttctggc cagcgaatga caagaacaag attccacatt 2221 tccgtgtaga ggcttgccat cgaatgtgag cgggcgggcc gcggacccga caaaaccctt 2281 acgacgtggt aagaaaaacg tggcgggcac tgtccctgta gcctgaagac cagcaggaga 2341 cgatcggaag catcacagca caggatcccg cgtctcgaac agagcgcgca gaggaacgct 2401 gaaggtctcg cctctgtcgc acctcagcgc ggcatacacc acaataacca cctgacgaat 2461 gcgcttggtt cttcgtccat tagcgaagcg tccggttcac acacgtgcca cgttggcgag 2521 gtggcaggtg acaatgatcg gtggagctga tggtcgaaac gttcacagcc tagggatatc 2581 gtgaaaactc gctcgaccgc ccgcgtcccg caggcagcga tgacgtgtgc gtgacctggg 2641 tgtttcgtcg aaaggccagc aaccccaaat cgcaggcgat ccggagattg ggatctgatc 2701 cgagcttgga ccagatcccc cacgatgcgg cacgggaact gcatcgactc ggcgcggaac 2761 ccagctttcg taaatgccag attggtgtcc gataccttga tttgccatca gcgaaacaag 2821 acttcagcag cgagcgtatt tggcgggcgt gctaccaggg ttgcatacat tgcccatttc 2881 tgtctggacc gctttaccgg cgcagagggt gagttgatgg ggttggcagg catcgaaacg 2941 cgcgtgcatg gtgtgtgtgt ctgttttcgg ctgcacaatt tcaatagtcg gatgggcgac 3001 ggtagaattg ggtgttgcgc tcgcgtgcat gcctcgcccc gtcgggtgtc atgaccggga 3061 ctggaatccc ccctcgcgac cctcctgcta acgctcccga ctctcccgcc cgcgcgcagg 3121 atagactcta gttcaaccaa tcgacaacta gtaacaatgg ccaccgcatc cactttctcg 3181 gcgttcaatg cccgctgcgg cgacctgcgt cgctcggcgg gctccgggcc ccggcgccca 3241 gcgaggcccc tccccgtgcg cgggcgcgcc tcctcctccc tgtccccctc cctgaagccc 3301 aagtccatcc ccaacggcgg cttccaggtg aaggccaacg cctccgcgca ccccaaggcg 3361 aacggcagcg cggtgaccct gaagtcgggc tccctgaaca cccaggagga cacgctcagc 3421 tcgtcccccc cccccgcgc gttcttcaac cagctgcccg actggagcat gctgctgacc 3481 gcgatcacca cggtcttcgt ggcgcccgag aagcgctgga ccatgttcga ccgcaagtcg 3541 aagcgcccca acatgctgat ggactccttc ggcctggagc gcgtggtcca ggacggcctg 3601 gtgttccgcc agagcttctc gatccgctcc tacgagatct gcgcggaccg caccgcgagc 3661 atcgagacgg tgatgaacca cgtccaggag acctcgctga ccagtgcaa gtccatcggc 3721 ctgctggacg acggcttcgg ccgcagcccc gagatgtgca agcgcgacct gatctgggtg 3781 gtcacccgca tgaagatcat ggtgaaccgc taccccacgt ggggcgacac catcgaggtc 3841 tcgacgtggc tgtcccagag cggcaagatc ggcggcggcc gcgactggct gatctcggac 3901 tgcaacaccg gcgagatcct ggtgcgcgcg acgtccgtct acgcgatgat gaaccagaag 3961 acccgccgct tcagcaagct gccccacgag gtgcgccagg agttcgcgcc ccacttcctg 4021 gactcgcccc ccgcgatcga ggacaacgac ggcaagctgc agaagttcga cgtcaagacg 4081 ggcgactcca tccgcaaggg cctgacccc ggctggtacg acctggacgt gaaccagcac 4141 gtgagcaacg tcaagtacat cggctggatc ctggagtcga tgcccaccga ggtcctggag 4201 acgcaggagc tgtgctccct gaccctggag taccgccgcg agtgcggccg cgactcggtg 4261 ctggagagcg tcaccagcat ggaccccctcg aaggtgggcg accgcttcca gtaccgccac 4321 ctgctgcgcc tggaggacgg cgcggacatc atgaagggcc gcaccgagtg gcgccccaag 4381 aacgcgggca cgaacggcgc gatctccacc ggcaagacga tggactacaa ggaccacgac 4441 ggcgactaca aggaccacga catcgactac aaggacgacg acgacaagtg attaattaac
```

-continued

```
4501 tcgaggcagc agcagctcag atagtatcga cacactctgg acgctggtcg tgtgatggac
4561 tgttgccgcc acacttgctg ccttgacctg tgaatatccc tgccgctttt atcaaacagc
4621 ctcagtgtgt ttgatcttgt gtgtacgcgc ttttgcgagt tgctagctgc ttgtgctatt
4681 tgcgaatacc accccagca tccccttccc tcgtttcata tcgcttgcat cccaaccgca
4741 acttatctac gctgtcctgc tatccctcag cgctgctcct gctcctgctc actgcccctc
4801 gcacagcctt ggtttgggct ccgcctgtat tctcctggta ctgcaacctg taaaccagca
4861 ctgcaatgct gatgcacggg aagtagtggg atgggaacac aaatggaaag cttgagctcc
4921 agcgccatgc cacgcccttt gatggcttca agtacgatta cggtgttgga ttgtgtgttt
4981 gttgcgtagt gtgcatggtt tagaataata cacttgattt cttgctcacg gcaatctcgg
5041 cttgtccgca ggttcaaccc catttcggag tctcaggtca gccgcgcaat gaccagccgc
5101 tacttcaagg acttgcacga caacgccgag gtgagctatg tttaggactt gattggaaat
5161 tgtcgtcgac gcatattcgc gctccgcgac agcacccaag caaaatgtca agtgcgttcc
5221 gatttgcgtc cgcaggtcga tgttgtgatc gtcggcgccg gatccgccgg tctgtcctgc
5281 gcttacgagc tgaccaagca ccctgacgtc cgggtacgcg agctgagatt cgattagaca
5341 taaattgaag attaaacccg tagaaaaatt tgatggtcgc gaaactgtgc tcgattgcaa
5401 gaaattgatc gtcctccact ccgcaggtcg ccatcatcga gcagggcgtt gctcccggcg
5461 gcggcgcctg gctgggggga cagctgttct cggccatgtg tgtacgtaga aggatgaatt
5521 tcagctggtt tcgttgcac agctgtttgt gcatgatttg tttcagacta ttgttgaatg
5581 tttttagatt tcttaggatg catgatttgt ctgcatgcga ct
```

SEQ ID NO: 64
Nucleotide sequence of pSZ4440
THI4a5'::CrTUB2_ScSUC2_PmPGH::AMT1-1p_CpSAD1tp-
CpalFATB2_ExtB_Flag_PmEF1::THI4a3'

| Nucleotide positions | Element name |
|---|---|
| 2723-3166 | PmPGH 3'UTR |
| 5327-5732 | PmEF1 3'UTR |
| 1118-2716 | ScSUC2o |
| 3966-5318 | CpalFATB2__ExtB with transit peptide |
| 3387-3958 | pPmAMT11 |
| 794-1105 | CrTUB2 promoter |

-continued

| Nucleotide positions | Element name |
|---|---|
| 1-787 | THI4a 5' flanking sequence |
| 5739-6441 | THI4a 3' flanking sequence |
| 5247-5318 | Flag |

```
  1 ccctcaactg cgacgctggg aaccttctcc gggcaggcga tgtgcgtggg tttgcctcct
 61 tggcacggct ctacaccgtc gagtacgcca tgaggcggtg atggctgtgt cggttgccac
121 ttcgtccaga gacggcaagt cgtccatcct ctgcgtgtgt ggcgcgacgc tgcagcagtc
181 cctctgcagc agatgagcgt gactttggcc atttcacgca ctcgagtgta cacaatccat
241 ttttcttaaa gcaaatgact gctgattgac cagatactgt aacgctgatt tcgctccaga
301 tcgcacagat agcgaccatg ttgctgcgtc tgaaaatctg gattccgaat tcgaccctgg
361 cgctccatcc atgcaacaga tggcgacact tgttacaatt cctgtcaccc atcggcatgg
421 agcaggtcca cttagattcc cgatcaccca cgcacatctc gctaatagtc attcgttcgt
481 gtcttcgatc aatctcaagt gagtgtgcat ggatcttggt tgacgatgcg gtatgggttt
541 gcgccgctgg ctgcagggtc tgcccaaggc aagctaaccc agctcctctc cccgacaata
601 ctctcgcagg caaagccggt cacttgcctt ccagattgcc aataaactca attatggcct
661 ctgtcatgcc atccatgggt ctgatgaatg gtcacgctcg tgtcctgacc gttccccagc
```

-continued

```
 721 ctctggcgtc ccctgccccg cccaccagcc cacgccgcgc ggcagtcgct gccaaggctg
 781 tctcggaggt acccttttctt gcgctatgac acttccagca aaaggtaggg cgggctgcga
 841 gacggcttcc cggcgctgca tgcaacaccg atgatgcttc gaccccccga agctccttcg
 901 gggctgcatg ggcgctccga tgccgctcca gggcgagcgc tgtttaaata gccaggcccc
 961 cgattgcaaa gacattatag cgagctacca aagccatatt caaacaccta gatcactacc
1021 acttctacac aggccactcg agcttgtgat cgcactccgc taaggggcg cctcttcctc
1081 ttcgtttcag tcacaacccg caaactctag aatatcaatg ctgctgcagg ccttcctgtt
1141 cctgctggcc ggcttcgccg ccaagatcag cgcctccatg acgaacgaga cgtccgaccg
1201 cccccctggtg cacttcaccc ccaacaaggg ctggatgaac gaccccaacg gcctgtggta
1261 cgacgagaag gacgccaagt ggcacctgta cttccagtac aacccgaacg acaccgtctg
1321 ggggacgccc ttgttctggg gccacgccac gtccgacgac ctgaccaact gggaggacca
1381 gcccatcgcc atcgccccga gcgcaacga ctccggcgcc ttctccggct ccatggtggt
1441 ggactacaac aacacctccg gcttcttcaa cgacaccatc gacccgcgcc agcgctgcgt
1501 ggccatctgg acctacaaca ccccggagtc cgaggagcag tacatctcct acagcctgga
1561 cggcggctac accttcaccg agtaccagaa gaaccccgtg ctggccgcca actccaccca
1621 gttccgcgac ccgaaggtct tctggtacga gccctcccag aagtggatca tgaccgcggc
1681 caagtcccag gactacaaga tcgagatcta ctcctccgac gacctgaagt cctggaagct
1741 ggagtccgcg ttcgccaacg agggcttcct cggctaccag tacgagtgcc ccggcctgat
1801 cgaggtcccc accgagcagg accccagcaa gtcctactgg gtgatgttca tctccatcaa
1861 ccccggcgcc ccggccggcg gctccttcaa ccagtacttc gtcggcagct tcaacggcac
1921 ccacttcgag gccttcgaca accagtcccg cgtggtggac ttcggcaagg actactacgc
1981 cctgcagacc ttcttcaaca ccgacccgac ctacgggagc gccctgggca tcgcgtgggc
2041 ctccaactgg gagtactccg ccttcgtgcc caccaacccc tggcgctcct ccatgtccct
2101 cgtgcgcaag ttctcccctca caccgagta ccaggccaac ccggagacgg agctgatcaa
2161 cctgaaggcc gagccgatcc tgaacatcag caacgccggc ccctggagcc ggttcgccac
2221 caacaccacg ttgacgaagg ccaacagcta caacgtcgac ctgtccaaca gcaccggcac
2281 cctggagttc gagctggtgt acgccgtcaa caccacccag acgatctcca agtccgtgtt
2341 cgcggacctc tccctctggt tcaagggcct ggaggacccc gaggagtacc tccgcatggg
2401 cttcgaggtg tccgcgtcct ccttcttcct ggaccgcggg aacagcaagg tgaagttcgt
2461 gaaggagaac ccctacttca ccaaccgcat gagcgtgaac aaccagccct tcaagagcga
2521 gaacgacctg tcctactaca aggtgtacgg cttgctggac cagaacatcc tggagctgta
2581 cttcaacgac ggcgacgtcg tgtccaccaa cacctacttc atgaccaccg gaacgccct
2641 gggctccgtg aacatgacga cggggggtgga caacctgttc tacatcgaca gttccaggt
2701 gcgcgaggtc aagtgacaat tgacgcccgc gcggcgcacc tgacctgttc tctcgagggc
2761 gcctgttctg ccttgcgaaa caagcccctg gagcatgcgt gcatgatcgt ctctggcgcc
2821 ccgccgcgcg gtttgtcgcc ctcgcgggcg ccgcggccgc gggggcgcat tgaaattgtt
2881 gcaaaccccca cctgacagat tgagggccca ggcaggaagg cgttgagatg gaggtacagg
2941 agtcaagtaa ctgaaagttt ttatgataac taacaacaaa gggtcgtttc tggccagcga
3001 atgacaagaa caagattcca catttccgtg tagaggcttg ccatcgaatg tgagcgggcg
3061 ggccgcggac ccgacaaaac ccttacgacg tggtaagaaa aacgtggcgg gcactgtccc
3121 tgtagcctga agaccagcag gagacgatcg gaagcatcac agcacaggat cccgcgtctc
```

-continued

```
3181 gaacagagcg cgcagaggaa cgctgaaggt ctcgcctctg tcgcacctca gcgcggcata
3241 caccacaata accacctgac gaatgcgctt ggttcttcgt ccattagcga agcgtccggt
3301 tcacacacgt gccacgttgg cgaggtggca ggtgacaatg atcggtggag ctgatggtcg
3361 aaacgttcac agcctaggga tatcgagtgc ggaggggccg gccgacccttt tgatgccgca
3421 accacacata cgtgttgtta tagtctagta gtacagtact gcaagcacca acttgaacct
3481 caagatggtc cgtcgaccca gctccagttt gcaacgaagg tcgggcgggt attggagatc
3541 cagatcaaag cgtaaatgcg accctctccc gaagagactt catgcgtgtg tcctgaagtg
3601 catgaaaaca ttccaggcag cgactcgtgc tccaggctgg cgttctttgc gacttgttgg
3661 cccgcttcgc agtcggacct aggggcctga ttccgcggtc gcgttgatga cacagaaacc
3721 aacggacgac ccatgtgaca ccggggactg aatcacagct gcccccaggg gctagggcat
3781 tcgagctgat acattgataa cgctagacga agtgcactgc ggcggtaaaa agctctattt
3841 gtgccatcac agcgccttgc gtggcttcag gagcgcttga cgcgctgcat ttctgaagtc
3901 gaaagcccta gtcgccagga ggagggtcga ctcgcccgca gttcgggaac gtttggacca
3961 ctagtatggc caccgcctcc accttctccg ccttcaacgc ccgctgcggc gacctgcgcc
4021 gctccgccgg ctccggcccc cgccgccccg cccgcccct gccgtgcgc ggccgcgcct
4081 cctccctgtc cgtgcccttc aagcccaagt ccaaccacaa cggcggcttc caggtgaagg
4141 ccaacgcctc cgcgcacccc aaggcgaacg gcagcgcggt gtcgctgaag tcgggctccc
4201 tggagaccca ggaggacaag acgagcagct cgtcccccc ccccgcacg ttcatcaacc
4261 agctgccgt gtggagcatg ctgctgtcgg cggtgaccac ggtcttcggc gtggccgaga
4321 agcagtggcc catgctggac cgcaagtcca agcgccccga catgctggtc gagcccctgg
4381 gcgtggaccg catcgtctac gacggcgtga gcttccgcca gtcgttctcc atccgcagct
4441 acgagatcgg cgccgaccgc accgcctcga tcgagacgct gatgaacatg ttccaggaga
4501 cctccctgaa ccactgcaag atcatcggcc tgctgaacga cggcttcggc cgcacgcccg
4561 agatgtgcaa gcgcgacctg atctgggtcg tgaccaagat gcagatcgag gtgaaccgct
4621 accccacgtg gggcgacacc atcgaggtca acacgtgggt gagcgcctcg ggcaagcacg
4681 gcatgggccg cgactggctg atctccgact gccacaccgg cgagatcctg atccgcgcga
4741 cgagcgtctg ggcgatgatg aaccagaaga cccgccgcct gtcgaagatc ccctacgagg
4801 tgcgccagga gatcgagccc cagttcgtcg actccgcccc cgtgatcgtg gacgaccgca
4861 agttccacaa gctggacctg aagacggcg acagcatctg caacggcctg accccccgct
4921 ggacggacct ggacgtgaac cagcacgtca acaacgtgaa gtacatcggc tggatcctgc
4981 agtcggtccc caccgaggtg ttcgagacgc aggagctgtg cggcctgacc ctggagtacc
5041 gccgcgagtg cggccgcgac tccgtgctgg agagcgtcac ggccatggac ccctcgaagg
5101 agggcgaccc ctccctgtac cagcacctgc tgcgcctgga ggacggcgcg gacatcgtga
5161 agggccgcac cgagtggcgc cccaagaacg ccggcgccaa gggcgccatc ctgacgggca
5221 agaccagcaa cggcaactcg atctccatgg actacaagga ccacgacggc gactacaagg
5281 accacgacat cgactacaag gacgacgacg acaagtgatt aattaacgcc accctgaagc
5341 ctgtgaagga cttcacggcc cagatccaga ccctggacat ccccggcgag gtcaaggccg
5401 gatactcccc catcggcttt gtgcgctgcg gccgctccgc ctgccgcatc tccaagatca
5461 actggaaggt cggcaaggag accggtggca agaagctgga ggagcccac agcctcaagg
5521 ccaacgagat ggctgaggtc gtgtttgagc ccgtccagcc cctggtcgtc gactccttca
```

```
5581 agaactgcga gggtctgtcc cgcattgcct tcctggacgg caacaccgcc gtcatgctgg 5641 gcaaggtggt ctccacctcc gccaagtaga gagggacacc tcttcttgtc ctctctggaa 5701 aagctcgcat gtgagtgccc acacgttctg tagagctcca gcgccatgcc acgcctttg 5761 atggcttcaa gtacgattac ggtgttggat tgtgtgtttg ttgcgtagtg tgcatggttt 5821 agaataatac acttgatttc ttgctcacgg caatctcggc ttgtccgcag gttcaacccc 5881 atttcggagt ctcaggtcag ccgcgcaatg accagccgct acttcaagga cttgcacgac 5941 aacgccgagg tgagctatgt ttaggacttg attggaaatt gtcgtcgacg catattcgcg 6001 ctccgcgaca gcacccaagc aaaatgtcaa gtgcgttccg atttgcgtcc gcaggtcgat 6061 gttgtgatcg tcggcgccgg atccgccggt ctgtcctgcg cttacgagct gaccaagcac 6121 cctgacgtcc gggtacgcga gctgagattg gattagacat aaattgaaga ttaaacccgt 6181 agaaaaattt gatggtcgcg aaactgtgct cgattgcaag aaattgatcg tcctccactc 6241 cgcaggtcgc catcatcgag cagggcgttg ctcccggcgg cggcgcctgg ctgggggggac 6301 agctgttctc ggccatgtgt gtacgtagaa ggatgaattt cagctggttt tcgttgcaca 6361 gctgtttgtg catgatttgt ttcagactat tgttgaatgt ttttagatttt cttaggatgc 6421 atgatttgtc tgcatgcgac t
```

SEQ ID NO: 65 - Nucleotide sequence of pSZ4442 THI4a5'::CrTUB2_ScSUC2_PmPGH::PmSAD2-2ver2_CpSAD1tp-CpalFATB2_ExtB_Flag_PmAHCY::THI4a3'

| Nucleotide positions | Element name |
| --- | --- |
| 794-1105 | CrTUB2 promoter |
| 3385-4113 | PmSAD22 promoter ver2 |
| 5481-5935 | PmAHCY 3'UTR |
| 2723-3166 | PmPGH 3'UTR |
| 1118-2716 | ScSUC2o |
| 4120-5472 | CpalFATB2_ExtB with transit peptide |
| 1-787 | THI4a 5' flanking sequence |
| 3173-3378 | THI4a 3' flanking sequence |
| 5401-5472 | Flag |

```
  1 ccctcaactg cgacgctggg aaccttctcc gggcaggcga tgtgcgtggg tttgcctcct 61 tggcacggct ctacaccgtc gagtacgcca tgaggcggtg atggctgtgt cggttgccac 121 ttcgtccaga gacggcaagt cgtccatcct ctgcgtgtgt ggcgcgacgc tgcagcagtc 181 cctctgcagc agatgagcgt gactttggcc atttcacgca ctcgagtgta cacaatccat 241 ttttcttaaa gcaaatgact gctgattgac cagatactgt aacgctgatt tcgctccaga 301 tcgcacagat agcgaccatg ttgctgcgtc tgaaaatctg gattccgaat tcgaccctgg 361 cgctccatcc atgcaacaga tggcgacact tgttacaatt cctgtcaccc atcggcatgg 421 agcaggtcca cttagattcc cgatcaccca cgcacatctc gctaatagtc attcgttcgt 481 gtcttcgatc aatctcaagt gagtgtgcat ggatcttggt tgacgatgcg gtatgggttt 541 gcgccgctgg ctgcagggtc tgcccaaggc aagctaaccc agctcctctc cccgacaata 601 ctctcgcagg caaagccggt cacttgcctt ccagattgcc aataaactca attatggcct 661 ctgtcatgcc atccatgggt ctgatgaatg gtcacgctcg tgtcctgacc gttccccagc 721 ctctggcgtc ccctgccccg cccaccagcc cacgccgcgc ggcagtcgct gccaaggctg 781 tctcggaggt acccttttctt gcgctatgac acttccagca aaaggtaggg cgggctgcga 841 gacggcttcc cggcgctgca tgcaacaccg atgatgcttc gaccccccga agctccttcg 901 gggctgcatg ggcgctccga tgccgctcca gggcgagcgc tgtttaaata gccaggcccc 961 cgattgcaaa gacattatag cgagctacca aagccatatt caaacaccta gatcactacc
```

-continued

```
1021 acttctacac aggccactcg agcttgtgat cgcactccgc taaggggggcg cctcttcctc
1081 ttcgtttcag tcacaacccg caaactctag aatatcaatg ctgctgcagg ccttcctgtt
1141 cctgctggcc ggcttcgccg ccaagatcag cgcctccatg acgaacgaga cgtccgaccg
1201 cccctggtg cacttcaccc ccaacaaggg ctggatgaac accccaacg gcctgtggta
1261 cgacgagaag gacgccaagt ggcacctgta cttccagtac aacccgaacg acaccgtctg
1321 ggggacgccc ttgttctggg ccacgccac gtccgacgac ctgaccaact gggaggacca
1381 gcccatcgcc atcgccccga agcgcaacga ctccggcgcc ttctccggct ccatggtggt
1441 ggactacaac aacacctccg gcttcttcaa cgacaccatc gacccgcgcc agcgctgcgt
1501 ggccatctgg acctacaaca ccccggagtc cgaggagcag tacatctcct acagcctgga
1561 cggcggctac accttcaccg agtaccagaa gaaccccgtg ctggccgcca actccaccca
1621 gttccgcgac ccgaaggtct tctggtacga gccctccag aagtggatca tgaccgcggc
1681 caagtcccag gactacaaga tcgagatcta ctcctccgac gacctgaagt cctggaagct
1741 ggagtccgcg ttcgccaacg agggcttcct cggctaccag tacgagtgcc ccggcctgat
1801 cgaggtcccc accgagcagg accccagcaa gtcctactgg gtgatgttca tctccatcaa
1861 ccccggcgcc ccggccggcg gctccttcaa ccagtacttc gtcggcagct caacggcac
1921 ccacttcgag gccttcgaca accagtcccg cgtggtggac ttcggcaagg actactacgc
1981 cctgcagacc ttcttcaaca ccgacccgac ctacgggagc gccctgggca tcgcgtgggc
2041 ctccaactgg gagtactccg ccttcgtgcc caccaacccc tggcgctcct ccatgtccct
2101 cgtgcgcaag ttctccctca cacccgagta ccaggccaac ccggagacgg agctgatcaa
2161 cctgaaggcc gagccgatcc tgaacatcag caacgccggc ccctggagcc ggttcgccac
2221 caacaccacg ttgacgaagg ccaacagcta caacgtcgac ctgtccaaca gcaccggcac
2281 cctggagttc gagctggtgt acgccgtcaa caccacccag acgatctcca gtccgtgtt
2341 cgcggacctc tccctctggt tcaagggcct ggaggacccc gaggagtacc tccgcatggg
2401 cttcgaggtg tccgcgtcct ccttcttcct ggaccgcggg aacagcaagg tgaagttcgt
2461 gaaggagaac ccctacttca ccaaccgcat gagcgtgaac aaccagccct caagagcga
2521 gaacgacctg tcctactaca aggtgtacgg cttgctggac cagaacatcc tggagctgta
2581 cttcaacgac ggcgacgtcg tgtccaccaa cacctacttc atgaccaccg gaacgccct
2641 gggctccgtg aacatgacga cggggggtgga caacctgttc tacatcgaca agttccaggt
2701 gcgcgaggtc aagtgacaat tgacgcccgc gcggcgcacc tgacctgttc tctcgagggc
2761 gcctgttctg ccttgcgaaa caagcccctg gagcatgcgt gcatgatcgt ctctggcgcc
2821 ccgccgcgcg gtttgtcgcc ctcgcgggcg ccgcggccgc gggggcgcat tgaaattgtt
2881 gcaaaccccca cctgacagat tgagggccca ggcaggaagg cgttgagatg gaggtacagg
2941 agtcaagtaa ctgaaagttt ttatgataac taacaacaaa gggtcgtttc tggccagcga
3001 atgacaagaa caagattcca catttccgtg tagaggcttg ccatcgaatg tgagcgggcg
3061 ggccgcggac ccgacaaaac ccttacgacg tggtaagaaa aacgtggcgg gcactgtccc
3121 tgtagcctga agaccagcag gagacgatcg gaagcatcac agcacaggat cccgcgtctc
3181 gaacagagcg cgcagaggaa cgctgaaggt ctcgcctctg tcgcacctca gcgcggcata
3241 caccacaata accacctgac gaatgcgctt ggttcttcgt ccattagcga agcgtccggt
3301 tcacacacgt gccacgttgg cgaggtggca ggtgacaatg atcggtggag ctgatggtcg
3361 aaacgttcac agcctaggga tatcctggct cgggcctcgt gctggcactc cctcccatgc
```

-continued

```
3421 cgacaacctt tctgctgtca ccacgaccca cgatgcaacg cgacacgacc cggtgggact
3481 gatcggttca ctgcacctgc atgcaattgt cacaagcgca tactccaatc gtatccgttt
3541 gatttctgtg aaaactcgct cgaccgcccg cgtcccgcag gcagcgatga cgtgtgcgtg
3601 acctgggtgt tcgtcgaaa ggccagcaac cccaaatcgc aggcgatccg gagattggga
3661 tctgatccga gcttggacca gatccccac gatgcggcac gggaactgca tcgactcggc
3721 gcggaaccca gctttcgtaa atgccagatt ggtgtccgat accttgattt gccatcagcg
3781 aaacaagact tcagcagcga gcgtatttgg cgggcgtgct accaggggttg catacattgc
3841 ccatttctgt ctggaccgct ttaccggcgc agagggtgag ttgatggggt tggcaggcat
3901 cgaaacgcgc gtgcatggtg tgtgtgtctg ttttcggctg cacaatttca atagtcggat
3961 gggcgacggt agaattgggt gttgcgctcg cgtgcatgcc tcgccccgtc gggtgtcatg
4021 accgggactg gaatccccc tcgcgaccct cctgctaacg ctcccgactc tcccgcccgc
4081 gcgcaggata gactctagtt caaccaatcg acaactagta tggccaccgc ctccaccttc
4141 tccgccttca acgcccgctg cggcgacctg cgccgctccg ccggctccgg ccccgccgc
4201 cccgcccgcc cctgcccgt gcgcggccgc gcctcctccc tgtccgtgcc cttcaagccc
4261 aagtccaacc acaacggcgg cttccaggtg aaggccaacg cctccgcgca ccccaaggcg
4321 aacggcagcg cggtgtcgct gaagtcgggc tccctggaga cccaggagga caagacgagc
4381 agctcgtccc cccccccg cacgttcatc aaccagctgc ccgtgtggag catgctgctg
4441 tcggcggtga ccacggtctt cggcgtggcc gagaagcagt ggcccatgct ggaccgcaag
4501 tccaagcgcc ccgacatgct ggtcgagccc ctgggcgtgg accgcatcgt ctacgacggc
4561 gtgagcttcc gccagtcgtt ctccatccgc agctacgaga tcggcgccga ccgcaccgcc
4621 tcgatcgaga cgctgatgaa catgttccag gagacctccc tgaaccactg caagatcatc
4681 ggcctgctga cgacggctt cggccgcacg cccgagatgt gcaagcgcga cctgatctgg
4741 gtcgtgacca agatgcagat cgaggtgaac cgctacccca cgtggggcga caccatcgag
4801 gtcaacacgt gggtgagcgc ctcgggcaag cacggcatgg gccgcgactg gctgatctcc
4861 gactgccaca ccggcgagat cctgatccgc gcgacgagcg tctgggcgat gatgaaccag
4921 aagacccgcc gcctgtcgaa gatcccctac gaggtgcgcc aggagatcga gccccagttc
4981 gtcgactccg ccccgtgat cgtggacgac cgcaagttcc acaagctgga cctgaagacg
5041 ggcgacagca tctgcaacgg cctgacccc cgctggacgg acctggacgt gaaccagcac
5101 gtcaacaacg tgaagtacat cggctggatc ctgcagtcgg tccccaccga ggtgttcgag
5161 acgcaggagc tgtgcggcct gaccctggag taccgccgcg agtgcggccg cgactccgtg
5221 ctggagagcg tcacgccat ggaccctcg aaggagggcg accgctccct gtaccagcac
5281 ctgctgcgcc tggaggacgg cgcggacatc gtgaagggcc gcaccgagtg gcgccccaag
5341 aacgccggcg ccaagggcgc catcctgacg ggcaagacca gcaacggcaa ctcgatctcc
5401 atggactaca aggaccacga cggcgactac aaggaccacg acatcgacta caaggacgac
5461 gacgacaagt gattaattaa atgcggggag tgaaggggga ggaaggaggc gtggctggcg
5521 atcgggtggt cgagattgta gattcacgat agggttcgtg tgtctttgtg acgctcaatc
5581 aatcgatcga tcgatcttcc cgacgcatag tcgccgcctc ttgttgttcc cgtgaaataa
5641 atatgtaacc aataaaaaca gacactctgc atggggcata catagaccga ggagtcgtcg
5701 ctcaaacctg atcgctgccc ccagccatgt gtcaagatga tattttcg tttcaaacac
5761 ggtcgggcac ctgcccca tctctaccctc catcgcgaga cagtcgtcgg gctcgcggcg
5821 atcgcggatc acacacaatt taatcatgtg ccactattag tattacgcgt actcaacacc
```

-continued

```
5881 cactccctag tatacacaca caactcggca accagcagat catcctgtgg tcccgagagc
5941 tccagcgcca tgccacgccc tttgatggct tcaagtacga ttcggtgtt ggattgtgtg
6001 tttgttgcgt agtgtgcatg gtttagaata atacacttga tttcttgctc acggcaatct
6061 cggcttgtcc gcaggttcaa ccccatttcg gagtctcagg tcagccgcgc aatgaccagc
6121 cgctacttca aggacttgca cgacaacgcc gaggtgagct atgtttagga cttgattgga
6181 aattgtcgtc gacgcatatt cgcgctccgc gacagcaccc aagcaaaatg tcaagtgcgt
6241 tccgatttgc gtccgcaggt cgatgttgtg atcgtcggcg ccggatccgc cggtctgtcc
6301 tgcgcttacg agctgaccaa gcaccctgac gtccgggtac gcgagctgag attcgattag
6361 acataaattg aagattaaac ccgtagaaaa atttgatggt cgcgaaactg tgctcgattg
6421 caagaaattg atcgtcctcc actccgcagg tcgccatcat cgagcagggc gttgctcccg
6481 gcggcggcgc ctggctgggg ggacagctgt tctcggccat gtgtgtacgt agaaggatga
6541 atttcagctg gttttcgttg cacagctgtt tgtgcatgat ttgtttcaga ctattgttga
6601 atgtttttag atttcttagg atgcatgatt tgtctgcatg cgact
```

SEQ ID NO: 66 - KAS_II_genomic_allele_1_-_KASII-allele_1_CDS
ATGCAGACCGCGCACCAGCGGCCCCCGACCGAGGGGCACTGCTTCGGTGCGAGGCTGCCCACGGCGTCG
AGGCGGGCGGTGCGCCGGGCATGGTCCCGCATCGCGCGCGCGGCGGCCGCGGCCGACGCAAACCCCGCC
CGCCCTGAGCGCCGCGTGGTCATCACGGGCCAGGGCGTGGTGACCAGCCTGGGCCAGACGATCGAGCAG
TTTTACAGCAGCCTGCTGGAGGGCGTGAGCGGCATCTCGCAGATACAGAAGTTCGACACCACGGGCTAC
ACGACGACGATCGCGGGCGAGATCAAGTCGCTGCAGCTGGACCCGTACGTGCCCAAGCGCTGGGCGAAG
CGCGTGGACGACGTGATAAAGTACGTCTACATCGCGGGCAAGCAGGCGCTGGAGAGCGCCGGCCTGCCG
ATCGAGGCGGCGGGGCTGGCGGGCGCGGGGCTGGACCCGGCGCTGTGCGGCGTGCTCATCGGCACCGCC
ATGGCGGGCATGACGTCTTTCGCGGCGGGCGTGGAGGCGCTGACGCGCGGCGGCGTGCGCAAGATGAAC
CCCTTTTGCATCCCCTTCTCCATCTCCAACATGGGCGGCGCGATGCTGGCGATGGACATCGGCTTCATG
GGCCCCAACTACTCCATCTCCACGGCCTGCGCGACGGGCAACTACTGCATCCTGGGCGCGGCGGACCAC
ATCCGGCGCGGCGACGCAAACGTGATGCTGGCCGGCGGCGCGGACGCGGCCATCATCCCCTCGGGCATC
GGCGGCTTCATCGCGTGCAAGGCGCTGAGCAAGCGCAACGACGAGCCCGAGCGCGCGAGCCGGCCCTGG
GACGCCGACCGCGACGGCTTCGTCATGGGCGAGGGCGCCGGCGTGCTGGTGCTGGAGGAGCTGGAGCAC
GCCAAGCGCCGCGGCGCGACCATTTTGGCTGAATTAGTTGGCGGCGCGGCCACCTCGGACGCGCACCAC
ATGACCGAGCCCGACCCGCAGGGCCGCGGCGTGCGCCTCTGCCTCGAGCGCGCGCTCGAGCGCGCGCGC
CTCGCGCCCGAGCGCGTCGGCTACGTCAACGCGCACGGCACCAGCACGCCCGCGGGCGACGTGGCCGAG
TACCGCGCCATCCGCGCCGTCATCCCGCAGGACTCACTACGCATCAACTCCACAAAGTCCATGATCGGG
CACCTGCTCGGCGGCGCCGGCGCGGTCGAGGCCGTGGCCGCCATCCAGGCCCTGCGCACCGGCTGGCTC
CACCCCAACTTGAACCTCGAGAACCCCGCGCCTGGCGTCGACCCCGTCGTGCTCGTGGGCCGCGGAAG
GAGCGCGCCGAAGACCTGGACGTCGTCCTCTCCAACTCCTTTGGCTTTGGCGGGCACAATTCGTGCGTC
ATCTTCCGAAAGTACGACGAGTGA SEQ ID NO: 67 - KAS_II_genomic_allele_1_-_KASII-
allele_1_CDS_translation
MQTAHQRPPTEGHCFGARLPTASRRAVRRAWSRIARAAAAADANPARPERRVVITGQGVVTSLGQTIEQ

FYSSLLEGVSGISQIQKFDTTGYTTTIAGEIKSLQLDPYVPKRWAKRVDDVIKYVYIAGKQALESAGLP

IEAAGLAGAGLDPALCGVLIGTAMAGMTSFAAGVEALTRGGVRKMNPFCIPFSISNMGGAMLAMDIGFM

GPNYSISTACATGNYCILGAADHIRRGDANVMLAGGADAAIIPSGIGGFIACKALSKRNDEPERASRPW

DADRDGFVMGEGAGVLVLEELEHAKRRGATILAELVGGAATSDAHHMTEPDPQGRGVRLCLERALERAR

LAPERVGYVNAHGTSTPAGDVAEYRAIRAVIPQDSLRINSTKSMIGHLLGGAGAVEAVAAIQALRTGWL

HPNLNLENPAPGVDPVVLVGPRKERAEDLDVVLSNSFGFGGHNSCVIFRKYDE

SEQ ID NO: 68 - KAS_II_genomic_allele_2_-_KASII-allele_2_CDS
ATGCAGACCGCGCACCAGCGGCCCCCGACCGAGGGGCACTGCTTCGGTGCGAGGCTGCCCACGGCGTCG

AGGCGGGCGGTGCGCCGGGCGTGGTCCCGCATCGCGCGCGCGGCGGCCGCGGCCGACGCGACCCCCGCC

CGCCCTCCGCGCCGCGTGGTCGTGACGGGCCAGGGCGTGGTGACCAGCCTGGGCCAGACGATCGAGCAG

TTTTACAGCAGCCTGCTGGAGGGCGTGAGCGGCATCTCGCAGATCCAAAAGTTTGACACCACGGGCTAC

ACGACGACGATCGCGGGCGAGATCAAGTCGCTGCAGCTGGACCCGTACGTGCCCAAGCGCTGGGCCAAG

CGCGTGGACGACGTCATCAAGTACGTCTACATCGCGGGCAAGCAGGCGCTGGAGAACGCGGGGCTGCCG

ATCGAGGCGGCGGGGCTGGCGGGCGCGGGGCTGGACCCCGCGCTGTGCGGCGTGCTCATCGGCACCGCC

ATGGCGGGCATGACGTCCTTCGCGGCGGGCGTGGAGGCGCTGACGCGCGGCGGCGTGCGCAAGATGAAC

CCCTTTTGCATCCCCTTCTCCATCTCCAACATGGGCGGCGCGATGCTGGCGATGGACATCGGCTTCATG

GGCCCCAACTACTCCATCTCCACGGCCTGCGCGACGGGCAACTACTGCATCCTGGGCGCGGCGGACCAC

ATCCGGCGCGGCGACGCGGACGTGATGCTGGCCGGCGGCGCGGACGCGGCCATCATCCCCTCGGGCATC

GGCGGCTTCATCGCGTGCAAGGCGCTGAGCAAGCGCAACGACGAGCCCGAGCGCGCGAGCCGGCCCTGG

GACGCCGACCGCGACGGCTTCGTCATGGGCGAGGGCGCCGGCGTGCTGGTGCTGGAGGAGCTGGAGCAC

GCCAAGCGCCGGCGCGACCATCCTGGCCGAATTCGTCGGCGGCGCGGCCACCTCGGACGCGCACCAC

ATGACCGAGCCGGACCCGCAGGGCCGCGGCGTGCGCCTCTGCCTCGAACGCGCGCTCGAGCGCGCGCGC

CTCGCGCCCGAGCGCGTCGGCTACGTCAACGCGCACGGCACCAGCACGCCCGCGGGCGACGTGGCCGAG

TACCGCGCCATCCGCGCCGTCATCCCGCAGGACTCGCTGCGCATCAACTCCACCAAGTCCATGATCGGG

CACCTGCTCGGCGGCGCCGGCGCGGTCGAGGCCGTGGCCGCCATCCAGGCCCTGCGCACCGGCTGGCTC

CACCCCAACCTCAACCTCGAGAACCCCGCACCCGGGGTCGACCCCGTCGTGCTCGTGGGCCGCGCAAG

GAGCGCGCCGAAGACCTCGACGTCGTCCTCTCCAACTCCTTTGGCTTCGGCGGGCACAACTCGTGCGTC

ATCTTCCAAAAGTACGACGAGTGA

SEQ ID NO: 69 - KAS_II_genomic_allele_2_-_KASII-
allele_2_CDS_translation
MQTAHQRPPTEGHCFGARLPTASRRAVRRAWSRIARAAAAADATPARPPRRVVVTGQGVVTSLGQTIEQ

FYSSLLEGVSGISQIQKFDTTGYTTTIAGEIKSLQLDPYVPKRWAKRVDDVIKYVYIAGKQALENAGLP

IEAAGLAGAGLDPALCGVLIGTAMAGMTSFAAGVEALTRGGVRKMNPFCIPFSISNMGGAMLAMDIGFM

GPNYSISTACATGNYCILGAADHIRRGDADVMLAGGADAAIIPSGIGGFIACKALSKRNDEPERASRPW

DADRDGFVMGEGAGVLVLEELEHAKRRGATILAEFVGGAATSDAHHMTEPDPQGRGVRLCLERALERAR

LAPERVGYVNAHGTSTPAGDVAEYRAIRAVIPQDSLRINSTKSMIGHLLGGAGAVEAVAAIQALRTGWL

HPNLNLENPAPGVDPVVLVGPRKERAEDLDVVLSNSFGFGGHNSCVIFQKYDE

What is claimed is:

1. A mutagenized microalgal strain of *Prototheca moriformis* having at least a 5% improvement in oil titer, relative to a parental microalgal strain, wherein the mutagenized microalgal strain has a higher rate of survival in 8 to 10 mM salicylhydroxamic acid (SHAM) than the parental microalgal strain,
wherein the mutagenized microalgal strain is capable of producing oil having a higher percentage of C18:1 than the parental microalgal strain, wherein the mutagenized microalgal strain is further resistant to an inhibitor of a β-ketoacyl-ACP synthase (KAS), wherein the inhibitor of the KAS comprises cerulenin.

2. The mutagenized microalgal strain of claim 1, wherein the parental microalgal strain is mutagenized, optionally mutagenized chemically or by exposure to radiation.

3. The mutagenized microalgal strain according claim 1, wherein the mutagenized microalgal strain:
   a) has an at least 10% improvement in percentage of C18:1;
   b) is capable of producing fatty acids comprising at least 70% C18:1;
   c) is capable of producing 10 to 90% triglyceride by dry cell weight; or
   d) is capable of producing at least 50% triglyceride by dry cell weight.

4. The mutagenized microalgal strain according to claim 1, wherein the mutagenized microalgal strain is a genetically engineered strain, wherein:
   a) the mutagenized microalgal strain comprises at least one exogenous fatty acid biosynthesis gene, optionally wherein the mutagenized microalgal strain comprises one or more of an exogenous gene selected from the group consisting of an acyl-ACP thioesterase, a fatty acid desaturase and a β-ketoacyl-ACP synthase (KAS); or
   b) the mutagenized microalgal strain is genetically engineered to produce an altered fatty acid chain length or saturation distribution via one or more of the introduction of a gene encoding an active exogenous thioesterase, introduction of a gene encoding an active exogenous fatty acid desaturase, introduction of a gene encoding an active exogenous β-ketoacyl-ACP synthase (KAS), suppression of an endogenous thioesterase or suppression of an endogenous fatty acid desaturase.

5. The mutagenized microalgal strain according to claim 4, wherein the exogenous acyl-ACP thioesterase:
   a) is from a plant selected from the group consisting of *Cuphea palustris, Cinnamomum camphora, Umbellularia californica, Cuphea hookeriana, Cuphea lanceolata, Iris germanica, Myristica fragrans* and *Ulmus americana*;
   b) has at least about 60% sequence identity to a polypeptide selected from the group consisting of SEQ ID NO:21, SEQ ID NO:15, SEQ ID NO:17, SEQ ID NO:19, SEQ ID NO:23, SEQ ID NO:25, SEQ ID NO:27, SEQ ID NO:29 and SEQ ID NO:31; or
   c) is encoded by a polynucleotide having at least about 60% sequence identity to a polynucleotide selected from the group consisting of SEQ ID NO:22, SEQ ID NO:16, SEQ ID NO:18, SEQ ID NO:20, SEQ ID NO:24, SEQ ID NO:26, SEQ ID NO:28, SEQ ID NO:30 and SEQ ID NO:32.

6. The mutagenized microalgal strain according to claim 4, wherein the exogenous fatty acid desaturase is selected from the group consisting of stearoyl-ACP desaturase 2B (SAD2B), delta 12 fatty acid desaturase (Δ12FAD) and stearoyl-ACP desaturase 2A (SAD2A).

7. The mutagenized microalgal strain according to claim 4, wherein:
   a) the β-ketoacyl-ACP synthase (KAS) is encoded by a polynucleotide having at least about 60% sequence identity to a polynucleotide selected from the group consisting of SEQ ID NO:66 and SEQ ID NO:68; or
   b) suppression of the endogenous fatty acid desaturase is accomplished by introduction of a polynucleotide having at least about 60% sequence identity to a polynucleotide selected from the group consisting of SEQ ID NO:42, SEQ ID NO:45 and SEQ ID NO:48.

8. The mutagenized microalgal strain according to claim 4, wherein the mutagenized microalgal strain is genetically engineered to produce the altered fatty acid chain length or saturation distribution via suppression of the endogenous thioesterase, optionally wherein the introduced gene comprises KASII, optionally further wherein the β-ketoacyl-ACP synthase (KAS) is encoded by a polynucleotide having at least about 60% sequence identity to a polynucleotide selected from the group consisting of SEQ ID NO:66 and SEQ ID NO:68.

9. A method for producing a mutagenized microalgal strain of *Prototheca moriformis* having at least a 5% improvement in oil titer, relative to a parental microalgal strain, the method comprising cultivating the parental microalgal strain in the presence of:
   8 to 10 mM salicylhydroxamic acid (SHAM); and
   isolating a mutant of the parental microalgal strain that has a higher rate of survival than the parental microalgal strain in 8 to 10 mM salicylhydroxamic acid (SHAM),
   wherein the mutagenized microalgal strain is further resistant to an inhibitor of a β-ketoacyl-ACP synthase (KAS) to produce oil having a higher percentage of C18:1 than the parental microalgal strain,
   wherein the inhibitor of the KAS comprises cerulenin.

10. The method according to claim 9, wherein the mutagenized microalgal strain is capable of producing:
   a) 10 to 90% triglyceride by dry cell weight; or
   b) at least 50% triglyceride by dry cell weight.

* * * * *

UNITED STATES PATENT AND TRADEMARK OFFICE
CERTIFICATE OF CORRECTION

PATENT NO. : 11,352,602 B2
APPLICATION NO. : 15/562356
DATED : June 7, 2022
INVENTOR(S) : Janice Lau Wee et al.

Page 1 of 1

It is certified that error appears in the above-identified patent and that said Letters Patent is hereby corrected as shown below:

In the Claims

In Column 289, Line 1, in Claim 6: please replace "(412FAD)" with "(Δ12FAD)".

Signed and Sealed this
Sixteenth Day of August, 2022

Katherine Kelly Vidal
*Director of the United States Patent and Trademark Office*

SEQUENCE LISTING

<160> NUMBER OF SEQ ID NOS: 69

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic primer"

<400> SEQUENCE: 1
caaccacgtc ttcaaagcaa                                           20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tccggtgtgt tgtaagtcca                                           20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
ttgtcggaat gtcatatcaa                                           20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
aacgcctttg tacaactgca                                           20

<210> SEQ ID NO 5
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ctgacccgac ctatgggagc gctcttggc                                 29

<210> SEQ ID NO 6
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
cttgacttcc ctcacctgga atttgtcg                                  28

<210> SEQ ID NO 7
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 7
gtggccatat ggacttacaa                                                  20

<210> SEQ ID NO 8
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
caagggctgg atgaatgacc ccaatggact gtggtacgac g                          41

<210> SEQ ID NO 9
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
cacccgtcgt catgttcacg gagcccagtg cg                                    32

<210> SEQ ID NO 10
<211> LENGTH: 2615
<212> TYPE: DNA
<213> ORGANISM: Saccharomyces cerevisiae

<400> SEQUENCE: 10
gaattcccca acatggtgga gcacgacact ctcgtctact ccaagaatat caaagataca      60
gtctcagaag accaaagggc tattgagact tttcaacaaa gggtaatatc gggaaacctc     120
ctcggattcc attgcccagc tatctgtcac ttcatcaaaa ggacagtaga aaaggaaggt     180
ggcacctaca aatgccatca ttgcgataaa ggaaaggcta tcgttcaaga tgcctctgcc     240
gacagtggtc ccaaagatgg accccaccc acgaggagca tcgtggaaaa agaagacgtt     300
ccaaccacgt cttcaaagca agtggattga tgtgaacatg gtggagcacg acactctcgt     360
ctactccaag aatatcaaag atacagtctc agaagaccaa agggctattg agacttttca     420
acaaagggta atatcgggaa acctcctcgg attccattgc ccagctatct gtcacttcat     480
caaaaggaca gtagaaaagg aaggtggcac ctacaaatgc catcattgcg ataaaggaaa     540
ggctatcgtt caagatgcct ctgccgacag tggtcccaaa gatggacccc acccacgag     600 gagcatcgtg gaaaagaag acgttccaac cacgtcttca aagcaagtgg attgatgtga     660
tatctccact gacgtaaggg atgacgcaca atcccactat ccttcgcaag acccttcctc     720
tatataagga agttcatttc atttggagag gacacgctga atcaccagt ctctctctac     780 aaatctatct ctggcgcgcc atatcaatgc ttcttcaggc ttttctttt cttcttgctg     840 gttttgctgc caagatcagc gcctctatga cgaacgaaac ctcggataga ccacttgtgc     900
actttacacc aaacaagggc tggatgaatg accccaatgg actgtggtac gacgaaaaag     960
atgccaagtg gcatctgtac tttcaataca acccgaacga tactgtctgg gggacgccat    1020
```

-continued

```
tgttttgggg ccacgccacg tccgacgacc tgaccaattg ggaggaccaa ccaatagcta    1080
tcgctccgaa gaggaacgac tccggagcat tctcgggttc catggtggtt gactacaaca    1140
atacttccgg cttttcaac gataccattg acccgagaca acgctgcgtg gccatatgga     1200
cttacaacac accggagtcc gaggagcagt acatctcgta tagcctggac ggtggataca    1260
cttttacaga gtatcagaag aaccctgtgc ttgctgcaaa ttcgactcag ttccgagatc    1320
cgaaggtctt ttggtacgag ccctcgcaga agtggatcat gacagcggca aagtcacagg    1380
actacaagat cgaaatttac tcgtctgacg accttaaatc ctggaagctc gaatccgcgt    1440
tcgcaaacga gggctttctc ggctaccaat acgaatgccc aggcctgata gaggtcccaa    1500
cagagcaaga tcccagcaag tcctactggg tgatgtttat ttccattaat ccaggagcac    1560
cggcaggagg ttctttaat cagtacttcg tcggaagctt taacggaact catttcgagg     1620
catttgataa ccaatcaaga gtagttgatt ttggaaagga ctactatgcc ctgcagactt    1680
tcttcaatac tgacccgacc tatgggagcg ctcttggcat tgcgtgggct tctaactggg    1740
agtattccgc attcgttcct acaaacccttt ggaggtcctc catgtcgctc gtgaggaaat   1800
tctctctcaa cactgagtac caggccaacc cggaaaccga actcataaac ctgaaagccg    1860
aaccgatcct gaacattagc aacgctgccc cctggagccg gtttgcaacc aacaccacgt    1920
tgacgaaagc caacagctac aacgtcgatc tttcgaatag caccggtaca cttgaatttg    1980
aactggtgta tgccgtcaat accacccaaa cgatctcgaa gtcggtgttc gcggacctct    2040
ccctctggtt taaaggcctg gaagaccccg aggagtacct cagaatgggt ttcgaggttt    2100
ctgcgtcctc cttcttcctt gatcgcggga acagcaaagt aaaatttgtt aaggagaacc    2160
catattttac caacaggatg agcgttaaca accaaccatt caagagcgaa acgacctgt    2220 cgtactacaa agtgtatggt ttgcttgatc aaaatatcct ggaactctac ttcaacgatg    2280
gtgatgtcgt gtccaccaac acatacttca tgacaaccgg gaacgcactg ggctccgtga    2340
acatgacgac gggtgtggat aacctgttct acatcgacaa attccaggtg agggaagtca    2400
agtgagatct gtcgatcgac aagctcgagt ttctccataa taatgtgtga gtagttccca    2460
gataagggaa ttagggttcc tatagggttt cgctcatgtg ttgagcatat aagaaaccct    2520
tagtatgtat ttgtatttgt aaaatacttc tatcaataaa atttctaatt cctaaaacca    2580
aaatccagta ctaaaatcca gatccccgcga attaa                              2615
```

<210> SEQ ID NO 11
<211> LENGTH: 3681
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

```
gcccttgtc atcgttggca tgcttttgc gtatgtacca tatgttgaat gtataatacg       60
aacggttgac cgtctgagat gcgagctttg ggtcttgtca aatgcgtggc cgcacggctc    120
cctcgcaccc agccccgagg cgtcgcgcac ctggcgagga gcagaccac gccaagaaag     180 tctagtccag catgtaacaa catcaggcaa tgtgacgttt tcggttcccg atttctctgc    240
cgctctttga cggcaggcac gggcgagcaa ccggcggcgc tcgcgtcagg cacgatggat    300
gcggcgctgc ccacctgtca atgtacccca ccagtctgtc gatcgctaca agcaaccttg    360
tgctccacat tcccacttgc agacagtcta gtcgattttg ccaagctgga tgtgaggatt    420
```

```
ggccatatct tggaggccaa gattcacccg gatgctgatg ggtacgtacg cgagccaggc    480
aggcagctgc gttgactttc tgattggcac aaagctttgg ctactctcaa taccaaccac    540 gtgcccttc tgcacacctg cttccttctg atgaccactc gccacgcatg tcgcagtctg    600
tacgtcgagc agatcgacct cggcgaggag ggggcccctc gcaccatcgt gagtggcctg    660
gtccggcacg tgaccctgga ggaccttgtc ggccggcggg tggtggtgct ggccaacctc    720
aagcctcgga gcatgcgcgg ggtcaaatcg gctgggatgc tgctctgcgc cgccaacgcg    780
gatcacaccg cggtggagcc gctgcgggtc ccggacgccg ccgtgacggg ggagcgggtc    840
tgggcggggg acgaggcact cctgtccacg gagcctgcca cacccaatca ggtaaggaca    900
cgttattggt gcgcatggtg cgaatgcgtg gtctgacctg ctgtgggtat gtgttgtggg    960
attggaaacc gaatgagggc cgttcaggat tgagcccttg gccccaccct gctcatcctc   1020
tcacgcccgc aggtccagaa gaagaaaatc tgggaggcag tacagccgct gctgagagtg   1080
aacgcccagg gatcgctac tgtggcagga gaggctatgg tgaccagtgc ggggccactg   1140
accgcgccca cgctggttga cgccgcgatt cctgacgcg agcgactgat tcttgacctt   1200
tgagaagcca ccacagcacc attttcattg ttcatccttg atttcagtac gacttctcac   1260
catttcagta ctgtaggacc cccaaaatag tgtgatcacg ctcgcaaggc acctgtgtga   1320
tcacggggaa gggcgaattc cttcttgcg ctatgacact tccagcaaaa ggtagggcgg   1380
gctgcgagac ggcttcccgg cgctgcatgc aacaccgatg atgcttcgac ccccgaagc   1440 tccttcgggg ctgcatgggc gctccgatgc cgctccaggg cgagcgctgt ttaaatagcc   1500
aggcccccga ttgcaaagac attatagcga gctaccaaag ccatattcaa acacctagat   1560
cactaccact tctacacagg ccactcgagc ttgtgatcgc actccgctaa ggggcgcct    1620 cttcctcttc gtttcagtca caacccgcaa acggcgcgcc atgctgctgc aggccttcct   1680
gttcctgctg gccggcttcg ccgccaagat cagcgcctcc atgacgaacg agacgtccga   1740 ccgcccctg gtgcacttca cccccaacaa gggctggatg aacgacccca acggcctgtg   1800
gtacgacgag aaggacgcca gtggcacct gtacttccag tacaacccga cgacaccgt   1860 ctgggggacg cccttgttct ggggccacgc cacgtccgac gacctgacca actgggagga   1920
ccagcccatc gccatcgccc cgaagcgcaa cgactccggc gccttctccg gctccatggt   1980
ggtggactac aacaacacct ccggcttctt caacgacacc atcgacccgc gccagcgctg   2040
cgtggccatc tggacctaca acaccccgga gtccgaggag cagtacatct cctacagcct   2100
ggacggcggc tacaccttca ccgagtacca gaagaacccc gtgctggccg ccaactccac   2160
ccagttccgc gacccgaagg tcttctggta cgagccctcc cagaagtgga tcatgaccgc   2220
ggccaagtcc caggactaca agatcgagat ctactcctcc gacgacctga agtcctggaa   2280
gctggagtcc gcgttcgcca acgagggctt cctcggctac cagtacgagt gccccggcct   2340
gatcgaggtc cccaccgagc aggacccag caagtcctac tgggtgatgt tcatctccat   2400
caaccccggc gcccggccg gcggctcctt caaccagtac ttcgtcggca gcttcaacgg   2460
cacccacttc gaggccttcg acaaccagtc ccgcgtggtg gacttcggca aggactacta   2520
cgccctgcag accttcttca acaccgaccc gacctacggg agcgccctgg gcatcgcgtg   2580
ggcctccaac tgggagtact ccgccttcgt gccaccaac ccctggcgct cctccatgtc   2640
cctcgtcgcg aagttctccc tcaacaccga gtaccaggcc aacccggaga cggagctgat   2700
caacctgaag gccgagccga tcctgaacat cagcaacgcc ggccctgga gccggttcgc   2760
```

| | |
|---|---:|
| caccaacacc acgttgacga aggccaacag ctacaacgtc gacctgtcca acagcaccgg | 2820 |
| caccctggag ttcgagctgg tgtacgccgt caacaccacc cagacgatct ccaagtccgt | 2880 |
| gttcgcggac ctctccctct ggttcaaggg cctggaggac cccgaggagt acctccgcat | 2940 |
| gggcttcgag gtgtccgcgt cctccttctt cctggaccgc gggaacagca aggtgaagtt | 3000 |
| cgtgaaggag aacccctact tcaccaaccg catgagcgtg aacaaccagc ccttcaagag | 3060 |
| cgagaacgac ctgtcctact acaaggtgta cggcttgctg gaccagaaca tcctggagct | 3120 |
| gtacttcaac gacggcgacg tcgtgtccac caacacctac ttcatgacca ccgggaacgc | 3180 |
| cctgggctcc gtgaacatga cgacggggt ggacaacctg ttctacatcg acaagttcca | 3240 |
| ggtgcgcgag gtcaagtgat taattaactc gaggcagcag cagctcggat agtatcgaca | 3300 |
| cactctggac gctggtcgtg tgatggactg ttgccgccac acttgctgcc ttgacctgtg | 3360 |
| aatatccctg ccgcttttat caaacagcct cagtgtgttt gatcttgtgt gtacgcgctt | 3420 |
| ttgcgagttg ctagctgctt gtgctatttg cgaataccac cccagcatc cccttccctc | 3480 |
| gtttcatatc gcttgcatcc caaccgcaac ttatctacgc tgtcctgcta tccctcagcg | 3540 |
| ctgctcctgc tcctgctcac tgcccctcgc acagccttgg tttgggctcc gcctgtattc | 3600 |
| tcctggtact gcaacctgta accagcact gcaatgctga tgcacgggaa gtagtgggat | 3660 |
| gggaacacaa atggaaagct t | 3681 |

<210> SEQ ID NO 12
<211> LENGTH: 3669
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

| | |
|---|---:|
| cccgtgatca cacaggtgcc ttgcgagcgt gatcacacta ttttgggggt cctacagtac | 60 |
| tgaaatggtg agaagtcgta ctgaaatcaa ggatgaacaa tgaaaatggt gctgtggtgg | 120 |
| cttctcaaag gtcaagaatc agtcgctcgc gtcaggaaat cgcggcgtca accagcgtgg | 180 |
| gcgcggtcag tggccccgca ctggtcacca tagcctctcc tgccacagta gcgatcccct | 240 |
| gggcgttcac tctcagcagc ggctgtactg cctcccagat tttcttcttc tggacctgcg | 300 |
| ggcgtgagag gatgagcagg gtggggccaa gggctcaatc ctgaacggcc ctcattcggt | 360 |
| ttccaatccc acaacacata cccacagcag gtcagaccac gcattcgcac catgcgcacc | 420 |
| aaataacgtg tccttacctg attgggtgtg gcaggctccg tggacaggag tgcctcgtcc | 480 |
| cccgcccaga cccgctcccc cgtcacggcg gcgtccggga cccgcagcgg ctccaccgcg | 540 |
| gtgtgatccg cgttggcggc gcagagcagc atcccagccg atttgacccc gcgcatgctc | 600 |
| cgaggcttga ggttggccag caccaccacc cgccggccga caaggtcctc cagggtcacg | 660 |
| tgccggacca ggccactcac gatggtgcga gggcccccct cctcgccgag gtcgatctgc | 720 |
| tcgacgtaca gactgcgaca tgcgtggcga gtggtcatca gaaggaagca ggtgtgcaga | 780 |
| aggggcacgt ggttggtatt gagagtagcc aaagctttgt gccaatcaga aagtcaacgc | 840 |
| agctgcctgc ctggctcgcg tacaattcct ttcttgcgct atgacacttc cagcaaaagg | 900 |
| tagggcgggc tgcgagacgg cttcccggcg ctgcatgcaa caccgatgat gcttcgaccc | 960 |
| cccgaagctc cttcggggct gcatgggcgc tccgatgccg ctccagggcg agcgctgttt | 1020 |
| aaatagccag gccccgatt gcaaagacat tatagcgagc taccaaagcc atattcaaac | 1080 |

```
acctagatca ctaccacttc tacacaggcc actcgagctt gtgatcgcac tccgctaagg    1140
gggcgcctct tcctcttcgt ttcagtcaca acccgcaaac ggcgcgccat gctgctgcag    1200
gccttcctgt tcctgctggc cggcttcgcc gccaagatca gcgcctccat gacgaacgag    1260
acgtccgacc gccccctggt gcacttcacc cccaacaagg gctggatgaa cgaccccaac    1320
ggcctgtggt acgacgagaa ggacgccaag tggcacctgt acttccagta caacccgaac    1380
gacaccgtct gggggacgcc cttgttctgg gccacgcca cgtccgacga cctgaccaac    1440
tgggaggacc agcccatcgc catcgccccg aagcgcaacg actccggcgc cttctccggc    1500
tccatggtgg tggactacaa caacacctcc ggcttcttca cgacaccat cgacccgcgc    1560 cagcgctgcg tggccatctg gacctacaac accccggagt ccgaggagca gtacatctcc    1620
tacagcctgg acgcggcta caccttcacc gagtaccaga gaaccccgt gctggccgcc    1680 aactccaccc agttccgcga cccgaaggtc ttctggtacg agccctccca gaagtggatc    1740
atgaccgcgg ccaagtccca ggactacaag atcgagatct actcctccga cgacctgaag    1800
tcctggaagc tggagtccgc gttcgccaac gagggcttcc tcggctacca gtacgagtgc    1860
cccggcctga tcgaggtccc caccgagcag gaccccagca gtcctactg ggtgatgttc    1920 atctccatca accccggcgc cccggccggc ggctccttca ccagtactt cgtcggcagc    1980 ttcaacggca cccacttcga ggccttcgac aaccagtccc gcgtggtgga cttcggcaag    2040
gactactacg ccctgcagac cttcttcaac accgacccga cctacgggag cgccctgggc    2100
atcgcgtggg cctccaactg ggagtactcc gccttcgtgc ccaccaaccc ctggcgctcc    2160
tccatgtccc tcgtgcgcaa gttctccctc aacaccgagt accaggccaa cccggagacg    2220
gagctgatca acctgaaggc cgagccgatc ctgaacatca gcaacgccgg cccctggagc    2280
cggttcgcca ccaacaccac gttgacgaag gccaacagct acaacgtcga cctgtccaac    2340
agcaccggca ccctggagtt cgagctggtg tacgccgtca acaccaccca gacgatctcc    2400
aagtccgtgt tcgcggacct ctccctctgg ttcaagggcc tggaggaccc cgaggagtac    2460
ctccgcatgg gcttcgaggt gtccgcgtcc tccttcttcc tggaccgcgg gaacagcaag    2520
gtgaagttcg tgaaggagaa ccccctacttc accaaccgca tgagcgtgaa caaccagccc    2580
ttcaagagcg agaacgacct gtcctactac aaggtgtacg gcttgctgga ccagaacatc    2640
ctggagctgt acttcaacga cggcgacgtc gtgtccacca acacctactt catgaccacc    2700
gggaacgccc tgggctccgt gaacatgacg acggggggtgg acaacctgtt ctacatcgac    2760
aagttccagg tgcgcgaggt caagtgatta attaactcga ggcagcagca gctcggatag    2820
tatcgacaca ctctggacgc tggtcgtgtg atggactgtt gccgccacac ttgctgcctt    2880
gacctgtgaa tatccctgcc gcttttatca aacagcctca gtgtgtttga tcttgtgtgt    2940
acgcgctttt gcgagttgct agctgcttgt gctatttgcg aataccaccc ccagcatccc    3000
cttccctcgt ttcatatcgc ttgcatccca accgcaactt atctacgctg tcctgctatc    3060
cctcagcgct gctcctgctc ctgctcactg cccctcgcac agccttggtt tgggctccgc    3120
ctgtattctc ctggtactgc aacctgtaaa ccagcactgc aatgctgatg cacgggaagt    3180
agtgggatgg gaacacaaat ggaaagcttg agctcggtac ccgtacccat cagcatccgg    3240
gtgaatcttg gcctccaaga tatggccaat cctcacatcc agcttggcaa aatcgactag    3300
actgtctgca gtgggaatg tggagcacaa ggttgcttgt agcgatcgac agactggtgg    3360
ggtacattga caggtgggca gcgccgcatc catcgtgcct gacgcgagcg ccgccggttg    3420
```

```
ctcgcccgtg cctgccgtca agagcggca gagaaatcgg gaaccgaaaa cgtcacattg    3480
cctgatgttg ttacatgctg gactagactt tcttggcgtg ggtctgctcc tcgccaggtg    3540
cgcgacgcct cggggctggg tgcgagggag ccgtgcggcc acgcatttga caagacccaa    3600
agctcgcatc tcagacggtc aaccgttcgt attatacatt caacatatgg tacatacgca    3660
aaaagcatg                                                            3669
```

<210> SEQ ID NO 13
<211> LENGTH: 3850
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

```
tttggcccccg ctttccagct ccggatctgc tggcgtccgc cgcgagacgt gacatcgcac     60
gtcgccggga gcgccagctt gatcacttgg caggggccg tgctctacaa ataccaggcc    120
ccgcggcggt cagttcgcac atccaatacc tgccgagcca tcttgcctac acttttatc    180 gactcctcta ctctgttcgc gagagcgctc ggtccaggct tggaattcgc cgaattcagc    240
tcgatcagtc gcttctgcaa ctgatctcgg ccgttcgcag actgcctttt ctcagcttgt    300
caggtagcga gttgttgttt tatatttatt cgatttcatc tgtgttgcat gtcttgttcg    360
tgctgtgcgt tctttctggg ccgcgctgtc gggtcgcatg ggctagctgt actcatgtta    420
gtcatgccgg tccgacccttg ttcgaggaag gccccacact gagcgtgccc tctttctaca    480
ccccttgtgc agaaattaga tagaaagcag aattccttcc ttgcgctatg acacttccag    540
caaaaggtag ggcgggctgc gagacggctt cccggcgctg catgcaacac cgatgatgct    600 tcgaccccccc gaagctcctt cggggctgca tgggcgctcc gatgccgctc cagggcgagc    660
gctgtttaaa tagccaggcc cccgattgca aagacattat agcgagctac caaagccata    720
ttcaaacacc tagatcacta ccacttctac acaggccact cgagcttgtg atcgcactcc    780
gctaaggggg cgcctcttcc tcttcgtttc agtcacaacc cgcaaacggc gcgccatgct    840
gctgcaggcc ttcctgttcc tgctggccgg cttcgccgcc aagatcagcg cctccatgac    900
gaacgagacg tccgaccgcc cctggtgca cttcaccccc aacaagggct ggatgaacga    960
ccccaacggc ctgtggtacg acgagaagga cgccaagtgg cacctgtact ccagtacaa    1020 cccgaacgac accgtctggg ggacgccctt gttctggggc cacgccacgt ccgacgacct    1080
gaccaactgg gaggaccagc ccatcgccat cgccccgaag cgcaacgact ccggcgcctt    1140
ctccggctcc atggtggtgg actacaacaa cacctccggc ttcttcaacg acaccatcga    1200
cccgcgccag cgctgcgtgg ccatctggac ctacaacacc ccggagtccg aggagcagta    1260
catctcctac agcctggacg gcggctacac cttcaccgag taccagaaga cccccgtgct    1320
ggccgccaac tccacccagt tccgcgaccc gaaggtcttc tggtacgagc cctcccagaa    1380
gtggatcatg accgcggcca gtcccagga ctacaagatc gagatctact cctccgacga    1440
cctgaagtcc tggaagctgg agtccgcgtt cgccaacgag ggcttcctcg gctaccagta    1500
cgagtgcccc ggcctgatcg aggtccccac cgagcaggac cccagcaagt cctactgggt    1560
gatgttcatc tccatcaacc ccggcgcccc ggcggcggc tccttcaacc agtacttcgt    1620
cggcagcttc aacggcaccc acttcgaggc cttcgacaac cagtcccgcg tggtggactt    1680
cggcaaggac tactacgccc tgcagacctt cttcaacacc gacccgacct acgggagcgc    1740
```

```
cctgggcatc gcgtgggcct ccaactggga gtactccgcc ttcgtgccca ccaacccctg    1800
gcgctcctcc atgtccctcg tgcgcaagtt ctccctcaac accgagtacc aggccaaccc    1860
ggagacggag ctgatcaacc tgaaggccga gccgatcctg aacatcagca cgccggccc    1920 ctggagccgg ttcgccacca acaccacgtt gacgaaggcc aacagctaca acgtcgacct    1980
gtccaacagc accggcaccc tggagttcga gctggtgtac gccgtcaaca ccacccagac    2040
gatctccaag tccgtgttcg cggacctctc cctctggttc aagggcctgg aggaccccga    2100
ggagtacctc cgcatgggct tcgaggtgtc cgcgtcctcc ttcttcctgg accgcgggaa    2160
cagcaaggtg aagttcgtga aggagaaccc ctacttcacc aaccgcatga gcgtgaacaa    2220
ccagcccttc aagagcgaga cgacctgtc ctactacaag gtgtacggct gctggacca    2280 gaacatcctg gagctgtact caacgacgcg cgacgtcgtg tccaccaaca cctacttcat    2340
gaccaccggg aacgccctgg gctccgtgaa catgacgacg ggggtggaca acctgttcta    2400
catcgacaag ttccaggtgc gcgaggtcaa gtgattaatt aactcgaggc agcagcagct    2460
cggatagtat cgacacactc tggacgctgg tcgtgtgatg gactgttgcc gccacacttg    2520
ctgccttgac ctgtgaatat ccctgccgct tttatcaaac agcctcagtg tgtttgatct    2580
tgtgtgtacg cgcttttgcg agttgctagc tgcttgtgct atttgcgaat accaccccca    2640
gcatcccctt ccctcgtttc atatcgcttg catcccaacc gcaacttatc tacgctgtcc    2700
tgctatccct cagcgctgct cctgctcctg ctcactgccc ctcgcacagc cttggtttgg    2760
gctccgcctg tattctcctg gtactgcaac ctgtaaacca gcactgcaat gctgatgcac    2820
gggaagtagt gggatgggaa cacaaatgga ccgacacgcc cccggcccag gtccagttct    2880
cctgggtctt ccagaggccc gtcgccatgt aaagtggcag agattggcgc ctgattcgat    2940
ttggatccaa ggatctccaa tcggtgatgg ggactgagtg cccaactacc acccttgcac    3000
tatcgtcctc gcactattta ttcccacctt ctgctcgccc tgccgggcga ttgcgggcgt    3060
ttctgcccct gacgtatcaa tttcgcccct gctggcgcga ggattcttca ttctaataag    3120
aactcactcc cgccagctct gtacttttcc tgcggggccc ctgcatggct tgttcccaat    3180
gcttgctcga tcgacggcgc ccattgccca cggcgctgcc gcatccatgt gaagaaacac    3240
ggaagagtgc gaagactgga agtgaattaa gagtataaga agaggtacca agggattctc    3300
aggtgctctt aggaacggct tttccttcgc caagagaaac tgctactgct cgtgtcgcca    3360
cggtggtcaa gccgcccat ctgcgatcca ccaggcccat ccgcggactc gcgatcagcc    3420
tgctggatcc ggactgccga cctgaccgct cgcatccacc attacaaccc tccaattgga    3480
caccactccc acgtcctaaa gttcaccatg caagctgatc gatcgcattc gccgatgcac    3540
tcgcctgcca cagaggtgtg cgcttcggac tagcgtgcag gcgccccgag gccaccagca    3600
tgcaccgatg gaagcgggca cggccgctgc tccaggtcgc tggctcgctc agacccatag    3660
caacctccgc tgcgtcccta aatgtcacac agagcgtctt tgatgggtac ggatgggaga    3720
gaatctgatt gggcattgct ggtgcagtgc aggaagatgg caagtgcaca gtcagtcatg    3780
ctgtacaaac tggtgcctcg tagtattgac tcgtatagtg catagtatca tgcatggtcg    3840
ttacttgcaa                                                          3850
```

<210> SEQ ID NO 14
<211> LENGTH: 3108
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 14

```
tttggccccg ctttccagct ccggatctgc tggcgtccgc cgcgagacgt gacatcgcac      60
gtcgccggga gcgccagctt gatcacttgg caggggccg tgctctacaa ataccaggcc      120
ccgcggcgt cagttcgcac atccaatacc tgccgagcca tcttgcctac acttttatc       180
gactcctcta ctctgttcgc gagagcgctc ggtccaggct tggaattcgc cgaattcagc    240
tcgatcagtc gcttctgcaa ctgatctcgg ccgttcgcag actgcctttt ctcagcttgt    300
caggtagcga gttgttgttt tatatttatt cgatttcatc tgtgttgcat gtcttgttcg    360
tgctgtgcgt tctttctggg ccgcgctgtc gggtcgcatg ggctagctgt actcatgtta    420
gtcatgccgg tccgaccttg ttcgaggaag gccccacact gagcgtgccc tctttctaca    480
ccccttgtgc agaaattaga tagaaagcaa tgctgctgca ggccttcctg ttcctgctgg    540
ccggcttcgc cgccaagatc agcgcctcca tgacgaacga gacgtccgac cgcccctgg    600
tgcacttcac ccccaacaag ggctggatga acgaccccaa cggcctgtgg tacgacgaga    660
aggacgccaa gtggcacctg tacttccagt acaacccgaa cgacaccgtc tggggacgc    720
ccttgttctg gggccacgcc acgtccgacg acctgaccaa ctgggaggac cagcccatcg    780
ccatcgcccc gaagcgcaac gactccggcg ccttctccgg ctccatggtg gtggactaca    840
acaacacctc cggcttcttc aacgacacca tcgacccgcg ccagcgctgc gtggccatct    900
ggacctacaa caccccggag tccgaggagc agtacatctc ctacagcctg gacggcggct    960
acacttcac cgagtaccag aagaaccccg tgctggccgc caactccacc cagttccgcg   1020
acccgaaggt cttctggtac gagccctccc agaagtggat catgaccgcg gccaagtccc   1080
aggactacaa gatcgagatc tactcctccg acgacctgaa gtcctggaag ctggagtccg   1140
cgttcgccaa cgagggcttc ctcggctacc agtacgagtg ccccggcctg atcgaggtcc   1200
ccaccgagca ggaccccagc aagtcctact gggtgatgtt catctccatc aaccccggcg   1260
ccccggccgg cggctccttc aaccagtact tcgtcggcag cttcaacggc acccacttcg   1320
aggccttcga caaccagtcc cgcgtggtgg acttcggcaa ggactactac gccctgcaga   1380
ccttcttcaa caccgacccg acctacggga gcgccctggg catcgcgtgg gcctccaact   1440
gggagtactc cgccttcgtg cccaccaacc cctggcgctc ctccatgtcc ctcgtgcgca   1500
agttctccct caacaccgag taccaggcca cccggagac ggagctgatc aacctgaagg   1560
ccgagccgat cctgaacatc agcaacgccg gccctggag ccggttcgcc accaacacca   1620
cgttgacgaa ggccaacagc tacaacgtcg acctgtccaa cagcaccggc accctggagt   1680
tcgagctggt gtacgccgtc aacaccaccc agacgatctc caagtccgtg ttcgcggacc   1740
tctccctctg gttcaagggc ctggaggacc ccgaggagta cctccgcatg ggcttcgagg   1800
tgtccgcgtc ctccttcttc ctggaccgcg ggaacagcaa ggtgaagttc gtgaaggaga   1860
accccctactt caccaaccgc atgagcgtga caaccagcc cttcaagagc gagaacgacc   1920
tgtcctacta caaggtgtac ggcttgctgg accagaacat cctggagctg tacttcaacg   1980
acggcgacgt cgtgtccacc aacacctact tcatgaccac cgggaacgcc ctgggctccg   2040
tgaacatgac gacggggtg gacaacctgt tctacatcga caagttccag gtgcgcgagg   2100
tcaagtgacc gacacgcccc cggcccaggt ccagttctcc tgggtcttcc agaggcccgt   2160
cgccatgtaa agtggcagag attggcgcct gattcgattt ggatccaagg atctccaatc   2220
```

```
ggtgatgggg actgagtgcc caactaccac ccttgcacta tcgtcctcgc actatttatt    2280
cccaccttct gctcgccctg ccgggcgatt gcgggcgttt ctgcccttga cgtatcaatt    2340
tcgcccctgc tggcgcgagg attcttcatt ctaataagaa ctcactcccg ccagctctgt    2400
acttttcctg cggggcccct gcatggcttg ttcccaatgc ttgctcgatc gacggcgccc    2460
attgcccacg gcgctgccgc atccatgtga agaaacacgg aagagtgcga agactggaag    2520
tgaattaaga gtataagaag aggtaccaag ggattctcag gtgctcttag gaacggcttt    2580
tccttcgcca agagaaactg ctactgctcg tgtcgccacg gtggtcaagc cgccccatct    2640
gcgatccacc aggcccatcc gcggactcgc gatcagcctg ctggatccgg actgccgacc    2700
tgaccgctcg catccaccat acaaccctc caattggaca ccactcccac gtcctaaagt     2760
tcaccatgca agctgatcga tcgcattcgc cgatgcactc gcctgccaca gaggtgtgcg    2820
cttcggacta gcgtgcaggc gccccgaggc caccagcatg caccgatgga agcgggcacg    2880
gccgctgctc caggtcgctg gctcgctcag acccatagca acctccgctg cgtccctaaa    2940
tgtcacacag agcgtctttg atgggtacgg atgggagaga atctgattgg gcattgctgg    3000
tgcagtgcag gaagatggca agtgcacagt cagtcatgct gtacaaactg gtgcctcgta    3060
gtattgactc gtatagtgca tagtatcatg catggtcgtt acttgcaa                 3108
```

<210> SEQ ID NO 15
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Pro Asp Trp Ser Met Leu Phe Ala Val Ile
        35                  40                  45

Thr Thr Ile Phe Ser Ala Ala Glu Lys Gln Trp Thr Asn Leu Glu Trp
    50                  55                  60

Lys Pro Lys Pro Asn Pro Gln Leu Leu Asp Asp His Phe Gly Pro
65                  70                  75                  80

His Gly Leu Val Phe Arg Arg Thr Phe Ala Ile Arg Ser Tyr Glu Val
                85                  90                  95

Gly Pro Asp Arg Ser Thr Ser Ile Val Ala Val Met Asn His Leu Gln
            100                 105                 110

Glu Ala Ala Leu Asn His Ala Lys Ser Val Gly Ile Leu Gly Asp Gly
        115                 120                 125

Phe Gly Thr Thr Leu Glu Met Ser Lys Arg Asp Leu Ile Trp Val Val
    130                 135                 140

Lys Arg Thr His Val Ala Val Glu Arg Tyr Pro Ala Trp Gly Asp Thr
145                 150                 155                 160

Val Glu Val Glu Cys Trp Val Gly Ala Ser Gly Asn Asn Gly Arg Arg
                165                 170                 175

His Asp Phe Leu Val Arg Asp Cys Lys Thr Gly Glu Ile Leu Thr Arg
            180                 185                 190

```
Cys Thr Ser Leu Ser Val Met Met Asn Thr Arg Thr Arg Arg Leu Ser
            195                 200                 205
Lys Ile Pro Glu Glu Val Arg Gly Glu Ile Gly Pro Ala Phe Ile Asp
        210                 215                 220
Asn Val Ala Val Lys Asp Glu Glu Ile Lys Lys Pro Gln Lys Leu Asn
225                 230                 235                 240
Asp Ser Thr Ala Asp Tyr Ile Gln Gly Gly Leu Thr Pro Arg Trp Asn
            245                 250                 255
Asp Leu Asp Ile Asn Gln His Val Asn Asn Ile Lys Tyr Val Asp Trp
        260                 265                 270
Ile Leu Glu Thr Val Pro Asp Ser Ile Phe Glu Ser His His Ile Ser
    275                 280                 285
Ser Phe Thr Ile Glu Tyr Arg Arg Glu Cys Thr Met Asp Ser Val Leu
    290                 295                 300
Gln Ser Leu Thr Thr Val Ser Gly Gly Ser Ser Glu Ala Gly Leu Val
305                 310                 315                 320
Cys Glu His Leu Leu Gln Leu Glu Gly Gly Ser Glu Val Leu Arg Ala
            325                 330                 335
Lys Thr Glu Trp Arg Pro Lys Leu Thr Asp Ser Phe Arg Gly Ile Ser
        340                 345                 350
Val Ile Pro Ala Glu Ser Ser Val
        355                 360

<210> SEQ ID NO 16
<211> LENGTH: 4653
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga agggtcaag tgcaaacacg ggcatgccac agcacgggca ccggggagtg     420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
caatgtggtg gataggatgc aagtggagcg aataccaaac cctctggctg cttgctgggt     720
tgcatggcat cgcaccatca gcaggagcgc atgcgaaggg actggcccca tgcacgccat     780
gccaaaccgg agcgcaccga gtgtccacac tgtcaccagg cccgcaagct ttgcagaacc     840
atgctcatgg acgcatgtag cgctgacgtc ccttgacggc gctcctctcg ggtgtgggaa     900
acgcaatgca gcacaggcag cagaggcggc ggcagcagag cggcggcagc agcggcgggg     960
gccacccttc ttgcgggtgc gcgccccagc cagcggtgat gcgctgatcc caaacgagtt    1020
```

```
cacattcatt tgcatgcctg agaagcgag gctggggcct ttgggctggt gcagcccgca      1080
atggaatgcg ggaccgccag gctagcagca aaggcgcctc ccctactccg catcgatgtt      1140
ccatagtgca ttggactgca tttgggtggg gcggccggct gtttctttcg tgttgcaaaa      1200
cgcgccagct cagcaacctg tcccgtgggt ccccgtgcc gatgaaatcg tgtgcacgcc      1260
gatcagctga ttgcccggct cgcgaagtag gcgccctcct ttctgctcgc cctctctccg      1320
tcccgcctct agaatatcaa tgatcgagca ggacggcctc cacgccggct ccccgccgc      1380 ctgggtggag cgcctgttcg gctacgactg ggcccagcag accatcggct gctccgacgc      1440
cgccgtgttc cgcctgtccg cccagggccg ccccgtgctg ttcgtgaaga ccgacctgtc      1500
cggcgccctg aacgagctgc aggacgaggc cgcccgcctg tcctggctgg ccaccaccgg      1560
cgtgccctgc gccgccgtgc tggacgtggt gaccgaggcc ggccgcgact ggctgctgct      1620
gggcgaggtg cccggccagg acctgctgtc ctcccacctg gcccccgccg agaaggtgtc      1680
catcatggcc gacgccatgc gccgcctgca caccctggac cccgccacct gcccttcga      1740 ccaccaggcc aagcaccgca tcgagcgcgc ccgcacccgc atggaggccg gctggtgga      1800 ccaggacgac ctggacgagg agcaccaggg cctggccccc gccgagctgt tcgcccgcct      1860
gaaggcccgc atgcccgacg gcgaggacct ggtggtgacc cacggcgacg cctgcctgcc      1920
caacatcatg gtggagaacg gccgcttctc cggcttcatc gactgcggcc gctgggcgt      1980 ggccgaccgc taccaggaca tcgccctggc cacccgcgac atcgccgagg agctgggcgg      2040
cgagtgggcc gaccgcttcc tggtgctgta cggcatcgcc gcccccgact cccagcgcat      2100
cgccttctac cgcctgctgg acgagttctt ctgacaattg gcagcagcag ctcggatagt      2160
atcgacacac tctggacgct ggtcgtgtga tggactgttg ccgccacact tgctgccttg      2220
acctgtgaat atccctgccg cttttatcaa acagcctcag tgtgtttgat cttgtgtgta      2280
cgcgcttttg cgagttgcta gctgcttgtg ctatttgcga ataccacccc cagcatcccc      2340
ttccctcgtt tcatatcgct tgcatcccaa ccgcaactta tctacgctgt cctgctatcc      2400
ctcagcgctg ctcctgctcc tgctcactgc ccctcgcaca gccttggttt gggctccgcc      2460
tgtattctcc tggtactgca acctgtaaac cagcactgca atgctgatgc acgggaagta      2520
gtgggatggg aacacaaatg gaggatcccg cgtctcgaac agagcgcgca gaggaacgct      2580
gaaggtctcg cctctgtcgc acctcagcgc ggcatacacc acaataacca cctgacgaat      2640
gcgcttggtt cttcgtccat tagcgaagcg tccggttcac acacgtgcca cgttggcgag      2700
gtggcaggtg acaatgatcg gtggagctga tggtcgaaac gttcacagcc tagggatatc      2760
gaattccttt cttgcgctat gacacttcca gcaaaaggta gggcgggctg cgagacggct      2820
tcccggcgct gcatgcaaca ccgatgatgc ttcgaccccc cgaagctcct tcggggctgc      2880
atgggcgctc cgatgccgct ccagggcgag cgctgtttaa atagccaggc cccgattgc      2940 aaagacatta tagcgagcta ccaaagccat attcaaacac ctagatcact accacttcta      3000
cacaggccac tcgagcttgt gatcgcactc cgctaagggg gcgcctcttc ctcttcgttt      3060
cagtcacaac ccgcaaacac tagtatggct atcaagacga acaggcagcc tgtggagaag      3120
cctccgttca cgatcgggac gctgcgcaag gccatcccg cgcactgttt cgagcgctcg      3180
gcgcttcgtg ggcgcgcccc cgactggtcc atgctgttcg ccgtgatcac caccatcttc      3240
tccgccgccg agaagcagtg gaccaacctg gagtggaagc caagcccaa ccccccag      3300 ctgctggacg accacttcgg cccccacggc ctggtgttcc gccgcacctt cgccatccgc      3360
agctacgagg tgggccccga ccgctccacc agcatcgtgg ccgtgatgaa ccacctgcag      3420
```

```
gaggccgccc tgaaccacgc caagtccgtg ggcatcctgg gcgacggctt cggcaccacc    3480
ctggagatgt ccaagcgcga cctgatctgg gtggtgaagc gcacccacgt ggccgtggag    3540
cgctaccccg cctggggcga caccgtggag gtggagtgct gggtgggcgc ctccggcaac    3600 aacgccgcc gccacgactt cctggtgcgc gactgcaaga ccggcgagat cctgacccgc    3660
tgcacctccc tgagcgtgat gatgaacacc cgcacccgcc gcctgagcaa gatccccgag    3720
gaggtgcgcg gcgagatcgg ccccgccttc atcgacaacg tggccgtgaa ggacgaggag    3780
atcaagaagc cccagaagct gaacgactcc accgccgact acatccaggg cggcctgacc    3840
ccccgctgga cgacctgga catcaaccag cacgtgaaca acatcaagta cgtggactgg    3900
atcctggaga ccgtgcccga cagcatcttc gagagccacc acatctcctc cttcaccatc    3960
gagtaccgcc gcgagtgcac catggacagc gtgctgcagt ccctgaccac cgtgagcggc    4020
ggctcctccg aggccggcct ggtgtgcgag cacctgctgc agctggaggg cggcagcgag    4080
gtgctgcgcg ccaagaccga gtggcgcccc aagctgaccg actccttccg cggcatcagc    4140
gtgatccccg ccgagtccag cgtgatggac tacaaggacc acgacggcga ctacaaggac    4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc ctcagtgtgt ttgatcttgt    4380
gtgtacgcgc ttttgcgagt tgctagctgc ttgtgctatt tgcgaatacc accccagca    4440 tccccttccc tcgtttcata tcgcttgcat cccaaccgca acttatctac gctgtcctgc    4500
tatccctcag cgctgctcct gctcctgctc actgcccctc gcacagcctt ggtttgggct    4560
ccgcctgtat tctcctggta ctgcaacctg taaaccagca ctgcaatgct gatgcacggg    4620
aagtagtggg atgggaacac aaatggaaag ctt                                 4653
```

<210> SEQ ID NO 17
<211> LENGTH: 360
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Pro Asp Trp Ser Met Leu Phe Ala Val Ile
        35                  40                  45

Thr Thr Ile Phe Ser Ala Ala Glu Lys Gln Trp Thr Asn Leu Glu Trp
    50                  55                  60

Lys Pro Lys Pro Lys Leu Pro Gln Leu Leu Asp Asp His Phe Gly Leu
65                  70                  75                  80

His Gly Leu Val Phe Arg Arg Thr Phe Ala Ile Arg Ser Tyr Glu Val
                85                  90                  95

Gly Pro Asp Arg Ser Thr Ser Ile Leu Ala Val Met Asn His Met Gln
            100                 105                 110

Glu Ala Thr Leu Asn His Ala Lys Ser Val Gly Ile Leu Gly Asp Gly
        115                 120                 125
```

```
Phe Gly Thr Thr Leu Glu Met Ser Lys Arg Asp Leu Met Trp Val Val
130                 135                 140
Arg Arg Thr His Val Ala Val Glu Arg Tyr Pro Thr Trp Gly Asp Thr
145                 150                 155                 160
Val Glu Val Glu Cys Trp Ile Gly Ala Ser Gly Asn Asn Gly Met Arg
                165                 170                 175
Arg Asp Phe Leu Val Arg Asp Cys Lys Thr Gly Glu Ile Leu Thr Arg
                180                 185                 190
Cys Thr Ser Leu Ser Val Leu Met Asn Thr Arg Thr Arg Arg Leu Ser
                195                 200                 205
Thr Ile Pro Asp Glu Val Arg Gly Glu Ile Gly Pro Ala Phe Ile Asp
210                 215                 220
Asn Val Ala Val Lys Asp Asp Glu Ile Lys Lys Leu Gln Lys Leu Asn
225                 230                 235                 240
Asp Ser Thr Ala Asp Tyr Ile Gln Gly Gly Leu Thr Pro Arg Trp Asn
                245                 250                 255
Asp Leu Asp Val Asn Gln His Val Asn Asn Leu Lys Tyr Val Ala Trp
                260                 265                 270
Val Phe Glu Thr Val Pro Asp Ser Ile Phe Glu Ser His His Ile Ser
275                 280                 285
Ser Phe Thr Leu Glu Tyr Arg Arg Glu Cys Thr Arg Asp Ser Val Leu
290                 295                 300
Arg Ser Leu Thr Thr Val Ser Gly Gly Ser Ser Glu Ala Gly Leu Val
305                 310                 315                 320
Cys Asp His Leu Leu Gln Leu Glu Gly Gly Ser Glu Val Leu Arg Ala
                325                 330                 335
Arg Thr Glu Trp Arg Pro Lys Leu Thr Asp Ser Phe Arg Gly Ile Ser
                340                 345                 350
Val Ile Pro Ala Glu Pro Arg Val
355                 360

<210> SEQ ID NO 18
<211> LENGTH: 4653
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga agggtcaag tgcaaacacg gcatgccac agcacgggca ccggggagtg     420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
```

```
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc     840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgcccagc cagcggtgat cgctgatcc caaacgagtt      1020 cacattcatt tgcatgcctg gagaagcgag gctggggcct ttgggctggt gcagcccgca    1080
atggaatgcg ggaccgccag gctagcagca aggcgcctc ccctactccg catcgatgtt     1140
ccatagtgca ttggactgca tttgggtggg gcggccggct gtttcttcg tgttgcaaaa     1200 cgcgccagct cagcaacctg tcccgtgggt ccccgtgcc gatgaaatcg tgtgcacgcc     1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc     1380 ctgggtggag cgcctgttcg gctacgactg ggcccagcag accatcggct gctccgacgc    1440
cgccgtgttc cgcctgtccg cccagggccg cccgtgctg ttcgtgaaga ccgacctgtc     1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
catcatggcc gacgccatgc gccgcctgca caccctggac cccgccacct gccccttcga    1740
ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860 gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt     1980 ggccgaccgc taccaggaca tcgccctggc cacccgcgac atcgccgagg agctgggcgg    2040
cgagtgggcc gaccgcttcc tggtgctgta cggcatcgcc gccccgact cccagcgcat     2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaggta gggcgggctg cgagacggct     2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
```

```
cagtcacaac ccgcaaacac tagtatggct atcaagacga acaggcagcc tgtggagaag    3120
cctccgttca cgatcgggac gctgcgcaag gccatcccg cgcactgttt cgagcgctcg    3180
gcgcttcgtg ggcgcgcccc cgactggtcc atgctgttcg ccgtgatcac caccatcttc    3240
agcgccgccg agaagcagtg gaccaacctg gagtggaagc ccaagcccaa gctgccccag    3300
ctgctggacg accacttcgg cctgcacggc ctggtgttcc gccgcacctt cgccatccgc    3360
tcctacgagg tgggccccga ccgcagcacc tccatcctgg ccgtgatgaa ccacatgcag    3420
gaggccaccc tgaaccacgc caagagcgtg ggcatcctgg gcgacggctt cggcaccacc    3480
ctggagatgt ccaagcgcga cctgatgtgg gtggtgcgcc gcacccacgt ggccgtggag    3540
cgctacccca cctggggcga caccgtggag gtggagtgct ggatcggcgc cagcggcaac    3600
aacggcatgc gccgcgactt cctggtgcgc gactgcaaga ccggcgagat cctgaccccg    3660
tgcacctccc tgagcgtgct gatgaacacc cgcacccgcc gcctgagcac catccccgac    3720
gaggtgcgcg cgagatcgg ccccgccttc atcgacaacg tggccgtgaa ggacgacgag    3780
atcaagaagc tgcagaagct gaacgactcc accgccgact acatccaggg cggcctgacc    3840
ccccgctgga cgacctgga cgtgaaccag cacgtgaaca acctgaagta cgtggcctgg    3900
gtgttcgaga ccgtgcccga cagcatcttc gagtcccacc acatcagctc cttcaccctg    3960
gagtaccgcc gcgagtgcac ccgcgactcc gtgctgcgca gcctgaccac cgtgagcggc    4020
ggcagctccg aggccggcct ggtgtgcgac cacctgctgc agctggaggg cggcagcgag    4080
gtgctgcgcg cccgcaccga gtggcgcccc aagctgaccg actccttccg cggcatcagc    4140
gtgatccccg ccgagccccg cgtgatggac tacaaggacc acgacggcga ctacaaggac    4200
cacgacatcg actacaagga cgacgacgac aagtgatgac tcgaggcagc agcagctcgg    4260
atagtatcga cacactctgg acgctggtcg tgtgatggac tgttgccgcc acacttgctg    4320
ccttgacctg tgaatatccc tgccgctttt atcaaacagc tcagtgtgt ttgatcttgt    4380 gtgtacgcgc ttttgcgagt tgctagctgc ttgtgctatt tgcgaatacc accccagca    4440 tccccttccc tcgtttcata tcgcttgcat cccaaccgca acttatctac gctgtcctgc    4500
tatccctcag cgctgctcct gctcctgctc actgcccctc gcacagcctt ggtttggct   4560 ccgcctgtat tctcctggta ctgcaacctg taaaccagca ctgcaatgct gatgcacggg    4620
aagtagtggg atgggaacac aaatggaaag ctt    4653
```

<210> SEQ ID NO 19
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Gln Leu Pro Asp Trp Ser Arg Leu Leu Thr
        35                  40                  45

Ala Ile Thr Thr Val Phe Val Lys Ser Lys Arg Pro Asp Met His Asp
    50                  55                  60
```

```
Arg Lys Ser Lys Arg Pro Asp Met Leu Val Asp Ser Phe Gly Leu Glu
 65                  70                  75                  80

Ser Thr Val Gln Asp Gly Leu Val Phe Arg Gln Ser Phe Ser Ile Arg
                 85                  90                  95

Ser Tyr Glu Ile Gly Thr Asp Arg Thr Ala Ser Ile Glu Thr Leu Met
            100                 105                 110

Asn His Leu Gln Glu Thr Ser Leu Asn His Cys Lys Ser Thr Gly Ile
        115                 120                 125

Leu Leu Asp Gly Phe Gly Arg Thr Leu Glu Met Cys Lys Arg Asp Leu
130                 135                 140

Ile Trp Val Val Ile Lys Met Gln Ile Lys Val Asn Arg Tyr Pro Ala
145                 150                 155                 160

Trp Gly Asp Thr Val Glu Ile Asn Thr Arg Phe Ser Arg Leu Gly Lys
                165                 170                 175

Ile Gly Met Gly Arg Asp Trp Leu Ile Ser Asp Cys Asn Thr Gly Glu
            180                 185                 190

Ile Leu Val Arg Ala Thr Ser Ala Tyr Ala Met Met Asn Gln Lys Thr
        195                 200                 205

Arg Arg Leu Ser Lys Leu Pro Tyr Glu Val His Gln Glu Ile Val Pro
210                 215                 220

Leu Phe Val Asp Ser Pro Val Ile Glu Asp Ser Asp Leu Lys Val His
225                 230                 235                 240

Lys Phe Lys Val Lys Thr Gly Asp Ser Ile Gln Lys Gly Leu Thr Pro
                245                 250                 255

Gly Trp Asn Asp Leu Asp Val Asn Gln His Val Ser Asn Val Lys Tyr
            260                 265                 270

Ile Gly Trp Ile Leu Glu Ser Met Pro Thr Glu Val Leu Glu Thr Gln
        275                 280                 285

Glu Leu Cys Ser Leu Ala Leu Glu Tyr Arg Arg Glu Cys Gly Arg Asp
290                 295                 300

Ser Val Leu Glu Ser Val Thr Ala Met Asp Pro Ser Lys Val Gly Val
305                 310                 315                 320

Arg Ser Gln Tyr Gln His Leu Leu Arg Leu Glu Asp Gly Thr Ala Ile
                325                 330                 335

Val Asn Gly Ala Thr Glu Trp Arg Pro Lys Asn Ala Gly Ala Asn Gly
            340                 345                 350

Ala Ile Ser Thr Gly Lys Thr Ser Asn Gly Asn Ser Val Ser
        355                 360                 365

<210> SEQ ID NO 20
<211> LENGTH: 4668
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
```

```
cagcagtgtc agcaaaggta gcagtttgcc agaatgatcg gttcagctgt taatcaatgc    360
cagcaagaga agggggtcaag tgcaaacacg ggcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc    840 atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960 gccaccccttc ttgcggggtc gcgcccagc cagcggtgat gcgctgatcc caaacgagtt   1020
cacattcatt tgcatgcctg gagaagcgag gctggggcct ttgggctggt gcagcccgca   1080
atggaatgcg ggaccgccag gctagcagca aaggcgcctc ccctactccg catcgatgtt   1140
ccatagtgca ttgactgca tttggtgggg gcggccggct gtttctttcg tgttgcaaaa   1200
cgcgccagct cagcaacctg tcccgtgggt ccccgtgcc gatgaaatcg tgtgcacgcc   1260
gatcagctga ttgcccggct cgcgaagtag gcgccctcct ttctgctcgc cctctctccg   1320
tcccgcctct agaatatcaa tgatcgagca ggacggcctc cacgccggct ccccgccgc    1380 ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacagggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gccccgccg agaaggtgtc   1680 catcatggcc gacgccatgc gccgcctgca caccctggac cccgccacct gcccccttcga   1740 ccaccaggcc aagcaccgca tcgagcgcgc ccgcacccgc atggaggccg gcctggtgga   1800
ccaggacgac ctggacgagg agcaccaggg cctggccccc gccgagctgt tcgcccgcct   1860
gaaggcccgc atgcccgacg gcgaggacct ggtggtgacc cacggcgacg cctgcctgcc   1920
caacatcatg gtggagaacg gccgcttctc cggcttcatc gactgcggcc gctgggcgt   1980 ggccgaccgc taccaggaca tcgccctggc caccgcgac atcgccgagg agctgggcgg   2040
cgagtgggcc gaccgcttcc tggtgctgta cggcatcgcc gcccccgact cccagcgcat   2100
cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg cttttatcaa acagcctcag tgtgtttgat cttgtgtgta   2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctc ctcctgctcc tgctcactgc ccctcgcaca gccttggttt gggctccgcc   2460
tgtattctcc tggtactgca acctgtaaac cagcactgca atgctgatgc acgggaagta   2520
gtgggatggg aacacaaatg gaggatcccg cgtctcgaac agagcgcgca gaggaacgct   2580
gaaggtctcg cctctgtcgc acctcagcgc ggcatacacc acaataacca cctgacgaat   2640
gcgcttggtt cttcgtccat tagcgaagcg tccggttcac acacgtgcca cgttggcgag   2700
```

```
gtggcaggtg acaatgatcg gtggagctga tggtcgaaac gttcacagcc tagggatatc   2760
gaattccttt cttgcgctat gacacttcca gcaaaaggta gggcgggctg cgagacggct   2820
tcccggcgct gcatgcaaca ccgatgatgc ttcgaccccc cgaagctcct tcggggctgc   2880
atgggcgctc cgatgccgct ccagggcgag cgctgtttaa atagccaggc cccgattgc    2940 aaagacatta tagcgagcta ccaaagccat attcaaacac ctagatcact accacttcta   3000
cacaggccac tcgagcttgt gatcgcactc cgctaagggg gcgcctcttc ctcttcgttt   3060
cagtcacaac ccgcaaacac tagtatggct atcaagacga acaggcagcc tgtggagaag   3120
cctccgttca cgatcgggac gctgcgcaag gccatcccg cgcactgttt cgagcgctcg    3180
gcgcttcgtg ggcgcgccca gctgcccgac tggagccgcc tgctgaccgc catcaccacc   3240
gtgttcgtga agtccaagcg ccccgacatg cacgaccgca agtccaagcg ccccgacatg   3300
ctggtggaca gcttcggcct ggagtccacc gtgcaggacg gcctggtgtt ccgccagtcc   3360
ttctccatcc gctcctacga gatcggcacc gaccgcaccg ccagcatcga gaccctgatg   3420
aaccacctgc aggagacctc cctgaaccac tgcaagagca ccggcatcct gctggacggc   3480
ttcggccgca ccctggagat gtgcaagcgc gacctgatct gggtggtgat caagatgcag   3540
atcaaggtga accgctaccc cgcctggggc gacaccgtgg agatcaacac ccgcttcagc   3600
cgcctgggca gatcggcat gggccgcgac tggctgatct ccgactgcaa caccggcgag    3660
atcctggtgc gcgccaccag cgcctacgcc atgatgaacc agaagacccg ccgcctgtcc   3720
aagctgccct acgaggtgca ccaggagatc gtgcccctgt tcgtggacag ccccgtgatc   3780
gaggactccg acctgaaggt gcacaagttc aaggtgaaga ccggcgacag catccagaag   3840
ggcctgaccc ccggctggaa cgacctggac gtgaaccagc acgtgtccaa cgtgaagtac   3900
atcggctgga tcctggagag catgcccacc gaggtgctgg agacccagga gctgtgctcc   3960
ctggccctgg agtaccgccg cgagtgcggc cgcgactccg tgctggagag cgtgaccgcc   4020
atggaccccg gcaaggtggg cgtgcgctcc cagtaccagc acctgctgcg cctggaggac   4080
ggcaccgcca tcgtgaacgg cgccaccgag tggcgcccca gaacgccgg cgccaacggc    4140 gccatctcca ccggcaagac cagcaacggc aactccgtgt ccatggacta caaggaccac   4200
gacggcgact acaaggacca cgacatcgac tacaaggacg acgacgacaa gtgactcgag   4260
gcagcagcag ctcggatagt atcgacacac tctggacgct ggtcgtgtga tggactgttg   4320
ccgccacact tgctgccttg acctgtgaat atccctgccg cttttatcaa acagcctcag   4380
tgtgtttgat cttgtgtgta cgcgcttttg cgagttgcta gctgcttgtg ctatttgcga   4440
ataccacccc cagcatcccc ttccctcgtt tcatatcgct tgcatcccaa ccgcaactta   4500
tctacgctgt cctgctatcc ctcagcgctg ctcctgctcc tgctcactgc ccctcgcaca   4560
gccttggttt gggctccgcc tgtattctcc tggtactgca acctgtaaac cagcactgca   4620
atgctgatgc acgggaagta gtgggatggg aacacaaatg gaaagctt               4668
```

<210> SEQ ID NO 21
<211> LENGTH: 393
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Pro Ala Asn Gly Ser Ala Val Thr Leu Lys
        35                  40                  45

Ser Gly Ser Leu Asn Thr Gln Glu Asp Thr Leu Ser Ser Pro Pro
50                  55                  60

Pro Arg Ala Phe Phe Asn Gln Leu Pro Asp Trp Ser Met Leu Leu Thr
65                  70                  75                  80

Ala Ile Thr Thr Val Phe Val Ala Pro Glu Lys Arg Trp Thr Met Phe
                85                  90                  95

Asp Arg Lys Ser Lys Arg Pro Asn Met Leu Met Asp Ser Phe Gly Leu
                100                 105                 110

Glu Arg Val Val Gln Asp Gly Leu Val Phe Arg Gln Ser Phe Ser Ile
            115                 120                 125

Arg Ser Tyr Glu Ile Cys Ala Asp Arg Thr Ala Ser Ile Glu Thr Val
        130                 135                 140

Met Asn His Val Gln Glu Thr Ser Leu Asn Gln Cys Lys Ser Ile Gly
145                 150                 155                 160

Leu Leu Asp Asp Gly Phe Gly Arg Ser Pro Glu Met Cys Lys Arg Asp
                165                 170                 175

Leu Ile Trp Val Val Thr Arg Met Lys Ile Met Val Asn Arg Tyr Pro
                180                 185                 190

Thr Trp Gly Asp Thr Ile Glu Val Ser Thr Trp Leu Ser Gln Ser Gly
            195                 200                 205

Lys Ile Gly Met Gly Arg Asp Trp Leu Ile Ser Asp Cys Asn Thr Gly
210                 215                 220

Glu Ile Leu Val Arg Ala Thr Ser Val Tyr Ala Met Met Asn Gln Lys
225                 230                 235                 240

Thr Arg Arg Phe Ser Lys Leu Pro His Glu Val Arg Gln Glu Phe Ala
                245                 250                 255

Pro His Phe Leu Asp Ser Pro Ala Ile Glu Asp Asn Asp Gly Lys
                260                 265                 270

Leu Gln Lys Phe Asp Val Lys Thr Gly Asp Ser Ile Arg Lys Gly Leu
            275                 280                 285

Thr Pro Gly Trp Tyr Asp Leu Asp Val Asn Gln His Val Ser Asn Val
        290                 295                 300

Lys Tyr Ile Gly Trp Ile Leu Glu Ser Met Pro Thr Glu Val Leu Glu
305                 310                 315                 320

Thr Gln Glu Leu Cys Ser Leu Thr Leu Glu Tyr Arg Arg Glu Cys Gly
                325                 330                 335

Arg Asp Ser Val Leu Glu Ser Val Thr Ser Met Asp Pro Ser Lys Val
                340                 345                 350

Gly Asp Arg Phe Gln Tyr Arg His Leu Leu Arg Leu Glu Asp Gly Ala
            355                 360                 365

Asp Ile Met Lys Gly Arg Thr Glu Trp Arg Pro Lys Asn Ala Gly Thr
370                 375                 380

Asn Gly Ala Ile Ser Thr Gly Lys Thr
385                 390

<210> SEQ ID NO 22
<211> LENGTH: 4686
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 22

```
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga aggggtcaag tgcaaacacg ggcatgccac agcacgggca ccggggagtg     420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
caatgtggtg gataggatgc aagtggagcg aataccaaac cctctggctg cttgctgggt     720
tgcatggcat cgcaccatca gcaggagcgc atgcgaaggg actggcccca tgcacgccat     780
gccaaaccgg agcgcaccga gtgtccacac tgtcaccagg cccgcaagct tgcagaacc      840
atgctcatgg acgcatgtag cgctgacgtc ccttgacggc gctcctctcg ggtgtgggaa     900
acgcaatgca gcacaggcag cagaggcggc ggcagcagag cggcggcagc agcggcgggg     960
gccacccttc ttgcggggtc gcgccccagc cagcggtgat gcgctgatcc caaacgagtt    1020
cacattcatt tgcatgcctg agaagcgag gctgggcct ttgggctggt gcagcccgca    1080
atggaatgcg ggaccgccag gctagcagca aggcgcctc ccctactccg catcgatgtt     1140
ccatagtgca ttggactgca tttgggtggg gcggccggct gtttctttcg tgttgcaaaa    1200
cgcgccagct cagcaacctg tcccgtgggt ccccgtgcc gatgaaatcg tgtgcacgcc     1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc     1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
catcatggcc gacgccatgc gccgcctgca caccctggac cccgccacct gccccttcga    1740
ccaccaggcc aagcaccgca tcgagcgcgc ccgcacccgc atggaggccg gctggtgga     1800
ccaggacgac ctggacgagg agcaccaggg cctggcccc gccgagctgt cgcccgcct      1860
gaaggcccgc atgcccgacg cgcgaggacct ggtggtgacc cacggcgacg cctgcctgcc    1920
caacatcatg gtggagaacg gccgcttctc cggcttcatc gactgcggcc gcctgggcgt    1980
ggccgaccgc taccaggaca tcgccctggc caccgcgac atcgccgagg agctgggcgg    2040
cgagtgggcc gaccgcttcc tggtgctgta cggcatcgcc gccccgact cccagcgcat     2100
cgccttctac cgcctgctgg acgagttctt ctgacaattg gcagcagcag ctcggatagt    2160
```

```
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc cccgattgc     2940 aaagacatta tagcgagcta ccaaaagccat attcaaacac ctagatcact accacttcta   3000
cacaggccac tcgagcttgt gatcgcactc cgctaagggg gcgcctcttc ctcttcgttt    3060
cagtcacaac ccgcaaacac tagtatggct atcaagacga acaggcagcc tgtgagaag    3120 cctccgttca cgatcgggac gctgcgcaag gccatccccg cgcactgttt cgagcgctcg    3180
gcgcttcgtg ggcgcgcccc cgcgaacggc agcgcggtga ccctgaagtc gggctccctg    3240
aacacccagg aggacacgct gagctcgtcc cccccccccc gcgcgttctt caaccagctg    3300
cccgactgga gcatgctgct gaccgcgatc accacggtct tcgtggcgcc cgagaagcgc    3360
tggaccatgt tcgaccgcaa gtcgaagcgc cccaacatgc tgatggactc cttcggcctg    3420
gagcgcgtgg tccaggacgg cctggtgttc cgccagagct ctcgatccg ctcctacgag     3480 atctgcgcgg accgcaccgc gagcatcgag acggtgatga ccacgtccca ggagacctcg    3540
ctgaaccagt gcaagtccat cggcctgctg gacgacggct tcggccgcag ccccgagatg    3600
tgcaagcgcg acctgatctg ggtggtcacc cgcatgaaga tcatggtgaa ccgctacccc    3660
acgtggggcg acaccatcga ggtctcgacg tggctgtccc agagcggcaa gatcggcatg    3720
ggccgcgact ggctgatctc ggactgcaac accggcgaga tcctggtgcg cgcgacgtcc    3780
gtctacgcga tgatgaacca gaagacccgc cgcttcagca agctgcccca cgaggtgcgc    3840
caggagttcg cgccccactt cctggactcg ccccccgcga tcgaggacaa cgacggcaag    3900
ctgcagaagt tcgacgtcaa gacgggcgac tccatccgca agggcctgac ccccggctgg    3960
tacgacctgg acgtgaacca gcacgtgagc aacgtcaagt acatcggctg gatcctggag    4020
tcgatgccca ccgaggtcct ggagacgcag gagctgtgct ccctgaccct ggagtaccgc    4080
cgcgagtgcg gccgcgactc ggtgctggag agcgtcacca gcatggaccc ctcgaaggtg    4140
ggcgaccgct tccagtaccg ccacctgctg cgcctggagg acggcgcgga catcatgaag    4200
ggccgcaccg agtggcgccc caagaacgcg ggcacgaacg gcgcgatctc caccggcaag    4260
acgtgactcg aggcagcagc agctcggata gtatcgacac actctggacg ctggtcgtgt    4320
gatggactgt tgccgccaca cttgctgcct tgacctgtga atatccctgc cgcttttatc    4380
aaacagcctc agtgtgtttg atcttgtgtg tacgcgcttt tgcgagttgc tagctgcttg    4440
tgctatttgc gaataccacc cccagcatcc ccttccctcg tttcatatcg cttgcatccc    4500
```

-continued

```
aaccgcaact tatctacgct gtcctgctat ccctcagcgc tgctcctgct cctgctcact    4560
gccccccgca cagccttggt ttgggctccg cctgtattct cctggtactg caacctgtaa    4620
accagcactg caatgctgat gcacgggaag tagtgggatg ggaacacaaa tggaaagctt    4680
gagctc                                                               4686
```

<210> SEQ ID NO 23
<211> LENGTH: 408
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 23

```
Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Pro Ala Asn Gly Ser Ala Val Asn Leu Lys
        35                  40                  45

Ser Gly Ser Leu Asn Thr Gln Glu Asp Thr Ser Ser Pro Pro Pro
    50                  55                  60

Arg Ala Phe Leu Asn Gln Leu Pro Asp Trp Ser Met Leu Leu Thr Ala
65                  70                  75                  80

Ile Thr Thr Val Phe Val Ala Ala Glu Lys Gln Trp Thr Met Leu Asp
                85                  90                  95

Arg Lys Ser Lys Arg Pro Asp Met Leu Val Asp Ser Val Gly Leu Lys
            100                 105                 110

Ser Ile Val Arg Asp Gly Leu Val Ser Arg Gln Ser Phe Leu Ile Arg
        115                 120                 125

Ser Tyr Glu Ile Gly Ala Asp Arg Thr Ala Ser Ile Glu Thr Leu Met
    130                 135                 140

Asn His Leu Gln Glu Thr Ser Ile Asn His Cys Lys Ser Leu Gly Leu
145                 150                 155                 160

Leu Asn Asp Gly Phe Gly Arg Thr Pro Gly Met Cys Lys Asn Asp Leu
                165                 170                 175

Ile Trp Val Leu Thr Lys Met Gln Ile Met Val Asn Arg Tyr Pro Thr
            180                 185                 190

Trp Gly Asp Thr Val Glu Ile Asn Thr Trp Phe Ser Gln Ser Gly Lys
        195                 200                 205

Ile Gly Met Ala Ser Asp Trp Leu Ile Ser Asp Cys Asn Thr Gly Glu
    210                 215                 220

Ile Leu Ile Arg Ala Thr Ser Val Trp Ala Met Met Asn Gln Lys Thr
225                 230                 235                 240

Arg Arg Phe Ser Arg Leu Pro Tyr Glu Val Arg Gln Glu Leu Thr Pro
                245                 250                 255

His Phe Val Asp Ser Pro His Val Ile Glu Asp Asn Asp Gln Lys Leu
            260                 265                 270

His Lys Phe Asp Val Lys Thr Gly Asp Ser Ile Arg Lys Gly Leu Thr
        275                 280                 285

Pro Arg Trp Asn Asp Leu Asp Val Asn Gln His Val Ser Asn Val Lys
    290                 295                 300

Tyr Ile Gly Trp Ile Leu Glu Ser Met Pro Ile Glu Val Leu Glu Thr
305                 310                 315                 320
```

Gln Glu Leu Cys Ser Leu Thr Val Glu Tyr Arg Arg Glu Cys Gly Met
                325                 330                 335

Asp Ser Val Leu Glu Ser Val Thr Ala Val Asp Pro Ser Glu Asn Gly
            340                 345                 350

Gly Arg Ser Gln Tyr Lys His Leu Leu Arg Leu Glu Asp Gly Thr Asp
        355                 360                 365

Ile Val Lys Ser Arg Thr Glu Trp Arg Pro Lys Asn Ala Gly Thr Asn
    370                 375                 380

Gly Ala Ile Ser Thr Ser Thr Ala Lys Thr Ser Asn Gly Asn Ser Ala
385                 390                 395                 400

Ser Asp Asp Asp Lys Leu Gly
                405

<210> SEQ ID NO 24
<211> LENGTH: 1239
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
actagtatgg ctatcaagac gaacaggcag cctgtggaga agcctccgtt cacgatcggg    60
acgctgcgca aggccatccc cgcgcactgt ttcgagcgct cggcgcttcg tgggcgcgcc   120
cccgcgaacg gcagcgcggt gaacctgaag tcgggctccc tgaacacccc aggaggacacg   180 agctcgtccc cccccccccg cgcgttcctg aaccagctgc ccgactggag catgctgctg   240
accgcgatca ccaccgtctt cgtggcggcg gagaagcagt ggacgatgct ggaccgcaag   300
tcgaagcgcc ccgacatgct ggtggactcc gtcggcctga gagcatcgt gcgcgacggc   360 ctggtctcgc gccagtcctt cctgatccgc agctacgaga tcggcgcgga ccgcaccgcg   420
tcgatcgaga ccctgatgaa ccacctgcag gagacgtcca tcaaccactg caagagcctg   480
ggcctgctga cgacggcttc ggccgcacc cccggcatgt gcaagaacga cctgatctgg   540
gtgctgacca agatgcagat catggtcaac cgctacccca cgtggggcga caccgtcgag   600
atcaacacgt ggttctcgca gtccggcaag atcggcatgg cgagcgactg gctgatctcg   660
gactgcaaca ccggcgagat cctgatccgc gcgacctccg tgtgggcgat gatgaaccag   720
aagacgcgcc gcttcagccg cctgccctac gaggtccgcc aggagctgac cccccacttc   780
gtggactcgc ccacgtcat cgaggacaac gaccagaagc tgcacaagtt cgacgtgaag   840
accggcgact ccatccgcaa gggcctgacg ccccgctgga cgacctgga cgtcaaccag   900 cacgtgtcga acgtgaagta catcggctgg atcctggagt ccatgcccat cgaggtcctg   960
gagacccagg agctgtgctc gctgaccgtg gagtaccgcc gcgagtgcgg catggactcc  1020
gtgctggagt cggtcacggc ggtggacccc agcgagaacg gcggccgcag ccagtacaag  1080
cacctgctgc gcctggagga cggcaccgac atcgtcaagt cgcgcaccga gtggcgcccc  1140
aagaacgcgg gcacgaacgg cgcgatctcc accagcaccg cgaagacgtc gaacggcaac  1200
tccgcgagcg atgacgatga caagctggga tgactcgag                          1239

<210> SEQ ID NO 25
<211> LENGTH: 399
<212> TYPE: PRT
<213> ORGANISM: Artificial Sequence
<220> FEATURE:

-continued

<221> NAME/KEY: source
<223> OTHER INFORMATION: /note="Description of Artificial Sequence: Synthetic polypeptide"

<400> SEQUENCE: 25

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ala Gln Ala Ala Thr Arg Val Asn Gly Ser
        35                  40                  45

Lys Val Gly Leu Lys Thr Asp Thr Asn Lys Leu Glu Asp Ala Pro Phe
    50                  55                  60

Ile Pro Ser Ser Ala Pro Arg Thr Phe Tyr Asn Gln Leu Pro Asp Trp
65                  70                  75                  80

Ser Val Leu Leu Ala Ala Ile Thr Thr Ile Phe Leu Ala Ala Glu Lys
                85                  90                  95

Gln Trp Thr Leu Ile Asp Trp Lys Arg Gly Pro Asp Met Leu Ser
                100                 105                 110

Asp Ala Phe Gly Leu Pro Lys Ile Ile Glu Asn Gly Leu Leu Tyr Arg
            115                 120                 125

Gln Lys Phe Ser Ile Arg Ser Tyr Glu Ile Gly Ala Asp Gln Thr Ala
        130                 135                 140

Ser Ile Glu Thr Leu Met Asn His Leu Gln Glu Thr Ala Leu Asn His
145                 150                 155                 160

Val Lys Cys Ala Gly Leu Leu Gly Asn Gly Phe Gly Ser Thr Pro Glu
                165                 170                 175

Met Ser Lys Met Asn Leu Ile Trp Val Val Thr Lys Met Gln Val Leu
            180                 185                 190

Val Glu His Tyr Pro Ser Trp Gly Asp Val Ile Glu Val Asp Thr Trp
        195                 200                 205

Ala Ala Ala Ser Gly Lys Asn Gly Met Arg Arg Asp Trp His Val Arg
    210                 215                 220

Asp Trp Gln Thr Gly Gln Thr Ile Met Arg Ala Ser Ser Asn Trp Val
225                 230                 235                 240

Met Met Asn Gln Asn Thr Arg Arg Leu Ser Lys Phe Pro Glu Glu Val
                245                 250                 255

Arg Ala Glu Ile Glu Pro Tyr Phe Met Glu Arg Ala Pro Val Ile Asp
            260                 265                 270

Asp Asp Asn Arg Lys Leu Pro Lys Leu Asp Asp Thr Ala Asp His
        275                 280                 285

Val Arg Asn Gly Leu Thr Pro Arg Trp Ser Asp Leu Asp Val Asn Gln
    290                 295                 300

His Val Lys Asn Val Lys Tyr Ile Gly Trp Ile Leu Glu Ser Ala Pro
305                 310                 315                 320

Ile Ser Ile Leu Glu Ser His Glu Leu Ala Ser Met Thr Leu Glu Tyr
                325                 330                 335

Arg Arg Glu Cys Gly Arg Asp Ser Val Leu Gln Ser Leu Thr Ser Val
            340                 345                 350

Ser Asn Asn Cys Thr Asp Gly Ser Glu Glu Leu Pro Ile Glu Cys Gln
        355                 360                 365

His Leu Leu Arg Asn Glu Gly Ser Glu Ile Val Lys Gly Arg Thr
    370                 375                 380

Glu Trp Arg Pro Lys Lys Cys Gly Pro Phe Gly Ala Gly Arg Pro
```

-continued

<210> SEQ ID NO 26
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
actagtatgg ccaccgcatc cactttctcg gcgttcaatg cccgctgcgg cgacctgcgt      60
cgctcggcgg gctccgggcc ccggcgccca gcgaggcccc tccccgtgcg cgggcgcgcc     120
gcccaggcgg ccacccgcgt gaacggcagc aaggtgggcc tgaagaccga caccaacaag     180
ctggaggacg cgcccttcat ccctcgtcc gcccccgca ccttctacaa ccagctgccc      240
gactggagcg tcctgctggc ggccatcacc accatcttcc tggcggccga aagcagtgg      300
accctgatcg actggaagcg cggcggcccc gacatgctgt cggacgcgtt cggcctgccc     360
aagatcatcg agaacggcct gctgtaccgc cagaagttct ccatccgcag ctacgagatc     420
ggcgccgacc agaccgcctc gatcgagacc ctgatgaacc acctgcagga gaccgcgctg     480
aaccacgtca gtgcgccgg cctgctgggc aacggcttcg gctccacccc cgagatgagc     540
aagatgaacc tgatctgggt ggtcaccaag atgcaggtgc tggtcgagca ctaccccgtcg    600
tggggcgacg tgatcgaggt ggacacctgg gcggccgcgt ccggcaagaa cggcatgcgc     660
cgcgactggc acgtccgcga ctggcagacc ggccagacca tcatgcgcgc cagctcgaac     720
tgggtgatga tgaaccagaa caccccgccgc ctgtccaagt tccccgagga ggtccgcgcc   780
gagatcgagc cctacttcat ggagcgcgcc ccgtgatcg acgacgacaa ccgcaagctg     840
cccaagctgg acgacgacac cgcggaccac gtgcgcaacg gcctgacccc ccgctggagc    900
gacctggacg tgaaccagca cgtcaagaac gtgaagtaca tcggctggat cctggagtcg     960
gccccatct ccatcctgga gagccacgag ctggcctcga tgaccctgga gtaccgccgc    1020
gagtgcggcc gcgactccgt cctgcagagc ctgacctcgg tgtccaacaa ctgcaccgac    1080
ggcagcgagg agctgcccat cgagtgccag cacctgctgc gcaacgaggg cggctcggag    1140
atcgtcaagg gccgcaccga gtggcgcccc aagaagtgcg gccccttcgg cgccggccgc   1200
ccctgactcg ag                                                        1212
```

<210> SEQ ID NO 27
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 27

Met Ala Ile Lys Thr Asn Arg Gln Pro Val Glu Lys Pro Pro Phe Thr
1               5                   10                  15

Ile Gly Thr Leu Arg Lys Ala Ile Pro Ala His Cys Phe Glu Arg Ser
            20                  25                  30

Ala Leu Arg Gly Arg Ala Ala Asn Ala His Thr Val Pro Lys Ile Asn
        35                  40                  45

Gly Asn Lys Ala Gly Leu Leu Thr Pro Met Glu Ser Thr Lys Asp Glu
    50                  55                  60

```
Asp Ile Val Ala Ala Pro Thr Val Ala Pro Lys Arg Thr Phe Ile Asn
 65                  70                  75                  80

Gln Leu Pro Asp Trp Ser Met Leu Leu Ala Ile Thr Thr Ile Phe
             85                  90                  95

Leu Ala Ala Glu Lys Gln Trp Thr Asn Leu Asp Trp Lys Pro Arg Arg
            100                 105                 110

Pro Asp Met Leu Val Asp Phe Asp Pro Phe Ser Leu Gly Arg Phe Val
            115                 120                 125

Gln Asp Gly Leu Ile Phe Arg Gln Asn Phe Ser Ile Arg Ser Tyr Glu
130                 135                 140

Ile Gly Ala Asp Arg Thr Ala Ser Ile Glu Thr Leu Met Asn His Leu
145                 150                 155                 160

Gln Glu Thr Ala Leu Asn His Val Arg Cys Ile Gly Leu Leu Asp Asp
                165                 170                 175

Gly Phe Gly Ser Thr Pro Glu Met Thr Arg Arg Asp Leu Ile Trp Val
            180                 185                 190

Val Thr Arg Met Gln Val Leu Val Asp Arg Tyr Pro Ser Trp Gly Asp
            195                 200                 205

Val Ile Glu Val Asp Ser Trp Val Thr Pro Ser Gly Lys Asn Gly Met
210                 215                 220

Lys Arg Glu Trp Phe Leu Arg Asp Cys Lys Thr Gly Glu Ile Leu Thr
225                 230                 235                 240

Arg Ala Thr Ser Val Trp Val Met Met Asn Lys Arg Thr Arg Arg Leu
                245                 250                 255

Ser Lys Ile Pro Glu Glu Val Arg Val Glu Ile Glu Pro Tyr Phe Val
            260                 265                 270

Glu His Gly Val Leu Asp Glu Asp Ser Arg Lys Leu Pro Lys Leu Asn
            275                 280                 285

Asp Asn Thr Ala Asn Tyr Ile Arg Arg Gly Leu Ala Pro Arg Trp Ser
290                 295                 300

Asp Leu Asp Val Asn Gln His Val Asn Asn Val Lys Tyr Ile Gly Trp
305                 310                 315                 320

Ile Leu Glu Ser Val Pro Ser Ser Leu Leu Glu Ser His Glu Leu Tyr
                325                 330                 335

Gly Met Thr Leu Glu Tyr Arg Lys Glu Cys Gly Lys Asp Gly Leu Leu
            340                 345                 350

Gln Ser Leu Thr Ala Val Ala Ser Asp Tyr Gly Gly Gly Ser Leu Glu
            355                 360                 365

Ala Gly Val Glu Cys Asp His Leu Leu Arg Leu Glu Asp Gly Ser Glu
370                 375                 380

Ile Met Arg Gly Lys Thr Glu Trp Arg Pro Lys Arg Ala Ala Asn Thr
385                 390                 395                 400

Thr Tyr Phe Gly Ser Val Asp Asp Ile Pro Pro Ala Asn Asn Ala
                405                 410                 415

<210> SEQ ID NO 28
<211> LENGTH: 1260
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
```

```
actagtatgg ctatcaagac gaacaggcag cctgtggaga agcctccgtt cacgatcggg    60
acgctgcgca aggccatccc cgcgcactgt ttcgagcgct cggcgcttcg tgggcgcgcc   120
gccaacgccc acaccgtgcc aagatcaac  ggcaacaagg ccggcctgct gaccccatg    180
gagagcacca aggacgagga catcgtcgcg gcccccaccg tggcgcccaa gcgcaccttc   240
atcaaccagc tgcccgactg gtcgatgctg ctggccgcga tcaccaccat cttcctggcg   300
gccgagaagc agtggaccaa cctggactgg aagccccgcc gccccgacat gctggtcgac   360
ttcgaccctc tctccctggg ccgcttcgtg caggacggcc tgatcttccg ccagaacttc   420
agcatccgct cgtacgagat cggcgcggac cgcaccgcct ccatcgagac cctgatgaac   480
cacctgcagg agaccgcgct gaaccacgtc cgctgcatcg gcctgctgga cgacggcttc   540
ggcagcaccc ccgagatgac ccgccgcgac ctgatctggg tggtcacccg catgcaggtc   600
ctggtggacc gctacccctc gtggggcgac gtgatcgagg tcgactcctg ggtgaccccc   660
agcggcaaga acggcatgaa gcgcgagtgg ttcctgcgcg actgcaagac cggcgagatc   720
ctgacccgcg ccacctcggt ctgggtgatg atgaacaagc gcacccgccg cctgtccaag   780
atccccgagg aggtccgcgt ggagatcgag ccctacttcg tcgagcacgg cgtgctggac   840
gaggactcgc gcaagctgcc caagctgaac gacaacaccg ccaactacat ccgccgcggc   900
ctggcgcccc gctggtccga cctggacgtc aaccagcacg tgaacaacgt caagtacatc   960
ggctggatcc tggagagcgt gcccagcagc ctgctggagt cgcacgagct gtacggcatg  1020
accctggagt accgcaagga gtgcggcaag gacggcctgc tgcagtccct gaccgccgtc  1080
gccagcgact acgcggcgg  ctcgctggag gccggcgtgg agtgcgacca cctgctgcgc  1140
ctggaggacg gctccgagat catgcgcggc aagaccgagt ggcgccccaa gcgcgccgcg  1200
aacaccacct acttcggcag cgtcgacgac atccccccg  ccaacaacgc gtgactcgag  1260
```

<210> SEQ ID NO 29
<211> LENGTH: 362
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Gly Arg Ala Ser Met Leu Leu Ser Ala Val Thr Thr Val
        35                  40                  45

Phe Gly Val Ala Glu Lys Gln Trp Pro Met Leu Asp Arg Lys Ser Lys
    50                  55                  60

Arg Pro Asp Met Leu Val Glu Pro Leu Gly Val Asp Arg Ile Val Tyr
65                  70                  75                  80

Asp Gly Val Ser Phe Arg Gln Ser Phe Ser Ile Arg Ser Tyr Glu Ile
                85                  90                  95

Gly Ala Asp Arg Thr Ala Ser Ile Glu Thr Leu Met Asn Met Phe Gln
            100                 105                 110

Glu Thr Ser Leu Asn His Cys Lys Ile Ile Gly Leu Leu Asn Asp Gly
        115                 120                 125

Phe Gly Arg Thr Pro Glu Met Cys Lys Arg Asp Leu Ile Trp Val Val

```
                130                 135                 140
Thr Lys Met Gln Ile Glu Val Asn Arg Tyr Pro Thr Trp Gly Asp Thr
145                 150                 155                 160

Ile Glu Val Asn Thr Trp Val Ser Ala Ser Gly Lys His Gly Met Gly
                165                 170                 175

Arg Asp Trp Leu Ile Ser Asp Cys His Thr Gly Glu Ile Leu Ile Arg
                180                 185                 190

Ala Thr Ser Val Trp Ala Met Met Asn Gln Lys Thr Arg Arg Leu Ser
                195                 200                 205

Lys Ile Pro Tyr Glu Val Arg Gln Glu Ile Glu Pro Gln Phe Val Asp
                210                 215                 220

Ser Ala Pro Val Ile Val Asp Asp Arg Lys Phe His Lys Leu Asp Leu
225                 230                 235                 240

Lys Thr Gly Asp Ser Ile Cys Asn Gly Leu Thr Pro Arg Trp Thr Asp
                245                 250                 255

Leu Asp Val Asn Gln His Val Asn Asn Val Lys Tyr Ile Gly Trp Ile
                260                 265                 270

Leu Gln Ser Val Pro Thr Glu Val Phe Glu Thr Gln Glu Leu Cys Gly
                275                 280                 285

Leu Thr Leu Glu Tyr Arg Arg Glu Cys Gly Arg Asp Ser Val Leu Glu
                290                 295                 300

Ser Val Thr Ala Met Asp Pro Ser Lys Glu Gly Asp Arg Ser Leu Tyr
305                 310                 315                 320

Gln His Leu Leu Arg Leu Glu Asp Gly Ala Asp Ile Val Lys Gly Arg
                325                 330                 335

Thr Glu Trp Arg Pro Lys Asn Ala Gly Ala Lys Gly Ala Ile Leu Thr
                340                 345                 350

Gly Lys Thr Ser Asn Gly Asn Ser Ile Ser
                355                 360

<210> SEQ ID NO 30
<211> LENGTH: 1101
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
actagtatgg ccaccgcatc cactttctcg gcgttcaatg cccgctgcgg cgacctgcgt      60
cgctcggcgg gctccgggcc ccggcgccca gcgaggcccc tccccgtgcg cgggcgcgcc     120
agcatgctgc tgtcggcggt gaccacggtc ttcggcgtgg ccgagaagca gtggcccatg     180
ctggaccgca agtccaagcg ccccgacatg ctggtcgagc ccctgggcgt ggaccgcatc     240
gtctacgacg gcgtgagctt ccgccagtcg ttctccatcc gcagctacga gatcggcgcc     300
gaccgcaccg cctcgatcga gacgctgatg aacatgttcc aggagacctc cctgaaccac     360
tgcaagatca tcggcctgct gaacgacggc ttcggccgca cgcccgagat gtgcaagcgc     420
gacctgatct gggtcgtgac caagatgcag atcgaggtga accgctaccc cacgtggggc     480
gacaccatcg aggtcaacac gtgggtgagc gcctcgggca gcacggcat gggccgcgac     540 tggctgatct ccgactgcca caccggcgag atcctgatcc gcgcgacgag cgtctgggcg     600
atgatgaacc agaagacccg ccgcctgtcg aagatcccct acgaggtgcg ccaggagatc     660
gagccccagt tcgtcgactc cgccccccgtg atcgtggacg accgcaagtt ccacaagctg     720
```

```
gacctgaaga cgggcgacag catctgcaac ggcctgaccc cccgctggac ggacctggac    780
gtgaaccagc acgtcaacaa cgtgaagtac atcggctgga tcctgcagtc ggtccccacc    840
gaggtgttcg agacgcagga gctgtgcggc ctgaccctgg agtaccgccg cgagtgcggc    900
cgcgactccg tgctggagag cgtcacggcc atggaccct cgaaggaggg cgaccgctcc     960
ctgtaccagc acctgctgcg cctggaggac ggcgcggaca tcgtgaaggg ccgcaccgag   1020
tggcgcccca agaacgccgg cgccaagggc gccatcctga cgggcaagac cagcaacggc   1080
aactcgatct cctgactcga g                                              1101
```

<210> SEQ ID NO 31
<211> LENGTH: 369
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 31

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Pro Ala Arg Pro Leu
            20                  25                  30

Pro Val Arg Gly Arg Ala Gln Leu Pro Asp Trp Ser Met Leu Leu Ala
        35                  40                  45

Ala Ile Thr Thr Leu Phe Leu Ala Ala Glu Lys Gln Trp Met Met Leu
50                  55                  60

Asp Trp Lys Pro Lys Arg Pro Asp Met Leu Val Asp Pro Phe Gly Leu
65                  70                  75                  80

Gly Arg Phe Val Gln Asp Gly Leu Val Phe Arg Asn Asn Phe Ser Ile
                85                  90                  95

Arg Ser Tyr Glu Ile Gly Ala Asp Arg Thr Ala Ser Ile Glu Thr Leu
            100                 105                 110

Met Asn His Leu Gln Glu Thr Ala Leu Asn His Val Lys Ser Val Gly
        115                 120                 125

Leu Leu Glu Asp Gly Leu Gly Ser Thr Arg Glu Met Ser Leu Arg Asn
130                 135                 140

Leu Ile Trp Val Val Thr Lys Met Gln Val Ala Val Asp Arg Tyr Pro
145                 150                 155                 160

Thr Trp Gly Asp Glu Val Gln Val Ser Ser Trp Ala Thr Ala Ile Gly
                165                 170                 175

Lys Asn Gly Met Arg Arg Glu Trp Ile Val Thr Asp Phe Arg Thr Gly
            180                 185                 190

Glu Thr Leu Leu Arg Ala Thr Ser Val Trp Val Met Met Asn Lys Leu
        195                 200                 205

Thr Arg Arg Ile Ser Lys Ile Pro Glu Glu Val Trp His Glu Ile Gly
210                 215                 220

Pro Ser Phe Ile Asp Ala Pro Pro Leu Pro Thr Val Glu Asp Gly
225                 230                 235                 240

Arg Lys Leu Thr Arg Phe Asp Glu Ser Ser Ala Asp Phe Ile Arg Lys
                245                 250                 255

Gly Leu Thr Pro Arg Trp Ser Asp Leu Asp Ile Asn Gln His Val Asn
            260                 265                 270

Asn Val Lys Tyr Ile Gly Trp Leu Leu Glu Ser Ala Pro Pro Glu Ile
```

|   |   |   | 275 |   |   |   | 280 |   |   |   | 285 |   |   |
|---|---|---|---|---|---|---|---|---|---|---|---|---|---|

His Glu Ser His Glu Ile Ala Ser Leu Thr Leu Glu Tyr Arg Arg Glu
    290                 295                 300

Cys Gly Arg Asp Ser Val Leu Asn Ser Ala Thr Lys Val Ser Asp Ser
305                 310                 315                 320

Ser Gln Leu Gly Lys Ser Ala Val Glu Cys Asn His Leu Val Arg Leu
            325                 330                 335

Gln Asn Gly Glu Ile Val Lys Gly Arg Thr Val Trp Arg Pro Lys
        340                 345                 350

Arg Pro Leu Tyr Asn Asp Gly Ala Val Val Asp Val Pro Ala Lys Thr
            355                 360                 365

Ser

<210> SEQ ID NO 32
<211> LENGTH: 1122
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
actagtatgg ccaccgcatc cactttctcg gcgttcaatg cccgctgcgg cgacctgcgt    60
cgctcggcgg gctccgggcc ccggcgccca gcgaggcccc tccccgtgcg cgggcgcgcc   120
cagctgcccg actggagcat gctgctggcc gcgatcacca ccctgttcct ggcggccgag   180
aagcagtgga tgatgctgga ctggaagccc aagcgccccg acatgctggt ggaccccttc   240
ggcctgggcc gcttcgtgca ggacggcctg gtgttccgca caacttcag catccgcagc    300 tacgagatcg gcgcggaccg caccgccagc atcgagaccc tgatgaacca cctgcaggag   360
accgccctga accacgtgaa gagcgtgggc ctgctggagg acggcctggg cagcacccgc   420
gagatgagcc tgcgcaacct gatctgggtg gtgaccaaga tgcaggtggc ggtggaccgc   480
taccccacct ggggcgacga ggtgcaggtg agcagctggg cgaccgccat cggcaagaac   540
ggcatgcgcc gcgagtggat cgtgaccgac ttccgcaccg gcgagaccct gctgcgcgcc   600
accagcgtgt gggtgatgat gaacaagctg acccgccgca tcagcaagat ccccgaggag   660
gtgtggcacg agatcggccc cagcttcatc gacgcgcccc cctgcccac cgtggaggac   720 gacggccgca agctgacccg cttcgacgag agcagcgccg acttcatccg caagggcctg   780 acccccgct ggagcgacct ggacatcaac cagcacgtga caacgtgaa gtacatcggc    840 tggctgctgg agagcgcgcc ccccgagatc cacgagagcc acgagatcgc cagcctgacc   900
ctggagtacc gccgcgagtg cggccgcgac agcgtgctga cagcgccac caaggtgagc   960 gacagcagcc agctgggcaa gagcgccgtg gagtgcaacc acctggtgcg cctgcagaac  1020
ggcggcgaga tcgtgaaggg ccgcaccgtg tggcgcccca gcgcccccct gtacaacgac  1080
ggcgccgtgg tggacgtgcc cgccaagacc agctgactcg ag                     1122

<210> SEQ ID NO 33
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

```
<400> SEQUENCE: 33
actagtatgg ctatcaagac gaacaggcag cctgtggaga agcctccgtt cacgatcggg    60
acgctgcgca aggccatccc cgcgcactgt ttcgagcgct cggcgcttcg tgggcgcgcc   120

<210> SEQ ID NO 34
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 34
actagtatgg ccaccgcatc cactttctcg gcgttcaatg cccgctgcgg cgacctgcgt    60
cgctcggcgg gctccgggcc ccggcgccca gcgaggcccc tccccgtgcg cgggcgcgcc   120

<210> SEQ ID NO 35
<211> LENGTH: 6207
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 35
gctcttcggc cgccgccact cctgctcgag cgcgcccgac tcgcgctccg cctgcgcccg    60
cgcgtgcgcc gccagcgcct tggccttttc gccgcgctcg tgcgcgtcgc tgatgtccat   120
caccaggtcc atgaggtctg ccttgcgccg gctgagccac tgcttcgtcc gggcggccaa   180
gaggagcatg agggaggact cctggtccag ggtcctgacg tggtcgcggc tctgggagcg   240
ggccagcatc atctggctct gccgcaccga ggccgcctcc aactggtcct ccagcagccg   300
cagtcgccgc cgaccctggc agaggaagac aggtgagggg ggtatgaatt gtacagaaca   360
accacgagcc ttgtctaggc agaatcccta ccagtcatgg ctttacctgg atgacggcct   420
gcgaacagct gtccagcgac cctcgctgcc gccgcttctc ccgcacgctt ctttccagca   480
ccgtgatggc gcgagccagc gccgcacgct ggcgctgcgc ttcgccgatc tgaggacagt   540
cggggaactc tgatcagtct aaaccccctt gcgcgttagt gttgccatcc tttgcagacc   600
ggtgagagcc gacttgttgt gcgccacccc ccacaccacc tcctcccaga ccaattctgt   660 caccttttttg gcgaaggcat cggcctcggc ctgcagagag gacagcagtg cccagccgct   720
gggggttggc ggatgcacgc tcaggtaccc tttcttgcgc tatgacactt ccagcaaaag   780
gtagggcggg ctgcgagacg gcttccggc gctgcatgca acaccgatga tgcttcgacc   840
ccccgaagct ccttcggggc tgcatgggcg ctccgatgcc gctccagggc gagcgctgtt   900
taaatagcca ggccccgat tgcaaagaca ttatagcgag ctaccaaagc catattcaaa   960
cacctagatc actaccactt ctacacaggc cactcgagct tgtgatcgca ctccgctaag  1020
ggggcgcctc ttcctcttcg tttcagtcac aacccgcaaa cggcgcgcca tgctgctgca  1080
ggccttcctg ttcctgctgg ccggcttcgc cgccaagatc agcgcctcca tgacgaacga  1140
gacgtccgac cgcccctgg tgcacttcac ccccaacaag ggctggatga acgacccaa   1200 cggcctgtgg tacgacgaga aggacgccaa gtggcacctg tacttccagt acaacccgaa  1260
cgacaccgtc tgggggacgc ccttgttctg gggccacgcc acgtccgacg acctgaccaa  1320
ctgggaggac cagcccatcg ccatcgcccc gaagcgcaac gactccggcg ccttctccgg  1380
```

-continued

```
ctccatggtg gtggactaca acaacacctc cggcttcttc aacgacacca tcgacccgcg    1440
ccagcgctgc gtggccatct ggacctacaa cacccggag tccgaggagc agtacatctc     1500
ctacagcctg gacggcggct acaccttcac cgagtaccag aagaaccccg tgctggccgc    1560
caactccacc cagttccgcg acccgaaggt cttctggtac gagccctccc agaagtggat    1620
catgaccgcg gccaagtccc aggactacaa gatcgagatc tactcctccg acgacctgaa    1680
gtcctggaag ctggagtccg cgttcgccaa cgagggcttc ctcggctacc agtacgagtg    1740
ccccggcctg atcgaggtcc ccaccgagca ggaccccagc aagtcctact gggtgatgtt    1800
catctccatc aaccccggcg ccccggccgg cggctccttc aaccagtact cgtcggcag     1860
cttcaacggc acccacttcg aggccttcga caaccagtcc cgcgtggtgg acttcggcaa    1920
ggactactac gccctgcaga ccttcttcaa caccgacccg acctacggga cgccctggg     1980
catcgcgtgg gcctccaact gggagtactc cgccttcgtg cccaccaacc cctggcgctc    2040
ctccatgtcc ctcgtgcgca gttctccct caacaccgag taccaggcca acccggagac     2100
ggagctgatc aacctgaagg ccgagccgat cctgaacatc agcaacgccg ccccctggag    2160
ccggttcgcc accaacacca cgttgacgaa ggccaacagc tacaacgtcg acctgtccaa    2220
cagcaccggc accctggagt cgagctggt gtacgccgtc aacaccaccc agacgatctc     2280
caagtccgtg ttcgcggacc tctccctctg gttcaagggc ctggaggacc ccgaggagta    2340
cctccgcatg ggcttcgagg tgtccgcgtc ctccttcttc ctggaccgcg ggaacagcaa    2400
ggtgaagttc gtgaaggaga ccccctactt caccaaccgc atgagcgtga acaaccagcc    2460
cttcaagagc gagaacgacc tgtcctacta caaggtgtac ggcttgctgg accagaacat    2520
cctggagctg tacttcaacg acggcgacgt cgtgtccacc aacacctact tcatgaccac    2580
cgggaacgcc ctgggctccg tgaacatgac gacggggtg gacaacctgt tctacatcga     2640
caagttccag gtgcgcgagg tcaagtgaca attggcagca gcagctcgga tagtatcgac    2700
acactctgga cgctggtcgt gtgatggact gttgccgcca cacttgctgc cttgacctgt    2760
gaatatccct gccgctttta tcaaacagcc tcagtgtgtt tgatcttgtg tgtacgcgct    2820
tttgcgagtt gctagctgct tgtgctattt gcgaatacca cccccagcat cccccttccct   2880
cgtttcatat cgcttgcatc ccaaccgcaa cttatctacg ctgtcctgct atccctcagc    2940
gctgctcctg ctcctgctca ctgccctcg cacagccttg gtttgggctc cgcctgtatt     3000
ctcctggtac tgcaacctgt aaaccagcac tgcaatgctg atgcacggga agtagtggga    3060
tgggaacaca aatggaggat cccgcgtctc gaacagagcg cgcagaggaa cgctgaaggt    3120
ctcgcctctg tcgcacctca gcgcggcata caccacaata accacctgac gaatgcgctt    3180
ggttcttcgt ccattagcga agcgtccggt tcacacacgt gccacgttgg cgaggtggca    3240
ggtgacaatg atcggtggag ctgatggtcg aaacgttcac agcctaggga tatcgaattc    3300
cttttcttgcg ctatgacact tccagcaaaa ggtagggcgg gctgcagac ggcttcccgg     3360
cgctgcatgc aacaccgatg atgcttcgac cccccgaagc tccttcgggg ctgcatgggc    3420
gctccgatgc cgctccaggg cgagcgctgt ttaaatagcc aggcccccga ttgcaaagac    3480
attatagcga gctaccaaag ccatattcaa acacctagat cactaccact tctacacagg    3540
ccactcgagc ttgtgatcgc actccgctaa ggggcgcct cttcctcttc gtttcagtca     3600
caacccgcaa acactagtat ggccaccgca tccactttct cggcgttcaa tgcccgctgc    3660
ggcgacctgc gtcgctcggc gggctccggg ccccggcgcc cagcgaggcc cctccccgtg    3720
```

```
cgcgggcgcg cccagctgcc cgactggagc atgctgctgg ccgcgatcac caccctgttc    3780
ctggcggccg agaagcagtg gatgatgctg gactggaagc caagcgccc cgacatgctg     3840
gtggacccct tcggcctggg ccgcttcgtg caggacggcc tggtgttccg caacaacttc    3900
agcatccgca gctacgagat cggcgcggac cgcaccgcca gcatcgagac cctgatgaac    3960
cacctgcagg agaccgccct gaaccacgtg aagagcgtgg gcctgctgga ggacggcctg    4020
ggcagcaccc gcgagatgag cctgcgcaac ctgatctggg tggtgaccaa gatgcaggtg    4080
gcggtggacc gctaccccac ctggggcgac gaggtgcagg tgagcagctg ggcgaccgcc    4140
atcggcaaga acggcatgcg ccgcgagtgg atcgtgaccg acttccgcac cggcgagacc    4200
ctgctgcgcg ccaccagcgt gtgggtgatg atgaacaagc tgacccgccg catcagcaag    4260
atccccgagg aggtgtggca cgagatcggc cccagcttca tcgacgcgcc cccctgccc    4320
accgtggagg acgacggccg caagctgacc cgcttcgacg agagcagcgc cgacttcatc    4380
cgcaagggcc tgaccccccg ctggagcgac ctggacatca accagcacgt gaacaacgtg    4440
aagtacatcg gctggctgct ggagagcgcg ccccccgaga tccacgagag ccacgagatc    4500
gccagcctga ccctggagta ccgccgcgag tgcggccgcg acagcgtgct gaacagcgcc    4560
accaaggtga gcgacagcag ccagctgggc aagagcgccg tggagtgcaa ccacctggtg    4620
cgcctgcaga acggcggcga gatcgtgaag ggccgcaccg tgtggcgccc caagcgcccc    4680
ctgtacaacg acggcgccgt ggtggacgtg cccgccaaga ccagcgatga cgatgacaag    4740
ctgggatgac tcgagttaat taactcgagg cagcagcagc tcggatagta tcgacacact    4800
ctggacgctg tcgtgtgat ggactgttgc cgccacactt gctgccttga cctgtgaata    4860
tccctgccgc tttttatcaaa cagcctcagt gtgtttgatc ttgtgtgtac gcgcttttgc    4920
gagttgctag ctgcttgtgc tatttgcgaa taccaccccc agcatcccct tccctcgttt    4980
catatcgctt gcatcccaac cgcaacttat ctacgctgtc ctgctatccc tcagcgctgc    5040
tcctgctcct gctcactgcc cctgcacag ccttggtttg gctccgcct gtattctcct     5100
ggtactgcaa cctgtaaacc agcactgcaa tgctgatgca cgggaagtag tgggatggga    5160
acacaaatgg aaagctgtag agctccttgt tttccagaag gagttgctcc ttgagccttt    5220
cattctcagc ctcgataacc tccaaagccg ctctaattgt ggagggggtt cgaatttaaa    5280
agcttggaat gttggttcgt gcgtctggaa caagcccaga cttgttgctc actgggaaaa    5340
ggaccatcag ctccaaaaaa cttgccgctc aaaccgcgta cctctgcttt cgcgcaatct    5400
gccctgttga atcgccacc acattcatat tgtgacgctt gagcagtctg taattgcctc    5460
agaatgtgga atcatctgcc ccctgtgcga gcccatgcca ggcatgtcgc gggcgaggac    5520
acccgccact cgtacagcag accattatgc tacctcacaa tagttcataa cagtgaccat    5580
atttctcgaa gctccccaac gagcacctcc atgctctgag tggccacccc ccggccctgg    5640
tgcttgcgga gggcaggtca accggcatgg ggctaccgaa atccccgacc ggatcccacc    5700
accccgcgca tgggaagaat ctctccccgg gatgtgggcc caccaccagc acaacctgct    5760
ggcccaggcg agcgtcaaac cataccacac aaatatcctt ggcatcggcc ctgaattcct    5820
tctgccgctc tgctacccgg tgcttctgtc gaagcaggg gttgctaggg atcgctccga    5880
gtccgcaaac ccttgtcgcg tggcggggct tgttcgagct tgttcgagct tgaagagcct    5940
ctagagtcga cctgcaggca tgcaagcttg gcgtaatcat ggtcatagct gtttcctgtg    6000
tgaaattgtt atccgctcac aattccacac aacatacgag ccggaagcat aaagtgtaaa    6060
gcctggggtg cctaatgagt gagctaactc acattaattg cgttgcgctc actgcccgct    6120
```

-continued

| | |
|---|---|
| ttccagtcgg gaaacctgtc gtgccagctg cattaatgaa tcggccaacg cgcggggaga | 6180 |
| ggcggtttgc gtattgggcg ctcttcc | 6207 |

<210> SEQ ID NO 36
<211> LENGTH: 5576
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 36

| | |
|---|---|
| gaattcgccc tcccgtgatc acacaggtgc cttgcgagcg tgatcacact attttggggg | 60 |
| tcctacagta ctgaaatggt gagaagtcgt actgaaatca aggatgaaca atgaaaatgg | 120 |
| tgctgtggtg gcttctcaaa ggtcaagaat cagtcgctcg cgtcaggaaa tcgcggcgtc | 180 |
| aaccagcgtg ggcgcggtca gtggccccgc actggtcacc atagcctctc ctgccacagt | 240 |
| agcgatcccc tgggcgttca ctctcagcag cggctgtact gcctcccaga ttttcttctt | 300 |
| ctggacctgc gggcgtgaga ggatgagcag ggtgggccaa ggctcaatc ctgaacggcc | 360 |
| ctcattcggt ttccaatccc acaacacata cccacagcag gtcagaccac gcattccacc | 420 |
| atgcgcacca ataacgtgtc cttacctgat tgggtgtggc aggctccgtg gacaggagtg | 480 |
| cctcgtcccc cgcccagacc cgctcccccg tcacggcggc gtccgggacc cgcagcggct | 540 |
| ccaccgcggt gtgatccgcg ttggcggcgc agagcagcat cccagccgat ttgaccccgc | 600 |
| gcatgctccg aggcttgagg ttggccagca ccaccaccg ccggccgaca aggtcctcca | 660 |
| gggtcacgtg ccggaccagg ccactcacga tggtgcgagg gccccctcc tcgccgaggt | 720 |
| cgatctgctc gacgtacaga ctgcgacatg cgtggcgagt ggtcatcaga aggaagcagg | 780 |
| tgtgcagaag gggcacgtgg ttggtattga gagtagccaa agctttgtgc caatcagaaa | 840 |
| gtcaacgcag ctgcctgcct ggctcgcgta caattccttt cttgcgctat gacacttcca | 900 |
| gcaaaaggta gggcgggctg cgagacggct tcccggcgct gcatgcaaca ccgatgatgc | 960 |
| ttcgaccccc cgaagctcct tcggggctgc atgggcgctc cgatgccgct ccagggcgag | 1020 |
| cgctgtttaa atagccaggc ccccgattgc aaagacatta tagcgagcta ccaaagcata | 1080 |
| ttcaaacacc tagatcacta ccacttctac acaggccact cgagcttgtg atcgcactcc | 1140 |
| gctaagggg cgcctcttcc cttcgtttca gtcacaaccc gcaaacggcg cgccatgctg | 1200 |
| ctgcaggcct tcctgttcct gctggccggc ttcgccgcca gatcagcgc ctccatgacg | 1260 |
| aacgagacgt ccgaccgccc cctggtgcac ttcaccccca caagggctg gatgaacgac | 1320 |
| cccaacggcc tgtggtacga cgagaaggac gccaagtggc acctgtactt ccagtacaac | 1380 |
| ccgaacgaca ccgtctgggg gacgcccttg ttctggggcc acgccacgtc cgacgacctg | 1440 |
| accaactggg aggaccagcc catcgccatc gccccgaagc gcaacgactc cggcgccttc | 1500 |
| tccggctcca tggtggtgga ctacaacaac acctccggct tcttcaacga caccatcgac | 1560 |
| ccgcgccagc gctgcgtggc catctggacc tacaacaccc cggagtccga ggagcagtac | 1620 |
| atctcctaca gcctggacgg cggctacacc ttcaccgagt accagaagaa ccccgtgctg | 1680 |
| gccgccaact ccacccagtt ccgcgacccg aaggtcttct ggtacgagcc ctcccagaag | 1740 |
| tggatcatga ccgcggccaa gtcccaggac tacaagatcg agatctactc ctccgacgac | 1800 |
| ctgaagtcct ggaagctgga gtccgcgttc gccaacgagg gcttcctcgg ctaccagtac | 1860 |

```
gagtgccccg gcctgatcga ggtccccacc gagcaggacc ccagcaagtc ctactgggtg    1920
atgttcatct ccatcaaccc cggcgccccg gccggcggct ccttcaacca gtacttcgtc    1980
ggcagcttca acggcaccca cttcgaggcc ttcgacaacc agtcccgcgt ggtggacttc    2040
ggcaaggact actacgccct gcagaccttc ttcaacaccg acccgaccta cgggagcgcc    2100
ctgggcatcg cgtgggcctc caactgggag tactccgcct tcgtgcccac caacccctgg    2160
cgctcctcca tgtccctcgt gcgcaagttc tccctcaaca ccgagtacca ggccaacccg    2220
gagacggagc tgatcaacct gaaggccgag ccgatcctga acatcagcaa cgccggcccc    2280
tggagccggt tcgccaccaa caccacgttg acgaaggcca acagctacaa cgtcgacctg    2340
tccaacagca ccggcaccct ggagttcgag ctggtgtacg ccgtcaacac cacccagacg    2400
atctccaagt ccgtgttcgc ggacctctcc ctctggttca agggcctgga ggaccccgag    2460
gagtacctcc gcatgggctt cgaggtgtcc gcgtcctcct tcttcctgga ccgcgggaac    2520
agcaaggtga agttcgtgaa ggagaacccc tacttcacca accgcatgag cgtgaacaac    2580
cagcccttca agagcgagaa cgacctgtcc tactacaagg tgtacggctt gctggaccag    2640
aacatcctgg agctgtactt caacgacggc gacgtcgtgt ccaccaacac ctacttcatg    2700
accaccggga acgccctggg ctccgtgaac atgacgacgg gggtggacaa cctgttctac    2760
atcgacaagt ccaggtgcg cgaggtcaag tgattaatta actcgaggca gcagcagctc    2820
ggatagtatc gacacactct ggacgctggt cgtgtgatgg actgttgccg ccacacttgc    2880
tgccttgacc tgtgaatatc cctgccgctt ttatcaaaca gcctcagtgt gtttgatctt    2940
gtgtgtacgc gcttttgcga gttgctagct gcttgtgcta tttgcgaata ccaccccag    3000 catcccctcc ctcgtttcat atcgcttgca tcccaaccgc aacttatcta cgctgtcctg    3060
ctatccctca cgctgctcc tgctcctgct cactgcccct cgcacagcct tggtttgggc    3120
tccgcctgta ttctcctggt actgcaacct gtaaaccagc actgcaatgc tgatgcacgg    3180
gaagtagtgg gatgggaaca caaatggaaa gcttgagctc cttctcttgcg ctatgacact    3240 tccagcaaaa ggtagggcgg gctgcgagac ggcttcccgg cgctgcatgc aacaccgatg    3300
atgcttcgac cccccgaagc tccttcgggg ctgcatgggc gctccgatgc cgctccaggg    3360
cgagcgctgt ttaaatagcc aggcccccga ttgcaaagac attatagcga gctaccaaag    3420
ccatattcaa acacctagat cactaccact tctacacagg ccactcgagc ttgtgatcgc    3480
actccgctaa gggggcgcct cttcctcttc gtttcagtca caacccgcaa acactagtat    3540
gacgttcggg gtcgccctcc cggccatggg ccgcggtgtc tcccttcccc ggcccagggt    3600
cgcggtgcgc gcccagtcgg cgagtcaggt tttggagagc gggcgcgccc ccgactggtc    3660
catgctgttc gccgtgatca ccaccatctt ctccgccgcc gagaagcagt ggaccaacct    3720
ggagtggaag cccaagccca accccccca gctgctggac gaccacttcg cccccacgg    3780 cctggtgttc cgccgcacct tcgccatccg cagctacgag gtgggccccg accgctccac    3840
cagcatcgtg gccgtgatga accacctgca ggaggccgcc ctgaaccacg ccaagtccgt    3900
gggcatcctg ggcgacggct tcggcaccac cctggagatg tccaagcgcg acctgatctg    3960
ggtggtgaag cgcacccacg tggccgtgga gcgctacccc gctggggcg acaccgtgga    4020 ggtggagtgc tgggtgggcg cctccggcaa caacggccgc cgccacgact tcctggtgcg    4080
cgactgcaag accggcgaga tcctgacccg ctgcacctcc ctgagcgtga tgatgaacac    4140
ccgcacccgc cgcctgagca agatccccga ggaggtgcgc ggcgagatcg ccccgccttt    4200
catcgacaac gtggccgtga aggacgagga gatcaagaag ccccagaagc tgaacgactc    4260
```

```
caccgccgac tacatccagg gcggcctgac cccccgctgg aacgacctgg acatcaacca    4320
gcacgtgaac aacatcaagt acgtggactg gatcctggag accgtgcccg acagcatctt    4380
cgagagccac cacatctcct ccttcaccat cgagtaccgc cgcgagtgca ccatggacag    4440
cgtgctgcag tccctgacca ccgtgagcgg cggctcctcc gaggccggcc tggtgtgcga    4500
gcacctgctg cagctggagg gcggcagcga ggtgctgcgc gccaagaccg agtggcgccc    4560
caagctgacc gactccttcc gcggcatcag cgtgatcccc gccgagtcca gcgtgatgga    4620
ctacaaggac cacgacggcg actacaagga ccacgacatc gactacaagg acgacgacga    4680
caagtgactc gaggcagcag cagctcggat agtatcgaca cactctggac gctggtcgtg    4740
tgatggactg ttgccgccac acttgctgcc ttgacctgtg aatatccctg ccgcttttat    4800
caaacagcct cagtgtgttt gatcttgtgt gtacgcgctt ttgcgagttg ctagctcttg    4860
tgctatttgc gaataccacc cccagcatcc ccttccctcg tttcatatcg cttgcatccc    4920
aaccgcaact tatctacgct gtcctgctat ccctcagcgc tgctcctgct cctgctcact    4980
gcccctcgca cagccttggt ttgggctccg cctgtattct cctggtactg caacctgtaa    5040
accagcactg caatgctgat gcacgggaag tagtgggatg ggaacacaaa tggaaagctg    5100
gtacccgtac ccatcagcat ccgggtgaat cttggcctcc aagatatggc caatcctcac    5160
atccagcttg gcaaaatcga ctagactgtc tgcaagtggg aatgtggagc acaaggttgc    5220
ttgtagcgat cgacagactg gtggggtaca ttgacaggtg ggcagcgccg catccatcgt    5280
gcctgacgcg agcgccgccg gttgctcgcc cgtgcctgcc gtcaaagagc ggcagagaaa    5340
tcgggaaccg aaaacgtcac attgcctgat gttgttacat gctggactag actttcttgg    5400
cgtgggtctg ctcctcgcca ggtgcgcgac gcctcggggc tgggtgcgag ggagccgtgc    5460
ggccacgcat ttgacaagac ccaaagctcg catctcagac ggtcaaccgt tcgtattata    5520
cattcaacat atggtacata cgcaaaaagc atgccaacga tgacataggc gaattc        5576
```

<210> SEQ ID NO 37
<211> LENGTH: 4674
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
ggtacccgcc tgcaacgcaa gggcagccac agccgctccc acccgccgct gaaccgacac      60
gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
cagcaagaga aggggtcaag tgcaaacacg gcatgccac agcacgggca ccggggagtg      420
gaatggcacc accaagtgtg tgcgagccag catcgccgcc tggctgtttc agctacaacg     480
gcaggagtca tccaacgtaa ccatgagctg atcaacactg caatcatcgg gcgggcgtga     540
tgcaagcatg cctggcgaag acacatggtg tgcggatgct gccggctgct gcctgctgcg     600
cacgccgttg agttggcagc aggctcagcc atgcactgga tggcagctgg gctgccactg     660
```

```
caatgtggtg ataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct tgcagaacc     840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgcccagc cagcggtgat cgctgatcc caaacgagtt     1020
cacattcatt tgcatgcctg agaagcgag gctggggcct ttgggctggt gcagcccgca    1080
atggaatgcg ggaccgccag gctagcagca aggcgcctc ccctactccg catcgatgtt    1140
ccatagtgca ttggactgca tttgggtggg gcggccggct gtttcttcg tgttgcaaaa    1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccggct ccccgccgc    1380
ctgggtggag cgcctgttcg gctacgactg ggcccagcag accatcggct gctccgacgc    1440
cgccgtgttc cgcctgtccg cccagggccg cccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
catcatggcc gacgccatgc ccgcctgca cccctggac cccgccacct gcccccttcga    1740
ccaccaggcc aagcaccgca tcgagcgcgc ccgcacccgc atggaggccg gctggtgga    1800
ccaggacgac ctggacgagg agcaccaggg cctggccccc gccgagctgt cgcccgcct    1860
gaaggcccgc atgcccgacg cgaggacct ggtggtgacc cacggcgacg cctgcctgcc    1920
caacatcatg gtggagaacg gccgcttctc cggcttcatc gactgcggcc gctgggcgt    1980
ggccgaccgc taccaggaca tcgccctggc cacccgcgac atcgccgagg agctgggcgg    2040
cgagtgggcc gaccgcttcc tggtgctgta cggcatcgcc gccccgact cccagcgcat    2100
cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg ctttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc cctcgcaca gccttggttt gggctccgcc    2460
tgtattctcc tggtactgca acctgtaaac cagcactgca atgctgatgc acggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgacccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
```

```
cagtcacaac ccgcaaacac tagtatggcc accgcatcca ctttctcggc gttcaatgcc    3120
cgctgcggcg acctgcgtcg ctcggcgggc tccgggcccc ggcgcccagc gaggcccctc    3180
cccgtgcgcg ggcgcgccca gctgcccgac tggagccgcc tgctgaccgc catcaccacc    3240
gtgttcgtga agtccaagcg ccccgacatg cacgaccgca agtccaagcg ccccgacatg    3300
ctggtggaca gcttcggcct ggagtccacc gtgcaggacg gcctggtgtt ccgccagtcc    3360
ttctccatcc gctcctacga gatcggcacc gaccgcaccg ccagcatcga gaccctgatg    3420
aaccacctgc aggagacctc cctgaaccac tgcaagagca ccggcatcct gctggacggc    3480
ttcggccgca ccctggagat gtgcaagcgc gacctgatct gggtggtgat caagatgcag    3540
atcaaggtga accgctaccc cgcctggggc gacaccgtgg agatcaacac ccgcttcagc    3600
cgcctgggca gatcggcat gggccgcgac tggctgatct ccgactgcaa caccggcgag    3660
atcctggtgc gcgccaccag cgcctacgcc atgatgaacc agaagacccg ccgcctgtcc    3720
aagctgccct acgaggtgca ccaggagatc gtgcccctgt tcgtggacag ccccgtgatc    3780
gaggactccg acctgaaggt gcacaagttc aaggtgaaga ccggcgacag catccagaag    3840
ggcctgaccc ccggctggaa cgacctggac gtgaaccagc acgtgtccaa cgtgaagtac    3900
atcggctgga tcctggagag catgcccacc gaggtgctgg agacccagga gctgtgctcc    3960
ctggccctgg agtaccgccg cgagtgcggc cgcgactccg tgctggagag cgtgaccgcc    4020
atggacccca gcaaggtggg cgtgcgctcc cagtaccagc acctgctgcg cctggaggac    4080
ggcaccgcca tcgtgaacgg cgccaccgag tggcgcccca gaacgccgg cgccaacggc    4140 gccatctcca ccggcaagac cagcaacggc aactccgtgt ccatggacta caaggaccac    4200
gacggcgact acaaggacca cgacatcgac tacaaggacg acgacgacaa gtgactcgag    4260
gcagcagcag ctcggatagt atcgacacac tctggacgct ggtcgtgtga tggactgttg    4320
ccgccacact tgctgccttg acctgtgaat atccctgccg cttttatcaa acagcctcag    4380
tgtgtttgat cttgtgtgta cgcgcttttg cgagttgcta gctgcttgtg ctatttgcga    4440
ataccacccc cagcatcccc ttccctcgtt tcatatcgct tgcatcccaa ccgcaactta    4500
tctacgctgt cctgctatcc ctcagcgctg ctcctgctcc tgctcactgc ccctcgcaca    4560
gccttggttt gggctccgcc tgtattctcc tggtactgca acctgtaaac cagcactgca    4620
atgctgatgc acgggaagta gtgggatggg aacacaaatg gaaagcttga gctc          4674
```

<210> SEQ ID NO 38
<211> LENGTH: 4656
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 38

```
ggtacccgcc tgcaacgcaa gggcagccac agccgctccc accogccgct gaaccgacac      60 gtgcttgggc gcctgccgcc tgcctgccgc atgcttgtgc tggtgaggct gggcagtgct     120
gccatgctga ttgaggcttg gttcatcggg tggaagctta tgtgtgtgct gggcttgcat     180
gccgggcaat gcgcatggtg gcaagagggc ggcagcactt gctggagctg ccgcggtgcc     240
tccaggtggt tcaatcgcgg cagccagagg gatttcagat gatcgcgcgt acaggttgag     300
cagcagtgtc agcaaaggta gcagtttgcc agaatgatcg gttcagctgt taatcaatgc     360
```

-continued

```
cagcaagaga agggtcaag tgcaaacacg gcatgccac agcacgggca ccggggagtg    420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcgggtc gcgccccagc cagcggtgat gcgctgatcc caaacgagtt    1020
cacattcatt tgcatgcctg gagaagcgag gctggggcct ttgggctggt gcagcccgca    1080
atggaatgcg ggaccgccag gctagcagca aaggcgcctc ccctactccg catcgatgtt    1140
ccatagtgca ttggactgca tttgggtggg gcggccggct gtttctttcg tgttgcaaaa    1200
cgcgccagct cagcaacctg tcccgtgggt ccccgtgcc gatgaaatcg tgtgcacgcc    1260
gatcagctga ttgcccggct cgcgaagtag gcgccctcct ttctgctcgc cctctctccg    1320
tcccgcctct agaatatcaa tgatcgagca ggacggcctc cacgccgcct cccccgccgc    1380
ctgggtggag cgcctgttcg gctacgactg ggcccagcag accatcggct gctccgacgc    1440
cgccgtgttc cgcctgtccg cccagggccg ccccgtgctg ttcgtgaaga ccgacctgtc    1500
cggcgccctg aacgagctgc aggacgaggc cgcccgcctg tcctggctgg ccaccaccgg    1560
cgtgccctgc gccgccgtgc tggacgtggt gaccgaggcc ggccgcgact ggctgctgct    1620
gggcgaggtg cccggccagg acctgctgtc ctcccacctg gcccccgccg agaaggtgtc    1680
catcatggcc gacgccatgc gccgcctgca cacctggac cccgccacct gcccttcga    1740 ccaccaggcc aagcaccgca tcgagcgcgc ccgcacccgc atggaggccg gcctggtgga    1800
ccaggacgac ctggacgagg agcaccaggg cctggccccc gccgagctgt cgcccgcct    1860 gaaggcccgc atgcccgacg gcgaggacct ggtggtgacc cacggcgacg cctgcctgcc    1920
caacatcatg gtggagaacg gccgcttctc cggcttcatc gactgcggcc gctgggcgt    1980 ggccgaccgc taccaggaca tcgccctggc cacccgcgac atcgccgagg agctgggcgg    2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt    2160
atcgacacac tctggacgct ggtcgtgtga tggactgttg ccgccacact tgctgccttg    2220
acctgtgaat atccctgccg cttttatcaa acagcctcag tgtgtttgat cttgtgtgta    2280
cgcgcttttg cgagttgcta gctgcttgtg ctatttgcga ataccacccc cagcatcccc    2340
ttccctcgtt tcatatcgct tgcatcccaa ccgcaactta tctacgctgt cctgctatcc    2400
ctcagcgctg ctcctgctcc tgctcactgc ccctcgcaca gccttggttt gggctccgcc    2460
tgtattctcc tggtactgca acctgtaaac cagcactgca atgctgatgc acggaagta    2520 gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
```

```
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggcc accgcatcca ctttctcggc gttcaatgcc    3120
cgctgcggcg acctgcgtcg ctcggcgggc tccgggcccc ggcgcccagc gaggcccctc    3180
cccgtgcgcg ggcgcgcccc cgactggtcc atgctgttcg ccgtgatcac caccatcttc    3240
agcgccgccg agaagcagtg gaccaacctg gagtggaagc ccaagcccaa gctgccccag    3300
ctgctggacg accacttcgg cctgcacggc ctggtgttcc gccgcacctt cgccatccgc    3360
tcctacgagg tgggccccga ccgcagcacc tccatcctgg ccgtgatgaa ccacatgcag    3420
gaggccaccc tgaaccacgc caagagcgtg ggcatcctgg cgacggcttc ggcaccacc    3480 ctggagatgt ccaagcgcga cctgatgtgg gtggtgcgcc gcacccacgt ggccgtggag    3540
cgctacccca cctggggcga caccgtggag gtggagtgct ggatcggcgc cagcggcaac    3600
aacggcatgc gccgcgactt cctggtgcgc gactgcaaga ccggcgagat cctgacccgc    3660
tgcacctccc tgagcgtgct gatgaacacc cgcacccgcc gcctgagcac catccccgac    3720
gaggtgcgcg gcgagatcgg ccccgccttc atcgacaacg tggccgtgaa ggacgacgag    3780
atcaagaagc tgcagaagct gaacgactcc accgccgact acatccaggg cggcctgacc    3840
ccccgctgga acgacctgga cgtgaaccag cacgtgaaca acctgaagta cgtggcctgg    3900
gtgttcgaga ccgtgcccga cagcatcttc gagtcccacc acatcagctc cttcaccctg    3960
gagtaccgcc gcgagtgcac ccgcgactcc gtgctgcgca gcctgaccac cgtgagcggc    4020
ggcagctccg aggccggcct ggtgtgcgac cacctgctgc agctggaggg cggcagcgag    4080
gtgctgcgcg cccgcaccga gtggcgcccc aagctgaccg actccttccg cggcatcagc    4140
gtgatccccg ccgagcccgc cgtgatggac tacaaggacc acgacggcga ctacaaggac    4200
cacgacatcg actacaagga cgacgacgac aagtgactcg aggcagcagc agctcggata    4260
gtatcgacac actctggacg ctggtcgtgt gatggactgt tgccgccaca cttgctgcct    4320
tgacctgtga atatccctgc cgcttttatc aaacagcctc agtgtgtttg atcttgtgtg    4380
tacgcgcttt tgcgagttgc tagctgcttg tgctatttgc gaataccacc cccagcatcc    4440
ccttccctcg tttcatatcg cttgcatccc aaccgcaact tatctacgct gtcctgctat    4500
ccctcagcgc tgctcctgct cctgctcact gccctcgca cagccttggt ttgggctccg    4560
cctgtattct cctggtactg caacctgtaa accagcactg caatgctgat gcacgggaag    4620
tagtgggatg ggaacacaaa tggaaagctt gagctc                              4656
```

<210> SEQ ID NO 39
<211> LENGTH: 4635
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39

```
ggtacccgcc tgcaacgcaa gggcagccac agccgctccc acccgccgct gaaccgacac    60
```

```
gtgcttgggc gcctgccgcc tgcctgccgc atgcttgtgc tggtgaggct gggcagtgct    120
gccatgctga ttgaggcttg gttcatcggg tggaagctta tgtgtgtgct gggcttgcat    180
gccgggcaat gcgcatggtg gcaagagggc ggcagcactt gctggagctg ccgcggtgcc    240
tccaggtggt tcaatcgcgg cagccagagg gatttcagat gatcgcgcgt acaggttgag    300
cagcagtgtc agcaaaggta gcagtttgcc agaatgatcg gttcagctgt taatcaatgc    360
cagcaagaga aggggtcaag tgcaaacacg gcatgccac agcacgggca ccggggagtg     420
gaatggcacc accaagtgtg tgcgagccag catcgccgcc tggctgtttc agctacaacg    480
gcaggagtca tccaacgtaa ccatgagctg atcaacactg caatcatcgg gcgggcgtga    540
tgcaagcatg cctggcgaag acacatggtg tgcggatgct gccggctgct gcctgctgcg    600
cacgccgttg agttggcagc aggctcagcc atgcactgga tggcagctgg gctgccactg    660
caatgtggtg gataggatgc aagtggagcg aataccaaac cctctggctg cttgctgggt    720
tgcatggcat cgcaccatca gcaggagcgc atgcgaaggg actggcccca tgcacgccat    780
gccaaaccgg agcgcaccga gtgtccacac tgtcaccagg cccgcaagct ttgcagaacc    840
atgctcatgg acgcatgtag cgctgacgtc ccttgacggc gctcctctcg ggtgtgggaa    900
acgcaatgca gcacaggcag cagaggcggc ggcagcagag cggcggcagc agcggcgggg    960
gccacccttc ttgcggggtc gcgccccagc cagcggtgat gcgctgatcc caaacgagtt   1020
cacattcatt tgcatgcctg gagaagcgag gctgggccct ttgggctggt gcagcccgca   1080
atggaatgcg ggaccgccag gctagcagca aaggcgcctc ccctactccg catcgatgtt   1140
ccatagtgca ttggactgca tttgggtggg gcggccggct gtttctttcg tgttgcaaaa   1200
cgcgccagct cagcaacctg tcccgtgggt ccccgtgcc gatgaaatcg tgtgcacgcc     1260
gatcagctga ttgcccggct cgcgaagtag gcgccctcct ttctgctcgc cctctctccg   1320
tcccgcctct agaatatcaa tgatcgagca ggacggcctc cacgccggct ccccgccgc    1380 ctgggtggag cgcctgttcg gctacgactg ggcccagcag accatcggct gctccgacgc   1440
cgccgtgttc cgcctgtccg cccagggccg ccccgtgctg ttcgtgaaga ccgacctgtc   1500
cggcgccctg aacgagctgc aggacgaggc cgcccgcctg tcctggctgg ccaccaccgg   1560
cgtgccctgc gccgccgtgc tggacgtggt gaccgaggcc ggccgcgact ggctgctgct   1620
gggcgaggtg cccggccagg acctgctgtc ctcccacctg gccccgccg agaaggtgtc    1680 catcatggcc gacgccatgc gccgcctgca caccctggac cccgccacct gccccttcga   1740
ccaccaggcc aagcaccgca tcgagcgcgc ccgcacccgc atggaggccg gcctggtgga   1800
ccaggacgac ctggacgagg agcaccaggg cctggccccc gccgagctgt cgcccgcct    1860 gaaggcccgc atgcccgacg cggaggacct ggtggtgacc cacggcgacg cctgcctgcc   1920
caacatcatg gtggagaacg gccgcttctc cggcttcatc gactgcggcc gcctgggcgt   1980
ggccgaccgc taccaggaca tcgccctggc caccccgcgac atcgccgagg agctgggcgg   2040
cgagtgggcc gaccgcttcc tggtgctgta cggcatcgcc gccccgact cccagcgcat    2100 cgccttctac cgcctgctgg acgagttctt ctgacaattg gcagcagcag ctcggatagt   2160
atcgacacac tctggacgct ggtcgtgtga tggactgttg ccgccacact tgctgccttg   2220
acctgtgaat atccctgccg ctttatcaa acagcctcag tgtgtttgat cttgtgtgta    2280
cgcgcttttg cgagttgcta gctgcttgtg ctatttgcga ataccacccc cagcatcccc   2340
ttccctcgtt tcatatcgct tgcatcccaa ccgcaactta tctacgctgt cctgctatcc   2400
ctcagcgctg ctcctgctcc tgctcactgc ccctcgcaca gccttggttt gggctccgcc   2460
```

-continued

```
tgtattctcc tggtactgca acctgtaaac cagcactgca atgctgatgc acgggaagta    2520
gtgggatggg aacacaaatg gaggatcccg cgtctcgaac agagcgcgca gaggaacgct    2580
gaaggtctcg cctctgtcgc acctcagcgc ggcatacacc acaataacca cctgacgaat    2640
gcgcttggtt cttcgtccat tagcgaagcg tccggttcac acacgtgcca cgttggcgag    2700
gtggcaggtg acaatgatcg gtggagctga tggtcgaaac gttcacagcc tagggatatc    2760
gaattccttt cttgcgctat gacacttcca gcaaaaggta gggcgggctg cgagacggct    2820
tcccggcgct gcatgcaaca ccgatgatgc ttcgaccccc cgaagctcct tcggggctgc    2880
atgggcgctc cgatgccgct ccagggcgag cgctgtttaa atagccaggc ccccgattgc    2940
aaagacatta tagcgagcta ccaaagccat attcaaacac ctagatcact accacttcta    3000
cacaggccac tcgagcttgt gatcgcactc cgctaagggg gcgcctcttc ctcttcgttt    3060
cagtcacaac ccgcaaacac tagtatggcc accgcatcca ctttctcggc gttcaatgcc    3120
cgctgcggcg acctgcgtcg ctcggcgggc tccgggcccc ggcgcccagc gaggcccctc    3180
cccgtgcgcg ggcgcgccca gctgcccgac tggagcatgc tgctggccgc gatcaccacc    3240
ctgttcctgg cggccgagaa gcagtggatg atgctggact ggaagcccaa gcgccccgac    3300
atgctggtgg accccttcgg cctgggccgc ttcgtgcagg acggcctggt gttccgcaac    3360
aacttcagca tccgcagcta cgagatcggc gcggaccgca ccgccagcat cgagaccctg    3420
atgaaccacc tgcaggagac cgccctgaac cacgtgaaga gcgtgggcct gctggaggac    3480
ggcctgggca gcaccgcgcga gatgagcctg cgcaacctga tctgggtggt gaccaagatg    3540
caggtggcgg tggaccgcta ccccacctgg ggcgacgagg tgcaggtgag cagctgggcg    3600
accgccatcg gcaagaacgg catgcgccgc gagtggatcg tgaccgactt ccgcaccggc    3660
gagaccctgc tgcgcgccac cagcgtgtgg gtgatgatga caagctgac ccgccgcatc    3720
agcaagatcc ccgaggaggt gtggcacgag atcggcccca gcttcatcga cgcgcccccc    3780
ctgcccaccg tggaggacga cggccgcaag ctgacccgct cgacgagag cagcgccgac    3840
ttcatccgca agggcctgac ccccgcgctg agcgacctgg acatcaacca gcacgtgaac    3900
aacgtgaagt acatcggctg gctgctggag agcgcgcccc ccgagatcca cgagagccac    3960
gagatcgcca gcctgacccct ggagtaccgc cgcgagtgcg gccgcgacag cgtgctgaac    4020
agcgccacca aggtgagcga cagcagccag ctgggcaaga gcgccgtgga gtgcaaccac    4080
ctggtgcgcc tgcagaacgg cggcgagatc gtgaagggcc gcaccgtgtg gcgcccccaag    4140
cgcccctgt acaacgacgg cgccgtggtg gacgtgcccg ccaagaccag cgatgacgat    4200
gacaagctgg gatgactcga ggcagcagca gctcggatag tatcgacaca ctctggacgc    4260
tggtcgtgtg atggactgtt gccgccacac ttgctgcctt gacctgtgaa tatccctgcc    4320
gctttatca aacagcctca gtgtgtttga tcttgtgtgt acgcgctttt gcgagttgct    4380
agctgcttgt gctatttgcg aataccaccc ccagcatccc cttccctcgt ttcatatcgc    4440
ttgcatccca accgcaactt atctacgctg tcctgctatc cctcagcgct gctcctgctc    4500
ctgctcactg cccctcgcac agccttggtt tgggctccgc ctgtattctc ctggtactgc    4560
aacctgtaaa ccagcactgc aatgctgatg cacgggaagt agtgggatgg aacacaaat    4620
ggaaagcttg agctc                                                    4635
```

<210> SEQ ID NO 40
<211> LENGTH: 1092
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 40

| | | | | | |
|---|---|---|---|---|---|
| gctcttcggg | tttgctcacc | cgcgaggtcg | acgcccagca | tggctatcaa | gacgaacagg | 60 |
| cagcctgtgg | agaagcctcc | gttcacgatc | gggacgctgc | gcaaggccat | ccccgcgcac | 120 |
| tgtttcgagc | gctcggcgct | tcgtagcagc | atgtacctgg | cctttgacat | cgcggtcatg | 180 |
| tccctgctct | acgtcgcgtc | gacgtacatc | gaccctgcgc | cggtgcctac | gtgggtcaag | 240 |
| tatggcgtca | tgtggccgct | ctactggttc | ttccaggtgt | gtgtgagggt | tgtggttgcc | 300 |
| cgtatcgagg | tcctggtggc | gcgcatgggg | agaaggcgc  | ctgtcccgct | gaccccccg  | 360 |
| gctaccctcc | cggcaccttc | cagggcgcct | tcggcacggg | tgtctgggtg | tgcgcgcacg | 420 |
| agtgcggcca | ccaggccttt | tcctccagcc | aggccatcaa | cgacggcgtg | ggcctggtgt | 480 |
| tccacagcct | gctgctggtg | ccctactact | cctggaagca | ctcgcaccgc | cgccaccact | 540 |
| ccaacacggg | gtgcctggac | aaggacgagg | tgtttgtgcc | gccgcaccgc | gcagtggcgc | 600 |
| acgagggcct | ggagtgggag | gagtggctgc | ccatccgcat | gggcaaggtg | ctggtcaccc | 660 |
| tgaccctggg | ctggccgctg | tacctcatgt | tcaacgtcgc | ctcgcggccg | tacccgcgct | 720 |
| tcgccaacca | ctttgacccg | tggtcgccca | tcttcagcaa | gcgcgaggta | cccttcttg  | 780 |
| cgctatgaca | cttccagcaa | aaggtagggc | gggctgcgag | acggcttccc | ggcgctgcat | 840 |
| gcaacaccga | tgatgcttcg | acccccgaa  | gctccttcgg | ggctgcatgg | gcgctccgat | 900 |
| gccgctccag | ggcgagcgct | gtttaaatag | ccaggccccc | gattgcaaag | acattatagc | 960 |
| gagctaccaa | agccatattc | aaacacctag | atcactacca | cttctacaca | ggccactcga | 1020 |
| gcttgtgatc | gcactccgct | aagggggcgc | ctcttcctct | tcgtttcagt | cacaacccgc | 1080 |
| aaacggcgcg | cc         |            |            |            |            | 1092 |

<210> SEQ ID NO 41
<211> LENGTH: 1400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41

| | | | | | |
|---|---|---|---|---|---|
| caattggcag | cagcagctcg | gatagtatcg | acacactctg | gacgctggtc | gtgtgatgga | 60 |
| ctgttgccgc | cacacttgct | gccttgacct | gtgaatatcc | ctgccgcttt | tatcaaacag | 120 |
| cctcagtgtg | tttgatcttg | tgtgtacgcg | cttttgcgag | ttgctagctg | cttgtgctat | 180 |
| ttgcgaatac | cacccccagc | atcccctttcc | ctcgtttcat | atcgcttgca | tcccaaccgc | 240 |
| aacttatcta | cgctgtcctg | ctatccctca | gcgctgctcc | tgctcctgct | cactgcccct | 300 |
| cgcacagcct | tggtttgggc | tccgcctgta | ttctcctggt | actgcaacct | gtaaaccagc | 360 |
| actgcaatgc | tgatgcacgg | gaagtagtgg | gatgggaaca | caaatggagc | atcgaggtgg | 420 |
| tcatctccga | cctcgcgttg | gtggcggtgc | tcagcgggct | cagcgtgctg | gccgcacca  | 480 |
| tgggctgggc | ctggctggtc | aagacctacg | tggtgcccta | catgatcgtg | aacatgtggc | 540 |
| tggtgctcat | cacgctgctc | cagcacacgc | acccggccct | gccgcactac | ttcgagaagg | 600 |
| actgggactg | gctacgcggc | gccatggcca | ccgtcgaccg | ctccatgggc | ccgcccttca | 660 |

```
tggacagcat cctgcaccac atctccgaca cccacgtgct gcaccacctc ttcagcacca    720
tcccgcacta ccacgccgag gaggcctccg ccgccatccg gccatcctg ggcaagtact     780 accaatccga cagccgctgg gtcggccgcg ccctgtggga ggactggcgc gactgccgct    840
acgtcgtccc cgacgcgccc gaggacgact ccgcgctctg gttccacaag tgagcgcgcc    900
tgcgcgagga cgcagaacaa cgctgccgcc gtgtcttttg cacgcgcgac tccggcgctt    960
cgctggtggc accccataa agaaaccctc aattctgttt gtggaagaca cggtgtaccc     1020
ccacccaccc acctgcacct ctattattgg tattattgac gcgggagtgg gcgttgtacc    1080
ctacaacgta gcttctctag ttttcagctg gctcccacca ttgtaaagag cctctagagt    1140
cgacctgcag gcatgcaagc ttggcgtaat catggtcata gctgtttcct gtgtgaaatt    1200
gttatccgct cacaattcca cacaacatac gagccggaag cataaagtgt aaagcctggg    1260
gtgcctaatg agtgagctaa ctcacattaa ttgcgttgcg ctcactgccc gctttccagt    1320
cgggaaacct gtcgtgccag ctgcattaat gaatcggcca acgcgcgggg agaggcggtt    1380
tgcgtattgg gcgctcttcc                                                1400
```

<210> SEQ ID NO 42
<211> LENGTH: 4091
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
gctcttcggg tttgctcacc cgcgaggtcg acgcccagca tggctatcaa gacgaacagg    60
cagcctgtgg agaagcctcc gttcacgatc gggacgctgc gcaaggccat ccccgcgcac    120
tgtttcgagc gctcggcgct tcgtagcagc atgtacctgg cctttgacat cgcggtcatg    180
tccctgctct acgtcgcgtc gacgtacatc gaccctgcgc cggtgcctac gtgggtcaag    240
tatggcgtca tgtggccgct ctactggttc ttccaggtgt gtgtgagggt gtgggttgcc    300
cgtatcgagg tcctggtggc gcgcatgggg gagaaggcgc ctgtcccgct gaccccccg    360 gctaccctcc cggcaccttc cagggcgcct tcggcacggg tgtctgggtg tgcgcgcacg    420
agtgcggcca ccaggccttt tcctccagcc aggccatcaa cgacgcgtg ggcctggtgt     480 tccacagcct gctgctggtg ccctactact cctggaagca ctcgcaccgc cgccaccact    540
ccaacacggg gtgcctggac aaggacgagg tgtttgtgcc gccgcaccgc gcagtggcgc    600
acgagggcct ggagtgggag gagtggctgc ccatccgcat gggcaaggtg ctggtcaccc    660
tgaccctggg ctggccgctg tacctcatgt tcaacgtcgc ctcgcggccg tacccgcgct    720
tcgccaacca ctttgacccg tggtcgccca tcttcagcaa gcgcgaggta ccctttcttg    780
cgctatgaca cttccagcaa aaggtagggc gggctgcgag acggcttccc ggcgctgcat    840
gcaacaccga tgatgcttcg accccccgaa gctccttcgg ggctgcatgg gcgctccgat    900
gccgctccag ggcgagcgct gttaaatag ccaggccccc gattgcaaag acattatagc     960
gagctaccaa agccatattc aaacacctag atcactacca cttctacaca ggccactcga    1020
gcttgtgatc gcactccgct aaggggcgc ctcttcctct tcgtttcagt cacaacccgc     1080
aaacggcgcg ccatgctgct gcaggccttc ctgttcctgc tggccggctt cgccgccaag    1140
atcagcgcct ccatgacgaa cgagacgtcc gaccgccccc tggtgcactt cacccccaac    1200
```

```
aagggctgga tgaacgaccc caacggcctg tggtacgacg agaaggacgc caagtggcac    1260
ctgtacttcc agtacaaccc gaacgacacc gtctggggga cgcccttgtt ctggggccac    1320
gccacgtccg acgacctgac caactgggag gaccagccca tcgccatcgc cccgaagcgc    1380
aacgactccg cgcccttctc cggctccatg gtggtggact acaacaacac ctccggcttc    1440
ttcaacgaca ccatcgaccc gcgccagcgc tgcgtggcca tctggaccta caacaccccg    1500
gagtccgagg agcagtacat ctcctacagc ctggacggcg gctacacctt caccgagtac    1560
cagaagaacc ccgtgctggc cgccaactcc acccagttcc gcgacccgaa ggtcttctgg    1620
tacgagccct cccagaagtg gatcatgacc gcggccaagt cccaggacta caagatcgag    1680
atctactcct ccgacgacct gaagtcctgg aagctggagt ccgcgttcgc caacgagggc    1740
ttcctcggct accagtacga gtgccccggc ctgatcgagg tccccaccga gcaggacccc    1800
agcaagtcct actgggtgat gttcatctcc atcaaccccg cgcccccggc cggcggctcc    1860
ttcaaccagt acttcgtcgg cagcttcaac ggcaccccact tcgaggcctt cgacaaccag    1920
tcccgcgtgg tggacttcgg caaggactac tacgccctgc agaccttctt caacaccgac    1980
ccgacctacg ggagcgccct gggcatcgcg tgggcctcca actgggagta ctccgccttc    2040
gtgcccacca cccctggcg ctcctccatg tccctcgtgc gcaagttctc cctcaacacc    2100
gagtaccagg ccaacccgga gacggagctg atcaacctga aggccgagcc gatcctgaac    2160
atcagcaacg ccggcccctg gagccggttc gccaccaaca ccacgttgac gaaggccaac    2220
agctacaacg tcgacctgtc caacagcacc ggcaccctgg agttcgagct ggtgtacgcc    2280
gtcaacacca cccagacgat ctccaagtcc gtgttcgcgg acctctcccct ctggttcaag    2340
ggcctggagg accccgagga gtacctccgc atgggcttcg aggtgtccgc gtcctccttc    2400
ttcctggacc gcgggaacag caaggtgaag ttcgtgaagg agaaccccta cttcaccaac    2460
cgcatgagcg tgaacaacca gcccttcaag agcgagaacg acctgtccta ctacaaggtg    2520
tacggcttgc tggaccagaa catcctggag ctgtacttca cgacggcga cgtcgtgtcc    2580
accaacacct acttcatgac caccgggaac gccctgggct ccgtgaacat gacgacgggg    2640
gtggacaacc tgttctacat cgacaagttc caggtgcgcg aggtcaagtg acaattggca    2700
gcagcagctc ggatagtatc gacacactct ggacgctggt cgtgtgatgg actgttgccg    2760
ccacacttgc tgccttgacc tgtgaatatc cctgccgctt ttatcaaaca gcctcagtgt    2820
gtttgatctt gtgtgtacgc gcttttgcga gttgctagct gcttgtgcta tttgcgaata    2880
ccaccccag catcccctc cctcgtttca tatcgcttgc atcccaaccg caacttatct    2940
acgctgtcct gctatccctc agcgctgctc ctgctcctgc tcactgcccc tcgcacagcc    3000
ttggtttggg ctccgcctgt attctcctgg tactgcaacc tgtaaaccag cactgcaatg    3060
ctgatgcacg ggaagtagtg ggatgggaac acaaatggag catcgaggtg gtcatctccg    3120
acctcgcgtt ggtggcggtg ctcagcgggc tcagcgtgct gggccgcacc atgggctggg    3180
cctggctggt caagacctac gtggtgccct acatgatcgt gaacatgtgg ctggtgctca    3240
tcacgctgct ccagcacacg cacccggccc tgccgcacta cttcgagaag gactgggact    3300
ggctacgcgg cgccatggcc accgtcgacc gctccatggg cccgcccttc atggacagca    3360
tcctgcacca catctccgac acccacgtgc tgcaccacct cttcagcacc atcccgcact    3420
accacgccga ggaggcctcc gccgccatcc ggcccatcct gggcaagtac taccaatccg    3480
acagccgctg ggtcggccgc gccctgtggg aggactggcg cgactgccgc tacgtcgtcc    3540
ccgacgcgcc cgaggacgac tccgcgctct ggttccacaa gtgagcgcgc ctgcgcgagg    3600
```

```
acgcagaaca acgctgccgc cgtgtctttt gcacgcgcga ctccggcgct tcgctggtgg    3660
cacccccata aagaaaccct caattctgtt tgtggaagac acggtgtacc cccacccacc    3720
cacctgcacc tctattattg gtattattga cgcgggagtg ggcgttgtac cctacaacgt    3780
agcttctcta gttttcagct ggctcccacc attgtaaaga gcctctagag tcgacctgca    3840
ggcatgcaag cttggcgtaa tcatggtcat agctgtttcc tgtgtgaaat tgttatccgc    3900
tcacaattcc acacaacata cgagccggaa gcataaagtg taaagcctgg ggtgcctaat    3960
gagtgagcta actcacatta attgcgttgc gctcactgcc cgctttccag tcgggaaacc    4020
tgtcgtgcca gctgcattaa tgaatcggcc aacgcgcggg gagaggcggt ttgcgtattg    4080
ggcgctcttc c                                                         4091
```

<210> SEQ ID NO 43
<211> LENGTH: 510
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
gctcttccgc ctggagctgg tgcagagcat gggtcagttt gcggaggaga gggtgctccc     60
cgtgctgcac cccgtggaca agctgtggca gccgcaggac ttcctgcccg accccgagtc    120
gcccgacttc gaggaccagg tggcggagct gcgcgcgcgc gccaaggacc tgcccgacga    180
gtactttgtg gtgctggtgg gcgacatgat cacggaggag gcgctgccga cctacatggc    240
catgctcaac accttggacg gtgtgcgcga cgacacgggc gcggctgacc acccgtgggc    300
gcgctggacg cggcagtggg tggccgagga gaaccggcac ggcgacctgc tgaacaagta    360
ctgttggctg acggggcgcg tcaacatgcg ggccgtggag gtgaccatca acaacctgat    420
caagagcggc atgaacccgc agacggacaa caacccttac ttgggcttcg tctacacctc    480
cttccaggag cgcgccacca agtaggtacc                                     510
```

<210> SEQ ID NO 44
<211> LENGTH: 1186
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 44

```
caattggcag cagcagctcg gatagtatcg acacactctg gacgctggtc gtgtgatgga     60
ctgttgccgc cacacttgct gccttgacct gtgaatatcc ctgccgcttt tatcaaacag    120
cctcagtgtg tttgatcttg tgtgtacgcg cttttgcgag ttgctagctg cttgtgctat    180
ttgcgaatac caccccagc atccccttcc ctcgtttcat atcgcttgca tcccaaccgc     240
aacttatcta cgctgtcctg ctatccctca gcgctgctcc tgctcctgct cactgcccct    300
cgcacagcct tggtttgggc tccgcctgta ttctcctggt actgcaacct gtaaaccagc    360
actgcaatgc tgatgcacgg gaagtagtgg gatgggaaca caaatggaag gatcgtagag    420
ctccagccac ggcaacaccg cgcgcctggc ggccagcac ggcgacaagg gcctgagcaa     480
gatctgcggg ctgatcgcca gcgacgaggg ccggcacaga atcgcctaca cgcgcatcgt    540
```

| | |
|---|---:|
| ggacgagttc ttccgcctcg accccgaggg cgccgtcgcc gcctacgcca acatgatgcg | 600 |
| caagcagatc accatgcccg cgcacctcat ggacgacatg ggccacggcg aggccaaccc | 660 |
| gggccgcaac ctcttcgccg acttctccgc cgtcgccgag aagatcgacg tctacgacgc | 720 |
| cgaggactac tgccgcatcc tggagcacct caacgcgcgc tggaaggtgg acgagcgcca | 780 |
| ggtcagcggc caggccgccg cggaccagga gtacgttctg ggcctgcccc agcgcttccg | 840 |
| gaaactcgcc gagaagaccg ccgccaagcg caagcgcgtc gcgcgcaggc ccgtcgcctt | 900 |
| ctcctggaga gaagagcctc tagagtcgac ctgcaggcat gcaagcttgg cgtaatcatg | 960 |
| gtcatagctg tttcctgtgt gaaattgtta tccgctcaca attccacaca acatacgagc | 1020 |
| cggaagcata aagtgtaaag cctggggtgc ctaatgagtg agctaactca cattaattgc | 1080 |
| gttgcgctca ctgcccgctt tccagtcggg aaacctgtcg tgccagctgc attaatgaat | 1140 |
| cggccaacgc gcggggagag gcggtttgcg tattgggcgc tcttcc | 1186 |

<210> SEQ ID NO 45
<211> LENGTH: 3615
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 45

| | |
|---|---:|
| gctcttccgc ctggagctgg tgcagagcat gggtcagttt gcggaggaga gggtgctccc | 60 |
| cgtgctgcac cccgtggaca agctgtggca gccgcaggac ttcctgcccg accccgagtc | 120 |
| gcccgacttc gaggaccagg tggcggagct gcgcgcgcgc gccaaggacc tgcccgacga | 180 |
| gtactttgtg gtgctggtgg gcgacatgat cacggaggag gcgctgccga cctacatggc | 240 |
| catgctcaac accttggacg tgtgcgcga cgacacgggc gcggctgacc acccgtgggc | 300 |
| gcgctggacg cggcagtggg tggccgagga gaaccgcac ggcgacctgc tgaacaagta | 360 |
| ctgttggctg acggggcgcg tcaacatgcg ggccgtggag gtgaccatca acaacctgat | 420 |
| caagagcgga atgaacccgc agacggacaa caacccttac ttgggcttcg tctacacctc | 480 |
| cttccaggag cgcgccacca agtaggtacc ctttcttgcg ctatgacact tccagcaaaa | 540 |
| ggtagggcgg gctgcgagac ggcttcccgg cgctgcatgc aacaccgatg atgcttcgac | 600 |
| cccccgaagc tccttcgggg ctgcatgggc gctccgatgc cgctccaggg cgagcgctgt | 660 |
| ttaaatagcc aggcccccga ttgcaaagac attatagcga gctaccaaag ccatattcaa | 720 |
| acacctagat cactaccact tctacacagg ccactcgagc ttgtgatcgc actccgctaa | 780 |
| gggggcgcct cttcctcttc gtttcagtca aacccgcaa acggcgcgcc atgctgctgc | 840 |
| aggccttcct gttcctgctg gccggcttcg ccgccaagat cagcgcctcc atgacgaacg | 900 |
| agacgtccga ccgcccctg gtgcacttca ccccaacaa gggctggatg aacgacccca | 960 |
| acggcctgtg gtacgacgag aaggacgcca agtggcacct gtacttccag tacaacccga | 1020 |
| acgacaccgt ctgggggacg cccttgttct ggggccacgc cacgtccgac gacctgacca | 1080 |
| actgggagga ccagcccatc gccatcgccc cgaagcgcaa cgactccggc gccttctccg | 1140 |
| gctccatggt ggtggactac aacaacacct ccggcttctt caacgacacc atcgacccgc | 1200 |
| gccagcgctg cgtggccatc tggacctaca acacccccga gtccgaggag cagtacatct | 1260 |
| cctacagcct ggacgcggc tacaccttca ccgagtacca gaagaacccc gtgctggccg | 1320 |
| ccaactccac ccagttccgc gacccgaagg tcttctggta cgagccctcc cagaagtgga | 1380 |

-continued

```
tcatgaccgc ggccaagtcc caggactaca agatcgagat ctactcctcc gacgacctga    1440
agtcctggaa gctggagtcc gcgttcgcca acgagggctt cctcggctac cagtacgagt    1500
gccccggcct gatcgaggtc cccaccgagc aggaccccag caagtcctac tgggtgatgt    1560
tcatctccat caaccccggc gccccggccg gcggctcctt caaccagtac ttcgtcggca    1620
gcttcaacgg caccactttc gaggccttcg acaaccagtc ccgcgtggtg gacttcggca    1680
aggactacta cgccctgcag accttcttca acaccgaccc gacctacggg agcgccctgg    1740
gcatcgcgtg ggcctccaac tgggagtact ccgccttcgt gcccaccaac ccctggcgct    1800
cctccatgtc cctcgtgcgc aagttctccc tcaacaccga gtaccaggcc aacccggaga    1860
cggagctgat caacctgaag gccgagccga tcctgaacat cagcaacgcc ggcccctgga    1920
gccggttcgc caccaacacc acgttgacga aggccaacag ctacaacgtc gacctgtcca    1980
acagcaccgg caccctggag ttcgagctgg tgtacgccgt caacaccacc cagacgatct    2040
ccaagtccgt gttcgcggac ctctccctct ggttcaaggg cctggaggac cccgaggagt    2100
acctccgcat gggcttcgag gtgtccgcgt cctccttctt cctggaccgc gggaacagca    2160
aggtgaagtt cgtgaaggag aaccccctact tcaccaaccg catgagcgtg aacaaccagc    2220
ccttcaagag cgagaacgac ctgtcctact acaaggtgta cggcttgctg gaccagaaca    2280
tcctggagct gtacttcaac gacggcgacg tcgtgtccac caacacctac ttcatgacca    2340
ccgggaacgc cctgggctcc gtgaacatga cgacggggt ggacaacctg ttctacatcg    2400
acaagttcca ggtgcgcgag gtcaagtgac aattggcagc agcagctcgg atagtatcga    2460
cacactctgg acgctggtcg tgtgatggac tgttgccgcc acacttgctg ccttgacctg    2520
tgaatatccc tgccgctttt atcaaacagc ctcagtgtgt ttgatcttgt gtgtacgcgc    2580
ttttgcgagt tgctagctgc ttgtgctatt tgcgaatacc accccccagca tccccttccc    2640 tcgtttcata tcgcttgcat cccaaccgca acttatctac gctgtcctgc tatccctcag    2700
cgctgctcct gctcctgctc actgcccctc gcacagcctt ggtttgggct ccgcctgtat    2760
tctcctggta ctgcaacctg taaaccagca ctgcaatgct gatgcacggg aagtagtggg    2820
atgggaacac aaatggaagg atcgtagagc tccagccacg gcaacaccgc gcgcctggcg    2880
gccgagcacg gcgacaaggg cctgagcaag atctgcgggc tgatcgccag cgacgagggc    2940
cggcacgaga tcgcctacac gcgcatcgtg gacgagttct tccgcctcga ccccgagggc    3000
gccgtcgccg cctacgccaa catgatgcgc aagcagatca ccatgcccgc gcacctcatg    3060
gacgacatgg gccacggcga ggccaacccg gccgcaacc tcttcgccga cttctccgcc    3120
gtcgccgaga agatcgacgt ctacgacgcc gaggactact gccgcatcct ggagcacctc    3180
aacgcgcgct ggaaggtgga cgagcgcag gtcagcggcc aggccgccgc ggaccaggag    3240
tacgttctgg gcctgcccca gcgcttccgg aaactcgccg agaagaccgc cgccaagcgc    3300
aagcgcgtcg cgcgcaggcc cgtcgccttc tcctggagag aagagcctct agagtcgacc    3360
tgcaggcatg caagcttggc gtaatcatgg tcatagctgt ttcctgtgtg aaattgttat    3420
ccgctcacaa ttccacacaa catacgagcc ggaagcataa agtgtaaagc ctggggtgcc    3480
taatgagtga gctaactcac attaattgcg ttgcgctcac tgcccgcttt ccagtcggga    3540
aacctgtcgt gccagctgca ttaatgaatc ggccaacgcg cggggagagg cggtttgcgt    3600
attgggcgct cttcc                                                     3615
```

<210> SEQ ID NO 46

<211> LENGTH: 511
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46

```
gctcttcccg cctggagctg gtgcagagca tggggcagtt tgcggaggag agggtgctcc    60
ccgtgctgca ccccgtggac aagctgtggc agccgcagga cttcctgccc gaccccgagt   120
cgcccgactt cgaggaccag gtggcggagc tgcgcgcgcg cgccaaggac ctgcccgacg   180
agtactttgt ggtgctggtg ggcgacatga tcacggagga ggcgctgccg acctacatgg   240
ccatgctcaa caccttggac ggtgtgcgcg acgacacggg cgcggctgac cacccgtggg   300
cgcgctggac gcggcagtgg gtggccgagg agaaccggca cggcgacctg ctgaacaagt   360
actgttggct gacggggcgc gtcaacatgc gggccgtgga ggtgaccatc aacaacctga   420
tcaagagcgg catgaacccg cagacggaca acaacccta cttgggcttc gtctacacct    480
ccttccagga gcgcgccacc aagtaggtac c                                  511
```

<210> SEQ ID NO 47
<211> LENGTH: 761
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 47

```
cagccacggc aacaccgcgc gccttgcggc cgagcacggc gacaagaacc tgagcaagat    60
ctgcgggctg atcgccagcg acgagggccg gcacgagatc gcctacacgc gcatcgtgga   120
cgagttcttc cgcctcgacc ccgagggcgc cgtcgccgcc tacgccaaca tgatgcgcaa   180
gcagatcacc atgcccgcgc acctcatgga cgacatgggc acggcgagg ccaacccggg    240
ccgcaacctc ttcgccgact tctccgcggt cgccgagaag atcgacgtct acgacgccga   300
ggactactgc cgcatcctgg agcacctcaa cgcgcgctgg aaggtggacg agcgccaggt   360
cagcggccag gccgccgcgg accaggagta cgtcctgggc ctgccccagc gcttccggaa   420
actcgccgag aagaccgccg ccaagcgcaa gcgcgtcgcg cgcaggcccg tcgccttctc   480
ctggagaaga gcctctagag tcgacctgca ggcatgcaag cttggcgtaa tcatggtcat   540
agctgtttcc tgtgtgaaat tgttatccgc tcacaattcc acacaacata cgagccggaa   600
gcataaagtg taaagcctgg ggtgcctaat gagtgagcta actcacatta ttgcgttgc    660
gctcactgcc cgctttccag tcgggaaacc tgtcgtgcca gctgcattaa tgaatcggcc   720
aacgcgcggg gagaggcggt ttgcgtattg ggcgctcttc c                       761
```

<210> SEQ ID NO 48
<211> LENGTH: 3599
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 48

```
gctcttcccg cctggagctg gtgcagagca tggggcagtt tgcggaggag agggtgctcc    60
```

```
ccgtgctgca ccccgtggac aagctgtggc agccgcagga cttcctgccc gaccccgagt    120
cgcccgactt cgaggaccag gtggcggagc tgcgcgcgcg cgccaaggac ctgcccgacg    180
agtactttgt ggtgctggtg ggcgacatga tcacggagga ggcgctgccg acctacatgg    240
ccatgctcaa caccttggac ggtgtgcgcg acgacacggg cgcggctgac cacccgtggg    300
cgcgctggac gcggcagtgg gtggccgagg agaaccggca cggcgacctg ctgaacaagt    360
actgttggct gacggggcgc gtcaacatgc gggccgtgga ggtgaccatc aacaacctga    420
tcaagagcgg catgaacccg cagacggaca caaccccta cttgggcttc gtctacacct    480
ccttccagga gcgcgccacc aagtaggtac cctttcttgc gctatgacac ttccagcaaa    540
aggtagggcg ggctgcgaga cggcttcccg gcgctgcatg caacaccgat gatgcttcga    600
ccccccgaag ctccttcggg gctgcatggg cgctccgatg ccgctccagg gcgagcgctg    660
tttaaatagc caggcccccg attgcaaaga cattatagcg agctaccaaa gccatattca    720
aacacctaga tcactaccac ttctacacag gccactcgag cttgtgatcg cactccgcta    780
agggggcgcc tcttcctctt cgtttcagtc acaacccgca aacggcgcgc catgctgctg    840
caggccttcc tgttcctgct ggccggcttc gccgccaaga tcagcgcctc catgacgaac    900
gagacgtccg accgccccct ggtgcacttc accccccaaca agggctggat gaacgacccc    960
aacggcctgt ggtacgacga gaaggacgcc aagtggcacc tgtacttcca gtacaacccg    1020
aacgacaccg tctgggggac gcccttgttc tggggccacg ccacgtccga cgacctgacc    1080
aactgggagg accagcccat cgccatcgcc ccgaagcgca acgactccgg cgccttctcc    1140
ggctccatgg tggtggacta caacaacacc tccggcttct tcaacgacac catcgacccg    1200
cgccagcgct gcgtggccat ctggacctac aacaccccgg agtccgagga gcagtacatc    1260
tcctacagcc tggacggcgg ctacaccttc accgagtacc agaagaaccc cgtgctggcc    1320
gccaactcca cccagttccg cgaccccgaag gtcttctggt acgagccctc ccagaagtgg    1380
atcatgaccc ggccaagtc ccaggactac aagatcgaga tctactcctc cgacgacctg    1440
aagtcctgga gctggagtc cgcgttcgcc aacgagggct tcctcggcta ccagtacgag    1500
tgccccggcc tgatcgaggt ccccaccgag caggaccca gcaagtccta ctgggtgatg    1560
ttcatctcca tcaaccccgg cgccccggcc ggcggctcct tcaaccagta cttcgtcggc    1620
agcttcaacg gcacccactt cgaggccttc gacaaccagt cccgcgtggt ggacttcggc    1680
aaggactact acgccctgca gaccttcttc aacaccgacc cgacctacgg gagcgccctg    1740
ggcatcgcgt gggcctccaa ctgggagtac tccgccttcg tgcccaccaa ccctggcgc    1800 tcctccatgt ccctcgtgcg caagttctcc ctcaacaccg agtaccaggc caacccggag    1860
acggagctga tcaacctgaa ggccgagccg atcctgaaca tcagcaacgc cggccctgg    1920 agccggttcg ccaccaacac cacgttgacg aaggccaaca gctacaacgt cgacctgtcc    1980
aacagcaccg gcaccctgga gttcgagctg gtgtacgccg tcaacaccac ccagacgatc    2040
tccaagtccg tgttcgcgga cctctccctc tggttcaagg gcctggagga ccccgaggag    2100
tacctccgca tgggcttcga ggtgtccgcg tcctccttct tcctggaccg cgggaacagc    2160
aaggtgaagt tcgtgaagga gaaccccctac ttcaccaacc gcatgagcgt gaacaaccag    2220
cccttcaaga gcgagaacga cctgtcctac tacaaggtgt acggcttgct ggaccagaac    2280
atcctggagc tgtacttcaa cgacggcgac gtcgtgtcca ccaacaccta cttcatgacc    2340
accgggaacg ccctgggctc cgtgaacatg acgacggggg tggacaacct gttctacatc    2400
```

-continued

```
gacaagttcc aggtgcgcga ggtcaagtga caattggcag cagcagctcg gatagtatcg    2460
acacactctg gacgctggtc gtgtgatgga ctgttgccgc cacacttgct gccttgacct    2520
gtgaatatcc ctgccgcttt tatcaaacag cctcagtgtg tttgatcttg tgtgtacgcg    2580
cttttgcgag ttgctagctg cttgtgctat ttgcgaatac caccccccagc atcccccttcc   2640 ctcgtttcat atcgcttgca tcccaaccgc aacttatcta cgctgtcctg ctatccctca    2700
gcgctgctcc tgctcctgct cactgcccct cgcacagcct tggtttgggc tccgcctgta    2760
ttctcctggt actgcaacct gtaaaccagc actgcaatgc tgatgcacgg aagtagtgg     2820 gatgggaaca caaatggaca gccacggcaa caccgcgcgc cttgcggccg agcacggcga    2880
caagaacctg agcaagatct gcgggctgat cgccagcgac gagggccggc acgagatcgc    2940
ctacacgcgc atcgtggacg agttcttccg cctcgacccc gagggcgccg tcgccgccta    3000
cgccaacatg atgcgcaagc agatcaccat gcccgcgcac ctcatggacg acatgggcca    3060
cggcgaggcc aacccgggcc gcaacctctt cgccgacttc tccgcggtcg ccagaaagat    3120
cgacgtctac gacgccgagg actactgccg catcctggag cacctcaacg cgcgctggaa    3180
ggtggacgag cgccaggtca gcggccaggc cgccgcggac caggagtacg tcctgggcct    3240
gccccagcgc ttccggaaac tcgccgagaa gaccgccgcc aagcgcaagc gcgtcgcgcg    3300
caggcccgtc gccttctcct ggagaagagc ctctagagtc gacctgcagg catgcaagct    3360
tggcgtaatc atggtcatag ctgtttcctg tgtgaaattg ttatccgctc acaattccac    3420
acaacatacg agccggaagc ataaagtgta aagcctgggg tgcctaatga gtgagctaac    3480
tcacattaat tgcgttgcgc tcactgcccg ctttccagtc gggaaacctg tcgtgccagc    3540
tgcattaatg aatcggccaa cgcgcgggga gaggcggttt gcgtattggg cgctcttcc     3599
```

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
tcacttcatg ccggcggtcc                                                  20

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gcgctcctgc ttggctcgaa                                                  20

<210> SEQ ID NO 51
<211> LENGTH: 733
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 51

```
gctcttcgag acgtggtctg aatcctccag gcgggtttcc ccgagaaaga aagggtgccg      60
atttcaaagc agagccatgt gccgggccct gtggcctgtg ttggcgccta tgtagtcacc     120
ccccctcacc caattgtcgc cagtttgcgc aatccataaa ctcaaaactg cagcttctga     180
gctgcgctgt tcaagaacac ctctggggtt tgctcacccg cgaggtcgac gcccagcatg     240
gctatcaaga cgaacaggca gcctgtggag aagcctccgt tcacgatcgg gacgctgcgc     300
aaggccatcc ccgcgcactg tttcgagcgc tcggcgcttc gtagcagcat gtacctggcc     360
tttgacatcg cggtcatgtc cctgctctac gtcgcgtcga cgtacatcga ccctgcgccg     420
gtgcctacgt gggtcaagta tggcgtcatg tggccgctct actggttctt ccaggtgtgt     480
gtgagggttg tggttgcccg tatcgaggtc ctggtggcgc gcatggggga aaggcgcct      540 gtcccgctga ccccccccggc taccctcccg gcaccttcca gggcgccttc ggcacgggtg     600
tctgggtgtg cgcgcacgag tgcggccacc aggccttttc ctccagccag gccatcaacg     660
acggcgtggg cctggtgttc cacagcctgc tgctggtgcc ctactactcc tggaagcact     720
cgcaccgggt acc                                                         733
```

<210> SEQ ID NO 52
<211> LENGTH: 739
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52

```
ccgccaccac tccaacacgg ggtgcctgga caaggacgag gtgtttgtgc cgccgcaccg      60
cgcagtggcg cacgagggcc tggagtggga ggagtggctg cccatccgca tgggcaaggt     120
gctggtcacc ctgaccctgg ctggccgct gtacctcatg ttcaacgtcg cctcgcggcc     180
gtacccgcgc ttcgccaacc actttgaccc gtggtcgccc atcttcagca agcgcgagcg     240
catcgaggtg gtcatctccg acctggcgct ggtggcggtg ctcagcgggc tcagcgtgct     300
gggccgcacc atgggctggg cctggctggt caagacctac gtggtgccct acctgatcgt     360
gaacatgtgg ctcgtgctca tcacgctgct ccagcacacg cacccggcgc tgccgcacta     420
cttcgagaag gactgggact ggctgcgcgg cgccatggcc accgtggacc gctccatggg     480
cccgcccttc atggacaaca tcctgcacca catctccgac acccacgtgc tgcaccacct     540
cttcagcacc atcccgcact accacgccga ggaggcctcc gccgccatca ggcccatcct     600
gggcaagtac taccagtccg acagccgctg ggtcggccgc gccctgtggg aggactggcg     660
cgactgccgc tacgtcgtcc cggacgcgcc cgaggacgac tccgcgctct ggttccacaa     720
gtgagtgagt gagaagagc                                                   739
```

<210> SEQ ID NO 53
<211> LENGTH: 2327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53

```
ctttcttgcg ctatgacact tccagcaaaa ggtagggcgg gctgcgagac ggcttcccgg      60
```

-continued

```
cgctgcatgc aacaccgatg atgcttcgac cccccgaagc tccttcgggg ctgcatgggc      120
gctccgatgc cgctccaggg cgagcgctgt ttaaatagcc aggcccccga ttgcaaagac      180
attatagcga gctaccaaag ccatattcaa acacctagat cactaccact tctacacagg      240
ccactcgagc ttgtgatcgc actccgctaa ggggcgcct cttcctcttc gtttcagtca       300
caacccgcaa acggcgcgcc atgctgctgc aggccttcct gttcctgctg gccggcttcg      360
ccgccaagat cagcgcctcc atgacgaacg agacgtccga ccgcccctg gtgcacttca       420 ccccaacaa gggctggatg aacgaccca acggcctgtg gtacgacgag aaggacgcca        480
agtggcacct gtacttccag tacaacccga cgacaccgt ctgggggacg cccttgttct       540 gggccacgc cacgtccgac gacctgacca actgggagga ccagcccatc gccatcgccc      600
cgaagcgcaa cgactccggc gccttctccg gctccatggt ggtggactac aacaacacct     660
ccggcttctt caacgacacc atcgaccgc gccagcgctg cgtggccatc tggacctaca      720
acaccccgga gtccgaggag cagtacatct cctacagcct ggacggcggc tacaccttca    780
ccgagtacca gaagaacccc gtgctggccg ccaactccac ccagttccgc gacccgaagg    840
tcttctggta cgagccctcc cagaagtgga tcatgaccgc ggccaagtcc caggactaca    900
agatcgagat ctactcctcc gacgacctga agtcctggaa gctggagtcc gcgttcgcca    960
acgagggctt cctcggctac cagtacgagt gccccggcct gatcgaggtc cccaccgagc   1020
aggaccccag caagtcctac tgggtgatgt tcatctccat caaccccggc gccccggccg   1080
gcggctcctt caaccagtac ttcgtcggca gcttcaacgg cacccacttc gaggccttcg   1140
acaaccagtc ccgcgtggtg gacttcgcca aggactacta cgccctgcag accttcttca   1200
acaccgaccc gacctacggg agcgccctgg gcatcgcgtg ggcctccaac tgggagtact   1260
ccgccttcgt gcccaccaac ccctggcgct cctccatgtc cctcgtgcgc aagttctccc   1320
tcaacaccga gtaccaggcc aacccggaga cggagctgat caacctgaag gccgagccga   1380
tcctgaacat cagcaacgcc ggcccctgga gccggttcgc caccaacacc acgttgacga   1440
aggccaacag ctacaacgtc gacctgtcca acagcaccgg cacctggag ttcgagctgg    1500 tgtacgccgt caacaccacc cagacgatct ccaagtccgt gttcgcggac ctctccctct   1560
ggttcaaggg cctggaggac cccgaggagt acctccgcat gggcttcgag gtgtccgcgt   1620
cctccttctt cctggaccgc gggaacagca aggtgaagtt cgtgaaggag aaccccctact   1680 tcaccaaccg catgagcgtg aacaaccagc ccttcaagag cgagaacgac ctgtcctact   1740
acaaggtgta cggcttgctg gaccagaaca tcctggagct gtacttcaac gacggcgacg   1800
tcgtgtccac caacacctac ttcatgacca ccgggaacgc cctgggctcc gtgaacatga   1860
cgacgggggt ggacaacctg ttctacatcg acaagttcca ggtgcgcgag tcaagtgac    1920 aattggcagc agcagctcgg atagtatcga cacactctgg acgctggtcg tgtgatggac   1980
tgttgccgcc acacttgctg ccttgacctg tgaatatccc tgccgctttt atcaaacagc   2040
ctcagtgtgt ttgatcttgt gtgtacgcgc ttttgcgagt tgctagctgc ttgtgctatt   2100
tgcgaatacc accccagca tcccccttccc tcgtttcata tcgcttgcat cccaaccgca   2160
acttatctac gctgtcctgc tatccctcag cgctgctcct gctcctgctc actgcccctc   2220
gcacagcctt ggtttgggct ccgcctgtat tctcctggta ctgcaacctg taaaccagca   2280
ctgcaatgct gatgcacggg aagtagtggg atgggaacac aaatgga                 2327
```

<210> SEQ ID NO 54
<211> LENGTH: 735

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 54
gctcttcgag gggctggtct gaatccttca ggcgggtgtt acccgagaaa gaaagggtgc      60
cgatttcaaa gcagacccat gtgccgggcc ctgtggcctg tgttggcgcc tatgtagtca     120 cccccctca cccaattgtc gccagtttgc gcactccata aactcaaaac agcagcttct      180
gagctgcgct gttcaagaac acctctgggg tttgctcacc cgcgaggtcg acgcccagca     240
tggctatcaa gacgaacagg cagcctgtgg agaagcctcc gttcacgatc gggacgctgc     300
gcaaggccat ccccgcgcac tgtttcgagc gctcggcgct tcgtagcagc atgtacctgg     360
cctttgacat cgcggtcatg tccctgctct acgtcgcgtc gacgtacatc gaccctgcac     420
cggtgcctac gtgggtcaag tacggcatca tgtggccgct ctactggttc ttccaggtgt     480
gtttgagggt tttggttgcc cgtattgagg tcctggtggc gcgcatggag gagaaggcgc     540
ctgtcccgct gacccccccg gctacccctcc cggcaccttc cagggcgcct tcggcacggg    600
tgtctgggtg tgcgcgcacg agtgcggcca ccaggccttt cctccagcc aggccatcaa      660 cgacggcgtg ggcctggtgt tccacagcct gctgctggtg ccctactact cctggaagca     720
ctcgcaccgg gtacc                                                       735

<210> SEQ ID NO 55
<211> LENGTH: 739
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 55
ccgccaccac tccaacacgg ggtgcctgga caaggacgag gtgtttgtgc cgccgcaccg      60
cgcagtggcg cacgagggcc tggagtggga ggagtggctg cccatccgca tgggcaaggt     120
gctggtcacc ctgaccctgg gctggccgct gtacctcatg ttcaacgtcg cctcgcggcc     180
gtacccgcgc ttcgccaacc actttgaccc gtggtcgccc atcttcagca gcgcgagcg     240 catcgaggtg gtcatctccg acctggcgct ggtggcggtg ctcagcgggc tcagcgtgct     300
gggccgcacc atgggctggg cctggctggt caagacctac gtggtgccct acctgatcgt     360
gaacatgtgg ctcgtgctca tcacgctgct ccagcacacg cacccggcgc tgccgcacta     420
cttcgagaag gactgggact ggctgcgcgg cgccatggcc accgtggacc gctccatggg     480
cccgcccttc atggacaaca tcctgcacca catctccgac acccacgtgc tgcaccacct     540
cttcagcacc atcccgcact accacgccga ggaggcctcc gccgccatca ggcccatcct     600
gggcaagtac taccagtccg acagccgctg ggtcggccgc gccctgtggg aggactggcg     660
cgactgccgc tacgtcgtcc cggacgcgcc cgaggacgac tccgcgctct ggttccacaa     720
gtgagtgagt gagaagagc                                                    739

<210> SEQ ID NO 56
<211> LENGTH: 726
<212> TYPE: DNA
<213> ORGANISM: Cinnamomum camphora
```

<400> SEQUENCE: 56

```
gctcttcgcc gccgccactc ctgctcgagc gcgcccgcgc gtgcgccgcc agcgccttgg      60
cctttcgcc gcgctcgtgc gcgtcgctga tgtccatcac caggtccatg aggtctgcct     120
tgcgccggct gagccactgc ttcgtccggg cggccaagag gagcatgagg gaggactcct     180
ggtccagggt cctgacgtgg tcgcggctct gggagcgggc cagcatcatc tggctctgcc     240
gcaccgaggc cgcctccaac tggtcctcca gcagccgcag tcgccgccga ccctggcaga     300
ggaagacagg tgagggggt atgaattgta cagaacaacc acgagccttg tctaggcaga     360
atccctacca gtcatggctt tacctggatg acggcctgcg aacagctgtc cagcgaccct     420
cgctgccgcc gcttctcccg cacgcttctt tccagcaccg tgatggcgcg agccagcgcc     480
gcacgctggc gctgcgcttc gccgatctga ggacagtcgg ggaactctga tcagtctaaa     540
cccccttgcg cgttagtgtt gccatccttt gcagaccggt gagagccgac ttgttgtgcg     600
ccaccccccca caccacctcc tcccagacca attctgtcac cttttggcg aaggcatcgg     660
cctcggcctg cagagaggac agcagtgccc agccgctggg ggttggcgga tgcacgctca     720
ggtacc                                                                726
```

<210> SEQ ID NO 57
<211> LENGTH: 749
<212> TYPE: DNA
<213> ORGANISM: Cinnamomum camphora

<400> SEQUENCE: 57

```
gagctccttg ttttccagaa ggagttgctc cttgagcctt tcattctcag cctcgataac      60
ctccaaagcc gctctaattg tggagggggt tcgaatttaa agcttggaa tgttggttcg     120
tgcgtctgga acaagcccag acttgttgct cactgggaaa aggaccatca gctccaaaaa     180
acttgccgct caaaccgcgt acctctgctt tcgcgcaatc tgccctgttg aaatcgccac     240
cacattcata ttgtgacgct tgagcagtct gtaattgcct cagaatgtgg aatcatctgc     300
cccctgtgcg agcccatgcc aggcatgtcg cgggcgagga caccgccac tcgtacagca     360
gaccattatg ctacctcaca atagttcata acagtgacca tatttctcga agctccccaa     420
cgagcacctc catgctctga gtggccaccc ccggccctg gtgcttgcgg agggcaggtc     480
aaccggcatg ggctaccga aatccccgac cggatcccac caccccgcg atgggaagaa     540
tctctccccg ggatgtgggc ccaccaccag cacaacctgc tggcccaggc gagcgtcaaa     600
ccataccaca caaatatcct tggcatcggc cctgaattcc ttctgccgct ctgctacccg     660
gtgcttctgt ccgaagcagg ggttgctagg gatcgctccg agtccgcaaa cccttgtcgc     720
gtggcgggc ttgttcgagc ttgaagagc                                       749
```

<210> SEQ ID NO 58
<211> LENGTH: 3635
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

```
ctttcttgcg ctatgacact tccagcaaaa ggtagggcgg gctgcgagac ggcttcccgg      60
cgctgcatgc aacaccgatg atgcttcgac cccccgaagc tccttcgggg ctgcatgggc     120
gctccgatgc cgctccaggg cgagcgctgt ttaaatagcc aggcccccga ttgcaaagac     180
```

-continued

```
attatagcga gctaccaaag ccatattcaa acacctagat cactaccact tctacacagg    240
ccactcgagc ttgtgatcgc actccgctaa gggggcgcct cttcctcttc gtttcagtca    300
caacccgcaa actctagaat atcaatgatc gagcaggacg gcctccacgc cggctccccc    360
gccgcctggg tggagcgcct gttcggctac gactgggccc agcagaccat cggctgctcc    420
gacgccgccg tgttccgcct gtccgcccag ggccgccccg tgctgttcgt gaagaccgac    480
ctgtccggcg ccctgaacga gctgcaggac gaggccgccc gctgtcctg gctgccacc     540
accggcgtgc cctgcgccgc cgtgctggac gtggtgaccg aggccggccg cgactggctg    600
ctgctgggcg aggtgcccgg ccaggacctg ctgtcctccc acctggcccc cgccgagaag    660
gtgtccatca tggccgacgc catgcgccgc ctgcacaccc tggacccccgc cacctgcccc   720
ttcgaccacc aggccaagca ccgcatcgag cgcgcccgca cccgcatgga ggccggcctg    780
gtggaccagg acgacctgga cgaggagcac cagggcctgg cccccgccga gctgttcgcc    840
cgcctgaagg cccgcatgcc cgacggcgag gacctggtgg tgacccacgg cgacgcctgc    900
ctgcccaaca tcatggtgga gaacggccgc ttctccggct tcatcgactg cggccgcctg    960
ggcgtggccg accgctacca ggacatcgcc ctggccaccc gcgacatcgc cgaggagctg   1020
ggcggcgagt gggccgaccg cttcctggtg ctgtacggca tcgccgcccc cgactcccag   1080
cgcatcgcct tctaccgcct gctggacgag ttcttctgac aattggcagc agcagctcgg   1140
atagtatcga cacactctgg acgctggtcg tgtgatggac tgttgccgcc acacttgctg   1200
ccttgacctg tgaatatccc tgccgctttt atcaaacagc ctcagtgtgt ttgatcttgt   1260
gtgtacgcgc ttttgcgagt tgctagctgc ttgtgctatt tgcgaatacc acccccagca   1320
tccccttccc tcgttttcata tcgcttgcat cccaaccgca acttatctac gctgtcctgc   1380
tatccctcag cgctgctcct gctcctgctc actgcccctc gcacagcctt ggtttgggct   1440
ccgcctgtat tctcctggta ctgcaacctg taaaccagca ctgcaatgct gatgcacggg   1500
aagtagtggg atgggaacac aaatggagga tcccgcgtct cgaacagagc gcgcagagga   1560
acgctgaagg tctcgcctct gtcgcacctc agcgcggcat acaccacaat aaccacctga   1620
cgaatgcgct tggttcttcg tccattagcg aagcgtccgg ttcacacacg tgccacgttg   1680
gcgaggtggc aggtgacaat gatcggtgga gctgatggtc gaaacgttca cagcctaggg   1740
atatcgaatt cctttcttgc gctatgacac ttccagcaaa aggtagggcg ggctgcgaga   1800
cggcttcccg gcgctgcatg caacaccgat gatgcttcga ccccccgaag ctccttcggg   1860
gctgcatggg cgctccgatg ccgctccagg gcgagcgctg tttaaatagc caggcccccg   1920
attgcaaaga cattatagcg agctaccaaa gccatattca aacacctaga tcactaccac   1980
ttctacacag gccactcgag cttgtgatcg cactccgcta agggggcgcc tcttcctctt   2040
cgtttcagtc acaacccgca aacactagta tggccaccgc atccactttc tcggcgttca   2100
atgcccgctg cggcgacctg cgtcgctcgg cgggctccgg gccccggcgc ccagcgaggc   2160
ccctccccgt gcgcgggcgc gccccgact ggtccatgct gttcgccgtg atcaccacca   2220
tcttctccgc cgccgagaag cagtggacca acctggagtg gaagcccaag cccaaccccc   2280
cccagctgct ggacgaccac ttcggccccc acggcctggt gttccgccgc accttcgcca   2340
tccgcagcta cgaggtgggc cccgaccgct ccaccagcat cgtggccgtg atgaaccacc   2400
tgcaggaggc cgccctgaac cacgccaagt ccgtgggcat cctgggcgac ggcttcggca   2460
ccaccctgga gatgtccaag cgcgacctga tctgggtggt gaagcgcacc cacgtggccg   2520
```

```
tggagcgcta ccccgcctgg ggcgacaccg tggaggtgga gtgctgggtg ggcgcctccg      2580
gcaacaacgg ccgccgccac gacttcctgg tgcgcgactg caagaccggc gagatcctga      2640
cccgctgcac ctccctgagc gtgatgatga acacccgcac ccgccgcctg agcaagatcc      2700
ccgaggaggt gcgcggcgag atcggcccg ccttcatcga acgtggcc gtgaaggacg          2760 aggagatcaa gaagcccag aagctgaacg actccaccgc cgactacatc cagggcggcc       2820
tgaccccccg ctggaacgac ctggacatca ccagcacgt gaacaacatc aagtacgtgg       2880
actggatcct ggagaccgtg cccgacagca tcttcgagag ccaccacatc tcctccttca      2940
ccatcgagta ccgccgcgag tgcaccatgg acagcgtgct gcagtccctg accaccgtga      3000
gcggcggctc ctccgaggcc ggcctggtgt gcgagcacct gctgcagctg gagggcggca      3060
gcgaggtgct gcgcgccaag accgagtggc gccccaagct gaccgactcc ttccgcggca      3120
tcagcgtgat ccccgccgag tccagcgtga tggactacaa ggaccacgac ggcgactaca      3180
aggaccacga catcgactac aaggacgacg acgacaagtg actcgaggca gcagcagctc      3240
ggatagtatc gacacactct ggacgctggt cgtgtgatgg actgttgccg ccacacttgc      3300
tgccttgacc tgtgaatatc cctgccgctt ttatcaaaca gcctcagtgt gtttgatctt      3360
gtgtgtacgc gcttttgcga gttgctagct gcttgtgcta tttgcgaata ccaccccag      3420 catccccttc cctcgtttca tatcgcttgc atcccaaccg caacttatct acgctgtcct      3480
gctatccctc agcgctgctc ctgctcctgc tcactgcccc tcgcacagcc ttggtttggg      3540
ctccgcctgt attctcctgg tactgcaacc tgtaaaccag cactgcaatg ctgatgcacg      3600
ggaagtagtg ggatgggaac acaaatggaa agctt                                 3635

<210> SEQ ID NO 59
<211> LENGTH: 2678
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59
gctcttcccg caccggctgg ctccacccca acttgaacct cgagaacccc gcgcctggcg      60
tcgaccccgt cgtgctcgtg gggccgcgga aggagcgcgc cgaagacctg gacgtcgtcc      120
tctccaactc ctttggcttt ggcgggcaca attcgtgcgt cggtacccttc tcttgcgcta     180 tgacacttcc agcaaaaggt agggcgggct gcgagacggc ttcccggcgc tgcatgcaac     240
accgatgatg cttcgacccc ccgaagctcc ttcgggctg catgggcgct ccgatgccgc      300
tccagggcga gcgctgttta aatagccagg ccccgattg caaagacatt atagcgagct      360
accaaagcca tattcaaaca cctagatcac taccacttct acacaggcca ctcgagcttg      420
tgatcgcact ccgctaaggg ggcgcctctt cctcttcgtt tcagtcacaa cccgcaaacg      480
gcgcgccatg ctgctgcagg ccttcctgtt cctgctggcc ggcttcgccg ccaagatcag      540
cgcctccatg acgaacgaga cgtccgaccg ccccctggtg cacttcaccc caacaaggg     600 ctggatgaac gaccccaacg gcctgtggta cgacgagaag gacgccaagt ggcacctgta      660
cttccagtac aacccgaacg acaccgtctg ggggacgccc ttgttctggg gccacgccac      720
gtccgacgac ctgaccaact gggaggacca gcccatcgcc atcgcccga agcgcaacga      780 ctccggcgcc ttctcggct ccatggtggt ggactacaac aacacctccg gcttcttcaa       840
cgacaccatc gacccgcgcc agcgctgcgt ggccatctgg acctacaaca ccccggagtc      900
```

```
cgaggagcag tacatctcct acagcctgga cggcggctac accttcaccg agtaccagaa    960
gaaccccgtg ctggccgcca actccaccca gttccgcgac ccgaaggtct tctggtacga   1020
gccctcccag aagtggatca tgaccgcggc caagtcccag gactacaaga tcgagatcta   1080
ctcctccgac gacctgaagt cctggaagct ggagtccgcg ttcgccaacg agggcttcct   1140
cggctaccag tacgagtgcc ccggcctgat cgaggtcccc accgagcagg accccagcaa   1200
gtcctactgg gtgatgttca tctccatcaa ccccggcgcc ccggccggcg gctccttcaa   1260
ccagtacttc gtcggcagct tcaacggcac ccacttcgag gccttcgaca accagtcccg   1320
cgtggtggac ttcggcaagg actactacgc cctgcagacc ttcttcaaca ccgacccgac   1380
ctacgggagc gccctgggca tcgcgtgggc ctccaactgg gagtactccg ccttcgtgcc   1440
caccaacccc tggcgctcct ccatgtccct cgtgcgcaag ttctccctca caccgagta    1500
ccaggccaac ccggagacgg agctgatcaa cctgaaggcc gagccgatcc tgaacatcag   1560
caacgccggc ccctggagcc ggttcgccac caacaccacg ttgacgaagg ccaacagcta   1620
caacgtcgac ctgtccaaca gcaccggcac cctggagttc gagctggtgt acgccgtcaa   1680
caccacccag acgatctcca agtccgtgtt cgcggacctc tccctctggt tcaagggcct   1740
ggaggacccc gaggagtacc tccgcatggg cttcgaggtg tccgcgtcct ccttcttcct   1800
ggaccgcggg aacagcaagg tgaagttcgt gaaggagaac ccctacttca ccaaccgcat   1860
gagcgtgaac aaccagccct tcaagagcga gaacgacctg tcctactaca aggtgtacgg   1920
cttgctggac cagaacatcc tggagctgta cttcaacgac ggcgacgtcg tgtccaccaa   1980
caccctacttc atgaccaccg ggaacgccct gggctccgtg aacatgacga cggggtggga   2040
caacctgttc tacatcgaca agttccaggt gcgcgaggtc aagtgacaat tggcagcagc   2100
agctcggata gtatcgacac actctggacg ctggtcgtgt gatggactgt tgccgccaca   2160
cttgctgcct tgacctgtga atatcccctgc cgcttttatc aaacagcctc agtgtgtttg   2220
atcttgtgtg tacgcgcttt tgcgagttgc tagctgcttg tgctatttgc gaataccacc   2280
cccagcatcc ccttccctcg tttcatatcg cttgcatccc aaccgcaact tatctacgct   2340
gtcctgctat ccctcagcgc tgctcctgct cctgctcact gccctcgca cagccttggt   2400
ttgggctccg cctgtattct cctggtactg caacctgtaa accagcactg caatgctgat   2460
gcacgggaag tagtgggatg ggaacacaaa tggaggatcg tagagctcat cttccgaaag   2520
tacgacgagt gagcgagctg attctctttg agcggggtcg ggtggttcgg ggagagtgcg   2580
cggaaaggcg cagagacgtg cggccggccg tgtccctccg tcttcccctg gttggtgcta   2640
tagtaacctg cctgtgtcgc gtgcgcgtcg ggaagagc                            2678
```

<210> SEQ ID NO 60  
<211> LENGTH: 6696  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 60

```
gctcttcacc caactcagat aataccaata cccctccttc tcctcctcat ccattcagta     60
ccccccccct tctcttccca aagcagcaag gcgtggcctt acagaagaac aatcggcttc    120
cgccaaagtc gccgagcact gcccgacggc ggcgcgccca gcagcccgct tggccacaca    180
```

```
ggcaacgaat acattcaata gggggcctcg cagaatggaa ggagcggtaa agggtacagg      240
agcactgcgc acaaggggcc tgtgcaggag tgactgactg ggcgggcaga cggcgcaccg      300
cgggcgcagg caagcaggga agattgaagc ggcagggagg aggatgctga ttgaggggg      360 catcgcagtc tctcttggac ccgggataag gaagcaaata ttcggccggt tgggttgtgt      420
gtgtgcacgt tttcttcttc agagtcgtgg gtgtgcttcc agggaggata taagcagcag      480
gatcgaatcc cgcgaccagc gtttccccat ccagccaacc accctgtcgg tacccttct      540 tgcgctatga cacttccagc aaaaggtagg gcgggctgcg agacggcttc ccggcgctgc      600
atgcaacacc gatgatgctt cgaccccccg aagctccttc ggggctgcat gggcgctccg      660
atgccgctcc agggcgagcg ctgtttaaat agccaggccc ccgattgcaa agacattata      720
gcgagctacc aaagccatat tcaaacacct agatcactac cacttctaca caggccactc      780
gagcttgtga tcgcactccg ctaaggggc gcctcttcct cttcgtttca gtcacaaccc      840
gcaaacggcg cgccatgctg ctgcaggcct tcctgttcct gctggccggc ttcgccgcca      900
agatcagcgc ctccatgacg aacgagacgt ccgaccgccc cctggtgcac ttcaccccca      960
acaagggctg gatgaacgac cccaacggcc tgtggtacga cgagaaggac gccaagtggc     1020
acctgtactt ccagtacaac ccgaacgaca ccgtctgggg gacgcccttg ttctggggcc     1080
acgccacgtc cgacgacctg accaactggg aggaccagcc catcgccatc gccccgaagc     1140
gcaacgactc cggcgccttc tccggctcca tggtggtgga ctacaacaac acctccggct     1200
tcttcaacga caccatcgac ccgcgccagc gctgcgtggc catctggacc tacaacaccc     1260
cggagtccga ggagcagtac atctcctaca gcctggacgg cggctacacc ttcaccgagt     1320
accagaagaa ccccgtgctg gccgccaact ccacccagtt ccgcgacccg aaggtcttct     1380
ggtacgagcc ctcccagaag tggatcatga ccgcggccaa gtccaggac tacaagatcg     1440 agatctactc ctccgacgac ctgaagtcct ggaagctgga gtccgcgttc gccaacgagg     1500
gcttcctcgg ctaccagtac gagtgccccg gcctgatcga ggtccccacc gagcaggacc     1560
ccagcaagtc ctactgggtg atgttcatct ccatcaaccc cggcgccccg gccggcggct     1620
ccttcaacca gtacttcgtc ggcagcttca acggcaccca cttcgaggcc ttcgacaacc     1680
agtcccgcgt ggtggacttc ggcaaggact actacgccct gcagaccttc ttcaacaccg     1740
acccgaccta cgggagcgcc ctgggcatcg cgtgggcctc caactgggag tactccgcct     1800
tcgtgcccac caaccctgg cgctcctcca tgtccctcgt gcgcaagttc tccctcaaca     1860
ccgagtacca ggcaacccg agacggagc tgatcaacct gaaggccgag ccgatcctga     1920
acatcagcaa cgccggcccc tggagccggt tcgccaccaa caccacgttg acgaaggcca     1980
acagctacaa cgtcgacctg tccaacagca ccggcacccct ggagttcgag ctggtgtacg     2040
ccgtcaacac cacccagacg atctccaagt ccgtgttcgc ggacctctcc ctctggttca     2100
agggcctgga ggaccccgag gagtacctcc gcatgggctt cgaggtgtcc gcgtcctcct     2160
tcttcctgga ccgcgggaac agcaaggtga agttcgtgaa ggagaacccc tacttccacca     2220 accgcatgag cgtgaacaac cagcccttca agagcgagaa cgacctgtcc tactacaagg     2280
tgtacggctt gctggaccag aacatcctgg agctgtactt caacgacggc gacgtcgtgt     2340
ccaccaacac ctacttcatg accaccggga acgccctggg ctccgtgaac atgacgacgg     2400
gggtggacaa cctgttctac atcgacaagt ccaggtgcg cgaggtcaag tgacaattgg     2460
cagcagcagc tcgatagta tcgacacact ctggacgctg tcgtgtgat ggactgttgc     2520 cgccacactt gctgccttga cctgtgaata tccctgccgc tttatcaaa cagcctcagt     2580
```

```
gtgtttgatc ttgtgtgtac gcgcttttgc gagttgctag ctgcttgtgc tatttgcgaa    2640 taccacccc  agcatcccct tccctcgttt catatcgctt gcatcccaac cgcaacttat    2700
ctacgctgtc ctgctatccc tcagcgctgc tcctgctcct gctcactgcc cctcgcacag    2760
ccttggtttg ggctccgcct gtattctcct ggtactgcaa cctgtaaacc agcactgcaa    2820
tgctgatgca cgggaagtag tgggatggga acacaaatgg aggatcccgc gtctcgaaca    2880
gagcgcgcag aggaacgctg aaggtctcgc ctctgtcgca cctcagcgcg catacacca    2940 caataaccac ctgacgaatg cgcttggttc ttcgtccatt agcgaagcgt ccggttcaca    3000
cacgtgccac gttggcgagg tggcaggtga caatgatcgg tggagctgat ggtcgaaacg    3060
ttcacagcct agggatatca tagcgactgc taccccccga ccatgtgccg aggcagaaat    3120
tatatacaag aagcagatcg caattaggca catcgctttg cattatccac acactattca    3180
tcgctgctgc ggcaaggctg cagagtgtat ttttgtggcc caggagctga gtccgaagtc    3240
gacgcgacga gcggcgcagg atccgacccc tagacgagct ctgtcatttt ccaagcacgc    3300
agctaaatgc gctgagaccg gtctaaatc  atccgaaaag tgtcaaaatg gccgattggg    3360
ttcgcctagg acaatgcgct gcggattcgc tcgagtccgc tgccggccaa aaggcggtgg    3420
tacaggaagg cgcacggggc caaccctgcg aagccggggg cccgaacgcc gaccgccggc    3480
cttcgatctc gggtgtcccc ctcgtcaatt tcctctctcg ggtgcagcca cgaaagtcgt    3540
gacgcaggtc acgaaatccg gttacgaaaa acgcaggtct tcgcaaaaac gtgagggttt    3600
cgcgtctcgc cctagctatt cgtatcgccg ggtcagaccc acgtgcagaa aagcccttga    3660
ataacccggg accgtggtta ccgcgccgcc tgcaccaggg ggcttatata agcccacacc    3720
acacctgtct caccacgcat ttctccaact cgcgactttt cggaagaaat tgttatccac    3780
ctagtataga ctgccacctg caggaccttg tgtcttgcag tttgtattgg tcccggccgt    3840
cgagctcgac agatctgggc tagggttggc ctggccgctc ggcactcccc tttagccgcg    3900
cgcatccgcg ttccagaggt gcgattcggt gtgtggagca ttgtcatgcg cttgtggggg    3960
tcgttccgtg cgcggcgggt ccgccatggg cgccgacctg ggcccctaggg tttgttttcg    4020 ggccaagcga gccctctca  cctcgtcgcc cccccgcatt ccctctctct tgcagccttg    4080
ccactagtat ggccaccgca tccacttttct cggcgttcaa tgcccgctgc ggcgacctgc    4140
gtcgctcggc gggctccggg ccccggcgcc cagcgaggcc cctccccgtg cgcgggcgcg    4200
ccgccgccgc cgccgacgcc aaccccgccc gccccgagcg ccgcgtggtg atcaccggcc    4260
agggcgtggt gacctcctg  ggccagacca tcgagcagtt ctactcctcc ctgctggagg    4320
gcgtgtccgg catctcccag atccagaagt tcgacaccac cggctacacc accaccatcg    4380
ccggcgagat caagtccctg cagctggacc cctacgtgcc caagcgctgg gccaagcgcg    4440
tggacgacgt gatcaagtac gtgtacatcg ccggcaagca ggccctggag tccgccggcc    4500
tgcccatcga ggccgccggc ctggccgcg  cggcctgga  ccccgccctg tgcggcgtgc    4560
tgatcggcac cgccatggcc ggcatgacct ccttcgccgc cggcgtggag gccctgaccc    4620
gcggcggcgt gcgcaagatg aacccccttct gcatcccctt ctccatctcc aacatgggcg    4680
gcgccatgct ggccatggac atcggcttca tgggccccaa ctactccatc tccaccgcct    4740
gcgccaccgg caactactgc atcctgggcg ccgccgacca catccgccgc ggcgacgcca    4800
acgtgatgct ggccggcggc gccgacgccg ccatcatccc ctccggcatc ggcggcttca    4860
tcgcctgcaa ggccctgtcc aagcgcaacg acgagcccga gcgcgcctcc cgcccctggg    4920
```

| | |
|---|---|
| acgccgaccg cgacggcttc gtgatgggcg agggcgccgg cgtgctggtg ctggaggagc | 4980 |
| tggagcacgc caagcgccgc ggcgccacca tcctggccga gctggtgggc ggcgccgcca | 5040 |
| cctccgacgc ccaccacatg accgagcccg accccaggg ccgcggcgtg cgcctgtgcc | 5100 |
| tggagcgcgc cctggagcgc gcccgcctgg ccccgagcg cgtgggctac gtgaacgccc | 5160 |
| acggcacctc caccccgcc ggcgacgtgg ccgagtaccg cgccatccgc gccgtgatcc | 5220 |
| cccaggactc cctgcgcatc aactccacca agtccatgat cggccacctg ctgggcggcg | 5280 |
| ccggcgccgt ggaggccgtg gccgccatcc aggccctgcg caccggctgg ctgcacccca | 5340 |
| acctgaacct ggagaacccc gccccggcg tggaccccgt ggtgctggtg ggcccccgca | 5400 |
| aggagcgcgc cgaggacctg gacgtggtgc tgtccaactc cttcggcttc ggcggccaca | 5460 |
| actcctgcgt gatcttccgc aagtacgacg agatggacta caaggaccac gacggcgact | 5520 |
| acaaggacca cgacatcgac tacaaggacg acgacgacaa gtgaatcgat agatctctta | 5580 |
| aggcagcagc agctcggata gtatcgacac actctggacg ctggtcgtgt gatggactgt | 5640 |
| tgccgccaca cttgctgcct tgacctgtga atatccctgc cgcttttatc aaacagcctc | 5700 |
| agtgtgtttg atcttgtgtg tacgcgcttt tgcgagttgc tagctgcttg tgctatttgc | 5760 |
| gaataccacc cccagcatcc ccttccctcg tttcatatcg cttgcatccc aaccgcaact | 5820 |
| tatctacgct gtcctgctat ccctcagcgc tgctcctgct cctgctcact gcccctcgca | 5880 |
| cagccttggt ttgggctccg cctgtattct cctggtactg caacctgtaa accagcactg | 5940 |
| caatgctgat gcacgggaag tagtgggatg ggaacacaaa tggaaagctt aattaagagc | 6000 |
| tcttgttttc cagaaggagt tgctccttga gcctttcatt ctcagcctcg ataacctcca | 6060 |
| aagccgctct aattgtggag ggggttcgaa ccgaatgctg cgtgaacggg aaggaggagg | 6120 |
| agaaagagtg agcagggagg gattcagaaa tgagaaatga gaggtgaagg aacgcatccc | 6180 |
| tatgcccttg caatggacag tgtttctggc caccgccacc aagacttcgt gtcctctgat | 6240 |
| catcatgcga ttgattacgt tgaatgcgac ggccggtcag ccccggacct ccacgcaccg | 6300 |
| gtgctcctcc aggaagatgc gcttgtcctc cgccatcttg cagggctcaa gctgctccca | 6360 |
| aaactcttgg gcgggttccg gacggacggc taccgcgggt gcggccctga ccgccactgt | 6420 |
| tcggaagcag cggcgctgca tgggcagcgg ccgctgcggt gcgccacgga ccgcatgatc | 6480 |
| caccggaaaa gcgcacgcgc tggagcgcgc agaggaccac agagaagcgg aagagacgcc | 6540 |
| agtactggca agcaggctgg tcggtgccat ggcgcgctac taccctcgct atgactcggg | 6600 |
| tcctcggccg gctggcggtg ctgacaattc gtttagtgga gcagcgactc cattcagcta | 6660 |
| ccagtcgaac tcagtggcac agtgactccg ctcttc | 6696 |

<210> SEQ ID NO 61
<211> LENGTH: 993
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

| | |
|---|---|
| gatatctccc tccgtctctg cactctggcg cccctcctcc gtctcgtgga ctgacggacg | 60 |
| agagtctggg cgccgctttt ctatccacac cgcccttcc gcatcgaaga caccacccat | 120 |
| cgtgccgcca ggtcttcccc aatcaccgc cctgtggtcc tctctcccag ccgtgtttgg | 180 |
| tcgctgcgtc cacatttttc cattcgtgcc ccacgatcct cgcccatctt ggcgccttgg | 240 |

```
ataggcaccc ttttttcagc acgccctggt gtgtagcaca acctgacctc tctctaccgc    300
atcgcctccc tcccacacct cagttgactc cctcgtcgca cgttgcaccc gcaagctccc    360
catttcatcc tattgacaat cgcacactgt acatgtatgc tcattatttt gcaaaaaaac    420 aggggtcgg ttcactcctg gcagacgacg cggtgctgcc gcgcgccgct gaggcggcgt     480
cgcgacggca acaccatcg caccgcacgt cgacgagtca acccaccctg ctcaacggtg     540
atctccccat cgcgacaccc cccgtgaccg tactatgtgc gtccatacgc aacatgaaaa    600
ggaccttggt ccccggaggc ggcgagctcg taatcccgag gttggcccg cttccgctgg     660 acacccatcg catcttccgg ctcgcccgct gtcgagcaag cgccctcgtg cgcgcaaccc    720
ttgtggtgcc tgcccgcaga gccgggcata aaggcgagca ccacacccga accagtccaa    780
tttgctttct gcattcactc accaactttt acatccacac atcgtactac cacacctgcc    840
cagtcgggtt tgatttctat tgcaaaggtg cggggggtt ggcgcactgc gtgggttgtg     900
cagccggccg ccgcggctgt acccagcgat caggtagctt gggctgtatc ttctcaagca    960
ttaccttgtc ctgggcgtag gtttgccact agt                                993
```

<210> SEQ ID NO 62
<211> LENGTH: 1083
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
gatatcgaat tcggccgaca ggacgcgcgt caaaggtgct ggtcgtgtat gccctggccg     60
gcaggtcgtt gctgctgctg gttagtgatt ccgcaaccct gattttggcg tcttattttg    120
gcgtggcaaa cgctggcgcc cgcgagccgg gccggcggcg atgcggtgcc ccacggctgc    180
cggaatccaa gggaggcaag agcgcccggg tcagttgaag ggctttacgc gcaaggtaca    240
gccgctcctg caaggctgcg tggtggaatt ggacgtgcag gtcctgctga agttcctcca    300
ccgcctcacc agcggacaaa gcaccggtgt atcaggtccg tgtcatccac tctaaagaac    360
tcgactacga cctactgatg gccctagatt cttcatcaaa aacgcctgag acacttgccc    420
aggattgaaa ctccctgaag ggaccaccag ggcccctgag ttgttccttc cccccgtggc    480
gagctgccag ccaggctgta cctgtgatcg aggctggcgg gaaataggc ttcgtgtgct     540 caggtcatgg gaggtgcagg acagctcatg aaacgccaac aatcgcacaa ttcatgtcaa    600
gctaatcagc tatttcctct tcacgagctg taattgtccc aaaattctgg tctaccgggg    660
gtgatccttc gtgtacgggc ccttccctca accctaggta tgcgcgcatg cggtcgccgc    720
gcaactcgcg cgagggccga gggtttggga cgggccgtcc cgaaatgcag ttgcacccgg    780
atgcgtggca cctttttgc gataatttat gcaatggact gctctgcaaa attctggctc     840
tgtcgccaac cctaggatca gcggcgtagg atttcgtaat cattcgtcct gatggggagc    900
taccgactac cctaatatca gcccgactgc ctgacgccag cgtccacttt tgtgcacaca    960
ttccattcgt gcccaagaca tttcattgtg gtgcgaagcg tccccagtta cgtcacctg    1020 tttcccgacc tccttactgt tctgtcgaca gagcgggccc acaggccggt cgcagccact   1080
agt                                                                 1083
```

<210> SEQ ID NO 63

<211> LENGTH: 5622
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

| | | | | | |
|---|---|---|---|---|---|
| ccctcaactg | cgacgctggg | aaccttctcc | gggcaggcga | tgtgcgtggg | tttgcctcct | 60 |
| tggcacggct | ctacaccgtc | gagtacgcca | tgaggcggtg | atggctgtgt | cggttgccac | 120 |
| ttcgtccaga | gacggcaagt | cgtccatcct | ctgcgtgtgt | ggcgcgacgc | tgcagcagtc | 180 |
| cctctgcagc | agatgagcgt | gactttggcc | atttcacgca | ctcgagtgta | cacaatccat | 240 |
| tttcttaaa | gcaaatgact | gctgattgac | cagatactgt | aacgctgatt | cgctccaga | 300 |
| tcgcacagat | agcgaccatg | ttgctgcgtc | tgaaaatctg | gattccgaat | tcgaccctgg | 360 |
| cgctccatcc | atgcaacaga | tggcgacact | tgttacaatt | cctgtcaccc | atcggcatgg | 420 |
| agcaggtcca | cttagattcc | cgatcaccca | cgcacatctc | gctaatagtc | attcgttcgt | 480 |
| gtcttcgatc | aatctcaagt | gagtgtgcat | ggatcttggt | tgacgatgcg | gtatgggttt | 540 |
| gcgccgctgg | ctgcagggtc | tgcccaaggc | aagctaaccc | agctcctctc | cccgacaata | 600 |
| ctctcgcagg | caaagccggt | cacttgcctt | ccagattgcc | aataaactca | attatggcct | 660 |
| ctgtcatgcc | atccatgggt | ctgatgaatg | gtcacgctcg | tgtcctgacc | gttccccagc | 720 |
| ctctggcgtc | ccctgccccg | cccaccagcc | cacgccgcgc | ggcagtcgct | gccaaggctg | 780 |
| tctcggaggt | accctttctt | gcgctatgac | acttccagca | aaaggtaggg | cgggctgcga | 840 |
| gacggcttcc | cggcgctgca | tgcaacaccg | atgatgcttc | gaccccccga | agctccttcg | 900 |
| gggctgcatg | ggcgctccga | tgccgctcca | gggcgagcgc | tgtttaaata | gccaggcccc | 960 |
| cgattgcaaa | gacattatag | cgagctacca | aagccatatt | caaacaccta | gatcactacc | 1020 |
| acttctacac | aggccactcg | agcttgtgat | cgcactccgc | taaggggggcg | cctcttcctc | 1080 |
| ttcgtttcag | tcacaacccg | caaactctag | aatatcaatg | atcgagcagg | acggcctcca | 1140 |
| cgccggctcc | cccgccgcct | gggtggagcc | cctgttcggc | tacgactggg | cccagcagac | 1200 |
| catcggctgc | tccgacgccg | ccgtgttccg | cctgtccgcc | cagggccgcc | ccgtgctgtt | 1260 |
| cgtgaagacc | gacctgtccg | gcgccctgaa | cgagctgcag | gacgaggccg | cccgcctgtc | 1320 |
| ctggctggcc | accaccggcg | tgccctgcgc | cgccgtgctg | gacgtggtga | ccgaggccgg | 1380 |
| ccgcgactgg | ctgctgctgg | gcgaggtgcc | cggccaggac | ctgctgtcct | cccacctggc | 1440 |
| ccccgccgag | aaggtgtcca | tcatggccga | cgccatgcgc | cgcctgcaca | ccctggaccc | 1500 |
| cgccacctgc | cccttcgacc | accaggccaa | gcaccgcatc | gagcgcgccc | gcacccgcat | 1560 |
| ggaggccggc | ctggtggacc | aggacgacct | ggacgaggag | caccagggcc | tggcccccgc | 1620 |
| cgagctgttc | gcccgcctga | aggcccgcat | gcccgacggc | gaggacctgg | tggtgacccca | 1680 |
| cggcgacgcc | tgcctgccca | acatcatggt | ggagaacggc | cgcttctccg | gcttcatcga | 1740 |
| ctgcggccgc | ctgggcgtgg | ccgaccgcta | ccaggacatc | gccctggcca | cccgcgacat | 1800 |
| cgccgaggag | ctgggcggcg | agtgggccga | ccgcttcctg | gtgctgtacg | gcatcgccgc | 1860 |
| ccccgactcc | cagcgcatcg | ccttctaccg | cctgctggac | gagttcttct | gacaattgac | 1920 |
| gcccgcgcgg | cgcacctgac | ctgttctctc | gagggcgcct | gttctgcctt | gcgaaacaag | 1980 |
| cccctggagc | atgcgtgcat | gatcgtctct | ggcgccccgc | cgcgcggttt | gtcgccctcg | 2040 |
| cgggcgccgc | ggccgcgggg | gcgcattgaa | attgttgcaa | accccacctg | acagattgag | 2100 |

```
ggcccaggca ggaaggcgtt gagatggagg tacaggagtc aagtaactga aagttttat    2160 gataactaac aacaaagggt cgtttctggc cagcgaatga caagaacaag attccacatt    2220
tccgtgtaga ggcttgccat cgaatgtgag cgggcgggcc gcggacccga caaaacccctt   2280 acgacgtggt aagaaaaacg tggcgggcac tgtccctgta gcctgaagac cagcaggaga    2340
cgatcggaag catcacagca caggatcccg cgtctcgaac agagcgcgca gaggaacgct    2400
gaaggtctcg cctctgtcgc acctcagcgc ggcatacacc acaataacca cctgacgaat    2460
gcgcttggtt cttcgtccat tagcgaagcg tccggttcac acacgtgcca cgttggcgag    2520
gtggcaggtg acaatgatcg gtggagctga tggtcgaaac gttcacagcc tagggatatc    2580
gtgaaaactc gctcgaccgc ccgcgtcccg caggcagcga tgacgtgtgc gtgacctggg    2640
tgtttcgtcg aaaggccagc aaccccaaat cgcaggcgat ccggagattg ggatctgatc    2700
cgagcttgga ccagatcccc cacgatgcgg cacgggaact gcatcgactc ggcgcggaac    2760
ccagctttcg taaatgccag attggtgtcc gataccttga tttgccatca gcgaaacaag    2820
acttcagcag cgagcgtatt tggcgggcgt gctaccaggg ttgcatacat tgcccatttc    2880
tgtctggacc gctttaccgg cgcagagggt gagttgatgg ggttggcagg catcgaaacg    2940
cgcgtgcatg gtgtgtgtgt ctgttttcgg ctgcacaatt tcaatagtcg gatgggcgac    3000
ggtagaattg ggtgttgcgc tcgcgtgcat gcctcgcccc gtcgggtgtc atgacccggga   3060 ctggaatccc ccctcgcgac cctcctgcta acgctcccga ctctcccgcc cgcgcgcagg    3120
atagactcta gttcaaccaa tcgacaacta gtaacaatgg ccaccgcatc cactttctcg    3180
gcgttcaatg cccgctgcgg cgacctgcgt cgctcggcgg gctccgggcc ccggcgccca    3240
gcgaggcccc tccccgtgcg cgggcgcgcc tcctcctccc tgtccccctc cctgaagccc    3300
aagtccatcc ccaacggcgg cttccaggtg aaggccaacg cctccgcgca ccccaaggcg    3360
aacggcagcg cggtgaccct gaagtcgggc tccctgaaca cccaggagga cacgctcagc    3420 tcgtccccccc ccccccgcgc gttcttcaac cagctgcccg actggagcat gctgctgacc    3480
gcgatcacca cggtcttcgt ggcgcccgag aagcgctgga ccatgttcga ccgcaagtcg    3540
aagcgcccca acatgctgat ggactccttc ggcctggagc gcgtggtcca ggacggcctg    3600
gtgttccgcc agagcttctc gatccgctcc tacgagatct gcgcggaccg caccgcgagc    3660
atcgagacgg tgatgaacca cgtccaggag acctcgctga accagtgcaa gtccatcggc    3720
ctgctggacg acggcttcgg ccgcagcccc gagatgtgca agcgcgacct gatctgggtg    3780
gtcacccgca tgaagatcat ggtgaaccgc taccccacgt ggggcgacac catcgaggtc    3840
tcgacgtggc tgtcccagag cggcaagatc ggcggcggcc gcgactggct gatctcggac    3900
tgcaacaccg gcgagatcct ggtgcgcgcg acgtccgtct acgcgatgat gaaccagaag    3960
acccgccgct tcagcaagct gcccccacgag gtgcgccagg agttcgcgcc ccacttcctg    4020
gactcgcccc ccgcgatcga ggacaacgac ggcaagctgc agaagttcga cgtcaagacg    4080
ggcgactcca tccgcaaggg cctgacccccc ggctggtacg acctggacgt gaaccagcac    4140
gtgagcaacg tcaagtacat cggctggatc ctggagtcga tgcccaccga ggtcctggag    4200
acgcaggagc tgtgctccct gaccctggag taccgccgcg agtgcggccg cgactcggtg    4260
ctggagagcg tcaccagcat ggacccctcg aaggtgggcg accgcttcca gtaccgccac    4320
ctgctgcgcc tggaggacgg cgcggacatc atgaagggcc gcaccgagtg cgcccccaag    4380
aacgcgggca cgaacggcgc gatctccacc ggcaagacga tggactacaa ggaccacgac    4440
```

```
ggcgactaca aggaccacga catcgactac aaggacgacg acgacaagtg attaattaac    4500
tcgaggcagc agcagctcag atagtatcga cacactctgg acgctggtcg tgtgatggac    4560
tgttgccgcc acacttgctg ccttgacctg tgaatatccc tgccgctttt atcaaacagc    4620
ctcagtgtgt ttgatcttgt gtgtacgcgc ttttgcgagt tgctagctgc ttgtgctatt    4680
tgcgaatacc accccagca tccccttccc tcgtttcata tcgcttgcat cccaaccgca    4740
acttatctac gctgtcctgc tatccctcag cgctgctcct gctcctgctc actgcccctc    4800
gcacagcctt ggtttgggct ccgcctgtat tctcctggta ctgcaacctg taaaccagca    4860
ctgcaatgct gatgcacggg aagtagtggg atgggaacac aaatggaaag cttgagctcc    4920
agcgccatgc cacgcccttt gatggcttca agtacgatta cggtgttgga ttgtgtgttt    4980
gttgcgtagt gtgcatggtt tagaataata cacttgattt cttgctcacg gcaatctcgg    5040
cttgtccgca ggttcaaccc catttcggag tctcaggtca gccgcgcaat gaccagccgc    5100
tacttcaagg acttgcacga caacgccgag gtgagctatg tttaggactt gattggaaat    5160
tgtcgtcgac gcatattcgc gctccgcgac agcacccaag caaaatgtca agtgcgttcc    5220
gatttgcgtc cgcaggtcga tgttgtgatc gtcggcgccg gatccgccgg tctgtcctgc    5280
gcttacgagc tgaccaagca ccctgacgtc cgggtacgcg agctgagatt cgattagaca    5340
taaattgaag attaaacccg tagaaaaatt tgatggtcgc gaaactgtgc tcgattgcaa    5400
gaaattgatc gtcctccact ccgcaggtcg ccatcatcga gcagggcgtt gctcccggcg    5460
gcggcgcctg gctgggggga cagctgttct cggccatgtg tgtacgtaga aggatgaatt    5520
tcagctggtt ttcgttgcac agctgtttgt gcatgatttg tttcagacta ttgttgaatg    5580 ttttttagatt tcttaggatg catgatttgt ctgcatgcga ct                      5622
```

<210> SEQ ID NO 64
<211> LENGTH: 6441
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
ccctcaactg cgacgctggg aaccttctcc gggcaggcga tgtgcgtggg tttgcctcct     60
tggcacggct ctacaccgtc gagtacgcca tgaggcggtg atggctgtgt cggttgccac    120
ttcgtccaga gacggcaagt cgtccatcct ctgcgtgtgt ggcgcgacgc tgcagcagtc    180
cctctgcagc agatgagcgt gactttggcc atttcacgca ctcgagtgta cacaatccat    240
ttttcttaaa gcaaatgact gctgattgac cagatactgt aacgctgatt tcgctccaga    300
tcgcacagat agcgaccatg ttgctgcgtc tgaaaatctg gattccgaat tcgaccctgg    360
cgctccatcc atgcaacaga tggcgacact tgttacaatt cctgtcaccc atcggcatgg    420
agcaggtcca cttagattcc cgatcaccca cgcacatctc gctaatagtc attcgttcgt    480
gtcttcgatc aatctcaagt gagtgtgcat ggatcttggt tgacgatgcg gtatgggttt    540
gcgccgctgg ctgcagggtc tgcccaaggc aagctaaccc agctcctctc cccgacaata    600
ctctcgcagg caaagccggt cacttgcctt ccagattgcc aataaactca attatggcct    660
ctgtcatgcc atccatgggt ctgatgaatg gtcacgctcg tgtcctgacc gttccccagc    720
ctctggcgtc ccctgcccg cccaccagcc cacgccgcgc ggcagtcgct gccaaggctg    780
tctcggaggt acccctttctt gcgctatgac acttccagca aaaggtaggg cgggctgcga    840
```

```
gacggcttcc cggcgctgca tgcaacaccg atgatgcttc gacccccga agctccttcg    900
gggctgcatg ggcgctccga tgccgctcca gggcgagcgc tgtttaaata gccaggcccc    960
cgattgcaaa gacattatag cgagctacca aagccatatt caaacaccta gatcactacc   1020
acttctacac aggccactcg agcttgtgat cgcactccgc taaggggcg cctcttcctc    1080
ttcgtttcag tcacaacccg caaactctag aatatcaatg ctgctgcagg ccttcctgtt   1140
cctgctggcc ggcttcgccg ccaagatcag cgcctccatg acgaacgaga cgtccgaccg   1200
cccctggtg cacttcaccc ccaacaaggg ctggatgaac gaccccaacg gcctgtggta    1260
cgacgagaag gacgccaagt ggcacctgta cttccagtac aacccgaacg acaccgtctg   1320
ggggacgccc ttgttctggg gccacgccac gtccgacgac ctgaccaact gggaggacca   1380
gcccatcgcc atcgcccga agcgcaacga ctccggcgcc ttctccggct ccatggtggt    1440
ggactacaac aacacctccg gcttcttcaa cgacaccatc gacccgcgcc agcgctgcgt   1500
ggccatctgg acctacaaca ccccggagtc cgaggagcag tacatctcct acagcctgga   1560
cggcggctac accttcaccg agtaccagaa gaaccccgtg ctggccgcca actccaccca   1620
gttccgcgac ccgaaggtct tctggtacga gccctcccag aagtggatca tgaccgcggc   1680
caagtcccag gactacaaga tcgagatcta ctcctccgac gacctgaagt cctggaagct   1740
ggagtccgcg ttcgccaacg agggcttcct cggctaccag tacgagtgcc ccggcctgat   1800
cgaggtcccc accgagcagg accccagcaa gtcctactgg gtgatgttca ctccatcaa    1860
ccccggcgcc ccgccggcg gctccttcaa ccagtacttc gtcggcagct tcaacggcac    1920
ccacttcgag gccttcgaca accagtcccg cgtggtggac ttcggcaagg actactacgc   1980
cctgcagacc ttcttcaaca ccgacccgac ctacgggagc gccctgggca tcgcgtgggc   2040
ctccaactgg gagtactccg ccttcgtgcc caccaacccc tggcgctcct ccatgtccct   2100
cgtgcgcaag ttctccctca caccgagta ccaggccaac ccggagacgg agctgatcaa    2160
cctgaaggcc gagccgatcc tgaacatcag caacgccggc ccctggagcc ggttcgccac   2220
caacaccacg ttgacgaagg ccaacagcta caacgtcgac ctgtccaaca gcaccggcac   2280
cctggagttc gagctggtgt acgccgtcaa caccaccccag acgatctcca gtccgtgtt    2340
cgcggacctc tccctctggt tcaagggcct ggaggacccc gaggagtacc tccgcatggg   2400
cttcgaggtg tccgcgtcct ccttcttcct ggaccgcggg aacagcaagg tgaagttcgt   2460
gaaggagaac ccctacttca ccaaccgcat gagcgtgaac aaccagccct caagagcga    2520
gaacgacctg tcctactaca aggtgtacgg cttgctggac cagaacatcc tggagctgta   2580
cttcaacgac ggcgacgtcg tgtccaccaa cacctacttc atgaccaccg gaacgccct    2640
gggctccgtg aacatgacga cggggtgga caacctgttc tacatcgaca agttccaggt    2700
gcgcgaggtc aagtgacaat tgacgcccgc gcggcgcacc tgacctgttc tctcgagggc   2760
gcctgttctg ccttgcgaaa caagcccctg gagcatgcgt gcatgatcgt ctctggcgcc   2820
ccgccgcgcg gtttgtcgcc ctcgcgggcg ccgcggccgc ggggcgcat tgaaattgtt    2880
gcaaacccca cctgacagat tgagggccca ggcaggaagg cgttgagatg gaggtacagg    2940
agtcaagtaa ctgaaagttt ttatgataac taacaacaaa gggtcgtttc tggccagcga   3000
atgacaagaa caagattcca catttccgtg tagaggcttg ccatcgaatg tgagcgggcg   3060
ggccgcggac ccgacaaaac ccttacgacg tggtaagaaa aacgtggcgg gcactgtccc   3120
tgtagcctga agaccagcag gagacgatcg gaagcatcac agcacaggat cccgcgtctc   3180
```

```
gaacagagcg cgcagaggaa cgctgaaggt ctcgcctctg tcgcacctca gcgcggcata    3240
caccacaata accacctgac gaatgcgctt ggttcttcgt ccattagcga agcgtccggt    3300
tcacacacgt gccacgttgg cgaggtggca ggtgacaatg atcggtggag ctgatggtcg    3360
aaacgttcac agcctaggga tatcgagtgc ggaggggccg gccgacctttt tgatgccgca    3420
accacacata cgtgttgtta tagtctagta gtacagtact gcaagcacca acttgaacct    3480
caagatggtc cgtcgaccca gctccagttt gcaacgaagg tcgggcgggt attggagatc    3540
cagatcaaag cgtaaatgcg accctctccc gaagagactt catgcgtgtg tcctgaagtg    3600
catgaaaaca ttccaggcag cgactcgtgc tccaggctgg cgttctttgc gacttgttgg    3660
cccgcttcgc agtcggacct aggggcctga ttccgcggtc gcgttgatga cacagaaacc    3720
aacgacgac ccatgtgaca ccgggggactg aatcacagct gcccccaggg gctagggcat    3780
tcgagctgat acattgataa cgctagacga agtgcactgc ggcggtaaaa agctctattt    3840
gtgccatcac agcgccttgc gtggcttcag gagcgcttga cgcgctgcat ttctgaagtc    3900
gaaagcccta gtcgccagga ggaggtcga ctcgcccgca gttcgggaac gtttggacca    3960
ctagtatggc caccgcctcc accttctccg ccttcaacgc ccgctgcggc gacctgcgcc    4020
gctccgccgg ctccggcccc cgccgccccg cccgcccccct gccgtgcgc ggccgcgcct    4080
cctccctgtc cgtgcccttc aagcccaagt ccaaccacaa cggcggcttc caggtgaagg    4140
ccaacgcctc cgcgcacccc aaggcgaacg gcagcgcggt gtcgctgaag tcgggctccc    4200
tggagaccca ggaggacaag acgagcagct cgtcccccccc cccccgcacg ttcatcaacc    4260
agctgccgt gtggagcatg ctgctgtcgg cggtgaccac ggtcttcggc gtggccgaga    4320
agcagtggcc catgctggac cgcaagtcca gcgcccccga catgctggtc gagcccctgg    4380
gcgtggaccg catcgtctac gacggcgtga gcttccgcca gtcgttctcc atccgcagct    4440
acgagatcgg cgccgaccgc accgcctcga tcgagacgct gatgaacatg ttccaggaga    4500
cctcccctgaa ccactgcaag atcatcggcc tgctgaacga cggcttcggc cgcacgcccg    4560
agatgtgcaa gcgcgacctg atctgggtcg tgaccaagat gcagatcgag gtgaaccgct    4620
accccacgtg gggcgacacc atcgaggtca acacgtgggt gagcgcctcg ggcaagcacg    4680
gcatgggccg cgactggctg atctccgact gccacaccgg cgagatcctg atccgcgcga    4740
cgagcgtctg ggcgatgatg aaccagaaga cccgccgcct gtcgaagatc ccctacgagg    4800
tgcgccagga gatcgagccc cagttcgtcg actccgcccc cgtgatcgtg gacgaccgca    4860
agttccacaa gctggacctg aagacggcg acagcatctg caacggcctg accccccgct    4920
ggacggacct ggacgtgaac cagcacgtca acaacgtgaa gtacatcggc tggatcctgc    4980
agtcggtccc caccgaggtg ttcgagacgc aggagctgtg cggcctgacc ctggagtacc    5040
gccgcgagtg cggccgcgac tccgtgctgg agagcgtcac ggccatggac ccctcgaagg    5100
agggcgaccg ctcccctgtac cagcacctgc tgcgcctgga ggacggcgcg gacatcgtga    5160
agggccgcac cgagtggcgc cccaagaacg ccggcgccaa gggcgccatc ctgacgggca    5220
agaccagcaa cggcaactcg atctccatgg actacaagga ccacgacggc gactacaagg    5280
accacgacat cgactacaag gacgacgacg acaagtgatt aattaacgcc accctgaagc    5340
ctgtgaagga cttcacggcc cagatccaga ccctggacat ccccggcgag gtcaaggccg    5400
gatactcccc catcggcttt gtgcgctgcg ccgctccgc ctgccgcatc tccaagatca    5460
actggaaggt cggcaaggag accggtgcca agaagctgga ggagcccac agcctcaagg    5520
ccaacgagat ggctgaggtc gtgtttgagc ccgtccagcc cctggtcgtc gactccttca    5580
```

```
agaactgcga gggtctgtcc cgcattgcct tcctggacgg caacaccgcc gtcatgctgg    5640
gcaaggtggt ctccacctcc gccaagtaga gagggacacc tcttcttgtc ctctctggaa    5700
aagctcgcat gtgagtgccc acacgttctg tagagctcca gcgccatgcc acgcccttttg   5760 atggcttcaa gtacgattac ggtgttggat tgtgtgtttg ttgcgtagtg tgcatggttt    5820
agaataatac acttgatttc ttgctcacgg caatctcggc ttgtccgcag gttcaacccc    5880
atttcggagt ctcaggtcag ccgcgcaatg accagccgct acttcaagga cttgcacgac    5940
aacgccgagg tgagctatgt ttaggacttg attggaaatt gtcgtcgacg catattcgcg    6000
ctccgcgaca gcacccaagc aaaatgtcaa gtgcgttccg atttgcgtcc gcaggtcgat    6060
gttgtgatcg tcggcgccgg atccgccggt ctgtcctgcg cttacgagct gaccaagcac    6120
cctgacgtcc gggtacgcga gctgagattc gattagacat aaattgaaga ttaaacccgt    6180 agaaaattt gatggtcgcg aaactgtgct cgattgcaag aaattgatcg tcctccactc     6240
cgcaggtcgc catcatcgag cagggcgttg ctcccggcgg cggcgcctgg ctgggggggac   6300 agctgttctc ggccatgtgt gtacgtagaa ggatgaattt cagctggttt tcgttgcaca    6360
gctgtttgtg catgatttgt ttcagactat tgttgaatgt ttttagattt cttaggatgc    6420
atgatttgtc tgcatgcgac t                                              6441
```

<210> SEQ ID NO 65
<211> LENGTH: 6645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

```
ccctcaactg cgacgctggg aaccttctcc gggcaggcga tgtgcgtggg tttgcctcct      60
tggcacggct ctacaccgtc gagtacgcca tgaggcggtg atggctgtgt cggttgccac     120
ttcgtccaga gacggcaagt cgtccatcct ctgcgtgtgt ggcgcgacgc tgcagcagtc     180
cctctgcagc agatgagcgt gactttggcc atttcacgca ctcgagtgta cacaatccat     240 tttcttaaa gcaaatgact gctgattgac cagatactgt aacgctgatt tcgctccaga     300
tcgcacagat agcgaccatg ttgctgcgtc tgaaaatctg gattccgaat tcgaccctgg    360
cgctccatcc atgcaacaga tggcgacact tgttacaatt cctgtcaccc atcggcatgg    420
agcaggtcca cttagattcc cgatcaccca cgcacatctc gctaatagtc attcgttcgt    480
gtcttcgatc aatctcaagt gagtgtgcat ggatcttggt tgacgatgcg gtatgggttt    540
gcgccgctgg ctgcagggtc tgcccaaggc aagctaaccc agctcctctc cccgacaata    600
ctctcgcagg caaagccggt cacttgcctt ccagattgcc aataaactca attatggcct    660
ctgtcatgcc atccatgggt ctgatgaatg gtcacgctcg tgtcctgacc gttccccagc    720
ctctggcgtc ccctgccccg cccaccagcc cacgccgcgc ggcagtcgct gccaaggctg    780
tctcggaggt acccttctt gcgctatgac acttccagca aaaggtaggg cgggctgcga    840
gacggcttcc cggcgctgca tgcaacaccg atgatgcttc gaccccccga agctccttcg     900
gggctgcatg ggcgctccga tgccgctcca gggcgagcgc tgtttaaata gccaggcccc    960
cgattgcaaa gacattatag cgagctacca aagcctatatt caaacaccta gatcactacc   1020
acttctacac aggccactcg agcttgtgat cgcactccgc taaggggggcg cctcttcctc   1080
```

```
ttcgtttcag tcacaacccg caaactctag aatatcaatg ctgctgcagg ccttcctgtt    1140
cctgctggcc ggcttcgccg ccaagatcag cgcctccatg acgaacgaga cgtccgaccg    1200
cccctggtg cacttcaccc ccaacaaggg ctggatgaac gaccccaacg gcctgtggta     1260
cgacgagaag gacgccaagt ggcacctgta cttccagtac aacccgaacg acaccgtctg    1320
ggggacgccc ttgttctggg gccacgccac gtccgacgac ctgaccaact gggaggacca    1380
gcccatcgcc atcgcccga  agcgcaacga ctccggcgcc ttctccggct ccatggtggt    1440
ggactacaac aacacctccg gcttcttcaa cgacaccatc gacccgcgcc agcgctgcgt    1500
ggccatctgg acctacaaca ccccggagtc cgaggagcag tacatctcct acagcctgga    1560
cggcggctac accttcaccg agtaccagaa gaaccccgtg ctggccgcca actccaccca    1620
gttccgcgac ccgaaggtct tctggtacga gccctcccag aagtggatca tgaccgcggc    1680
caagtcccag gactacaaga tcgagatcta ctcctccgac gacctgaagt cctggaagct    1740
ggagtccgcg ttcgccaacg agggcttcct cggctaccag tacgagtgcc ccggcctgat    1800
cgaggtcccc accgagcagg accccagcaa gtcctactgg gtgatgttca tctccatcaa    1860
ccccggcgcc ccggccggcg gctccttcaa ccagtacttc gtcggcagct tcaacggcac    1920
ccacttcgag gccttcgaca accagtcccg cgtggtggac ttcggcaagg actactacgc    1980
cctgcagacc ttcttcaaca ccgacccgac ctacgggagc gccctgggca tcgcgtgggc    2040
ctccaactgg gagtactccg ccttcgtgcc caccaacccc tggcgctcct ccatgtccct    2100
cgtgcgcaag ttctccctca acaccgagta ccaggccaac ccggagacgg agctgatcaa    2160
cctgaaggcc gagccgatcc tgaacatcag caacgccggc ccctggagcc ggttcgccac    2220
caacaccacg ttgacgaagg ccaacagcta acgtcgac ctgtccaaca gcaccggcac     2280
cctggagttc gagctggtgt acgccgtcaa caccacccag acgatctcca agtccgtgtt    2340
cgcggacctc tccctctggt tcaagggcct ggaggacccc gaggagtacc tccgcatggg    2400
cttcgaggtg tccgcgtcct ccttcttcct ggaccgcggg aacagcaagg tgaagttcgt    2460
gaaggagaac ccctacttca ccaaccgcat gagcgtgaac aaccagccct tcaagagcga    2520
gaacgacctg tcctactaca aggtgtacgg cttgctggac cagaacatcc tggagctgta    2580
cttcaacgac ggcgacgtcg tgtccaccaa cacctacttc atgaccaccg gaacgccct    2640
gggctccgtg aacatgacga cggggtgga caacctgttc tacatcgaca agttccaggt    2700
gcgcgaggtc aagtgacaat tgacgcccgc gcggcgcacc tgacctgttc tctcgagggc    2760
gcctgttctg ccttgcgaaa caagcccctg agcatgcgt gcatgatcgt ctctggcgcc    2820
ccgccgcgcg gtttgtcgcc ctcgcgggcg ccgcggccgc ggggcgcat tgaaattgtt    2880
gcaaaccccca cctgacagat tgagggccca ggcaggaagg cgttgagatg gaggtacagg    2940
agtcaagtaa ctgaaagttt ttatgataac taacaacaaa gggtcgtttc tggccagcga    3000
atgacaagaa caagattcca catttccgtg tagaggcttg ccatcgaatg tgagcgggcg    3060
ggccgcggac ccgacaaaac ccttacgacg tggtaagaaa acgtggcgg gcactgtccc     3120
tgtagcctga agaccagcag gagacgatcg gaagcatcac agcacaggat cccgcgtctc    3180
gaacagagcg cgcagaggaa cgctgaaggt ctcgcctctg tcgcacctca gcgcggcata    3240
caccacaata accacctgac gaatgcgctt ggttcttcgt ccattagcga agcgtccggt    3300
tcacacacgt gccacgttgg cgaggtggca ggtgacaatg atcggtggag ctgatggtcg    3360
aaacgttcac agcctaggga tatcctggct cgggcctcgt gctggcactc cctcccatgc    3420
cgacaacctt tctgctgtca ccacgaccca cgatgcaacg cgacacgacc cggtgggact    3480
```

-continued

```
gatcggttca ctgcacctgc atgcaattgt cacaagcgca tactccaatc gtatccgttt    3540
gatttctgtg aaaactcgct cgaccgcccg cgtcccgcag gcagcgatga cgtgtgcgtg    3600
acctgggtgt tcgtcgaaa ggccagcaac cccaaatcgc aggcgatccg gagattggga    3660
tctgatccga gcttggacca gatccccccac gatgcggcac gggaactgca tcgactcggc    3720
gcggaaccca gctttcgtaa atgccagatt ggtgtccgat accttgattt gccatcagcg    3780
aaacaagact tcagcagcga gcgtatttgg cgggcgtgct accaggggttg catacattgc    3840 ccatttctgt ctggaccgct ttaccggcgc agagggtgag ttgatgggggt tggcaggcat    3900 cgaaacgcgc gtgcatggtg tgtgtgtctg ttttcggctg cacaatttca atagtcggat    3960
gggcgacggt agaattgggt gttgcgctcg cgtgcatgcc tcgccccgtc gggtgtcatg    4020
accgggactg gaatccccccc tcgcgaccct cctgctaacg ctcccgactc tcccgcccgc    4080
gcgcaggata gactctagtt caaccaatcg acaactagta tggccaccgc ctccaccttc    4140
tccgccttca cgcccgctg cggcgacctg cgccgctccg ccggctccgg ccccgccgc    4200 cccgcccgcc cctgcccgt gcgcggccgc gcctcctccc tgtccgtgcc cttcaagccc    4260
aagtccaacc acaacggcgg cttccaggtg aaggccaacg cctccgcgca ccccaaggcg    4320
aacggcagcg cggtgtcgct gaagtcgggc tccctggaga cccaggagga caagacgagc    4380
agctcgtccc ccccccccg cacgttcatc aaccagctgc ccgtgtggag catgctgctg    4440
tcggcggtga ccacggtctt cggcgtggcc gagaagcagt ggcccatgct ggaccgcaag    4500
tccaagcgcc ccgacatgct ggtcgagccc ctgggcgtgg accgcatcgt ctacgacggc    4560
gtgagcttcc gccagtcgtt ctccatccgc agctacgaga tcggcgccga ccgcaccgcc    4620
tcgatcgaga cgctgatgaa catgttccag gagacctccc tgaaccactg caagatcatc    4680
ggcctgctga cgacggctt cggccgcacg cccgagatgt gcaagcgcga cctgatctgg    4740
gtcgtgacca agatgcagat cgaggtgaac cgctaccccca cgtggggcga caccatcgag    4800
gtcaacacgt gggtgagcgc ctcgggcaag cacggcatgg ccgcgactg gctgatctcc    4860 gactgccaca ccggcgagat cctgatccgc gcgacgagcg tctgggcgat gatgaaccag    4920
aagacccgcc gcctgtcgaa gatcccctac gaggtgcgcc aggagatcga gccccagttc    4980
gtcgactccg cccccgtgat cgtggacgac cgcaagttcc acaagctgga cctgaagacg    5040
ggcgacagca tctgcaacgg cctgaccccc cgctggacgg acctggacgt gaaccagcac    5100
gtcaacaacg tgaagtacat cggctggatc ctgcagtcgg tccccaccga ggtgttcgag    5160
acgcaggagc tgtgcggcct gaccctggag taccgccgcg agtgcggccg cgactccgtg    5220
ctggagagcg tcacggccat ggaccccctcg aaggagggcg accgctccct gtaccagcac    5280
ctgctgcgcg tggaggacgg cgcggacatc gtgaagggcc gcaccgagtg gcgccccaag    5340
aacgccggcg ccaagggcgc catcctgacg ggcaagacca gcaacggcaa ctcgatctcc    5400
atggactaca aggaccacga cggcgactac aaggaccacg acatcgacta caaggacgac    5460
gacgacaagt gattaattaa atgcggggag tgaagggga ggaaggaggc gtggctggcg    5520
atcgggtggt cgagattgta gattcacgat agggttcgtg tgtctttgtg acgctcaatc    5580
aatcgatcga tcgatcttcc cgacgcatag tcgccgcctc ttgttgttcc cgtgaaataa    5640
atatgtaacc aataaaaaca gacactctgc atggggcata catagaccga ggagtcgtcg    5700
ctcaaacctg atcgctgccc ccagccatgt gtcaagatga tattttttccg tttcaaacac    5760 ggtcgggcac ctggccccac tctctacctc catcgcgaga cagtcgtcgg gctcgcggcg    5820
```

| | |
|---|---|
| atcgcggatc acacacaatt taatcatgtg ccactattag tattacgcgt actcaacacc | 5880 |
| cactccctag tatacacaca caactcggca accagcagat catcctgtgg tcccgagagc | 5940 |
| tccagcgcca tgccacgccc tttgatggct tcaagtacga ttacggtgtt ggattgtgtg | 6000 |
| tttgttgcgt agtgtgcatg gtttagaata atacacttga tttcttgctc acggcaatct | 6060 |
| cggcttgtcc gcaggttcaa ccccatttcg gagtctcagg tcagccgcgc aatgaccagc | 6120 |
| cgctacttca aggacttgca cgacaacgcc gaggtgagct atgtttagga cttgattgga | 6180 |
| aattgtcgtc gacgcatatt cgcgctccgc gacagcaccc aagcaaaatg tcaagtgcgt | 6240 |
| tccgatttgc gtccgcaggt cgatgttgtg atcgtcggcg ccggatccgc cggtctgtcc | 6300 |
| tgcgcttacg agctgaccaa gcaccctgac gtccgggtac gcgagctgag attcgattag | 6360 |
| acataaattg aagattaaac ccgtagaaaa atttgatggt cgcgaaactg tgctcgattg | 6420 |
| caagaaattg atcgtcctcc actccgcagg tcgccatcat cgagcagggc gttgctcccg | 6480 |
| gcggcggcgc ctggctgggg gacagctgt tctcggccat gtgtgtacgt agaaggatga | 6540 |
| atttcagctg gttttcgttg cacagctgtt tgtgcatgat ttgtttcaga ctattgttga | 6600 |
| atgttttag atttcttagg atgcatgatt tgtctgcatg cgact | 6645 |

<210> SEQ ID NO 66
<211> LENGTH: 1404
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 66

| | |
|---|---|
| atgcagaccg cgcaccagcg gcccccgacc gaggggcact gcttcggtgc gaggctgccc | 60 |
| acggcgtcga ggcgggcggt gcgccgggca tggtcccgca tcgcgcgcgc ggcggccgcg | 120 |
| gccgacgcaa accccgcccg ccctgagcgc gcgtggtca tcacgggcca gggcgtggtg | 180 |
| accagcctgg gccagacgat cgagcagttt tacagcagcc tgctggaggg cgtgagcggc | 240 |
| atctcgcaga tacagaagtt cgacaccacg ggctacacga cgacgatcgc gggcgagatc | 300 |
| aagtcgctgc agctggaccc gtacgtgccc aagcgctggg cgaagcgcgt ggacgacgtg | 360 |
| ataaagtacg tctacatcgc gggcaagcag gcgctggaga gcgccggcct gccgatcgag | 420 |
| gcggcgggc tggcgggcgc ggggctggac ccggcgctgt gcggcgtgct catcggcacc | 480 |
| gccatggcgg gcatgacgtc tttcgcggcg gcgtggagg cgctgacgcg cggcggcgtg | 540 |
| cgcaagatga ccccttttg catcccttc tccatctcca acatgggcgg cgcgatgctg | 600 |
| gcgatggaca tcggcttcat gggccccaac tactccatct ccacggcctg cgcgacgggc | 660 |
| aactactgca tcctgggcgc ggcggaccac atccggcgcg gcgacgcaaa cgtgatgctg | 720 |
| gccggcggcg cggacgcggc catcatcccc tcgggcatcg gcggcttcat cgcgtgcaag | 780 |
| gcgctgagca agcgcaacga cgagcccgag gcgcgcagcc ggcctgggga cgccgaccgc | 840 |
| gacggcttcg tcatgggcga gggcgccggc gtgctggtgc tggaggagct ggagcacgcc | 900 |
| aagcgccgcg gcgcgaccat tttggctgaa ttagttggcg gcgcggccac ctcggacgcg | 960 |
| caccacatga ccgagcccga cccgcagggc cgcggcgtgc gcctctgcct cgagcgcgcg | 1020 |
| ctcgagcgcg cgcgcctcgc gccgagcgc gtcggctacg tcaacgcgca cggcaccagc | 1080 |
| acgcccgcgg gcgacgtggc cgagtaccgc gccatccgcg ccgtcatccc gcaggactca | 1140 |
| ctacgcatca actccacaaa gtccatgatc gggcacctgc tcggcggcgc cggcgcggtc | 1200 |

```
gaggccgtgg ccgccatcca ggccctgcgc accggctggc tccacccaa cttgaacctc   1260 gagaaccccg cgcctggcgt cgaccccgtc gtgctcgtgg ggccgcggaa ggagcgcgcc   1320
gaagacctgg acgtcgtcct ctccaactcc tttggctttg gcgggcacaa ttcgtgcgtc   1380
atcttccgaa agtacgacga gtga                                         1404
```

<210> SEQ ID NO 67
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 67

```
Met Gln Thr Ala His Gln Arg Pro Pro Thr Glu Gly His Cys Phe Gly
1               5                   10                  15

Ala Arg Leu Pro Thr Ala Ser Arg Arg Ala Val Arg Arg Ala Trp Ser
            20                  25                  30

Arg Ile Ala Arg Ala Ala Ala Ala Asp Ala Asn Pro Ala Arg Pro
        35                  40                  45

Glu Arg Arg Val Val Ile Thr Gly Gln Gly Val Val Thr Ser Leu Gly
    50                  55                  60

Gln Thr Ile Glu Gln Phe Tyr Ser Ser Leu Leu Glu Gly Val Ser Gly
65                  70                  75                  80

Ile Ser Gln Ile Gln Lys Phe Asp Thr Thr Gly Tyr Thr Thr Thr Ile
                85                  90                  95

Ala Gly Glu Ile Lys Ser Leu Gln Leu Asp Pro Tyr Val Pro Lys Arg
            100                 105                 110

Trp Ala Lys Arg Val Asp Asp Val Ile Lys Tyr Val Tyr Ile Ala Gly
        115                 120                 125

Lys Gln Ala Leu Glu Ser Ala Gly Leu Pro Ile Glu Ala Ala Gly Leu
    130                 135                 140

Ala Gly Ala Gly Leu Asp Pro Ala Leu Cys Gly Val Leu Ile Gly Thr
145                 150                 155                 160

Ala Met Ala Gly Met Thr Ser Phe Ala Ala Gly Val Glu Ala Leu Thr
                165                 170                 175

Arg Gly Gly Val Arg Lys Met Asn Pro Phe Cys Ile Pro Phe Ser Ile
            180                 185                 190

Ser Asn Met Gly Gly Ala Met Leu Ala Met Asp Ile Gly Phe Met Gly
        195                 200                 205

Pro Asn Tyr Ser Ile Ser Thr Ala Cys Ala Thr Gly Asn Tyr Cys Ile
    210                 215                 220

Leu Gly Ala Ala Asp His Ile Arg Arg Gly Asp Ala Asn Val Met Leu
225                 230                 235                 240

Ala Gly Gly Ala Asp Ala Ile Ile Pro Ser Gly Ile Gly Gly Phe
                245                 250                 255

Ile Ala Cys Lys Ala Leu Ser Lys Arg Asn Asp Glu Pro Glu Arg Ala
            260                 265                 270

Ser Arg Pro Trp Asp Ala Asp Arg Asp Gly Phe Val Met Gly Glu Gly
        275                 280                 285

Ala Gly Val Leu Val Leu Glu Glu Leu Glu His Ala Lys Arg Arg Gly
    290                 295                 300

Ala Thr Ile Leu Ala Glu Leu Val Gly Gly Ala Ala Thr Ser Asp Ala
```

His His Met Thr Glu Pro Asp Pro Gln Gly Arg Gly Val Arg Leu Cys
            325                 330                 335

Leu Glu Arg Ala Leu Glu Arg Ala Arg Leu Ala Pro Glu Arg Val Gly
        340                 345                 350

Tyr Val Asn Ala His Gly Thr Ser Thr Pro Ala Gly Asp Val Ala Glu
    355                 360                 365

Tyr Arg Ala Ile Arg Ala Val Ile Pro Gln Asp Ser Leu Arg Ile Asn
370                 375                 380

Ser Thr Lys Ser Met Ile Gly His Leu Leu Gly Ala Gly Ala Val
385                 390                 395                 400

Glu Ala Val Ala Ala Ile Gln Ala Leu Arg Thr Gly Trp Leu His Pro
                405                 410                 415

Asn Leu Asn Leu Glu Asn Pro Ala Pro Gly Val Asp Pro Val Val Leu
            420                 425                 430

Val Gly Pro Arg Lys Glu Arg Ala Glu Asp Leu Asp Val Val Leu Ser
        435                 440                 445

Asn Ser Phe Gly Phe Gly Gly His Asn Ser Cys Val Ile Phe Arg Lys
    450                 455                 460

Tyr Asp Glu
465

<210> SEQ ID NO 68
<211> LENGTH: 1404
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
atgcagaccg cgcaccagcg gcccccgacc gaggggcact gcttcggtgc gaggctgccc      60
acggcgtcga ggcgggcggt gcgccgggcg tggtcccgca tcgcgcgcgc ggcggccgcg     120
gccgacgcga ccccgcccg ccctccgcgc cgcgtggtcg tgacgggcca gggcgtggtg     180
accagcctgg ccagacgat cgagcagttt tacagcagcc tgctggaggg cgtgagcggc     240
atctcgcaga tccaaaagtt tgacaccacg ggctacacga cgacgatcgc gggcgagatc     300
aagtcgctgc agctggaccc gtacgtgccc aagcgctggg ccaagcgcgt ggacgacgtc     360
atcaagtacg tctacatcgc gggcaagcag gcgctggaga cgcggggct gccgatcgag     420 gcggcgggc tggcgggcgc ggggctggac ccgcgctgt gcggcgtgct catcggcacc     480
gccatggcgg gcatgacgtc cttcgcggcg ggcgtggagg cgctgacgcg cggcggcgtg     540
cgcaagatga ccccttttg catccccttc tccatctcca acatgggcgg cgcgatgctg     600
gcgatggaca tcggcttcat gggccccaac tactccatct ccacggcctg cgcgacgggc     660
aactactgca tcctgggcgc ggcggaccac atccggcgcg cgacgcgga cgtgatgctg     720 gccggcggcg cggacgcggc catcatcccc tcgggcatcg cggcttcat cgcgtgcaag     780 gcgctgagca agcgcaacga cgagcccgag gcgcgagcc ggccctggga cgccgaccgc     840
gacggcttcg tcatgggcga gggcgccggc gtgctggtgc tggaggagct ggagcacgcc     900
aagcgccgcg gcgcgaccat cctggccgaa ttcgtcggcg gcgcggccac ctcggacgcg     960
caccacatga ccgagccgga cccgcagggc gcggcgtgc gcctctgcct gaacgcgcg    1020 ctcgagcgcg cgcgcctcgc gcccgagcgc gtcggctacg tcaacgcgca cggcaccagc    1080

```
acgcccgcgg gcgacgtggc cgagtaccgc gccatccgcg ccgtcatccc gcaggactcg    1140
ctgcgcatca actccaccaa gtccatgatc gggcacctgc tcggcggcgc cggcgcggtc    1200
gaggccgtgg ccgccatcca ggccctgcgc accggctggc tccacccaa cctcaacctc     1260 gagaaccccg cacccggggt cgaccccgtc gtgctcgtgg ggccgcgcaa ggagcgcgcc    1320
gaagacctcg acgtcgtcct ctccaactcc tttggcttcg gcgggcacaa ctcgtgcgtc    1380
atcttccaaa agtacgacga gtga                                           1404
```

<210> SEQ ID NO 69
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

```
Met Gln Thr Ala His Gln Arg Pro Pro Thr Glu Gly His Cys Phe Gly
1               5                   10                  15

Ala Arg Leu Pro Thr Ala Ser Arg Arg Ala Val Arg Ala Trp Ser
            20                  25                  30

Arg Ile Ala Arg Ala Ala Ala Ala Asp Ala Thr Pro Ala Arg Pro
        35                  40                  45

Pro Arg Arg Val Val Val Thr Gly Gln Gly Val Val Thr Ser Leu Gly
    50                  55                  60

Gln Thr Ile Glu Gln Phe Tyr Ser Ser Leu Leu Glu Gly Val Ser Gly
65                  70                  75                  80

Ile Ser Gln Ile Gln Lys Phe Asp Thr Thr Gly Tyr Thr Thr Thr Ile
                85                  90                  95

Ala Gly Glu Ile Lys Ser Leu Gln Leu Asp Pro Tyr Val Pro Lys Arg
            100                 105                 110

Trp Ala Lys Arg Val Asp Asp Val Ile Lys Tyr Val Tyr Ile Ala Gly
        115                 120                 125

Lys Gln Ala Leu Glu Asn Ala Gly Leu Pro Ile Glu Ala Ala Gly Leu
    130                 135                 140

Ala Gly Ala Gly Leu Asp Pro Ala Leu Cys Gly Val Leu Ile Gly Thr
145                 150                 155                 160

Ala Met Ala Gly Met Thr Ser Phe Ala Ala Gly Val Glu Ala Leu Thr
                165                 170                 175

Arg Gly Gly Val Arg Lys Met Asn Pro Phe Cys Ile Pro Phe Ser Ile
            180                 185                 190

Ser Asn Met Gly Gly Ala Met Leu Ala Met Asp Ile Gly Phe Met Gly
        195                 200                 205

Pro Asn Tyr Ser Ile Ser Thr Ala Cys Ala Thr Gly Asn Tyr Cys Ile
    210                 215                 220

Leu Gly Ala Ala Asp His Ile Arg Arg Gly Asp Ala Asp Val Met Leu
225                 230                 235                 240

Ala Gly Gly Ala Asp Ala Ala Ile Ile Pro Ser Gly Ile Gly Phe
                245                 250                 255

Ile Ala Cys Lys Ala Leu Ser Lys Arg Asn Asp Glu Pro Glu Arg Ala
            260                 265                 270

Ser Arg Pro Trp Asp Ala Asp Arg Asp Gly Phe Val Met Gly Glu Gly
        275                 280                 285
```

```
Ala Gly Val Leu Val Leu Glu Glu Leu Glu His Ala Lys Arg Arg Gly
    290                 295                 300

Ala Thr Ile Leu Ala Glu Phe Val Gly Gly Ala Ala Thr Ser Asp Ala
305                 310                 315                 320

His His Met Thr Glu Pro Asp Pro Gln Gly Arg Gly Val Arg Leu Cys
                325                 330                 335

Leu Glu Arg Ala Leu Glu Arg Ala Arg Leu Ala Pro Glu Arg Val Gly
                340                 345                 350

Tyr Val Asn Ala His Gly Thr Ser Thr Pro Ala Gly Asp Val Ala Glu
            355                 360                 365

Tyr Arg Ala Ile Arg Ala Val Ile Pro Gln Asp Ser Leu Arg Ile Asn
        370                 375                 380

Ser Thr Lys Ser Met Ile Gly His Leu Leu Gly Gly Ala Gly Ala Val
385                 390                 395                 400

Glu Ala Val Ala Ala Ile Gln Ala Leu Arg Thr Gly Trp Leu His Pro
                405                 410                 415

Asn Leu Asn Leu Glu Asn Pro Ala Pro Gly Val Asp Pro Val Val Leu
                420                 425                 430

Val Gly Pro Arg Lys Glu Arg Ala Glu Asp Leu Asp Val Val Leu Ser
            435                 440                 445

Asn Ser Phe Gly Phe Gly Gly His Asn Ser Cys Val Ile Phe Gln Lys
    450                 455                 460

Tyr Asp Glu
465
```